United States Patent
Yang et al.

(10) Patent No.: US 9,062,066 B2
(45) Date of Patent: Jun. 23, 2015

(54) ANTI-INFLAMMATORY COMPOUND HAVING INHIBITORY ACTIVITY AGAINST MULTIPLE TYROSINE KINASES AND PHARMACEUTICAL COMPOSITION CONTAINING SAME

(75) Inventors: Beom-Seok Yang, Seoul (KR); Yong-Zu Kim, Deajeon (KR); Tae-Kyo Park, Deajeon (KR); Sung-Ho Woo, Deajeon (KR); Hyang-Sook Lee, Deajeon (KR); Sun-Young Kim, Deajeon (KR); Jong-Un Cho, Deajeon (KR); Hong-Bum Lee, Deajeon (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 127 days.

(21) Appl. No.: 13/699,970

(22) PCT Filed: May 26, 2011

(86) PCT No.: PCT/KR2011/003873
§ 371 (c)(1),
(2), (4) Date: Nov. 26, 2012

(87) PCT Pub. No.: WO2011/149288
PCT Pub. Date: Dec. 1, 2011

(65) Prior Publication Data
US 2013/0072482 A1     Mar. 21, 2013

(30) Foreign Application Priority Data

May 26, 2010  (KR) .................. 10-2010-0049368
May 26, 2010  (WO) ............... PCT/KR2011/003332

(51) Int. Cl.
C07D 495/04     (2006.01)
(52) U.S. Cl.
CPC .................................. *C07D 495/04* (2013.01)
(58) Field of Classification Search
CPC .................................................. C07D 495/04
USPC ....................................... 514/233.8; 544/116
See application file for complete search history.

(56) References Cited

U.S. PATENT DOCUMENTS 6,492,383 B1    12/2002  Munchhof et al.

FOREIGN PATENT DOCUMENTS

| CN | 101268081 A | 9/2008 |
| JP | 2001-522853 | 11/2001 |
| WO | WO 99/24440 A1 | 5/1999 |
| WO | 2006/124874 A2 | 11/2006 |
| WO | 2006/124874 A3 | 11/2006 |
| WO | WO 2007/056214 A2 | 5/2007 |
| WO | WO 2010062038 | * 6/2010 |

OTHER PUBLICATIONS

RN 874830-25-8, STN File Registry, entered STN Feb. 21, 2006.*
International Search Report of Corresponding PCT Application PCT/KR2011/003873 mailed Feb. 6, 2012.
A. Martin-Kohler et al., "Furo [2, 3-*d*] pyrimidines and oxazolo [5, 4-*d*]pyrimidines as inhibitors of Receptor Tyrosine Kinases (RTK)", *Helvetica Chimica Acta*, vol. 87, No. 4, 2004, pp. 956-975.
Database: RN 930654-42-5 Registry, Entered into STN on Apr. 18, 2007, and RN 874830-25-8 Registry, Entered into STN on Feb. 21, 2006, Retrieved from STN international [online] on Jul. 9, 2010, 1 page.
R. G. Robinett et al, "The discovery of substituted 4-(3-hydroxyanilino)-quinolines as potent RET kinase inhibitors", *Bioorganic & Medicinal Chemistry Letters*, vol. 17, No. 21, Aug. 2007, pp. 5886-5893.
Extended European Search Report mailed Oct. 31, 2013 in corresponding European Application No. 11 78 6920.

* cited by examiner

*Primary Examiner* — Rebecca Anderson
(74) *Attorney, Agent, or Firm* — Goldilocks ZONE IP LAW

(57) ABSTRACT

The present invention is for the anti-inflammatory compounds that have an inhibitory activity against protein tyrosine kinases and their pharmaceutical composition(s) containing the compound as the active ingredient. Since the compounds of the present invention can inhibit multiple protein kinases associated with inflammatory diseases and immune disorders, they are useful for their prevention or treatment.

10 Claims, 10 Drawing Sheets

* Significantly different from the TNCB group by t-test (p<0.05)

* Significantly different from the TNCB group by t-test (p<0.05)

* Significantly different from the TNCB group by t-test (p<0.05)

ated fibroblast, epithelial cells or alpha smooth muscle cells at the inflammatory site contribute importantly to various pathologies of inflammatory diseases.

ANTI-INFLAMMATORY COMPOUND HAVING INHIBITORY ACTIVITY AGAINST MULTIPLE TYROSINE KINASES AND PHARMACEUTICAL COMPOSITION CONTAINING SAME

CROSS REFERENCE TO RELATED APPLICATION

This application is a U.S. national stage application of PCT/KR2011/003873 filed May 26, 2011 and claims the foreign priority benefit of International Patent Application No. PCT/KR2010/003332, filed on May 26, 2010, and Korean Application No. 10-2010-0049368, filed May 24, 2010, in the Korean Intellectual Property Office, the contents of all of which are incorporated herein by reference.

TECHNICAL FIELD

This invention describes compounds that contain hydroxyl (or methoxy) anilino thieno pyrimidine or hydroxyl (or methoxy) anilino thieno pyridine moiety as the common pharmacophore and have the inhibitory activity against multiple tyrosine kinases and their pharmaceutical compositions that contain the compounds as an effective component. The pharmaceutical compositions mentioned above can be used for prevention or therapeutic purpose of various inflammatory disease and immune disorder and for promotion of wound healing and suppression of scar formation.

BACKGROUND ART

Inflammatory reaction is mainly due to the activities of inflammatory immune cells. In various inflammatory diseases, it is often observed that activated inflammatory immune cells influence neighboring fibroblast, epithelial cells and/or alpha smooth muscle cells to be activated into myoblast type cells. When fibroblast, epithelial cells, or alpha smooth muscle cells are activated into myoblast type cells, they show an enhanced ability for proliferation and migration and secret a large amount of extracellular matrix proteins such as fiber collagens which finally lead to induction of tissue fibrosis and hypertrophy. When this phenoma occur in wound healing process following tissue injury, the area of fibrosis gives scar in the tissue.

Recent researches provided with the evidence that cooperative activities of activated inflammatory cells with activated fibroblast, epithelial cells or alpha smooth muscle cells at the inflammatory site contribute importantly to various pathologies of inflammatory diseases.

One of the representative examples for the pathological phenomenon can be found in the wound healing process which occurs after external or internal injury on the tissues of our body by external phycal impact or internal continuous inflammation. After tissue injury, inflammatory immune cells such as macrophage, neutrophil, eosinophil, mast cell penetrate into the injured site rapidly and become activated to secret various cytokines, which in turn activate the neighboring fibroblast, epithelial cells, or alpha smooth muscle cells into myoblast type cells. These myoblasts synthesize and secret a large amount of extracellular matrix protein which leads to scar formation and tissue fibrosis and hypertrophy. (Gurtner G C et al., Trends Cell Biol. 15: 599-607, 2005). This pathological mechanism is the fundamental reason for scar formation in skin wound and for tissue fibrosis in lung, kidney and blood vessel. In addition, even in atopic dermatitis, asthma, COPD, psorisis, kelloid, proliferative retinopathy, the cooperative activation between inflammatory immune cells and fibrotic cells such as fibroblast, epitherial cells, or alpha smooth muscle cells occurs and these cells cooperatively contribute to the development of the pathology.

For example, atopic dermatitis is one of allergic skin inflammatory response where overactivation of type 2 helper T cell pathway is involved. In atopic dermatitis, IgE level in blood increases and cytokines such as IL-4, and IL-13 are also elevated. Water content in epidermis decreases and an excessive amount of mast cells are recruited into inflammatory site to secret a large amount of immune modulator by their degranulation. Interestingly collagen accumulation in skin is observed in atopic dermatitis. In psoriasis and kelloid, which are another skin inflammatory disease, the activation of keratinocyte is also involved in the process of tissue fibrosis along with invasion and activation of inflammatory cells.

Asthma is an allergic inflammatory reaction similarly to atopic dermatitis and happens in airway. Recently, it was known that activations of thoratic fibroblast, epithelial cells and/or alpha smooth muscle cells make an important contribution to inflammatory diseases in thoratic organs such as asthma and COPD in addition to inflammatory cells. In arterosclerosis, liver fibrosis, kidney fibrosis, and proliferative retinopathy, activations of alpha smooth muscle cells, liver stellate cell, kidney fibroblast, mesangial cell, ocular fibroblast respectively are observed along with the activations of inflammatory immune cells such as macrophage and they are importantly involved in the pathology of the inflammatory diseases.

When inflammatory immune cells are activated, an increased migration and secretion of various immune modulatory chemicals and cytokines are generally observed. For example, activation of macrophages increases their invasive activity through tissue induced by chemokines, the expression of iNOS (inducible nitric oxide synthase) and the synthesis of NO (nitric oxide). In addition, an increased synthesis of cytokines such as TNF-alpha is also typically observed. One of the notable features is the increased expression of alpha smooth muscle actin when Fibroblast, epithelial cells or alpha smooth muscle cells become activated into myoblast type cells. In addition, the cellular activity of FAK and Akt1 is increased, which contributes directly to an increase in cellular proliferation and migration.

We, inventors paid attention to the fact that the synergistic activation between inflammatory immune cells and neighboring fibroblast epithelial cell, or alpha smooth muscle cells occurs in various hardly-curable inflammatory diseases. Therefore we intended to develop compounds to suppress potently both the activation of immune cells and the activation of fibroblast, epithelial cells, or alpha smooth muscle cells into activated myoblast type cell in order to prevent and cure various hardly-curable inflammatory diseases or immune disorder. To accomplish this goal, the inventors intended to develop small molecular weight compounds to inhibit strongly against the activities of protein kinses involved directly in cell signaling pathways which lead the activations of inflammatory immune cells as well as fibroblast, epithelial cell, and alpha smooth muscle cells.

Especially c-Src family tyrosine kinases can be considered as the target for this goal among the cellular kinases since they play an important role in the signaling to activate various inflammatory immune cells. In addition, discoidin domain receptor family tyrosine kinases are important for the activations of fibroblast epithelial cells, or alpha smooth muscle cells to increase their proliferation and secretion of extra cellular matrix proteins.

Therefore, the inventors of the present invention provide with small molecule inhibitors to inhibit both c-Src family tyrosine kinases and discoidin domain receptor family tyrosine kinases simultaneously.

Protein kinases refer to proteins to catalyze the reaction to transfer a phosphate group at gamma position of ATP to hydroxyl group of tyrosine, serine or threonine at a specific substrate protein. The kinases to transfer phosphate to tyrosine to produce phospho-tyrosine are called protein tyrosine kinases. In vertebrate animal cells, more than 500 proteins kinases are found. One of their important roles is to play a role in signal transduction pathways which respond to the internal or external stimuli and their regulated activity is necessary for the maintenance of cell homiosis. However their excessive expression, over-activity or reduced expression or activity is directly or indirectly associated with various diseases such as cancer and immune disorders. For example, an abnormal over-activity of a certain protein kinases was proved as one of the main reasons for abnormal over-proliferations, migration, metastasis, and over-production of cytokines in cancer and immune cells.

Some protein tyrosine kinases are known as directly involved in the cell signaling to activate inflammatory immune cells and inflammatory response. Of them, Src family tyrosine kinase is one of the most extensively studied kinases.

Src family tyrosine kinases are consisted of total 8 non-receptor tyrosine kinases including Fgr, Fyn, Yes, Blk, Hck, Lck, Lyn along with c-Src. Their multiple in vivo functions are well elucidated and especially their important roles in immune cells to carry out immunological reactions are confirmed (Okutani et al., Am. J. Physiol. Lung Cell Mol. Physiol. 291: 129-141, 2006). Among the family proteins, Hck, Fgr, and Lyn are important for the activation of inflammatory cells such as macrophage and neutrophil and their adhesion in inflammatory site. Lck is known to be expressed mostly in T-cells and it is activated in the down stream of T-cell receptor in T cell signaling where its activity plays a critical role for the receptor signaling. In addition, Hck, Lyn, and Fgr showed an increased expression when monocyte cells and macrophage are activated by for example LPS (lipo-polysaccharide). In addition, for example, when the expressions of Lyn, Fyn, Blk are inhibited, differentiation of immature B-cells into mature B-cells is suppressed in B-cell differentiation. Src family kinases are also indispensible for the accumulation of monocyte cells, macrophage, neutrophil cell in an inflammatory site and their activation as well as their participation to inflammatory reaction. Many cases of autoimmune and immunological diseases are associated with the activations of immune cells such as T-cell, B-cell, monocyte cell, and/or macrophage. In addition, other non-receptor tyrosine kinases are also important for the activations of inflammatory cells. Syk1 kinase is important for the activations of B cell, mastcell, macrophage, and monocyte cell. In addition, Btk1 is associated with the activations of macrophage, mast cell, and platelet. Therefore these three non-receptor tyrosine kinases of c-Src family, Syk1, Btk1 are considered as important major targets for developing drugs to suppress inflammatory reactions.

Discoidin domain receptor family (DDR) belongs to receptor tyrosine kinase family and consistes of type 1 and type 2 which have 89% homology in their kinase domain. These receptors have collagen as their activating ligand. DDR2 is important for cell migration, proliferation, and the increased synthesis of collagen when fibrblast cells are activated. It is also important for the activation of liver sellate cells which produce excessive collagen in liver cirrhosis, for the activation of synovial fibroblasts in joint tissue of arthritis and for the activation of arortic alpha smooth muscle cells of blood vessel wall in restenosis and arterosclerosis. DDR1 is also important for the proliferation of alpha smooth muscle cells in blood vessel and is involved in the tissue fibrosis by over-activation of fibroblast cells in kidney and lung. In addition, it plays a role for the accumulation of macrophage at inflammatory site in arterosclerosis, kidney fibrosis, and lung fibrosis.

We inventors synthesized small molecule compounds to have either thieno pyrimidine or thieno pyridine as a pharmacophore and have specific substituents around the pharmacophore to inhibit the activities of both c-Src family tyrosine kinases and discoidin domain receptor family tyrosine kinases simultaneously. Furthermore we confirmed that these compounds can inhibit both Src family tyrosine kinase activity that is important for the activation of cell signaling in immune cells and discoidin domain receptor family tyrosine kinase activity that is involved in the activations of fibroblast and alpha smooth muscle cells. Therefore we accomplished the present invention by confirming that these compounds are useful to cure various inflammatory diseases or immune disorder and to promote wound healing, and suppression of scar formation.

DISCLOSURE

Technical Problem

An object of the present invention is to provide new compounds to inhibit activities of both c-Src family tyrosine kinase and discoidin domain receptor family tyrosine kinase family activity simultaneously as well as their isomers, or their pharmaceutically acceptable salts.

Another object of the present invention is to provide a pharmaceutical composition for preventing or treating inflammatory disease, immune disorder, or tissue fibrosis and scar formation in wound healing process, comprising the compound, an isomer thereof or pharmaceutically acceptable salts thereof as an active ingredient.

Another object of the present invention is to provide a method for treating inflammatory disease or immune disorder comprising the step of administering into a patient a therapeutically effective amount of the compound, an isomer thereof or pharmaceutically acceptable salts thereof.

Another object of the present invention is to provide the method for preventing scar formation or promoting wound healing comprising the step of administering into a patient a therapeutically effective amount of the compound, an isomer thereof or pharmaceutically acceptable salts thereof.

Technical Solution

To achieve the goals in accordance with the purpose of the present invention, the present invention provides a compound of the chemical formula 1, isomers thereof or pharmaceutically acceptable salts thereof. In addition, the present invention provides with the usage of the compounds mentioned above, or their isomer or their salts that are pharmaceutically acceptable for prevention or therapeutic purpose of inflammatory diseases, immune disorder, wound healing promotion and/or suppression of scar formation.

[Chemical formula 1]

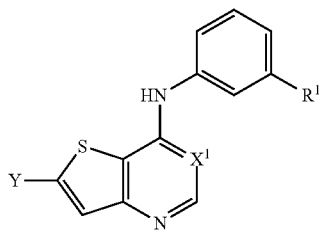

Wherein, $X^1$ is N or CH;

$R^1$ is —OH or —OCH$_3$;

Y is C$_{6-10}$ aryl substituted with R$^2$, or C$_{5-10}$ heteroaryl substituted with R$^2$ or N-methylpiperazinyl;

R$^2$ is —(CH$_2$)$_n$—R$^3$, —(CH$_2$)$_n$—C(O)—R$^3$, or —O(CH$_2$)$_n$—R$^3$;

R$^3$ is —H, —CN, halogen, C$_{1-3}$ alkyl, C$_{1-3}$ alkoxy, phenyl, pyridinyl, amino, di C$_{1-3}$ alkyl amino, di C$_{1-3}$ alkylamino, hydroxyl C$_{1-3}$ alkyl amino, carboxy C$_{1-3}$ alkyl amino, C$_{3-6}$ cycloalkyl C$_{1-3}$ alkylamino, pyrrolidinyl, hydroxyl pyrrolidinyl, hydroxyl C$_{1-3}$ alkylpyrrolidinyl, carboxypyrrolidinyl, piperidinyl, C$_{1-3}$ alkylpiperidinyl, di C$_{1-3}$ alkyl piperidinyl, piperazinyl, C$_{1-3}$ alkylpiperazinyl, C$_{1-4}$ alkoxycarbonylpiperazinyl, or morpholinyl; and n is an integer selected from 0 to 3.

In the preferred embodiment of the present invention, R$^3$ mentioned above is selected from —H, —CN, halogen, C$_{1-3}$ alkyl, C$_{1-3}$ alkoxy, phenyl, pyridinyl, amino, ethyl amino, diethylamino, pyrrolidinyl, piperidinyl, piperazinyl, morpholinyl or a group defined as the structural formula shown below.

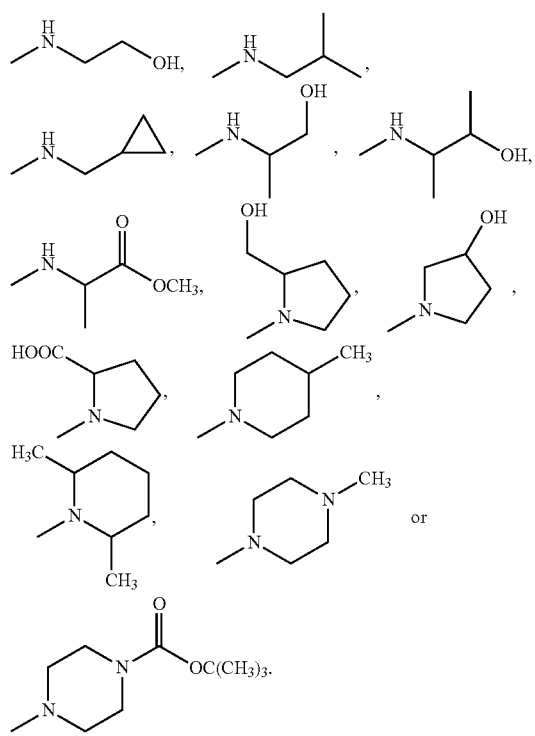

Advantageous Effects

The compounds of the present invention, their isomer or their pharmaceutically acceptable salts have the simultaneous inhibitory activities against both c-Src family tyrosine kinase and discoidin domain receptor family tyrosine kinase so that they can be used effectively to prevent and cure various inflammatory and immune diseases (especially inflammatory diseases accompanying tissue fibrosis), to promote healing in skin wound and to suppress scar formation.

BEST MODE

Figure 1:
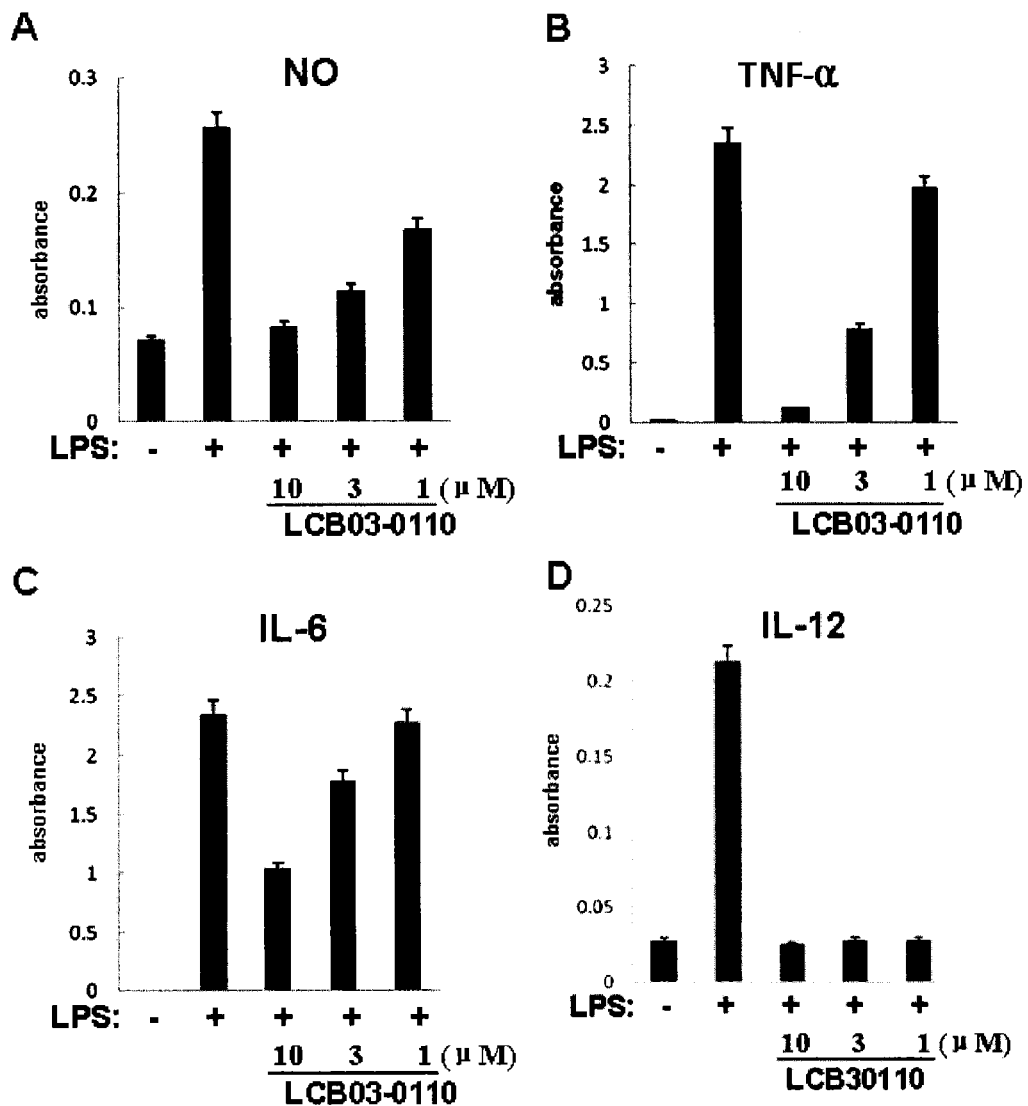
FIG. 1 shows graphs to depict the inhibitory effect of a compound mentioned in the preferred embodiment described in the present invention against NO and immune cytokines in activated macrophage.

We inventors define terms before describing the art of the present invention in detail.

The term "Src", as used herein, stands for Src protein tyrosine kinase that is expressed in various cells and induced in macrophage. Src is involved in the cell signaling to induce expressions of genes involved in inflammation, for example TNF-alpha which is induced in macrophage by the treatment of LPS.

The term "Yes", as used herein, stands for a tyrosine kinase that belongs to Src family tyrosine kinase and is expressed in various cells. Yes is involved in the cell signaling pathways of cytokines in immune and inflammatory cells.

The term "Fyn", as used herein, stands for a tyrosine kinase that belongs to Src family tyrosine kinase, expressed in, for example, T-cells, B-cells, NK cells, and mast cell. It is involved in the signaling pathway from T-cell receptor and cell adhesion and plays an important role in the degranulation and cytokine synthesis in mast cells.

The term "lck", as used herein, stands for a tyrosine kinase that belongs to Src family tyrosine kinase, expressed in for example T-cell and NK cell and plays a central role for the T cell activation and differentiation.

The term "Lyn", as used herein, stands for a tyrosine kinase that belongs to Src family tyrosine kinase, expressed broadly in T-cell, B-cell, NK cell, neutrophil, eosinophil, macrophage, monocyte, mast cell and dendritic cell and regulates B-cell activity.

The term "Hck", as used herein, stands for a tyrosine kinase that belongs to Src family tyrosine kinase, expressed in for example neutrophil, eosinophil, macrophage, monocyte, dendritic cell and mediates the cell signalings involved in the proliferation, differentiation and migration of these cells.

The term "Fgr", as used herein, stands for a tyrosine kinase that belongs to Src family tyrosine kinase, expressed in for example neutrophil, eosinophil, macrophage, monocyte, dendritic cell and involved in the cell signalings of B-cell receptor, FcR, and integrin family.

The term "Syk1", as used herein, stands for a tyrosine kinase that belongs to Src family tyrosine kinase, expressed broadly in T-cell, B-cell, mastcell, monocyte, and macrophage as well as fibroblast cell, epithelial cells, liver cell, neuronal cell, endotherial cell. It works at a down stream of Src family tyrosine kinase signaling pathway and play an important role in cell signaling of FceR receptor. Therefore it is regarded as one of the major targets for inflammatory diseases.

The term "Btk1", as used herein, stands for a tyrosine kinase that belongs to Tec family tyrosine kinase, expressed broadly in blood cells such as B-cell, mastcell, and macrophage. It is well known to play an important role in B-cell proliferation and differentiation and cell signaling to activate mastcell, macrophage, platelet, osteoblast cell.

The term "VEGFR2", as used herein, stands for a tyrosine kinase that belongs to VEGFR family tyrosine kinase, and is a major receptor for VEGF-A. This receptor plays an important role when endotherial cells differentiate from their precursor, mesodermal cells so that it is important for cell signalings of angiogenesis. Uncontrolled angiogenesis as well as inflammatory reaction contributes to the development of diseases such as diabetic retinopathy and rheumatis. Therefore the inhibition of this receptor is a valuable therapeutic target for cancer and inflammatory diseases where an uncontrolled and excessive angiogenesis is a serious problem.

The term "discoidin domain receptor family (DDR) tyrosine kinase", as used herein, consists of two types, that is DDR1 and DDR2. They have collagen as their ligand and become activated for autophosphorylating activity upon the ligand binding. Activation of DDR1 is involved in the differentiation of macrophage and the activations of epithelial cells and alpha smooth muscle cells. DDR2 is involved in the activation of fibroblast, liver stellate cells, cartilage cells, and alpha smooth muscle cells.

The present invention is described more in detail in the following.

The present invention provides a compound of the following chemical formula 1, an isomer thereof or pharmaceutically acceptable salts thereof. In addition, the present invention provides a pharmaceutical composition for preventing or treating inflammatory disease and immune disorder, or promoting wound healing and preventing scar formation, comprising the compound of the following chemical formula 1, an isomer thereof or pharmaceutically acceptable salts thereof as an active ingredient.

[Chemical formula 1]

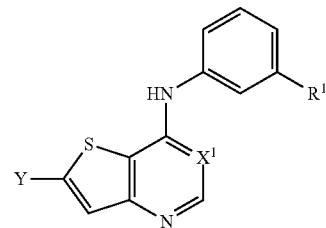

Wherein,
$X^1$ is N or CH;
$R^1$ is —OH, or —OCH$_3$;
Y is $C_{6-10}$ aryl substituted with $R^2$, or $C_{5-10}$ heteroaryl substituted with $R^2$ or N-methylpiperazinyl;
$R^2$ is —(CH$_2$)$_n$—$R^3$, —(CH$_2$)$_n$—C(O)—$R^3$, or —O(CH$_2$)$_n$—$R^3$;
$R^3$ is —H, —CN, halogen, $C_{1-3}$ alkyl, $C_{1-3}$ alkoxy, phenyl, pyridinyl, amino, $C_{1-3}$ alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkyl amino, pyrrolidinyl, hydroxyl pyrrolidinyl, hydroxyl $C_{1-3}$ alkyl pyrrolidinyl, carboxy pyrrolidinyl, piperidinyl, $C_{1-3}$ alkyl piperidinyl, di $C_{1-3}$ alkyl piperidinyl, piperazinyl, $C_{1-3}$ alkyl piperazinyl, $C_{1-4}$ alkoxy carbonyl piperazinyl, or morpholinyl; and n is an integer selected from 0 to 3.

In the preferred embodiment of the present invention, $R^3$ mentioned above is —H, —CN, halogen, $C_{1-3}$ alkyl, $C_{1-3}$ alkoxy, phenyl, pyridinyl, amino, ethylamino, diethylamino, pyrrolidinyl, piperidinyl, piperazinyl, morpholinyl or any one selected from the group consisting of the structural formula shown below.

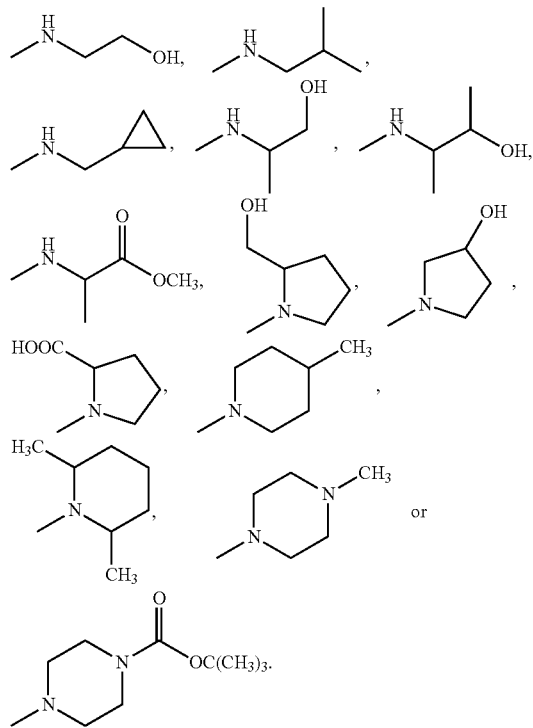

In addition, the compounds of chemical formula 1 in the present invention can be formulated as pharmaceutically acceptable salts and these pharmaceutically acceptable salts contain acids which can be formulated as an non-toxic acid salts including pharmaceutically-acceptable anions, for example, inorganic acids such as HCl, H2SO4, HNO3, H2PO4, HBr, HI, organic carboxylic acids such as tartaric acid, formic acid, citric acid, acetic acid, trichloroacetic acid, trifluoroacetic acid, glcuronic acid, benzoic acid, lactic acid, fumaric acid, maleic acid, and acid salts formulated by sulfonic acids such as methansulfonic acid, benzene sulfonic acid, p-toluene sulfonic acid or napthalene sulfonic acid. In the preferred embodiment of the present invention, the pharmaceutically-acceptable salts can be formulated using HCl or trifluoroacetic acid.

The representative compounds among the compounds denoted as chemical formula 1 are listed as the followings. The names inside of parenthesis are code names and used for the distinction of compounds in this invention.

3-(6-(phenylthieno[3,2-d]pyrimidine-4-ylamino)phenol (LCB 03-0008),
4-(4-(3-methoxyphenylamino)thieno[3,2-d]pyrimidine-6-yl)benzonitrile (LCB 03-0009),
4-(4-(3-hydroxyphenylamino)thieno[3,2-d]pyrimidine-6-yl)benzonitrile (LCB 03-0013),
3-(6-bromo-thieno[3,2-d]pyrimidine-4-nyl amino)-phenol (LCB 03-0015),
4-(4-(3-methoxyphenylamino)thieno[3,2-d]pyrimidine-6-yl)phenol (LCB 03-0016),
3-[6-(4-methoxyphenyl)-thieno[3,2-d]pyrimidine-4-nyl amino]-phenol (LCB 03-0017),
N-(3-methoxyphenyl)-6-(4-(2-morpholinoethoxy)phenyl) thieno[3,2-d]pyrimidine-4-amine (LCB 03-0018),
3-(6-(4-chlorophenyl)thieno[3,2-d]pyrimidine-4-yl amino) phenol (LCB 03-0019),
3-(6-(4-(2-morpholinoethoxy)phenyl)thieno[3,2-d]pyrimidine-4-ylamino)phenol (LCB 03-0020),
N-(3-methoxyphenyl)-6-(4-phenethoxyphenyl)thieno[3,2-d]pyrimidine-4-amine (LCB 03-0021),
N-(3-methoxyphenyl)-6-(4-(2-(pyridine-2-yl)ethoxy)phenyl)thieno[3,2-d]pyrimidine-4-amine (LCB 03-0022),
(6-furan-2-yl-thieno[3,2-d]pyrimidine-4-yl)-(3-methoxyphenol)-amine (LCB 03-0023),
(6-furan-3-yl-thieno[3,2-d]pyrimidine-4-yl)-(3-methoxyphenol)-amine (LCB 03-0024),
N-(3-methoxyphenyl)-6-(4-(2-(pyrrolidine-1-yl)ethoxy) phenyl)thieno[3,2-d]pyrimidine-4-amine (LCB 03-0026),
N-(3-methoxyphenyl)-6-(thiophene-2-yl)thieno[3,2-d]pyrimidine-4-amine (LCB 03-0027),
(3-methoxyphenyl)-(6-thiophene-3-yl-thieno[3,2-d]pyrimidine-4-yl)-amine (LCB 03-0028),
N-(3-methoxyphenyl)-6-(4-(2-(piperazine-1-yl)ethoxy)phenyl)thieno[3,2-d]pyrimidine-4-amine (LCB 03-0029),
(3-methoxyphenyl)-(6-thiophene-2-yl-thieno[3,2-d]pyrimidine-4-yl)-amine (LCB 03-0030),
3-(6-thiophene-3-yl-thieno[3,2-d]pyrimidine-4-ylamino)-phenol (LCB 03-0031),
3-((6-(4-(morpholinomethyl)phenyl)thieno[3,2-d]pyrimidine-4-ylamino)phenol (LCB 03-0032),
3-((6-(4-(piperazine-1-ylmethyl)phenyl)thieno[3,2-d]pyrimidine-4-ylamino)phenol (LCB 03-0033),
3-(6-(4-(pyrrolidine-1-ylmethyl)phenyl)thieno[3,2-d]pyrimidine-4-ylamino)phenol (LCB 03-0034),
3-((6-(4-(piperidine-ylmethyl)phenyl)thieno[3,2-d]pyrimidine-4-ylamino)phenol (LCB 03-0035),
3-((6-(4-((4-methylpiperazine-1-yl-methyl)phenyl)thieno[3,2-d]pyrimidine-4-ylamino)phenol (LCB 03-0036),
3-(6-(4-((diethylamino)methyl)phenyl)thieno[3,2-d]pyrimidine-4-ylamino)phenol (LCB 03-0037),
3-(6-(furan-2-yl)thieno[3,2-d]pyrimidine-4-ylamino)phenol (LCB 03-0038),
3-(6-(furan-2-yl)thieno[3,2-d]pyrimidine-4-ylamino)phenol (LCB 03-0039),
3-(6-(4-((cyclopropylmethylamino)methyl)phenyl)thieno[3,2-d]pyrimidine-4-ylamino)phenol (LCB 03-0040),
3-((6-(4-((isobutylamino)methyl)phenyl)thieno[3,2-d]pyrimidine-4-ylamino)phenol (LCB 03-0041),
3-((6-(4-((ethylamino)methyl)phenyl)thieno[3,2-d]pyrimidine-4-ylamino)phenol (LCB 03-0042),
3-((6-(4-(2-(pyrrolidine-1-yl)ethyl)phenyl)thieno[3,2-d]pyrimidine-4-ylamino)phenol (LCB 03-0043),
3-((6-(4-(2-(piperidine-1-yl)ethyl)phenyl)thieno[3,2-d]pyrimidine-4-ylamino)phenol (LCB 03-0044),
3-((6-(4-(2-(4-methylpiperazine-1-yl)ethyl)phenyl)thieno[3,2-d]pyrimidine-4-ylamino)phenol (LCB 03-0045),
3-(6-(4-(2-morpholinoethyl)phenyl)thieno[3,2-d]pyrimidine-4-ylamino)phenol (LCB 03-0046),
2-(4-(4-(3-hydroxyphenylamino)thieno[3,2-d]pyrimidine-6-yl)phenyl)-1-(4-methylpiperazine-1-yl)ethanone (LCB 03-0047),
2-(4-(4-(3-hydroxyphenylamino)thieno[3,2-d]pyrimidine-6-yl)phenyl)-1-(pyrrolidine-1-yl)ethanone (LCB 03-0049), N,N-diethyl-2-(4-(4-(3-hydroxyphenylamino)thieno[3,2-d]pyrimidine-6-yl)phenyl)acetamide (LCB 03-0050), 3-(4-(3-hydroxyphenylamino)thieno[3,2-d]pyrimidine-6-yl)benzoic acid (LCB 03-0051)

(4-(4-(3-hydroxyphenylamino)thieno[3,2-d]pyrimidine-6-yl)phenyl)(4-methylpiperazine-1-yl)methanone (LCB 03-0052), (3-(4-(3-hydroxyphenylamino)thieno[3,2-d]pyrimidine-6-yl)phenyl)pyrrolidine-1-yl)methanone (LCB 03-0053), N,N-diethyl-3-(4-(3-hydroxyphenylamino)thieno[3,2-d]pyrimidine-6-yl)benzamide (LCB 03-0054), (3-(4-(3-hydroxyphenylamino)thieno[3,2-d]pyrimidine-6-yl)phenyl(4-methylpiperazine-1-yl)methanone (LCB 03-0055), methyl 1-(4-(4-(3-hydroxyphenylamino)thieno[3,2-d]pyrimidine-6-yl)benzyl)pyrrolidine-2-carboxylate (LCB 03-0056), 3-(6-(4-(2-(hydroxymethyl)pyrrolidine-1-yl)methyl)phenyl)thieno[3,2-d]pyrimidine-4-ylamino)phenol (LCB 03-0057), 3-(6-(4-(4-methylpiperidine-1-yl)methyl)phenyl)thieno[3,2-d]pyrimidine-4-ylamino)phenol (LCB 03-0058), 3-(6-(4-(((2R,6S)-2,6-dimethylpiperidine-1-yl)methyl)phenyl)thieno[3,2-d]pyrimidine-4-ylamino)phenol (LCB 03-0059), 3-(6-(3-(piperidine-1-ylmethyl)phenyl)thieno[3,2-d]pyrimidine-4-ylamino)phenol (LCB 03-0060), 3-(6-(3-((4-methylpiperazine-1-yl)methyl)phenyl)thieno[3,2-d]pyrimidine-4-ylamino)phenol (LCB 03-0061), 3-(6-(3-(pyrrolidine-1-ylmethyl)phenyl)thieno[3,2-d]pyrimidine-4-ylamino)phenol (LCB 03-0062), 3-(6-(3-((diethylamino)methyl)phenyl)thieno[3,2-d]pyrimidine-4-ylamino)phenol (LCB 03-0063), 3-(6-(3-(piperazine-1-ylmethyl)phenyl)thieno[3,2-d]pyrimidine-4-ylamino)phenol (LCB 03-0064), 3-(6-(3-((ethylamino)methyl)phenyl)thieno[3,2-d]pyrimidine-4-ylamino)phenol (LCB 03-0065), 3-(6-(3-(morpholinomethyl)phenyl)thieno[3,2-d]pyrimidine-4-ylamino)phenol (LCB 03-0066), 3-(6-(3-((isobutylamino)methyl)phenyl)thieno[3,2-d]pyrimidine-4-ylamino)phenol (LCB 03-0067), 1-(4-(4-(3-hydroxyphenylamino)thieno[3,2-d]pyrimidine-6-yl)benzyl)pyrrolidine-2-carboxamide HCl salt (LCB 03-0068)

1-(4-(4-(3-hydroxyphenylamino)thieno[3,2-d]pyrimidine-6-yl)benzyl)pyrrolidine-2-carboxylic acid HCl salt (LCB 03-0069)

3-(6-(4-((2-hydroxyethylamino)methyl)phenyl)thieno[3,2-d]pyrimidine-4-ylamino)phenol (LCB 03-0070), methyl 2-(3-(4-(3-hydroxyphenylamino)thieno[3,2-d]pyrimidine-6-yl)benzamido)propanoate (LCB 03-0071)

1-(4-(4-(3-hydroxyphenylamino)thieno[3,2-d]pyrimidine-6-yl)benzyl)pyrrolidine-3-ol HCl salt (LCB 03-0072)

3-(6-(4-(ethoxymethyl)phenyl)thieno[3,2-d]pyrimidine-4-ylamino)phenol (LCB 03-0073), 4-(4-(3-hydroxyphenylamino)thieno[3,2-d]pyrimidine-6-yl)-N-(1-hydroxyprophane-2-yl)benzamide (LCB 03-0074), 2-(4-(4-(3-hydroxyphenylamino)thieno[3,2-d]pyrimidine-6-yl)benzamido) propanoic acid (LCB 03-0075)

3-(6-(3-(2-(pyrrolidine-1-yl)ethyl)phenyl)thieno[3,2-d]pyrimidine-4-ylamino)phenol (LCB 03-0076), 3-(6-(3-(2-(piperazine-1-yl)ethyl)phenyl)thieno[3,2-d]pyrimidine-4-ylamino)phenol (LCB 03-0079), 3-(2-(4-(pyrrolidine-1-ylmethyl)phenyl)thieno[3,2-b]pyridine-7-ylamino)phenol (LCB 03-0080), 3-(6-(4-morpholinophenyl)thieno[3,2-d]pyrimidine-4-ylamino)phenol (LCB 03-0082), 3-(2-(4-(morpholinomethyl)phenyl)thieno[3,2-b]pyridine-7-ylamino)phenol (LCB 03-0083), 3-(2-(4-((4-methylpiperazine-1-ylmethyl)phenyl)thieno[3,2-b]pyridine-7-ylamino)phenol (LCB 03-0084), 3-(6-(5-(pyrrolidine-1-ylmethyl)thiophene-2-yl)thieno[3,2-d]pyrimidine-4-ylamino)phenol (LCB 03-0085), 3-(6-(5-(pyrrolidine-1-ylmethyl)furan-2-yl)thieno[3,2-d]pyrimidine-4-ylamino)phenol (LCB 03-0086), 3-(6-(5-((4-methylpiperazine-1-yl)methyl)furan-2-yl)thieno[3,2-d]pyrimidine-4-ylamino)phenol (LCB 03-0087), 3-(6-(5-(piperidine-1-ylmethyl)furan-2-yl)thieno[3,2-d]pyrimidine-4-ylamino)phenol (LCB 03-0088), 3-(6-(5-(morpholinomethyl)furan-2-yl)thieno[3,2-d]pyrimidine-4-ylamino)phenol (LCB 03-0089), 3-(6-(5-(piperazine-1-ylmethyl)furan-2-yl)thieno[3,2-d]pyrimidine-4-ylamino)phenol (LCB 03-0090), 3-(6-(5-((ethylamino)methyl)furan-2-yl)thieno[3,2-d]pyrimidine-4-ylamino)phenol (LCB 03-0091), 3-(6-(5-((4-methylpiperazine-1-yl)methyl)thiophene-2-yl)thieno[3,2-d]pyrimidine-4-ylamino)phenol (LCB 03-0092), 3-(6-(5-(piperidine-1-ylmethyl)thiophene-2-yl)thieno[3,2-d]pyrimidine-4-ylamino)phenol (LCB 03-0093), 3-(6-(5-(piperazine-1-ylmethyl)thiophene-2-yl)thieno[3,2-d]pyrimidine-4-ylamino)phenol (LCB 03-0094), 3-(6-(5-((ethylamino)methyl)thiophene-2-yl)thieno[3,2-d]pyrimidine-4-ylamino)phenol (LCB 03-0095), 3-(2-(4-(piperidine-1-ylmethyl)phenyl)thieno[3,2-b]pyridine-7-ylamino)phenol (LCB 03-0097), 3-(2-(4-(piperazine-1-ylmethyl)phenyl)thieno[3,2-b]pyridine-7-ylamino)phenol (LCB 03-0098), 3-(2-(4-((ethylamino)methyl)phenyl)thieno[3,2-b]pyridine-7-ylamino)phenol (LCB 03-0099), 3-(2-(4-methylpiperazine-1-yl)thiazolo[4,5-d]pyrimidine-7-ylamino)phenol (LCB 03-0100), 3-(6-(4-(pyrrolidine-1-ylmethyl)thiophene-2-yl)thieno[3,2-d]pyrimidine-4-ylamino)phenol (LCB 03-0101), 3-(6-(4-((4-methylpiperazine-1-yl)methyl)thiophene-2-yl)thieno[3,2-d]pyrimidine-4-ylamino)phenol (LCB 03-0102), 3-(6-(4-(piperidine-1-ylmethyl)thiophene-2-yl)thieno[3,2-d]pyrimidine-4-ylamino)phenol (LCB 03-0103), 3-(6-(4-(morpholinomethyl)thiophene-2-yl)thieno[3,2-d]pyrimidine-4-ylamino)phenol Trifluoroacetic acid (LCB 03-0104)

3-(6-(4-(piperazine-1-ylmethyl)thiophene-2-yl)thieno[3,2-d]pyrimidine-4-ylamino)phenol Trifluoroacetic acid (LCB 03-0105)

3-(6-(4-((ethylaminomethyl)thiophene-2-yl)thieno[3,2-d]pyrimidine-4-ylamino)phenol (LCB 03-0106), 3-(2-(3-(pyrrolidine-1-ylmethyl)phenyl)thieno[3,2-b]pyridine-7-ylamino)phenol (LCB 03-0107), 3-(2-(3-((4-methylpiperazine-1-yl)methyl)phenyl)thieno[3,2-b]pyridine-7-ylamino)phenol (LCB 03-0108), 3-(2-(3-(piperidine-1-ylmethyl)phenyl)thieno[3,2-b]pyridine-7-ylamino)phenol (LCB 03-0109), 3-(2-(3-(morpholinomethyl)phenyl)thieno[3,2-b]pyridine-7-ylamino)phenol (LCB 03-0110), 3-(2-(3-(piperazine-1-ylmethyl)phenyl)thieno[3,2-b]pyridine-7-ylamino)phenol (LCB 03-0111), 3-(2-(3-((ethylamino)methyl)phenyl)thieno[3,2-b]pyridine-7-ylamino)phenol (LCB 03-0112), 3-(6-(4-(pyrrolidine-1-ylmethyl)furan-2-yl)thieno[3,2-d]pyrimidine-4-ylamino)phenol (LCB 03-0113).

3-(6-(4-((4-methylpiperazine-1-yl)furan-2-yl)thieno[3,2-d]pyrimidine-4-ylamino)phenol trifluoroacetic acid (LCB 03-0114) and 3-(6-(4-(piperidine-1-ylmethyl)furan-2-yl)thieno[3,2-d]pyrimidine-4-ylamino)phenol (LCB 03-0115)

In a preferred embodiment of the present invention, the compounds of the present invention include 3-(2-(3-(morpholinomethyl)phenyl)thieno[3,2-b]pyridine-7-ylamino)phenol which is denoted as LCB 03-0110.

The compounds of the present invention inhibits the activations of both immune cells involved in inflammatory diseases or immune disorder and fibrotic cells involved in wound healing reaction. In a preferred embodiment of the present invention, inventors found that this compound inhibits both Src family tyrosine kinase and discoidin domain receptor family tyrosine kinase simultaneously, and furthermore it inhibits potently Syk1 tyrosine kinase, Btk1 tyrosine kinase, EphA3 tyrosine kinase, FLT3 tyrosine kinase and VEGFR2 tyrosine kinase as well.

Syk1, Btk1, VEGFR2, EphA3, FLT3 are important for the activations of immune cells in inflammatory response and it was suggested that their inhibitors would be effective anti-inflammatory agents. Therefore the compounds denoted as chemical formula 1 can be effectively used for prevention and/or cure of various inflammatory diseases, tissue fibrosis, the diseases related to scar formation associated with inflammation, the promotion of skin wound healing and the suppression of scar formation since these compounds inhibits c-Src family tyrosine kinase as well as several kinases importantly involved in various inflammatory response so that the synthesis of NO and TNF-alpha in inflammatory cells such as macrophage are suppressed and in addition, they suppress the activations of fibroblast, epitherial cells, or alpha smooth muscle cells into myoblast type to inhibit the synthesis of alpha smooth muscle actin, and enhanced proliferation and migration of these cells because they can inhibit against discoidin domain receptor family tyrosine kinase activity.

In fact, the compounds of the present invention showed anti-inflammatory activity in mouse skin inflammatory model generated by treatment with oxazolone. In addition, when the representative compound, LCB 03-0110 among the compounds denoted as chemical formula I was treated into activated macrophage, the synthesis of iNOS protein, NO, and immune cytokine, TNF-alpha and the migration of macrophage into inflammatory site were suppressed, and in addition, the synthesis of TNF-alpha and IL-4 in mast cells and their degranulation were inhibited. Furthermore, its pharmaceutical activities such as the suppression of atopic dermatitis in the mouse model, the promotion of wound healing and suppression of scar formation in skin wound healing model, and the suppression of asthma in mouse asthma model induced by ovalbumin were confirmed. Therefore the provided compounds can be used effectively for prevention and/or cure of various inflammatory diseases, especially diseases related to tissue fibrosis and scar formation associated with inflammation, the promotion of skin wound healing and the suppression of scar formation.

In addition, the compounds of the present invention that have thieno pyridine as the pharmacophore showed a significantly enhanced activity for the suppression against macrophage activation that is related to inflammatory diseases and immune disorder and for the inhibition of fibroblast activation that occurs in wound healing process and exhibited a significantly enhanced efficacy in an animal model of skin inflammation as well when they were compared to the similar compounds which are not included in the definition by chemical formula 1 of the present invention (control compound 1, 2 and 3 described in the detailed description of the preferred embodiments for the present invention).

The considerable contributions made by the present invention are listed as the followings.

1) the compounds provided by the present invention are new compounds which never ever have been synthesized.

2) the compounds provided by the present invention can inhibit the activations of inflammatory cells like macrophage and the activations of fibroblast, epitherial cell or alpha smooth muscle cells into myoblast type cells simultaneously. Because of these activities, they can be used for prevention and/or cure of various inflammatory diseases or immune disorder such as dermatitis (contact and atopic dermatitis), asthma, COPD, psoriasis, proliferative retinopathy and the promotion of skin wound healing and prevention of scar formation. For this, in the detailed description of the preferred embodiments, the compounds of the present invention was confirmed directly to inhibit simultaneously both of c-Src family kinase and discoidin domain receptor family kinase activity which are importantly involved in the activation of inflammatory cells and the activation of fibroblast, epitherial cells or alpha smooth muscle cells.

3) the compounds provided by the present invention that have thieno pyridine as the pharmacophore and three similar control compounds that are not included in the definition depicted as chemical formula 1 of the present invention were compared for the inhibitory activities against src tyrosine kinase family and discoidin domain receptor family tyrosine kinase and the biomarkers in the activations of macrophage and fibroblast. From these results, inventors confirmed that the compounds provided by the present invention have significantly better efficacy than the similar control compounds.

4) the compounds provided by the present invention showed an excellent suppression activity against skin inflammation in the mouse model induced by oxazolone and especially LCB 03-0110, the representative compound of the present invention showed inhibitory efficacies against atopic dermatitis, asthma and scar formation in the corresponding disease animal models as described in the preferred embodiments of the present invention.

5) When the compounds provided by the present invention that have thieno pyridine as the pharmacophore and three similar control compounds that are not included in the definition depicted as chemical formula 1 of the present invention were compared for anti-inflammatory activity in skin inflammatory animal model induced by oxazolone, the compounds of the present invention showed a superior suppression activity to the structurally similar compounds.

In addition, the present invention provides a method for treating inflammatory disease comprising the step of administering into a subject a therapeutically effective amount of pharmaceutical composition comprising the compound of the chemical formula 1, an isomer thereof or pharmaceutically acceptable salts thereof as an active ingredient.

The present invention provides a method for treating immune disorder comprising the step of administering into a subject a therapeutically effective amount of pharmaceutical composition comprising the compound of the chemical formula 1, an isomer thereof or pharmaceutically acceptable salts thereof as an active ingredient.

In addition, the present invention provides a method for preventing scar formation or promoting of wound healing comprising the step of administering into a subject a therapeutically effective amount of pharmaceutical composition comprising the compound of the chemical formula 1, an isomer thereof or pharmaceutically acceptable salts thereof as an active ingredient.

For the pharmaceutical compositions of the present invention, the inflammatory diseases mentioned above are selected from atopic dermatitis, contact dematitis, psorisis, asthma, COPD, arthritis, allergic conjunctivitis, uveitis, iritis, keratitis, scleritis, episcleritis, eye inflammation, palpebritis, keratoconjunctivitis sicca, diabetic retinopathy, diabetic renal failure, and diabetic neuropathy although they are not restricted to such diseases listed above.

For the pharmaceutical compositions of the present invention, the immune disorder mentioned above are selected from disease groups such as rejection of organ transplantation and autoimmune disorder although they are not restricted to such diseases mentioned above.

For the pharmaceutical compositions of the present invention, wound diseases mentioned above are selected from trauma, burn wound, ulser, and diabetic foot ulser although they are not restricted to such diseases listed above.

For usage of the pharmaceutical compositions of the present invention, the compounds denoted as the chemical formula 1 in the present invention, their isomers, and their pharmaceuticall-acceptable salts to contain the compounds denoted as the chemical formula 1 in the present invention as the effective components can be used clinically after formulation by oral, non-oral, rectal, epidermal, ocular, nasal, iv, intramuscular, plaster and patch delivery type although they are not restricted to such listed formulation methods.

Such pharmaceutical formulations can be prepared easily by using conventional formulation methods as described for example, Remington, The Science and Practice of Pharmacy, 20th ed., 2000.

All such methods include the step to combine the active component with carrier comprised of one or more components. Generally the pharmaceutical formulation can be prepared as a preferred type by mixing completely the active component with either liquid carrier or solid carrier of fine particle or the both when necessary.

Oral formulations can be such as, for example, tablets, pills, hard/soft capsules, liquids, suspensions, sachets, granules, lozenges, which contain oils (eg, cottonseed oil, sesame oil, coconutfive days or peanut oil, edible oils), and suspending agents (example: Bontrager Cannes, alginate, acacia, dextran, sodium carboxy methyl cellulose, gelatin, methyl cellulose, hydroxypropylmethylcellulose, hydroxypropylcellulose, Carbomer, synthetic or natural gums such as polyvinylpyrrolidone) in addition to the effective component.

The formulation of tablet can be made by pressing or molding the active ingredient with optionally using one or more secondary ingredients. Tablet made by applying pressure can be generated by molding after mixing the active ingredients in the type of powder, granule, or free-flow with binder (for example, lactose, glucose, starch, gelatin, acacia gum, Bontrager Cannes gum, sodium alginate, carboxy methyl cellulose, methyl cellulose, hydroxypropylmethyl cellulose, polyethylrengeulsilicon, wax), lubricants (eg: Oleinphosphate, stearic acid salt, magnesium stearate, benzoic acid salt, acetic acid salt, sodium chloride), disintegrant (for example, starch, methyl cellulose, agar, bentonite, cross Carmelo sodium, sodium starch glycol, crospovidone), and dispersant (polysorbate 80). Molded tablet can be made by molding after mixing the active ingredient powder with a suitable non-active solvent.

The pharmaceutical composition containing the compounds represented by the chemical formula 1 as an active ingredient may be administered parenterally. Parenteral administration can be possible by vascular injection, transdermal, topical administration, rectal administration, intramuscular injection, plaster or patch type.

In particular, The formulation for the administration through can be made by disolving the active component in a sterile solution or by generating a suspension of the crystallites. In addition, Using biodegradable polymer composition or liposomes as shown Encyclopedia of Pharmaceutical Technology, vol. 2, 1989, can be used for eye treatment.

A suitable formulation for topical or ocular administration can include liquid or semi-liquid type of emulsion such as liniment, lotion, gel, cream or ointment, drop type of solution, or suspension.

In addition, the pharmaceutical compositions for the administration by oral or nasal absorption can be possibly formulated by power type, self-propelled spray aerosol or spray type.

The methods for such formulations can be referred to the general methods in Modern Pharmaceutics, 2<nd> ed., G. S. Banker and C T. Rhodes (Eds.), page 427-432, Marcel Dekker, New York; Modern Pharmaceutics, 3th ed., G. S. Banker and C T. Rhodes (Eds.), page 618-619 and 718-721, Marcel Dekker, New York and Encyclopedia of Pharmaceutical Technology vol. 10, J Swarbrick and J. C. Boylan (Eds), page 191-221, Marcel Dekker, New York.

As added to the aforementioned elements, pharmaceutical compositions that contain the compounds of chemical formula 1 can include one or more components of such as diluents, buffers, fragrances, coloring agents, surfactant, sinking agents, preservatives such as methyl hydroxybenzoic acid, emulsifying agent or similar material. When pharmaceutical active components being treated as a type of pharmaceutically acceptable salt using a non-toxic acid or base, the preferred salts can be generated as a water-soluble or a weakly water soluble type to achieve a desirable absorption corresponding to a particular case.

In addition, human dosage of the compounds of the present invention can vary depending on the patient's age, weight, gender, administration type, health status or the degree or diseases. Based on 70 kg weight of adult patients, it is typically 0.1 to 500 mg/kg body weight and may be administered once per day or several times in accordance with a doctor or pharmacist's judgment.

The synthetic scheme for the compounds of chemical formula 1 in the present invention can be provided as the following reaction formula 1. However, the synthetic method for the compounds of chemical formula 1 in the present invention is not restricted by the synthetic scheme of the reaction formula 1. Since the following synthetic scheme is well known to the people in the related field, the definitions of substituents in the following reaction are identical with the ones in the chemical formula 1 shown above if not denoted specifically.

The synthesis of compounds in chemical reaction 1 can be synthesized as follows;

7-chlorothienopyrimidine or 7-chlorothienopyridine derivative (II) is synthesized by chlorolination of compound of (1) with the scaffold of thienopyrimidinone, thienopyridinone or thiazolopyrimidinone, then bromination was carried out to synthesize the derivative of 2-bromo-7-chlorothienopyrimidine or 2-bromo-7-chloro thienopyridine derivative (III), then compound (V) was synthesized by a substitution reaction with aniline derivative (IV).

Compounds of chemical formula, 1-1, 1-2, and 1-3 with the scaffold of thienopyrimidine, thienopyridine or thiazolopyrimidine can be synthesized by Suzuki coupling from the compound (V).

[Chemical reactioin 1]
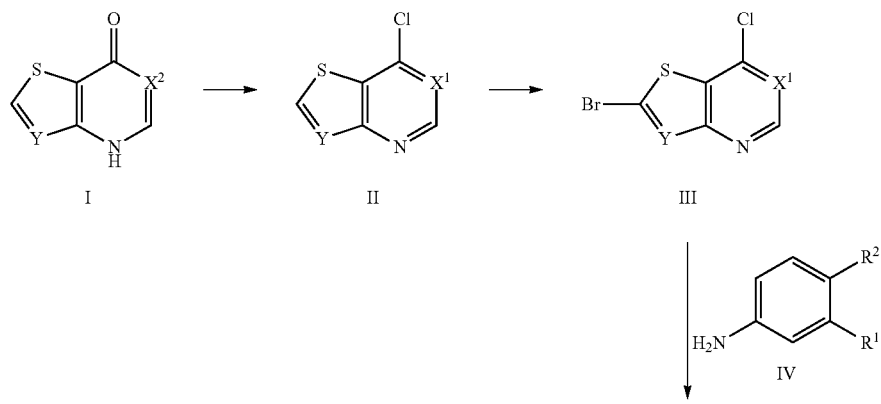
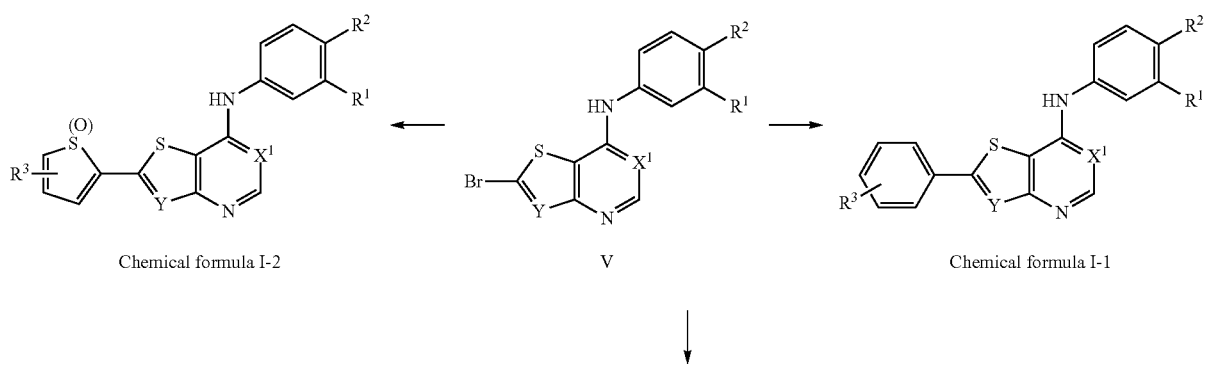
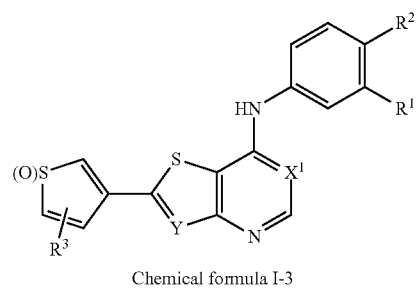
Chemical formula I-3

As a preferred embodiment of the synthesized method shown above, the scheme of the chemical reactions to synthesize the compounds of the present invention can be depicted as the following chemical reaction 2. The compounds shown in chemical reaction 2 can be used as starting materials for the synthesis of the compounds of the present invention. Because the transformation of the following synthetic method is familiar to the people in the related field, the definitions of substituents in the following reaction are identical with the ones in the chemical formula 1 shown above if not denoted specifically.

As a preferred embodiment of the synthetic method mentioned above, the chemical reaction to synthesize the compounds of the present invention was schematized and shown in chemical reaction 2 as below.

[Chemical reaction 2]

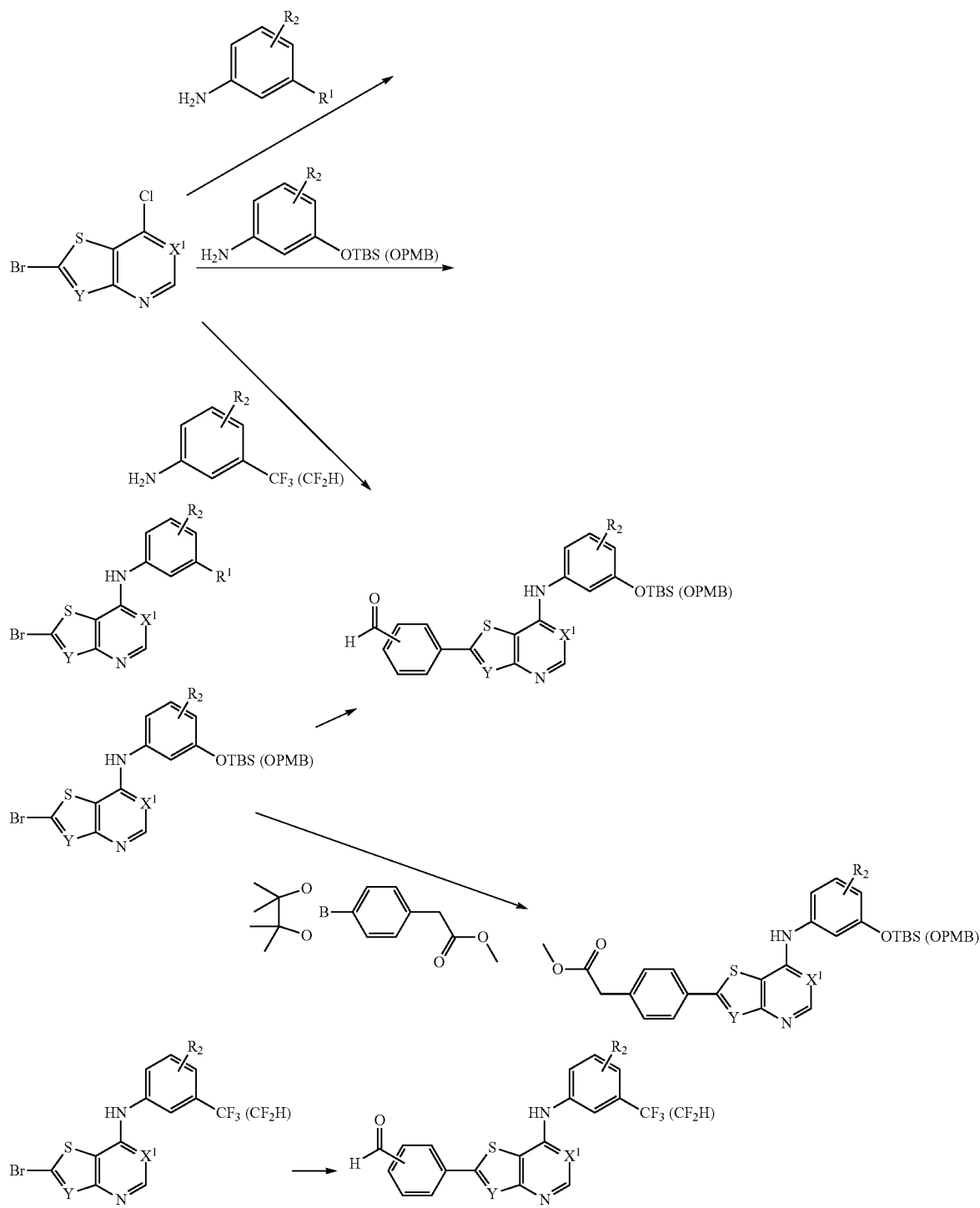

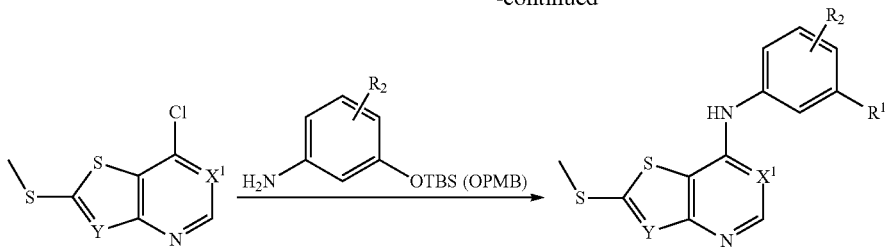

MODE FOR INVENTION

In the followings, the synthetic examples and the preferred embodiments were provided to describe the present invention more in detail. However the synthetic examples and the preferred embodiments are provided to explain the present invention in a more convenient way, but do not restrict the content of the present invention.

Preparation Example of each compound was described in the followings.

Preparation Example 1

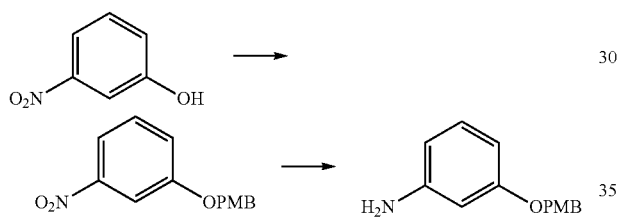

Preparation Example 1-1

The synthesis of 1-(4-(methoxybenzyloxy)-3-nitrobenzene

NaOH (0.54 g, 13.36 mmol) was added into 10 ml of degassed dimethylformamide at 0° C., then 3-nitrophenol (1.69 g, 12.14 mmol) dissolved in 7 ml of dimethylformamide was dropped slowly, and then para-methoxybenzylchloride (1.81 ml, 13.36 mmol) was added slowly. After stirred for 2 hours at the increased reaction temperature to room temperature, the reaction mixture was extracted using saturated ammonium chloride (100 ml) and ethylacetate (100 ml). The organic layer was washed twice using 100 ml of water, and dried using anhydrous sodium sulfate, then concentrated under vacuum. The resultant solid was solidified using n-hexane to obtain pale yellowish solid of 1-(4-methoxybenzyloxy)-3-nitrobenzene (2.85 g, 90%) finally.

$^1$H-NMR (600 MHz, CDCl$_3$); δ 7.83-7.81 (m, 2H), 7.42 (t, J=8.4 Hz, 1H), 7.37 (d, J=8.4 Hz, 2H), 7.28 (dd, J, 2.4, 8.4 Hz, 1H), 6.93 (d, J=8.4 Hz, 2H), 5.06 (s, 2H), 3.82 (s, 3H)

Preparation Example 1-2

The synthesis of 3-(4-methoxybenzyloxy)aniline

Fe (5.6 g, 100.28 mmol) was mixed with methanol:H$_2$O (15 ml:3 ml) and refluxed for 30 minutes. After the temperature is dropped to room temperature, 1-(4-methoxybenzyloxy)-3-nitrobenzene (1.3 g, 5.01 mmol) dissolved in 6 ml of methanol:H$_2$O (5:1) was added and then refluxed for 15 hours. Fe was removed using cellite, then the reaction mixture was washed using methanol and concentrated under vacuum to remove the solvent. After extraction with 100 ml of saturated ammonium chloride+150 ml of dichloromethane, the organic layer was washed with water. The organic solvent was concentrated under vacuum to obtain the title compound (1.14 g, 99%).

$^1$H-NMR (400 MHz, CDCl$_3$); δ 7.34 (d, J=7.2 Hz, 1H), 7.25 (s, 1H), 7.05-7.04 (m, 1H), 6.91-6.90 (m, 2H), 6.40-6.31 (m, 3H), 4.94 (s, 2H), 3.81 (s, 3H)

Preparation Example 2

The Synthesis of 3-(tert-butyldimethylsilyloxy)aniline

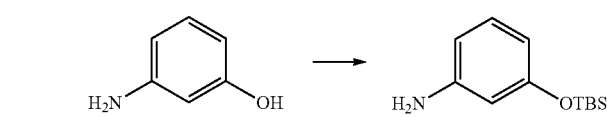 [SMILES: Nc1cccc(O)c1 ; CC(C)(C)[Si](C)(C)Oc1cccc(N)c1]

Chloro t-butyldimethylsilane (11 g, 72.98 mmol), 3-aminophenol (6.64 g, 60.81 mmol) and imidazole (5.38 g, 79.10 mmol) were added into 200 ml of dichloromethane. The mixture was stirred at room temperature for 15 hours. The reaction mixture was extracted using 200 ml of saturated ammonium chloride and 200 m of dichloromethane and the organic layer was washed twice using 200 ml of water. After concentrated under vacuum, the title compound (13.5 g, 99%) was obtained.

$^1$H-NMR (400 MHz, CDCl$_3$); δ 6.95 (t, J=8.0 Hz, 1H), 6.27-6.18 (m, 2H), 6.16-6.15 (m, 1H), 3.56 (brs, 2H), 0.90 (s, 9H), 0.11 (s, 6H); LC-MS 224 (MH+)

Preparation Example 3

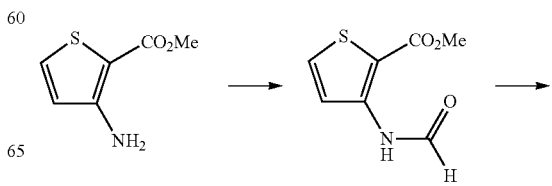

-continued

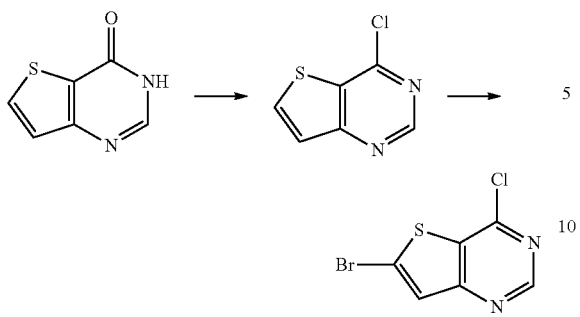

Preparation Example 3-1

The synthesis of methyl 3-formamidothiophene-2-carboxylate

Formic acid 125 ml, and ammonium acetate (15.9 g, 207 mmol) were added to methyl 3-amino-2-thiophene carboxylate (25 g, 159.04 mmol) and the mixture was refluxed for 4 hours. After lowering the temperature to room temperature, the synthesized solid was washed with water and the title compound (29 g, 98%) was obtained.

$^1$H-NMR (400 MHz, CDCl$_3$); δ 10.10 (br, 1H), 8.42 (s, 1H), 8.10 (d, J=5.6 Hz, 1H), 7.49 (d, J=5.2 Hz, 1H), 3.90 (s, 3H); LC-MS 186.20 (MH+)

Preparation Example 3-2

The synthesis of 3H-thieno[3,2-d]pyrimidine-4-one

After the compound (29 g, 156.6 mmol) synthesized in Preparation Example 3-1 was mixed with ammonium formate (29.7 g, 469.8 mmol) and formamide (38 ml, 939.5 mmol), the mixture was boiled for 20 hours at 140° C. The temperature of reaction mixture was lowered to room temperature, and the synthesized solid was washed with water. The title compound (15.7 g, 66%) of dark brown solid was obtained.

$^1$H-NMR (400 MHz, CDCl$_3$); δ 8.18 (d, J=5.2 Hz, 1H), 8.15 (s, 1H), 7.40 (d, J=5.2 Hz, 1H); LC-MS 153.0 (MH+)

Preparation Example 3-3

The synthesis of 4-chloro-thieno[3,2-d]pyrimidine

After dimethylformamide (15.4 ml, 197.13 mmol) was added into 150 ml of dichloroethane with lowering the temperature to 0° C., oxalyl chloride (25 4 ml, 295.70 mmol) was slowly added. When white gel type started to form, 3H-thieno[3,2-d]pyrimidine-4-one (15 g, 98.57 mmol) was added. After 2.5 hours of reflex of the reaction mixture, the temperature was lowed to room temperature. After adding water, the reaction mixture was extracted using dichloromethane (3×300 ml) and dried with anhydrous magnesium sulfate. After concentrated under vacuum, trituration was carried out with 200 ml of hexane and the title compound (16.7 g, 99%) was obtained as a dark brown solid.

$^1$H NMR (400 MHz, DMSO-d$_6$); δ 9.06 (s, 1H), 8.61 (d, J=5.2 Hz, 1H), 7.78 (d, J=5.2 Hz, 1H); LC-MS 173.2 (MH+)

Preparation Example 3-4

The synthesis of 6-bromo-4-chloro-thieno[3,2-d]pyrimidine

Lithum diisopropylamine (25 ml, 61.54 mmol) was added to 200 ml of tetrahydrofuran and after lowering the temperature to −78° C., 4-chloro-thieno[3,2-d]pyrimidine (5 g, 39.30 mmol) dissolved in 50 ml of tetrahydrofuran was slowly added into the mixture. After 20 minutes, 1,2-dibromo-1,1,2,2-tetrafluoroethane (11.45 g, 35.17 mmol) was slowly added. After 20 minutes of stirring at −78° C., the temperature was raised to room temperature and the stirring was continued for 2 hours further. The reaction mixture was added with water and extracted with chloroform (3×300 ml), then dried using anhydrous magnesium sulfate. After concentrated under vacuum, it was triturated with 200 ml of n-hexane and the title compound (6.5 g, 89.2%) was obtained as a dark brown solid.

$^1$H-NMR (400 MHz, CDCl$_3$); δ 8.94 (s, 1H), 7.62 (s, 1H); LC-MS: 249, 251 (MH+)

Preparation Example 4

The synthesis of 6-bromo-N-(3-(4-methoxybenzyloxy)phenyl)thieno[3,2-d]pyrimidine-4-amine

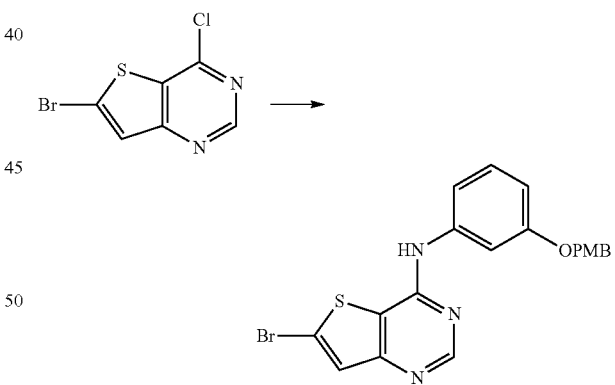

The compound (0.18 g, 0.80 mmol) obtained in the example of synthesis 3-4 was dissolved in 3 ml of dichloroethane and 3 ml of t-butanol and placed into a sealed tube followed by stirring for 3 days at 85° C. After cooled to room temperature, the synthesized pale brown solid was washed using diethyl ether to obtain the grey-colored title compound (0.25 g, 80%).

$^1$H-NMR (600 MHz, DMSO-d$_6$); δ 10.52 (brs, 1H), 8.70 (s, 1H), 7.73 (s, 1H), 7.44-7.27 (m, 5H), 6.95-6.88 (m, 3H), 5.04 (s, 2H), 3.75 (s, 3H); LC-MS: 443 (MH+)

The following compounds were synthesized using the methods similar to the one described above.

Preparation Example 5

6-bromo-N-(3-(t-butyldimethylsiloxy)phenyl)thieno[3,2-d]pyrimidine-4-amine

The synthesis of (6-bromo-N-(3-(tert-butyldimethylsilyloxy)phenyl)thieno[3,2-d]pyrimidin-4-amine)

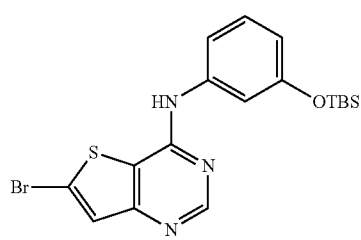 [SMILES: CC(C)(C)[Si](C)(C)Oc1cccc(Nc2ncnc3cc(Br)sc23)c1]

$^1$H-NMR (400 MHz, CDCl$_3$); δ 8.62 (s, 1H), 7.40 (s, 1H), 7.30-7.26 (m, 1H), 7.06-7.02 (m, 2H), 6.87-6.82 (m, 2H), 1.00 (s, 9H), 0.23 (s, 6H); LC-MS 439 (MH+)

Preparation Example 6

4-(4-(3-(t-butyldimethylsiloxy)phenylamino)thieno[3,2-d]pyrimidine-6-yl)benzadehyde The synthesis of (4-(4-(3-(tert-butyldimethylsilyloxy)phenylamino)thieno[3,2-d]pyrimidin-6-yl)benzaldehyde)

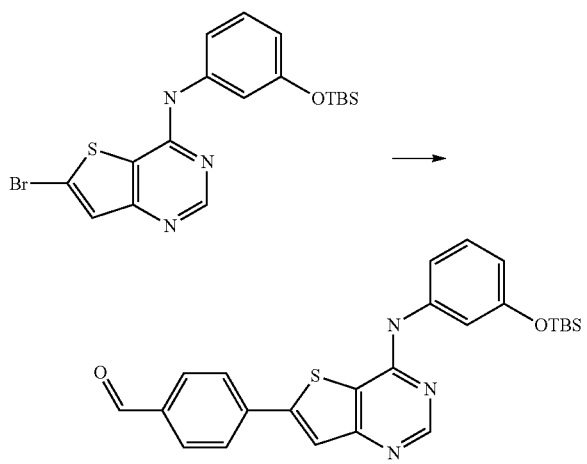

The compound (3.5 g, 8.02 mmol) synthesized from the example of synthesis 5, 4-formylphenyl boric acid (1.44 g, 9.62 mmol), palladium tetrakistriphenylphosphine (1.85 g, 1.60 mmol), and 2N sodium carbonate (8 ml, 16.04 mmol) were added into 30 ml of 1,4-dioxane and refluxed for 3 hours. After extracting the reaction mixture twice with 50 ml of saturated sodium bicarbonate and 150 ml of dichloromethane, the organic layer was further extracted twice using saturated sodium bicarbonate 150 ml and dried using anhydrous sodium sulfate followed by concentration under vacuum. After column chromatography (ethylacetate/n-hexane, 1/3), the title compound (2.1 g, 56.7%) of brown solid was obtained.

$^1$H-NMR (600 MHz, CDCl$_3$); δ 10.06 (s, 1H), 8.72 (s, 1H), 7.96 (d, J=8.4 Hz, 2H), 7.83 (d, J=8.4 Hz, 2H), 7.17 (s, 1H), 7.30-7.28 (m, 1H), 7.18 (s, 1H), 7.16-7.14 (m, 1H), 6.93 (brs, 1H), 6.79 (d, J=8.4 Hz, 1H), 0.96 (s, 9H), 0.21 (s, 6H); LC-MS: 462 (MH+)

Preparation Example 7

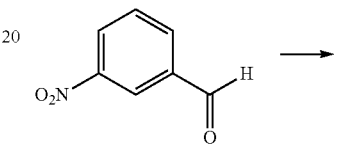

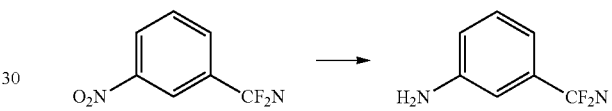

Preparation Example 7-1

The synthesis of 1-(difluoromethyl)-3-nitrobenzene

DAST (20 ml, 13.23 mmol) diluted in 5 ml of dichloromethane was slowly dropped at −78° C. into 3-nitrobenzaldehyde (1 g, 6.61 mmol) dissolved in 20 ml of dichloromethane and the mixture was stirred for 15 hours at room temperature. After adding 100 ml of water and extraction with 100 ml of dichloromethane, the organic layer was concentrated under vacuum and column chromatography (ethylacetate/n-hexane, 1/15) was carried out to obtain the title compound (1.11 g, 97.3%) as brown oil.

$^1$H-NMR (400 MHz, CDCl$_3$); δ 8.40 (s, 1H), 8.37-8.35 (m, 1H), 7.87 (d, J=7.6 Hz, 1H), 7.69 (t, J=8.0 Hz, 1H), 6.75 (t, J=56.0 Hz, 1H)

Preparation Example 7-2

The synthesis of 3-(difluoromethyl)aniline 100 mg of Fe was added intio 3 ml of acetic acid and refluxed for 15 minutes. After lowering the temperature into room temperature, the mixture was added with 1-(difluoromethyl)-3-nitrobenzene (0.2 g, 1.15 mmol) and refluxed again for 1 hour. After addition of 20 ml ethyl acetate, impurities were removed using cellite and the organic layer was concentrated under vacuum. After column chromatography (ethylacetate/n-hexane, 1/15), the title compound (0.16 g, 50%) was obtained.

¹H-NMR (600 MHz, CDCl₃); δ 7.22 (t, J=7.8 Hz, 1H), 6.86 (d, J=7.8 Hz, 1H), 6.81 (s, 1H), 6.77-6.75 (m, 1H), 6.54 (t, J=56 Hz, 1H), 3.91 (brs, 2H)

Preparation Example 8

6-bromo-N-(3-(trifluoromethyl)phenyl)thieno[3,2-d]pyrimidine-4-amine

The synthesis of 6-bromo-N-(3-(trifluoromethyl)phenyl)thieno[3,2-d]pyrimidine-4-amine

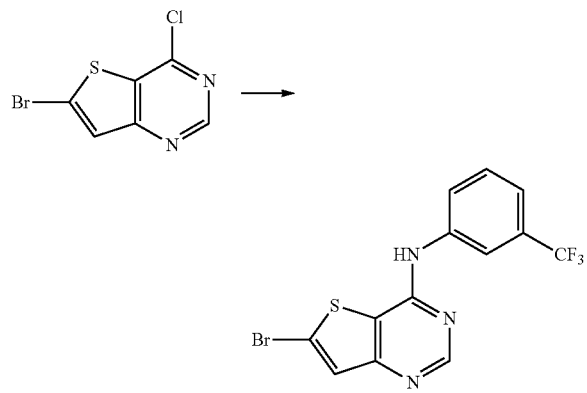

The compound (0.1 g, 0.40 mmol) prepared from example of synthesis 3-4 was dissolved in 2 ml of dichloroethane and 2 ml of t-butanol and added with 3-fluoromethyl aniline (55 μl, 0.44 mmol) followed by a reflux for 20 hours. The reaction mixture was concentrated under vacuum and the synthesized yellowish solid was washed using diethyl ether to obtain the title compound (0.12 g, 100%).

¹H-NMR (400 MHz, DMSO-d₆); δ 10.83 (brs, 1H), 8.76 (s, 1H), 8.20 (s, 1H), 8.09 (d, J=8.0 Hz, 1H), 7.78 (d, J=2.0 Hz, 1H), 7.66 (t, J=8.0 Hz, 1H), 7.53 (d, J=7.6 Hz, 1H); LC-MS: 323 (MH+)

The following compounds were synthesized by the methods similar to the ones described above.

Preparation Example 9

N-(3-(6-bromothieno[3,2-d]pyrimidine-4-ylamino)phenyl)-2,2,2-trifluoroacetamide

The synthesis of N-(3-(6-bromothieno[3,2-d]pyrimidin-4-ylamino)phenyl)-2,2,2-trifluoroacetamide)

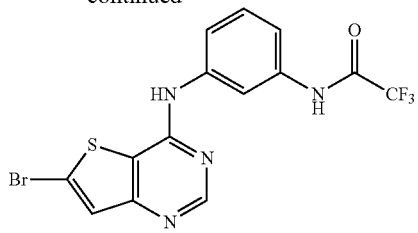

¹H-NMR (600 MHz, DMSO-d₆) δ 11.40 (brs, 1H), 8.70 (s, 1H), 7.74 (s, 1H), 7.62-7.60 (m, 2H), 7.49-7.44 (m, 2H); LC-MS: 419 (MH+2)

Preparation Example 10

6-bromo-N-(3-(difluoromethyl)phenyl)thieno[3,2-d]pyrimidine-4-amine

The synthesis of 6-bromo-N-(3-(difluoromethyl)phenyl)thieno[3,2-d]pyrimidin-4-amine

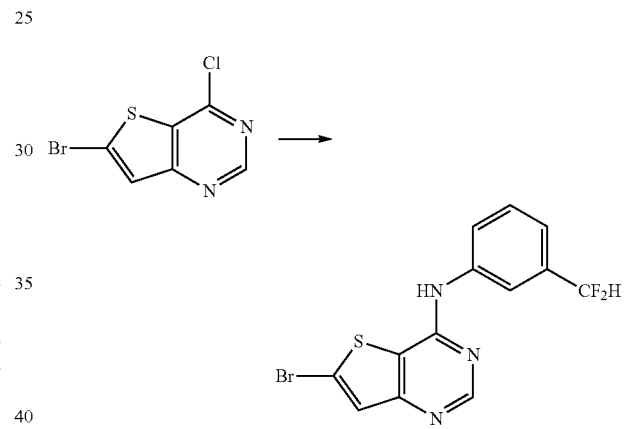

¹H-NMR (400 MHz, CDCl₃); δ 10.75 (brs, 1H), 8.74 (s, 1H), 7.98 (s, 1H), 7.94-7.92 (m, 1H), 7.77 (d, J=1.6 Hz, 1H), 7.57 (t, J=8.0 HZ, 1H), 7.40 (d, J 8.0 HZ, 1H), 7.09 (t, J=56 HZ, 1H)

Preparation Example 11

4-(4-(3-(trifluoromethyl)phenylamino)thieno[3,2-d]pyrimidine-6-yl)benzadehyde

The synthesis of 4-(4-(3-(trifluoromethyl)phenylamino)thieno[3,2-d]pyrimidin-6-yl)benzaldehyde

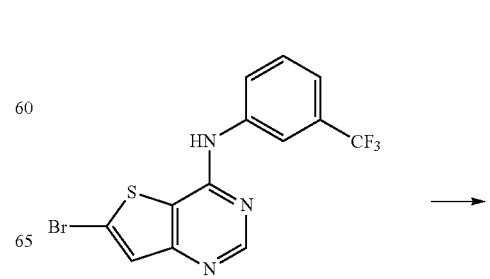

-continued

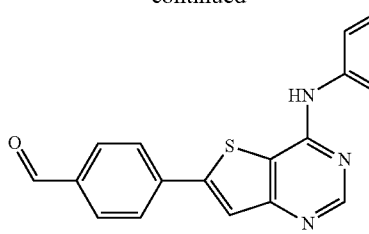

The title compound (64 mg, 86%) was obtained using the method similar to the one to prepare the compound of the example of synthesis 6 from the compound of the example 8 (60 mg, 0.18 mmol).

$^1$H-NMR (600 MHz, CDCl$_3$); δ 10.07 (s, 1H), 8.00-7.98 (m, 3H), 7.89-7.87 (m, 3H), 7.79 (s, 1H), 7.58-7.47 (m, 2H), 6.87 (brs, 1H)

Preparation Example 12

4-(4-(3-(difluoromethyl)phenylamino)thieno[3,2-d]pyrimidine-6-yl)benzadehyde

The synthesis of (4-(4-(3-(difluoromethyl)phenylamino)thieno[3,2-d]pyrimidin-6-yl)benzaldehyde)

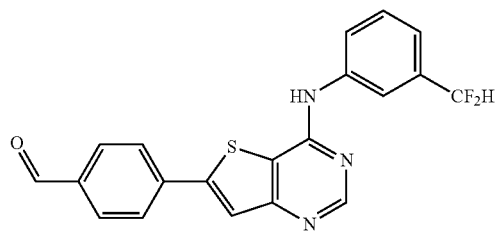 [SMILES: O=Cc1ccc(-c2cc3ncnc(Nc4cccc(C(F)F)c4)c3s2)cc1]

$^1$H-NMR (400 MHz, CDCl$_3$); δ 10.07 (s, 1H), 8.77 (s, 1H), 7.99 (d, J=8.4 Hz, 2H), 7.88 (d, J=8.4 Hz, 2H), 7.99-7.78 (m, 2H), 7.53 (t, J=7.6 Hz, 1H), 7.39 (d, J=7.6 Hz, 1H), 6.84 (brs, 1H), 6.71 (t, J=56 Hz, 1H)

Preparation Example 13

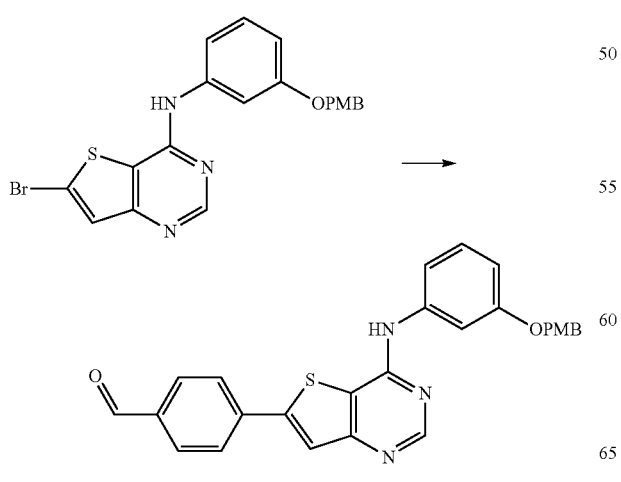

$^1$H-NMR (600 Hz, CDCl$_3$); δ 10.06 (s, 1H), 8.72 (s, 1H), 7.96 (d J=8.47 Hz, 2H), 7.83 (d, J=8.47 Hz, 2H), 7.71 (s, 1H), 7.38 (d, J=8.8 Hz, 2H), 7.30-7.28 (m, 1H), 7.18 (s, 1H), 7.16-7.14 (m, 1H), 6.95 (d, J=8.8 Hz, 2H), 6.93 (brs, 1H), 5.03 (s, 2H), 3.82 (s, 3H); LC-MS 346 (MH+)

Preparation Example 14

The synthesis of 4-chloro-3-(4-methoxybenzyloxy)aniline 1-amino-5-nitrophenol (2 g, 12.97 mmol), and sodium nitrite (0.9 g, 12.97 mol) were mixed with 10 ml of water and 30 ml of 48% HBF$_4$ and stirred for 30 minutes at room temperature, then copper chloride (I) (642 mg, 6.48 mmol) was further added, and heated at 80° C. for 3 hours. Ice-cold water at 0° C. was added, and the reaction mixture was extracted with 200 ml of saturated sodium bicarbonate and 200 ml of ethylacetate, then dried using anhydrous sodium sulfate, filtered and concentrated under vacuum. Column chromatography (n-hexane/ethylacetate, 15/1) was conducted to obtain two-chloro-5-nitrophenol (0.46 g, 23%). From 2-chloro-5-nitrophenol (0.36 g, 2.29 mmol), the title compound (0.167 g, 94%) was obtained using the method similar to the example of synthesis 9.

$^1$H-NMR (400 MHz, CDCl$_3$); δ 7.37 (d, J=8.8 Hz, 2H), 7.10 (d, J=8.8 Hz, 1H), 6.92 (d, J=10.8 Hz, 2H), 6.32 (d, J=2.4 Hz, 1H), 6.23 (dd, J=2.0, 8.4 Hz, 1H), 5.02 (s, 2H), 3.81 (s, 3H); LC-MS: 248 (MH+)

Preparation Example 15

The synthesis of 6-bromo-N-(4-chloro-3-(4-methoxybenzyloxy)phenyl)thieno[3,2-d]pyrimidine-4-amine

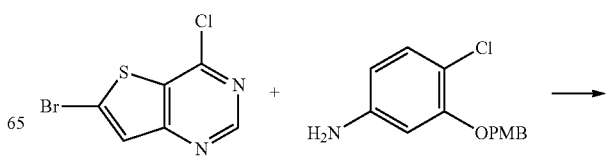

-continued

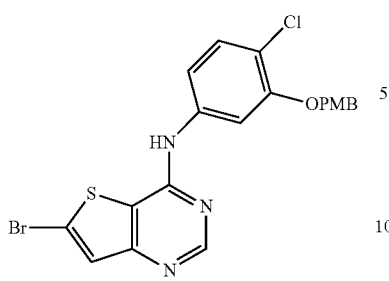

The title compound was obtained using the methods similar to the example of synthesis 8.

$^1$H-NMR (400 MHz, DMSO-d$_6$); δ 10.58 (brs, 1H), 8.72 (s, 1H), 7.75-7.73 (m, 2H), 7.43-7.38 (m, 4H), 6.97 (d, J=8.0 Hz, 2H), 5.12 (s, 2H), 3.76 (s, 3H); LC-MS: 477 (MH+)

Preparation Example 16

The synthesis of 4-(4-(4-chloro-3-(4-methoxybenzyloxy)phenylamino)thieno[3,2-d]pyrimidine-6-yl)benzadehyde

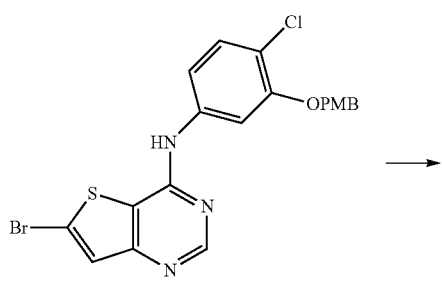

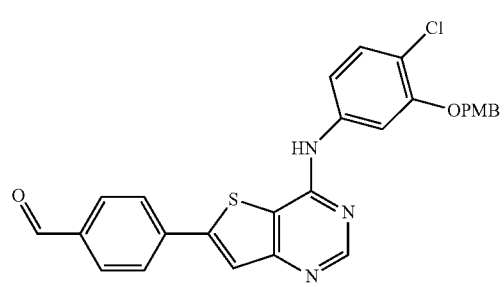

The title compound was obtained using the methods similar to the example of synthesis 6.

$^1$H NMR (600 MHz, CDCl$_3$); δ 10.05 (s, 1H), 8.62 (s, 1H), 7.98 (d, J=8.4 Hz, 2H), 7.90 (d, J=8.4 Hz, 2H), 7.76 (s, 1H), 7.49-7.48 (m, 1H), 7.41 (d, J=8.4 Hz, 2H), 7.16 (dd, J=1.8, 8.4 Hz, 1H), 6.94-6.90 (m, 4H), 5.13 (s, 2H), 3.79 (s, 3H); LC-MS 502 (MH+)

Preparation Example 17

3-(4-(3-(4-methoxybenzyloxy)phenylamino)thieno[3,2-d]pyrimidine-6-yl)benzadehyde The synthesis of (3-(4-(3-(4-methoxybenzyloxy)phenylamino)thieno[3,2-d]pyrimidin-6-yl)benzaldehyde)

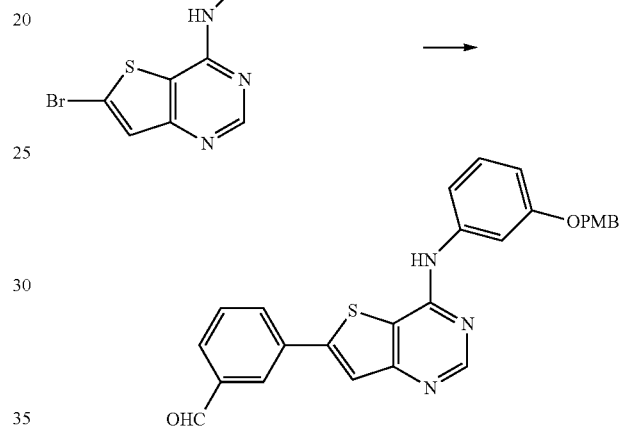

The synthesized compound (500 mg, 0.89 mmol) in Example 1, 3-formylphenylboric acid (160 mg, 1.06 mmol), and palladium tetrakistriphenylphosphine (21.7 mg, 0.02 mmol) were added sequentially into degassed 5 ml of dimethylformamide and 1.33 ml of 2N sodium carbonate was further added. After stirred at 80° C. for 15 hours, the reaction mixture was extracted with 50 ml of dichloromethane and 50 ml of saturated ammonium chloride. After the organic layer was extracted with 50 ml of saturated ammonium chloride twice more it was dried with sodium sulfate and concentrated under vacuum, then concentrated with 10 ml of diethylether to obtain the title compound (320 mg, 77%) as brown solid.

$^1$H NMR (600 MHz, CDCl$_3$); δ 10.09 (s, 1H), 8.73 (s, 1H), 8.17 (s, 1H), 7.94 (t, J=9.0 Hz, 1H), 7.69 (s, 1H), 7.65 (t, J=7.8 Hz, 1H), 7.37 (m, 3H), 7.33 (t, J=7.8 Hz, 3H), 7.11 (d, J=5.4 Hz, 1H), 6.90 (m, 3H), 6.79 (br, 1H), 5.04 (s, 2H), 3.80 (s, 3H); LC-MS 468 (MH+)

Preparation Example 18

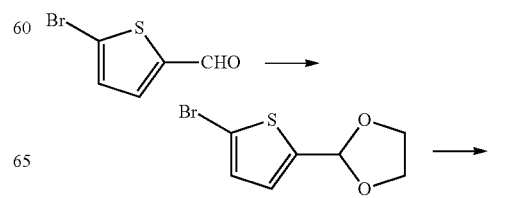

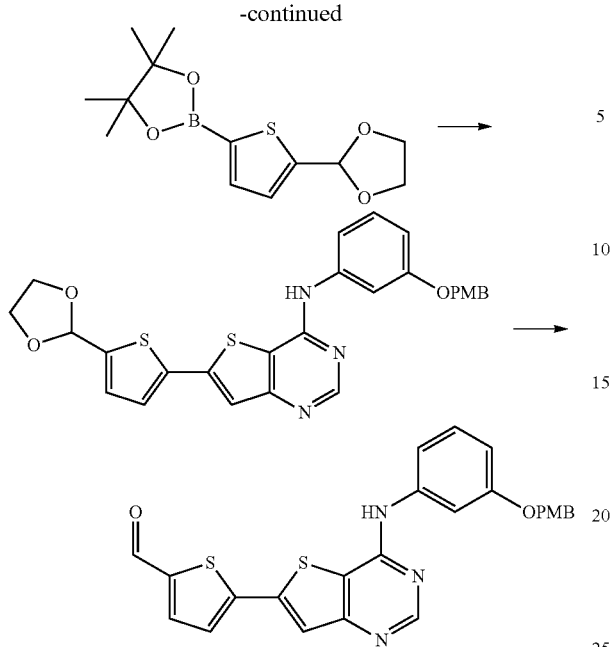

Preparation Example 18-1

The synthesis of 2-(5-bromothiophene-2-yl)-1,3-dioxolane 5-bromothiophene-2-carboxyaldehyde (2 g, 10.46 mmol) was dissolved in 30 ml of toluene. After adding para-toluenesulfonic acid (60 mg, 0.31 mmol) and ethyleneglycol (0.75 ml, 13.61 mmol), the mixture was stirred at dean-stark apparatus at 130° C. for 15 hours. After being cooled to room temperature, it was added with 20 ml of water and neutralized using saturated sodium bicarbonate solution followed by extraction using 100 ml of diethylether. After washing the organic layer with 50 ml of water and 50 ml of brine solution, it was dried using magnesium sulfate, filtered and concentrated under vacuum. The title compound (1.8 g, 73.1%) was obtained as brown oil.

$^1$H NMR (600 MHz, CDCl$_3$); δ 9.78 (s, 1H), 7.52 (d, J=3.6 Hz, 1H)

Preparation Example 18-2

6-(5-(1,3-dioxolane-2-yl)thiophene-2-yl)-N-(3-(4-methoxybenzyloxy)phenyl)thieno[3,2-d]pyrimidine-4-amine The synthesis of 6-(5-(1,3-dioxolan-2-yl)thiophene-2-yl)-N-(3-(4-methoxybenzyloxy)phenyl)thieno[3,2-d]pyrimidin-4-amine The compound (0.1 g, 0.35 mmol) obtained in example of synthesis 18-1, the compound (0.1 g, 0.22 mmol) obtained in example of synthesis 7, and PdCl$_2$(dppf)$_2$ (5 mg, 0.006 mmol) were placed under nitrogen gas and added with 5 ml of degassed dimethylformamide and 2N sodium carbonate (0.3 ml, 0.66 mmol) followed by stirred at 80° C. for 15 hours. The reaction mixture was extracted with 50 ml of dichloromethane and 50 ml of saturated ammonium chloride solution. The organic layer was extracted twice with 50 ml of saturated ammonium chloride solution, dried with sodium sulfate and concentrated under vacuum. After column chromatography (ethylacetate/n-hexane, 1/15), the title compound (39 mg, 34%) was obtained as brown solid.

$^1$H NMR (600 MHz, CDCl$_3$); δ 8.68 (s, 1H), 7.44 (s, 1H), 7.37 (d, J=7.8 Hz, 2H), 7.32-7.31 (m, 2H), 7.23-7.22 (m, 1H), 7.12 (d, J=3.0 Hz, 1H), 6.91 (d, J=7.8 Hz, 2H), 6.88-6.87 (m, 1H), 6.79 (s, 1H), 5.03 (s, 2H), 4.17-4.15 (m, 2), 4.06-4.04 (m, 2H), 3.08 (s, 3H); LC-MS 518 (MH+)

Preparation Example 18-31

5-(4-(3-(4-methoxybenzyloxy)phenylamino)thieno[3,2-d]pyrimidine-6-yl)thiophene-2-carboadehyde The synthesis of 5-(4-(3-(4-methoxybenzyloxy)phenylamino)thieno[3,2-d]pyrimidin-6-yl)thiophene-2-carbaldehyde The compound (0.27 g, 0.52 mmol) obtained in Preparation Example 18-2 was dissolved in 10 ml acetone, and added with para-toluenesulfonic acid (49 mg, 0.26 mmol) followed by stirring for 20 hours at room temperature. After neutralization by adding 50 ml of saturated sodium bicarbonate, the mixture was concentrated under vacuum. After 10 ml of water was added, the residue was stirred for 30 minutes and filtered. After the filtrate was solidified in 5 ml of dichloromethane and 1 ml of methanol, the title compound (240 mg, 85%) was obtained as yellowish solid.

$^1$H NMR (600 MHz, DMSO-d$_6$); δ 9.97 (brs, 1H), 8.63 (s, 1H), 8.23 (d, J=3.6 Hz, 1H), 8.00 (s, 1H), 7.86 (d, J=4.2 Hz, 1H), 7.59-7.58 (m, 1H), 7.40 (d, J=8.4 Hz, 2H), 7.37 (d, J=7.8 HZ, 1H), 7.27 (t, J=8.4 HZ, 1H), 6.95 (d, J=8.4 Hz, 2H), 6.78 (dd, J=1.8, 8.4 Hz, 1H), 5.03 (s, 2H), 3.75 (s, 3H); LC-MS 474 (MH+)

The following compounds were synthesized using the methods similar to the ones described above.

Preparation Example 19

5-(4-(3-(4-methoxybenzyloxy)phenylamino)thieno[3,2-d]pyrimidine-6-yl)furan-2-carboadehyde The synthesis of 5-(4-(3-(4-methoxybenzyloxy)phenylamino)thieno[3,2-d]pyrimidin-6-yl)furan-2-carbaldehyde

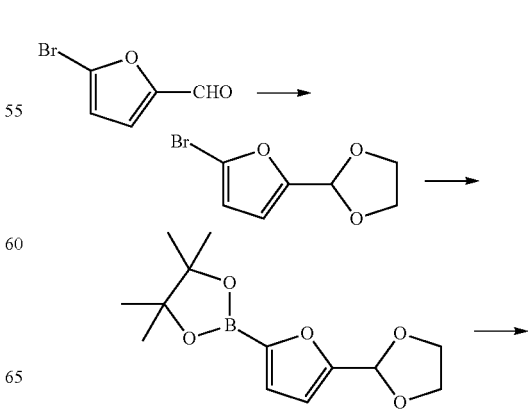

-continued 7.28 (t, J=8.0 HZ, 1H), 6.95 (d, J=8.4 Hz, 2H), 6.79-6.78 (m, 1H), 5.03 (s, 2H), 3.75 (s, 3H); LC-MS 458 (MH+)

Preparation Example 20

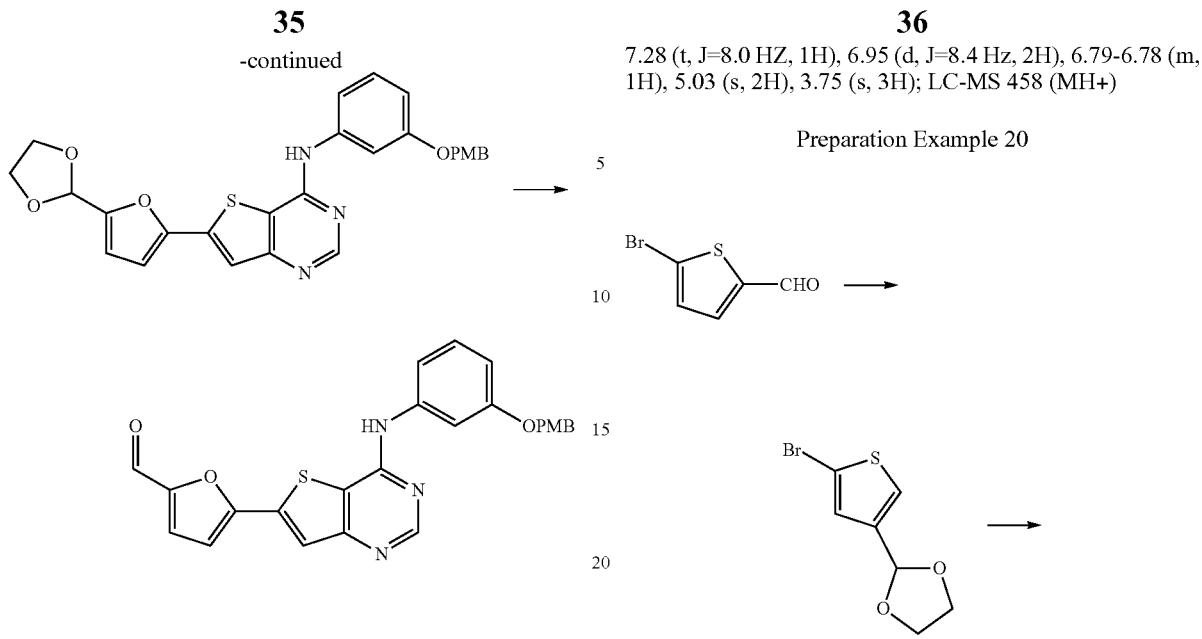

Preparation Example 19-1

The synthesis of 2-(5-bromofuran-2-yl)-1,3-dioxolane $^1$H NMR (600 MHz, CDCl$_3$); δ 6.41 (d, J=2.4 Hz, 1H), 6.28 (d, J=2.0 Hz, 1H), 5.87 (s, 1H), 4.15-4.10 (m, 2H), 4.03-4.00 (m, 2H)

Preparation Example 19-2

6-(5-(1,3-dioxolane-2-yl)furan-2-yl)-N-(3-(4-methoxybenzyloxy)phenyl)thieno[3,2-d]pyrimidine-4-amine)

The synthesis of 6-(5-(1,3-dioxolan-2-yl)furan-2-yl)-N-(3-(4-methoxybenzyloxy)phenyl)thieno[3,2-d]pyrimidin-4-amine $^1$H NMR (600 MHz, CDCl$_3$); δ 8.69 (s, 1H), 7.53 (s, 1H), 7.37 (d, J=9.0 Hz, 2H), 7.34-7.33 (m, 1H), 7.31 (t, J=7.8 Hz, 1H), 7.08-7.07 (m, 1H), 6.91 (d, J=9.0 Hz, 2H), 6.87-6.86 (m, 1H), 6.74 (brs, 1H), 6.71 (d, J=3.6 Hz, 1H), 6.55 (d, J=3.6 Hz, 1H), 5.99 (s, 1H), 5.03 (s, 2H), 4.17-4.15 (m, 2H), 4.07-4.04 (m, 3H), 3.80 (s, 4H); LC-MS 502 (MH+)

Preparation Example 19-3

5-(4-(3-(4-methoxybenzyloxy)phenylamino)thieno[3,2-d]pyrimidine-6-yl)furan-2-carboaldehyde The synthesis of 5-(4-(3-(4-methoxybenzyloxy)phenylamino)thieno[3,2-d]pyrimidin-6-yl)furan-2-carboaldehyde $^1$H NMR (400 MHz, DMSO-d$_6$); δ 9.80 (brs, 1H), 9.67 (s, 1H), 8.63 (s, 1H), 7.74 (d, J=4.0 Hz, 1H), 7.58 (s, 1H), 7.51 (d, J=4.0 Hz, 1H), 7.40 (d, J=8.8 Hz, 2H), 7.38-7.36 (m, 1H), Preparation Example 20-1

The synthesis of 2-(5-bromothiophene-3-yl)-1,3-dioxolane $^1$H-NMR (400 MHz, CDCl$_3$); δ 7.29 (d, J=1.6 Hz, 1H), 7.10 (d, J=1.6 Hz, 1H), 5.80 (s, 1H), 4.07-4.06 (m, 2H), 4.01-3.99 (m, 2H)

Preparation Example 20-2

6-(4-(1,3-dioxolane-2-yl)thiophene-2-yl)-N-(3-(4-methoxybenzyloxy)phenyl)thieno[3,2-d]pyrimidine-4-amine The synthesis of 6-(4-(1,3-dioxolan-2-yl)thiophene-2-yl)-N-(3-(4-methoxybenzyloxy)phenyl)thieno[3,2-d]pyrimidin-4-amine $^1$H-NMR (400 MHz, CDCl$_3$); δ 8.68 (s, 1H), 7.45 (d, J=4.4 Hz, 2H), 7.38 (m, 3H), 7.32 (s, 2H), 7.08 (d, J=8.8 Hz, 1H), 6.87 (m, 4H); LC-MS 518 (MH+)

Preparation Example 20-3

5-(4-(3-(4-methoxybenzyloxy)phenylamino)thieno[3,2-d]pyrimidine-6-yl)thiophene-3-carboadehyde The synthesis of 5-(4-(3-(4-methoxybenzyloxy)phenylamino)thieno[3,2-d]pyrimidin-6-yl)thiophene-3-carbaldehyde $^1$H-NMR (400 MHz, CDCl$_3$); δ 9.97 (s, 1H), 9.81 (s, 1H), 8.62 (s, 1H), 8.12 (d, J=4.0 Hz, 1H), 8.00 (s, 1H), 7.86 (d, J=4.0 Hz, 1H), 7.59 (s, 1H), 7.41 (d, J=5.6 Hz, 2H), 7.30 (m, 1H), 7.27 (m, 1H), 6.96 (d, J=8.8 Hz, 2H), 6.80 (m, 1H), 5.03 (s, 2H), 3.79 (s, 3H); LC-MS 474 (M+H+)

Preparation Example 211

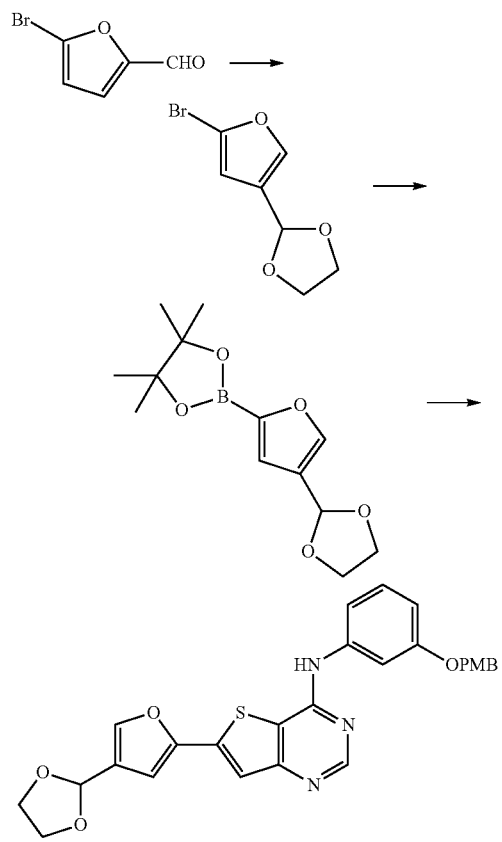

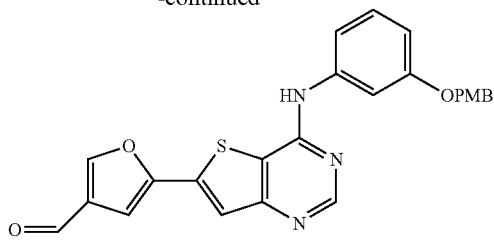

Preparation Example 21-1

The synthesis of 2-(5-bromofuran-3-yl)-1,3-dioxolane $^1$H-NMR (400 MHz, CDCl$_3$); δ 7.52 (s, 1H), 6.39 (s, 1H), 5.79 (s, 1H), 4.11-4.04 (m, 2H), 3.93-3.86 (m, 2H)

Preparation Example 21-2

6-(4-(1,3-dioxolane-2-yl)furan-2-yl)-N-(3-(4-methoxybenzyloxy)phenyl)thieno[3,2-d]pyrimidine-4-amine The synthesis of 6-(4-(1,3-dioxolan-2-yl)furan-2-yl)-N-(3-(4-methoxybenzyloxy)phenyl)thieno[3,2-d]pyrimidin-4-amine $^1$H-NMR (400 MHz, CDCl$_3$); δ 8.66 (s, 1H), 7.58 (s, 1H), 7.49 (s, 1H), 7.37-7.26 (m, 6H), 7.08 (d, J=7.2 Hz, 1H), 6.88 (m, 2H), 6.80 (s, 1H), 5.01 (s, 2H), 4.12-3.98 (m, 4H), 3.76 (s, 1H); LC-MS 502 (MH+)

Preparation Example 21-3

5-(4-(3-(4-methoxybenzyloxy)phenylamino)thieno[3,2-d]pyrimidine-6-yl)furan-3-carboadehyde The synthesis of 5-(4-(3-(4-methoxybenzyloxy)phenylamino)thieno[3,2-d]pyrimidin-6-yl)furan-3-carbaldehyde $^1$H-NMR (400 MHz, CDCl$_3$); δ 9.97 (s, 1H), 8.70 (s, 1H), 8.13 (s, 1H), 7.61 (s, 1H), 7.38-7.26 (m, 4H), 7.08 (m, 2H), 6.91 (m, 2H), 5.04 (s, 2H), 3.80 (s, 3H); LC MS 458 (MH+)

Preparation Example 22

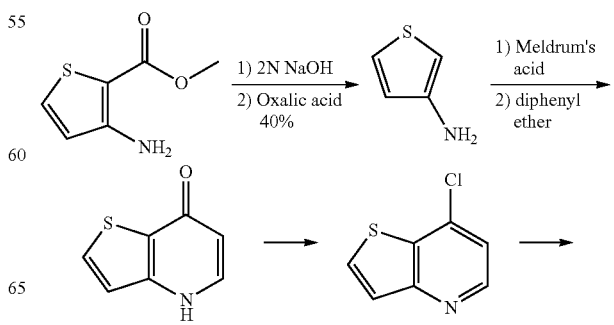

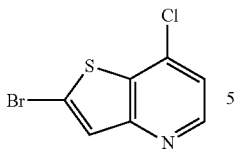

Preparation Example 22-1

The synthesis of thiophene-3-amine 10 g of methyl 3-amino-2-thiophenecarboxylate (63.61 mmol) was dissolved with 60 ml of 2N—NaOH and refluxed for 2 hours. After lowering to 0° C., conc HCl was added into the reaction mixture to adjust to pH 5. After the synthesized beige-colored solid was washed with water, it was dissolved in acetone 40 ml, and dried with magnesium sulfate. After filtration and concentration under vacuum, 50 ml of isopropyl alcohol and oxalic acid (6.3 g, 69.28 mmol) were added and the mixture was stirred at 38° C. for 45 minutes. After lowering the reaction mixture to 0° C., diethylether was added and the synthesized precipitate was filtered. After washing with diethylether, the title compound (2.54 g, 40.3%) was obtained.

$^1$H-NMR (400 MHz, CDCl$_3$); δ 7.13-7.11 (m, 1H), 6.65-6.63 (m, 1H), 6.17-6.16 (m, 1H), 3.60 (brs, 2H)

Preparation Example 22-2

The synthesis of 4H-thieno[3,2-b]pyridine-7-one

Trimethylorthoformate (14 ml, 128.07 mmol) was added to dimethyl-[1,3]dioxane-4,6-dione (4.61 g, 32.01 mmol) and the mixture was stirred for 1 hour at 30° C. Thiophene-3-amine (2.54 g, 25.61 mmol) was added slowly to the reaction mixture at room temperature until white precipitates were formed. After stirring the reaction mixture at 85° C. for 15 hours, the temperature was lowered to room temperature and 25 ml of isopropyl ether was added followed by stirring at room temperature for 1 hour. The synthesized purple solid (intermediate) was washed using isopropyl ether. The intermediate was dissolved in dichloromethane and potassium carbonate and stirred for 30 minutes. Solids were removed by filtration and the solution was concentrated to obtain 2,2-dimethyl-5-(thiophene-3-ylaminoethylene)-[1,3]dioxane-4,6-dione. 5 ml of 2,2-dimethyl-5-(thiophene-3-ylaminoethylene)-[1,3]dioxane-4,6-dione was added slowly to diphenyl ether at 259° C. and refluxed for 30 minutes. After cooling the reaction mixture to room temperature, it was added with isopropyl ether and stirred for 1 hour. The title compound of pale brown solid (2 g, 53%) was obtained.

$^1$H-NMR (600 MHz, DMSO-d$_6$); δ 12.15 (brs, 1H), 7.96 (d, J=8.4 Hz, 1H), 7.82 (d, J=10.8 Hz, 1H), 7.24 (d, J=7.8 Hz, 1H), 6.01 (d, J=10.8 Hz, 1H); LC-MS: 152 (MH+)

Preparation Example 22-3

The synthesis of 7-chloro-thieno[3,2-b]pyridine 30 ml of dichloromethane and 20 ml of dichloroethane in 250 ml round bottom flask were added with dimethylformamide (1.8 ml, 23.28 mmol) and oxalylchloride (2.9 ml, 33.86 mmol) was slowly dropped to the mixture at 0° C. After 4H-thieno[3,2-b]pyridine-7-one (1.6 g, 10.58 mmol) was added, the mixture was refluxed for 6 hours. After lowering the temperature to room temperature, the title compound of yellowish solid (1.7 g, 90%) was obtained.

$^1$H-NMR (400 MHz, CDCl$_3$); δ 8.61 (d, J=5.2 Hz, 1H), 7.81 (d, J=5.2 Hz, 1H), 7.30 (d, J=4.8 Hz, 1H)

Preparation Example 22-4

The synthesis of 2-bromo-7-chlorothieno[3,2-b]pyridine 20 ml of tetrahydrofuran and purified diisopropylamine (0.93 ml, 6.63 mmol) were placed in the 250 ml round bottom flask, filled with nitrogen, and dropped with n-butyllithium (2.45 ml, 6.12 mmol) at −78° C. After stirred for 10 minutes at 0° C., the temperature of the reaction mixture was lowered to −78° C. Then, 7-chloro-thieno[3,2-b]pyridine (0.87 g, 5.1 mmol) dissolved in 10 ml tetrahydrofuran was added using cannula. The reaction mixture was stirred for 10 minutes and 1,2-dibromo-1,1,2,2-tetrafluoromethane (2 g, 6.12 mmol) was added followed by stirred for 30 minutes. The temperature was gradually raised up to room temperature. After 1 hour, the reaction mixture was added with water and extracted with ethylacetate (30 ml×2). After being dried over magnesium sulfate, filtered and concentrated under vacuum, column chromatography (n-hexane/ethylacetate, 1/40) was carried out to obtain the title compound (1.12 mg, 88%).

$^1$H-NMR (600 MHz, DMSO-d$_6$); δ 8.64 (d, J=5.2 Hz, 1H), 7.94 (s, 1H), 7.61 (d, J=5.2 Hz, 1H)

Preparation Example 23

2-bromo-N-(3-(4-methoxybenzyloxy)phenyl)thieno[3,2-b]pyridine-7-amine

The synthesis of 2-bromo-N-(3-(4-methoxybenzyloxy)phenyl)thieno[3,2-b]pyridin-7-amine

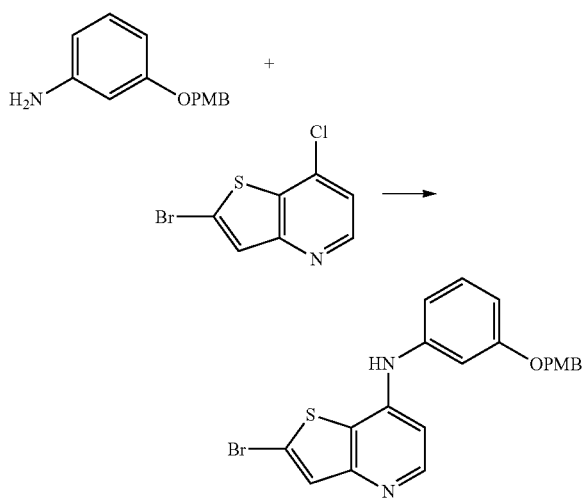

The compound (0.18 g, 0.80 mmol) obtained from Preparation Example 1 was dissolved in 3 ml of dichloroethane and 3 ml of t-butanol and placed into a sealed tube. The mixture was added with the synthesized compound (198 mg, 0.80 mmol) in example of synthesis 22-4 and stirred for next 3 days at 85° C. After cooling to room temperature, the synthesized pale brown solid was washed by diethylether and the title compound (0.25 g, 80%) was obtained as a gray solid.

$^1$H-NMR (400 MHz, CDCl$_3$); δ 8.32 (d, J=5.2 Hz, 1H), 7.50 (s, 1H), 7.34 (d, J=7.6 Hz, 2H), 7.29 (t, J=8.0 Hz, 1H), 6.92 (d, J=7.6 Hz, 2H), 6.83-6.80 (m, 4H), 5.00 (s, 2H), 3.82 (s, 3H)

Preparation Example 24

4-(7-(3-(4-methoxybenzyloxy)phenylamino)thieno[3,2-b]pyridine-2-yl)benzadehyde

The synthesis of 4-(7-(3-(4-methoxybenzyloxy)phenylamino)thieno[3,2-b]pyridin-2-yl)benzaldehyde

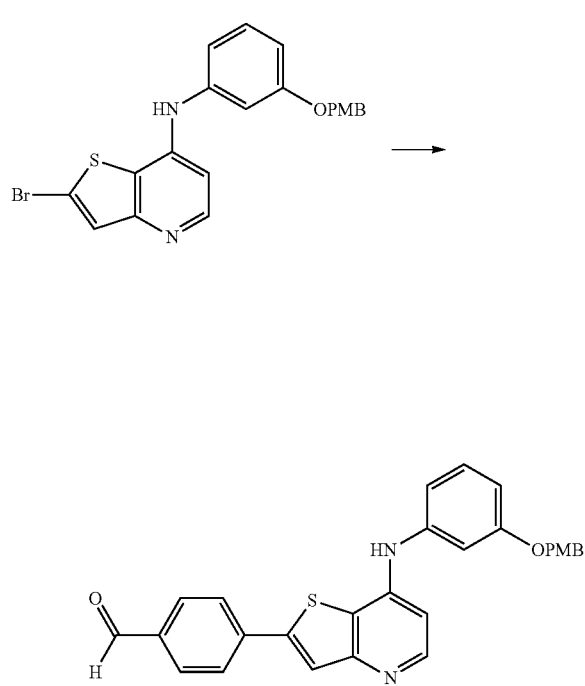

The compound (0.5 g, 0.89 mmol) obtained from the example of synthesis 22, 4-formylphenylboric acid (0.16 g, 1.06 mmol) and PdCl2 (dppf) 2 (21 mg, 0.03 mmol) were placed into the reaction vessel under nitrogen gas and 5 ml of degassed dimethylformamide and 2N sodium carbonate (0.9 ml, 1.78 mmol) were added. The mixture was stirred at 80° C. for 15 hours and extracted with 50 ml dichloromethane and 50 ml of saturated ammonium chloride solution. The organic layer was further extracted twice with 50 ml of saturated ammonium chloride solution, dried using anhydrous sodium sulfate and concentrated under vacuum. After trituration with 10 ml of diethylether, the title compound 320 mg (0.69 mmol, 77%) was obtained as a brown solid.

$^1$H-NMR (400 MHz, CDCl$_3$); δ 10.06 (s, 1H), 8.39 (d, J=3.6 Hz, 1H), 7.96 (d, J=5.2 Hz, 2H), 7.89-7.7.86 (m, 3H), 7.35 (d, J=5.6 Hz, 2H), 7.31 (t, J=5.2 Hz, 1H), 6.94-6.90 (m, 4H), 6.86 (d, J=5.2 Hz, 1H), 6.82 (d, J=5.2 Hz, 1H), 6.09 (s, 1H), 5.01 (s, 2H), 3.82 (s, 3H); LC-MS 467.0 (MH+)

Preparation Example 251

3-(7-(3-(4-methoxybenzyloxy)phenylamino)thieno[3,2-b]pyridine-2-yl)benzadehyde

The synthesis of 3-(7-(3-(4-methoxybenzyloxy)phenylamino)thieno[3,2-b]pyridin-2-yl)benzaldehyde

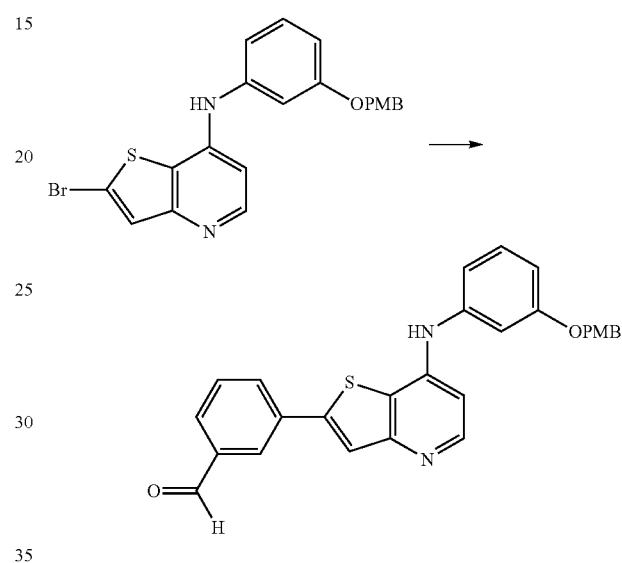

The compound (6.69 g, 15.63 mmol) obtained from example of synthesis 23, 3-formylphenylboric acid (2.7 g, 18.76 mmol), and PdCl2 (dppf) 2 (388 mg, 0.46 mmol) were placed into the reaction vessel under nitrogen gas. 70 ml of degassed dimethylformamide and 2N sodium carbonate (23 ml, 46.89 mmol) were added and the mixture was stirred at 80° C. for 15 hours. The reaction mixture were added with 250 ml of saturated ammonium chloride solution and 250 ml of dichloromethane, and extracted. The organic layer was further extracted twice with 150 ml of saturated ammonium chloride solution, dried using anhydrous sodium sulfate, and concentrated under vacuum. After trituration with 10 ml of diethylether, the title compound (2.5 g, 36%) was obtained as brown solid.

$^1$H-NMR (600 MHz, DMSO-d$_6$); δ 10.11 (s, 1H), 8.92 (s, 1H), 8.32-8.31 (m, 2H), 8.19 (d, J=8.4 Hz, 1H), 7.97 (s, 1H), 7.76 (d, J=7.8 Hz, 1H), 7.75 (t, J=7.8 Hz, 1H), 7.64-7.60 (m, 1H), 7.57-7.54 (m, 1H), 7.38 (d, J=8.4 Hz, 2H), 6.95 (d, J=8.4 Hz, 2H), 6.90-6.87 (m, 2H), 6.77 (dd, J=1.8 Hz, 7.8 Hz, 1H), 5.04 (s, 2H), 3.76 (s, 3H); LC-MS 467 (MH+)

Preparation Example 26

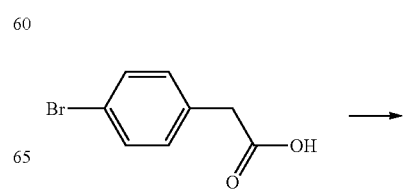

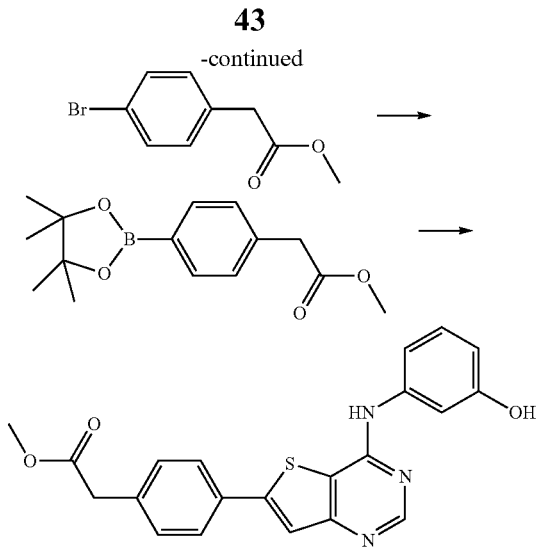

Preparation Example 26-1

The synthesis of methyl 2-(4-bromophenyl)acetate 20 ml acetonitrile was added to 4-bromophenylacetic acid (2 g, 9.3 mmol) and 1,8-diazabicyclo[5.4.0]undec-2-ene (1.7 g, 11.2 mmol) was added at 0° C. Iodomethane (1.98 g, 14.0 mmol) was slowly dropped to the mixture and stirred for 2 hours at room temperature. After the reaction is complete, the mixture was extracted using water (100 ml×2) and dichloromethane (100 ml). The title compound (1.7 g, 75%) was obtained by column chromatography (ethylacetate/n-hexane, 1/15).

$^1$H-NMR (600 MHz, CDCl$_3$); δ 7.45 (d, J=12.6 Hz, 2H), 7.15 (d, J=12.6 Hz, 2H), 3.69 (s, 3H), 3.58 (2H),

Preparation Example 26-2

Methyl 2-(4-(4-(3-hydroxyphenylamino)thieno[3,2-d]pyrimidine-6-yl)phenyl)acetate The synthesis of methyl 2-(4-(4-(3-hydroxyphenylamino)thieno[3,2-d]pyrimidin-6-yl)phenyl)acetate bis(pinacolate)diborane (1.95 g, 7.68 mmol), PdCl$_2$ dppf (171 mg, 0.21 mmol), and potassium acetate (2.06 g, 7.68 mmol) were placed in a reaction chamber and vacuum-dried. The compound (1.6 g, 7.0 mmol) synthesized in example of synthesis 18-1 was dissolved into 5 ml of degassed dimethylformamide and added into the reaction chamber followed by stirring at 85° C. for 15 hours. The reaction mixture was cooled to room temperature and added with 50 ml of ethylacetate and 50 ml of saturated ammonium chloride and extracted. The organic layer was washed with 50 ml of ammonium chloride twice, then dried using anhydrous magnesium sulfate, concentrated under vacuum. Deep brown oil type of methyl 2-(4-(4,4,5,5-tetramethyl-1,3,2-dioxaborane-2-yl)phenyl)acetate was obtained. this compound and the compound (1.8 g, 4.23 mmol) synthesized in example of synthesis 5-2, and PdCl$_2$ dppf (80 mg, 0.10 mmol) were added sequentially into 20 ml of degassed dimethylformamide and 2N sodium carbonate solution (2 ml, 6.52 mmol) was further added. The reaction mixture was stirred at 80° C. for 15 hours and cooled to room temperature. It was extracted with 100 ml of ethylacetate and 100 ml of saturated ammonium chloride. The organic layer was washed twice with 100 ml of saturated ammonium chloride, dried with anhydrous magnesium sulfate, and concentrated under vacuum. The title compound (A) (0.51 g, 40%) was obtained after column chromatography (ethylacetate/hexane, 1/2).

$^1$H-NMR (400 MHz, DMSO-d$_6$); δ 9.61 (brs, 1H), 9.43 (brs, 1H), 8.58 (s, 1H), 7.88 (s, 1H), 7.83 (d, J=8.0 Hz, 2H), 7.43 (d, J=8.4 Hz, 2H), 7.33-7.30 (m, 1H), 7.20-7.12 (m, 2H), 6.54-6.52 (m, 1H), 3.78 (s, 2H), 3.64 (s, 3H); LC-MS: 392 (MH+)

Preparation Example 27 methyl-2-(4-(4-(3-(t-butyldimethylsiloxy)phenylamino)thieno[3,2-d]pyrimidine-6-yl)phenyl)acetate The synthesis of methyl-2-(4-(4-(3-(tert-butyldimethylsilyloxy)phenylamino)thieno[3,2-d]pyrimidin-6-yl)phenyl)acetate

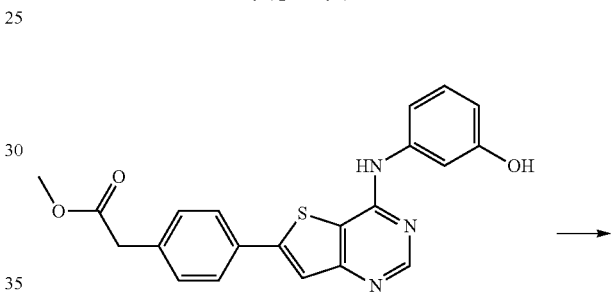

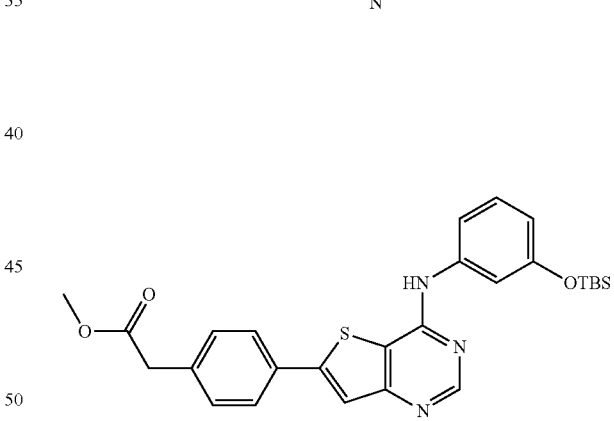

The compound (0.51 g, 1.30 mmol) prepared from example of synthesis 26-2 was dissolved in 10 ml of dichloromethane and 5 ml of dimethylformamide, imidazole (0.11 g, 1.69 mmol) and tert-butylchlorodimethyl silane (0.24 mg, 1.56 mmol). The mixture was stirred for 10 hours at room temperature. Saturated ammonium chloride solution (100 ml) was added to the reaction solution, which then was extracted with ethyl acetate (100 ml×2). The organic layer was washed with water (100 ml×2), dried using anhydrous sodium sulfate and concentrated under vacuum. After column chromatography (ethylacetate/n-hexane, 1:2), the title compound (0.49 g, 74.4%) as yellowish solid was obtained.

$^1$H-NMR (400 MHz, CDCl$_3$); δ 8.69 (s, 1H), 7.64 (d, J=8.0 Hz, 2H), 7.59 (s, 1H), 7.36 (d, J=8.0 Hz, 2H), 7.28-7.24 (m, 1H), 6.76 (brs, 1H), 7.19 (t, J=2.2 Hz, 1H), 7.16-7.16 (m, 1H), 6.76 (brs, 1H), 6.75-6.74 (m, 1H), 3.68 (s, 2H), 1.00 (s, H), 0.24 (s, 6H); LC-MS: 506 (MH+)

Preparation Example 28

4-(4-(3-(t-butyldimethylsiloxy)phenylamino)thieno [3,2-d]pyrimidine-6-yl)benzoic acid The synthesis of 4-(4-(3-(tert-butyldimethylsilyloxy) phenylamino)thieno[3,2-d]pyrimidin-6-yl)benzoic acid

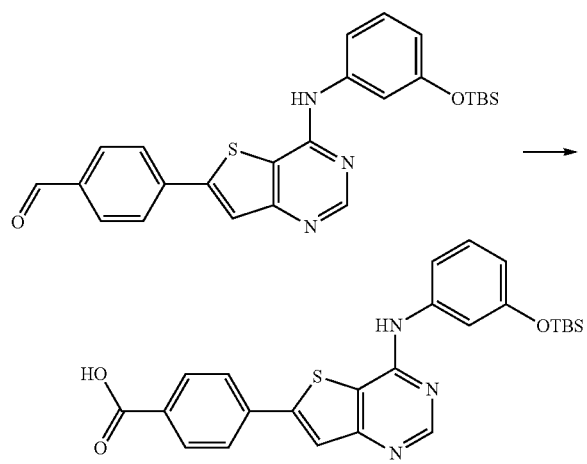

The compound (0.2 g, 0.46 mmol) synthesized in the example of synthesis 6 was dissolved into 2 ml of acetone and added with 0.4 ml of water and potassium permanganate (130 mg, 0.82 mmol). The mixture was stirred at room temperature for 3 hours. The mixture was extracted with 20 ml of 2N c HCl and 30 ml of ethyl acetate and washed twice with 30 ml of H₂O. After being dried with sodium sulfate, filtered and concentrated under vacuum, the title compound (0.2 g, 96%) was obtained as yellowish solid.

¹H-NMR (400 MHz, CDCl₃); δ 10.44 (brs, 1H), 8.78 (s, 1H), 8.12 (t, J=7.6 Hz, 1H), 8.05 (d, J=8.0 Hz, 2H), 7.69-7.59 (m, 3H), 7.48 (d, J=8.0 Hz, 1H), 7.43 (s, 1H), 7.33 (t, J=8.0 Hz, 1H), 6.74 (d, J=8.4 Hz, 1H), 1.01 (s, 9H), 0.28 (s, 6H); LC-MS: 478 (MH+)

Preparation Example 29

2-(4-(4-(3-(t-butyldimethylsiloxy)phenylamino) thieno[3,2-d]pyrimidine-6-yl)phenyl)acetic acid The synthesis of 2-(4-(4-(3-(tert-butyldimethylsilyloxy)phenylamino)thieno[3,2-d]pyrimidin-6-yl)phenyl)acetic acid

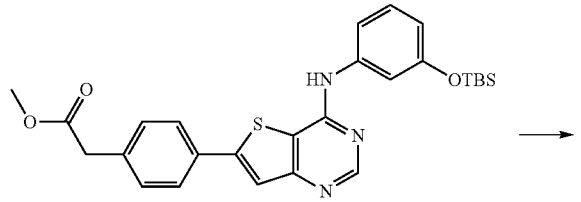

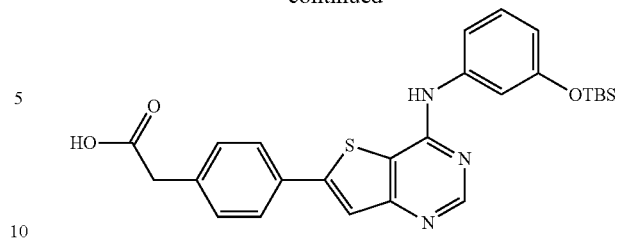

¹H-NMR (400 MHz, CDCl₃); δ 10.44 (br, 1H), 8.78 (s, 1H), 8.12 (t, J=7.6 Hz, 1H), 8.05 (d, J=8.0 Hz, 2H), 7.69-7.59 (m, 2H), 7.48 (d, J=8.0 Hz, 1H), 7.43 (s, 1H), 7.33 (t, J=8.0 Hz, 1H), 6.74 (d, J=8.4 Hz, 1H), 3.60 (s, 2H), 1.01 (s, 9H), 0.28 (s, 6H); LC-MS 478 (MH+)

Preparation Example 30

The synthesis of 1-bromo-4-(ethoxymethyl)benzene

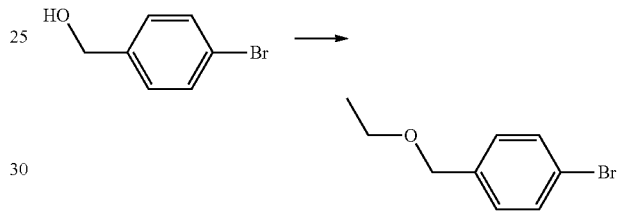

NaOH (0.1 g, 2.4 mmol) was added to 2 ml of degassed dimethylformamide and 4-bromobenzylalcohol (0.3 g, 1.6 mmol) was further added slowly. Iodoethane (0.14 ml, 1.76 mmol) was added at room temperature followed by stirring for 2 hours. The mixture was added with 50 ml of 2N c HCl and extracted with 50 ml of ethylacetate. The organic layer was washed twice with 50 ml of H₂O. After concentration under vacuum and column chromatography (ethylacetate/n-hexane, 1/10), the title compound (0.17 g, 48%) was obtained as yellowish oil.

¹H-NMR (600 MHz, CDCl₃); δ 7.46 (d, J=8.4 Hz, 2H), 7.21 (d, J=8.4 Hz, 2H), 4.45 (s, 2H), 3.55-3.51 (m, 2H), 1.28-1.23 (m, 3H)

Preparation Example 31 ethyl 4-amino-2-(methylthio)thiazole-5-carboxylate

The synthesis of ethyl 4-amino-2-(methylthio)thiazole-5-carboxylate

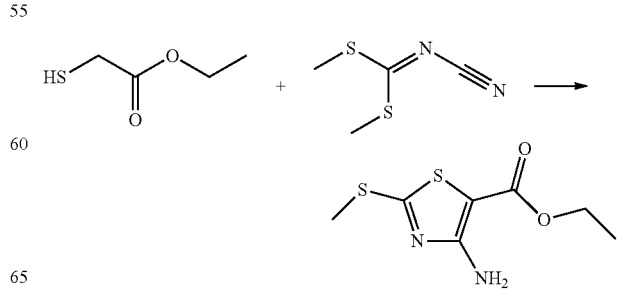

Ethyl 2-mercaptoacetate (50 g, 0.416 mol) was dissolved in 500 ml of dimethylformamide and added with dimethyl N-thienodithioimino carbonate (67 g, 0.416 mol) and diisopropylamine (112 ml, 0.624 mol). After heating at 100° C. for 5 hours, the mixture was extracted with 500 ml of saturated ammonium chloride and 500 ml of ethylacetate, dried with sodium sulfate, filtered and concentrated under vacuum. After washing the solid with n-hexane, the title compound (90 g, 99%) was obtained.

$^1$H-NMR (400 MHz, CDCl$_3$); δ 5.84 (brs, 2H), 4.26 (q, J=7.2 Hz, 2H), 2.63 (s, 3H), 1.32 (t, J=7.2 Hz, 3H); LC-MS 219 (MH+)

Preparation Example 32

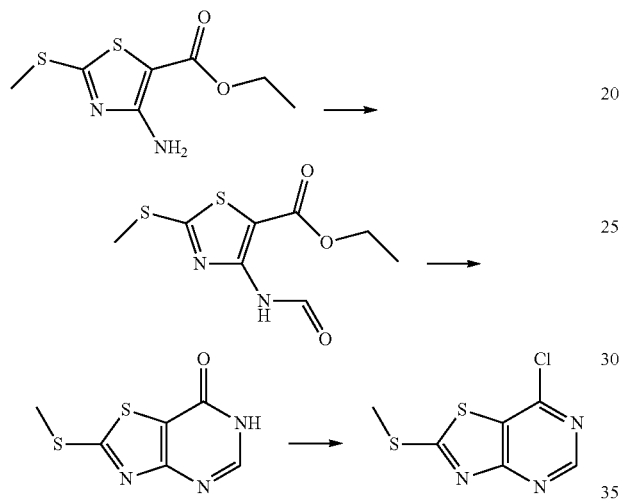

Preparation Example 32-1 ethyl 4-formamido-2-(methylthio)thiazole-5-carboxylate

The synthesis of ethyl 4-formamido-2-(methylthio)thiazole-5-carboxylate

The compound (30 g, 138.05 mole) synthesized in Preparation Example 31 and ammoniumacetate (13.8 g, 179.03 mol) were mixed with 200 ml of formic acid. After 46 hours of reflux, the mixture was concentrated under vacuum to remove the formic acid and extracted with ethylacetate and 300 ml of saturated sodium bicarbonate. The organic layer was dried with sodium sulfate, filtered and concentrated under vacuum. The title compound (29.5 g, 87.3%) was obtained as yellowish solid.

$^1$H-NMR (400 MHz, CDCl$_3$); δ 9.38 (s, 1H), 5.81 (brs, 1H), 4.32 (q, J=6.8 Hz, 2H), 2.70 (s, 3H), 1.35 (t, J=6.8 Hz, 3H); LC-MS 246 (MH+)

Preparation Example 32-2

2-(methylthio)thiazolo[4,5-d]pyrimidine-7-(6H)-one

The synthesis of 2-(methylthio)thiazolo[4,5-d]pyrimidin-7(6H)-one

The compound (29.5 g, 0.12 mol) synthesized in example of synthesis 32-1, ammonium formate (22.7 g, 0.36 mol), and formamide (28.7 ml, 0.72 mol) were mixed and the mixture was heated at 140° C. for 48 hours followed by adding 100 ml of water. After adding 200 ml of diethylether, it was stirred at room temperature for 30 minutes. The synthesized solid was washed with n-hexane to obtain the title compound (20.5 g, 85%) as yellowish solid.

$^1$H-NMR (400 MHz, DMSO-d$_6$); δ 8.83 (s, 1H), 8.60 (s, 1H), 3.38 (s, 3H); LC-MS 202 (MH+)

Preparation Example 32-3

7-chloro-2-(methylthio)thiazolo[4,5-d]pyrimidine

The synthesis of 7-chloro-2-(methylthio)thiazolo[4,5-d]pyrimidine

The compound (2 g, 9.93 mmol) synthesized in example of synthesis 32-2 and 4 ml of phosphoryl chloride were mixed and heated at 130° C. for 15 hours. After removing phosphorylchloride by concentration under vacuum, 100 ml of ice-cold water was added and stirred for 20 minutes. The synthesized solid was washed with 100 ml of water and n-hexane and the title compound (0.88 g, 40.4%) was obtained as yellowish solid.

$^1$H-NMR (400 MHz, CDCl$_3$); δ 8.95 (s, 1H), 2.90 (s, 3H); LC-MS 220 (MH+)

Preparation Example 33

N-(3-(4-methoxybenzyloxy)phenyl)-2-(methylthio) thiazolo[4,5-d]pyrimidine-7-amine The synthesis of N-(3-(4-methoxybenzyloxy)phenyl)-2-(methylthio)thiazolo[4,5-d]pyrimidin-7-amine

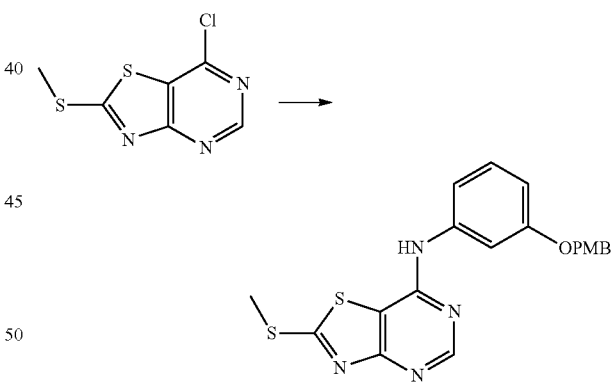

The compound (0.2 g, 0.91 mmol) synthesized in example of synthesis 32-3, the compound (0.23 g, 1.00 mmol) synthesized in example of synthesis 1, and diisopropylamine (0.2 ml, 1.09 mmol) were mixed with 2 ml of isopropylalcohol and heated at 80° C. for 20 hours. After removing isopropylalcohol by concentration under vacuum, 20 ml of dichloromethane and 2 ml of methanol was added and the mixture was concentrated under vacuum again to remove organic solvent followed by trituration using n-hexane and diethylether. The title compound (260 mg, 70%) was obtained as beige-colored solid.

$^1$H-NMR (400 MHz, CDCl$_3$); δ 8.65 (s, 1H), 7.36-7.30 (m, 3H), 7.07 (brs, 1H), 7.05-7.04 (m, 1H), 6.96-6.90 (m, 4H), 5.30 (s, 2H), 3.81 (s, 3H), 2.79 (s, 3H); LC-MS 412 (MH+)

The preferred embodiments described below are provided by the compounds synthesized in the example of synthesis described above.

Example 1

6-bromo-thieno[3,2-d]pyrimidine-4-nyl)-(3-methoxy-phenyl)-amine

The synthesis of (6-Bromo-thieno[3,2-d]pyrimidine-4-yl)-(3-methoxy-phenyl)-amine) (LCB03-0007)

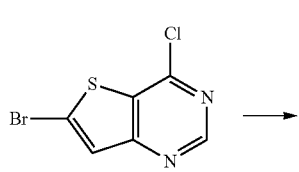

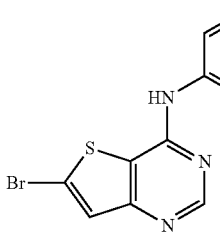

The compound (1 g, 4.00 mmol) synthesized in the example of synthesis 3-4, 0.9 ml diisopropylethylamine, and 0.56 ml of m-anisidine were added to 5 ml of isopropyl alcohol and refluxed for 12 hours followed by concentration under vacuum. The reaction mixture was added with 80 ml of ethylacetate and washed with 20 ml of water twice, and concentrated under vacuum. The solid was washed with n-hexane three times and concentrated under vacuum. The title compound (1.05 g, 78%) was obtained as pale yellowish solid.

$^1$H-NMR (400 MHz, CDCl$_3$); δ 7.41 (s, 1H), 7.34 (t, J=8.4 Hz, 1H), 7.20 (s, 1H), 7.10 (dd, J=2.0, 8.0 Hz, 1H), 7.03 (dd, J=2.0, 8.0 Hz, 1H), 6.89 (dd, J=2.4, 8.4 Hz, 1H), 3.85 (s, 3H); LC-MS 336, 338 (M+, MH+2)

Example 2

3-(6-bromo-thieno[3,2-d]pyrimidine-4-nylamino)-phenol

The synthesis of (3-(6-Bromo-thieno[3,2-d]pyrimidin-4-ylamino)-phenol) (LCB03-0015)

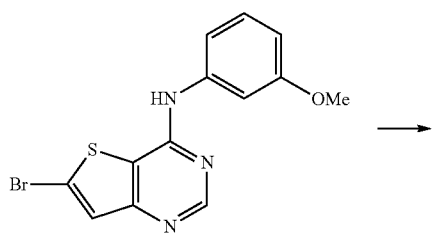

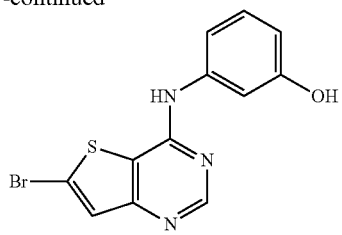

The compound (150 mg, 0.45 mmol) synthesized in the preferred embodiment 1 was dissolved in 5 ml of dichloromethane. Then it was added slowly with 0.89 ml of 1M borontribromide at 0° C. and stirred at room temperature for 12 hours. After being extracted with 30 ml of dichloromethane and 20 ml of sodium bicarbonate and concentrated under vacuum, column chromatography (dichloromethane/methanol, 20/1) was done to obtain the title compound (90 mg, 63%) as pale yellowish solid.

$^1$H NMR (400 MHz, DMSO-d$_6$); δ 8.60 (s, 1H), 7.65 (s, 1H), 7.19-7.15 (m, 1H), 7.09 (d, J=8.0 Hz, 1H), 7.77 (s, 1H), 6.61 (d, J=8.0 Hz, 1H), 3.83 (s, 3H); LC-MS 322, 324 (M+, MH+2)

Example 3

3-[6-(4-methoxyphenyl)-thieno[3,2-d]pyrimidine-4-nylamino]-1-phenol

The synthesis of (3-[6-(4-Methoxy-phenyl)-thieno[3,2-d]pyrimidin-4-ylamino]-phenol) (LCB03-0017)

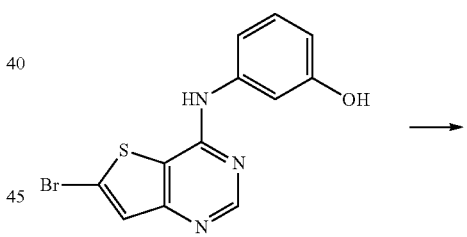

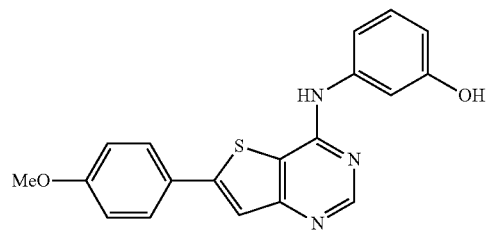

The compound (45 mg, 0.14 mmol) synthesized in the preferred embodiment 2, 4-methoxyphenylboric acid (22 mg, 0.15 mmol), 2M potassium carbonate (0.14 ml, 0.28 mmol), and 10 mg of paladiumtetrakistriphenylphosphine was mixed in 1 ml of 1,4-dioxane and refluxed for 3 hours. The mixture was washed with 20 ml of ethylacetate and 10 ml of sodium bicarbonate solution twice and concentrated under vacuum. After column chromatography (dichloromethane/methanol, 40/1), the title compound (27 mg, 57%) was obtained as yellowish solid.

$^1$H-NMR (400 MHz, CDCl$_3$); δ 9.55 (s, 1H), 9.43 (s, 1H), 8.58 (s, 1H), 7.81 (d, J=8.8 Hz, 2H), 7.77 (s, 1H), 7.32 (s, 1H), 7.19 (d, J=8.0 Hz, 1H), 7.16 (m, 1H), 7.09 (d, J=8.8 Hz, 2H), 6.52 (d, J=8.0 Hz, 1H), 3.83 (s, 3H); LC-MS 350 (MH+)

Example 4

(3-methoxyphenyl)-(6-thiophene-2-yl-thieno[3,2-d]pyrimidine-4-yl)-amine

The synthesis of ((3-Methoxyphenyl)-(6-thiophene-2-yl-thieno[3,2-d]pyrimidin-4-yl)-amine) (LCB03-0030)

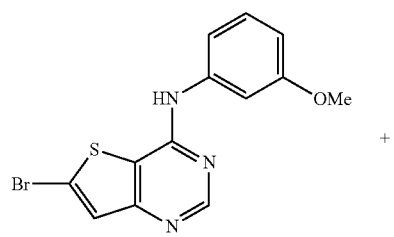

+

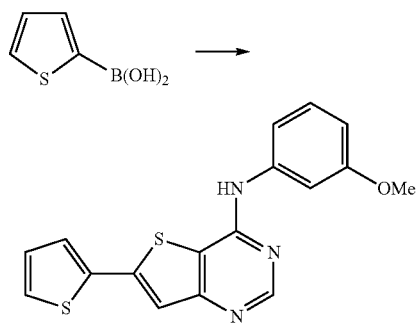

The compound (70 mg, 0.21 mmol) synthesized in the preferred embodiment 1, 2-thiopheneboric acid (20 mg, 0.23 mmol), 2M potassium carbonate (0.46 ml, 0.42 mmol), and 10 mg of paladiumtetrakistrinylphosphine were mixed in 1 ml of 1,4-dioxane and refluxed for 12 hours. After washing with 20 ml of ethylacetate and 10 ml of sodium bicarbonate solution twice followed by concentration under vacuum, column chromatography (ethylacetate/n-hexane, 1/1) was done to obtain the title compound (51 mg, 71%) as pale yellowish solid.

$^1$H-NMR (400 MHz, CDCl$_3$); δ 8.69 (s, 1H), 7.46 (s, 1H), 7.40 (dd, J=4.8, 0.8 Hz, 1H), 7.35 (dd, J=4.8, 0.8 Hz, 1H), 7.33 (t, J=8.0 Hz, 1H), 7.25 (t, J=2.4 Hz, 1H), 7.11-7.08 (m, 2H), 6.83-6.80 (m, 2H), 3.85 (s, 3H); LC-MS 340 (MH+)

The following compounds were synthesized by the methods to similar to the one of the preferred embodiment 4.

Example 5

(3-methoxyphenyl)-(6-thiophene-3-yl-thieno[3,2-d]pyrimidine-4-yl)-amine

The synthesis of ((3-Methoxyphenyl)-(6-thiophene-3-yl-thieno[3,2-d]pyrimidin-4-yl)-amine) (LCB03-0028)

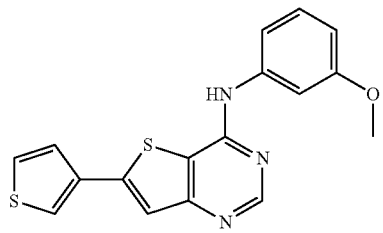 [SMILES: COc1cccc(Nc2ncnc3cc(-c4ccsc4)sc23)c1]

$^1$H-NMR (400 MHz, CDCl$_3$); δ 8.70 (s, 1H), 7.61-7.60 (m, 1H), 7.49 (s, 1H), 7.44-7.39 (m, 2H), 7.33 (t, J=8.0 Hz, 1H), 7.26-7.25 (m, 1H), 7.12-7.10 (m, 1H), 6.83-6.80 (m, 1H), 6.72 (s, 1H), 3.86 (s, 3H); LC-MS 340 (MH+)

Example 6

(6-furan-2-yl-thieno[3,2-d]pyrimidine-4-yl)-(3-methoxyphenol)-amine

The synthesis of ((6-Furan-2-yl-thieno[3,2-d]pyrimidin-4-yl)-(3-methoxyphenyl)-amine) (LCB03-0023)

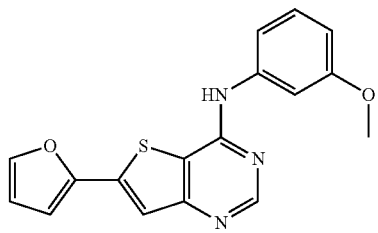 [SMILES: COc1cccc(Nc2ncnc3cc(-c4ccco4)sc23)c1]

$^1$H-NMR (400 MHz, CDCl$_3$); δ 8.70 (s, 1H), 7.52 (m, 2H), 7.40 (t, J=8.0 Hz, 1H), 7.25 (t, J=2.4 Hz, 1H), 7.11-7.08 (m,

1H), 6.84-6.81 (m, 1H), 6.78 (d, J=7.6 Hz, 1H), 6.73 (s, 1H), 6.53 (dd, J=3.6, 2.4 Hz, 1H), 3.86 (s, 3H); LC-MS 324 (MH+)

Example 7

(6-furan-3-yl-thieno[3,2-d]pyrimidine-4-yl)-(3-methoxyphenol)-amine

The synthesis of ((6-Furan-3-yl-thieno[3,2-d]pyrimidin-4-yl)-(3-methoxyphenyl)-amine) (LCB03-0024)

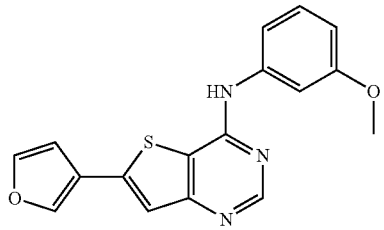

$^1$H-NMR (400 MHz, CDCl$_3$); δ 8.71 (s, 1H), 7.79 (s, 1H), 7.50 (t, J=1.6 Hz, 1H), 7.40 (s, 1H), 7.32 (t, J=8.0 Hz, 1H), 7.23 (t, J=1.6 Hz, 1H), 7.10-7.08 (m, 1H), 6.83-6.80 (m, 1H), 6.68 (dd, J=1.6, 0.8 Hz, 1H), 3.84 (s, 3H); LC-MS 324 (MH+)

Example 8

N-(3-methoxyphenyl)-6-phenylthieno[3,2-d]pyrimidine-4-amine

The synthesis of (N-(3-methoxyphenyl)-6-phenylthieno[3,2-d]pyrimidin-4-amine) (LCB03-0006)

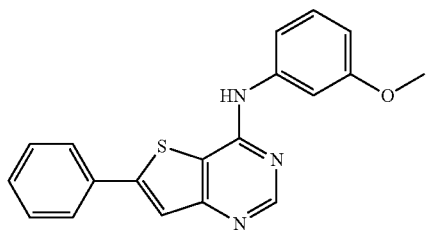 [SMILES: COc1cccc(Nc2ncnc3cc(-c4ccccc4)sc23)c1]

$^1$H-NMR (400 MHz, CDCl$_3$); δ 8.71 (s, 1H), 7.68 (d, J=6.8 Hz, 2H), 7.60 (s, 1H), 5.46-7.41 (m, 4H), 7.34-7.30 (m, 2H), 7.13-7.11 (m, 1H), 7.03 (brs, 1H), 6.82-6.80 (m, 1H), 3.48 (s, 3H); LC-MS: 334 (MH+)

Example 9

4-(4-(3-methoxyphenylamino)thieno[3,2-d]pyrimidine-6-yl)phenol

The synthesis of (4-(4-(3-methoxyphenylamino)thieno[3,2-d]pyrimidin-6-yl)phenol) (LCB03-0016)

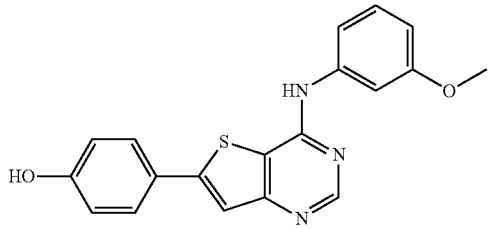

$^1$H-NMR (400 MHz, CDCl$_3$); δ 8.44 (s, 1H), 7.62 (d, J=8.8 Hz, 2), 7.42 (s, 1H), 7.32 (t, J=2.2 Hz, 1H), 7.25-7.19 (m, 2H), 6.85 (d, J=8.8 Hz, 2H), 6.74-6.71 (m, 1H), 3.79 (s, 3H); LC-MS 350 (MH+)

Example 10

4-(4-(3-methoxyphenylamino)thieno[3,2-d]pyrimidine-6-yl)benzonitrile

The synthesis of (4-(4-(3-methoxyphenylamino)thieno[3,2-d]pyrimidin-6-yl)benzonitrile) (LCB03-0009)

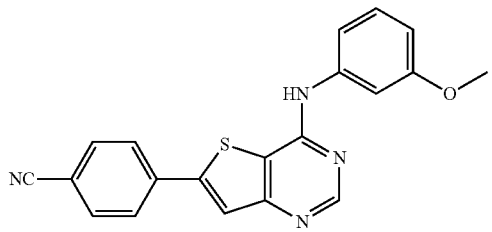 [SMILES: COc1cccc(Nc2ncnc3cc(-c4ccc(C#N)cc4)sc23)c1]

$^1$H-NMR (400 MHz, CDCl$_3$); δ 8.78 (s, 1H), 7.79-7.73 (m, 4H), 7.70 (s, 1H), 7.35 (t, J=8.4 Hz, 1H), 7.24-7.21 (m, 1H), 7.11-7.10 (m, 1H), 6.86-6.84 (m, 1H), 6.82 (brs, 1H), 3.86 (s, 3H); LC-MS 359 (MH+)

Example 11

N-(3-methoxyphenyl)-6-(thiophene-2-yl)thieno[3,2-d]pyrimidine-4-amine

The synthesis of (N-(3-methoxyphenyl)-6-(thiophene-2-yl)thieno[3,2-d]pyrimidin-4-amine) (LCB03-0027)

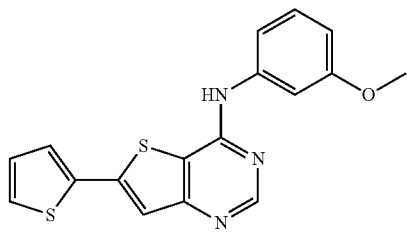 [SMILES: COc1cccc(Nc2ncnc3cc(-c4cccs4)sc23)c1]

$^1$H-NMR (400 MHz, CDCl$_3$); δ 8.69 (s, 1H), 7.46 (s, 1H), 7.40 (dd, J=4.8, 0.8 Hz, 1H), 7.35 (dd, J=4.8, 0.8 Hz, 1H), 7.33 (t, J=8.0 Hz, 1H), 7.25 (t, J=2.4 Hz, 1H), 7.11-7.08 (m, 2H), 6.83-6.80 (m, 2H), 3.85 (s, 3H); LC-MS 340 (MH+)

Example 12

3-(6-thiophene-2-yl-thieno[3,2-d]pyrimidine-4-ylamino)-phenol

The synthesis of (3-(6-Thiophene-2-yl-thieno[3,2-d]pyrimidin-4-ylamino)-phenol)

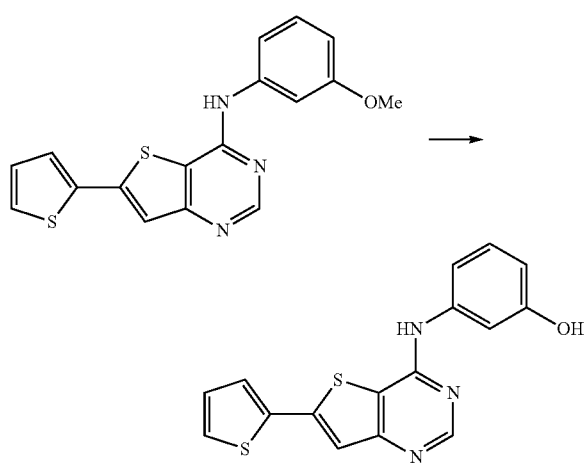

The compound (40 mg, 0.12 mmol) synthesized in the preferred embodiment 4 was dissolved in 2 ml of dichloromethane 2 ml and then added slowly with 0.3 ml of 1M boron tribromide at 0° C. followed by stirring for 12 hours at room temperature. Then the mixture was extracted with 12 ml of water, and 50 ml of ethylacetate 50 ml and concentrated under vacuum followed by column chromatography (dichloromethane/methanol, 20/1). The title compound (15 mg, 39%) was obtained as yellowish solid.

$^1$H-NMR (400 MHz, DMSO-d$_6$); δ 9.53 (s, 1H), 9.39 (s, 1H), 8.52 (s, 1H), 7.71 (d, J=1.2 Hz, 1H), 7.63 (s, 1H), 7.61 (d, J=1.2 Hz, 1H), 7.27 (s, 1H), 7.19-7.07 (m, 3H), 6.48-6.47 (m, 1H); LC-MS 326 (MH+)

The following compounds were synthesized by the method similar to the one described in the preferred embodiment 12 described above.

Example 13

3-(6-thiophene-3-yl-thieno[3,2-d]pyrimidine-4-ylamino)-phenol

The synthesis of (3-(6-Thiophene-3-yl-thieno[3,2-d]pyrimidin-4-ylamino)-phenol) (LCB03-0031)

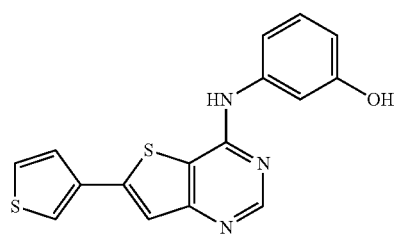 [SMILES: Oc1cccc(Nc2ncnc3cc(-c4ccsc4)sc23)c1]

$^1$H-NMR (400 MHz, DMSO-d$_6$); δ 10.89 (s, 1H), 8.86 (s, 1H), 8.21 (t, J=1.2 Hz, 1H), 7.76 (dd, J=4.8, 2.4 Hz, 1H), 7.72 (s, 1H), 7.61 (d, J=4.8 Hz, 1H), 7.21 (t, J=8.0 Hz, 1H), 7.08 (s, 1H), 7.05 (d, J=8.4 Hz, 1H), 6.68 (d, J=8.0 Hz, 1H); LC-MS 326 (MH+)

Example 14

3-(6-(phenylthieno[3,2-d]pyrimidine-4-ylamino)phenol

The synthesis of (3-(6-phenylthieno[3,2-d]pyrimidin-4-ylamino)phenol) (LCB03-0008)

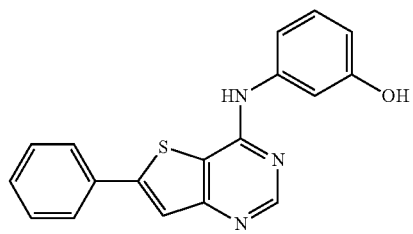 [SMILES: Oc1cccc(Nc2ncnc3cc(-c4ccccc4)sc23)c1]

$^1$H-NMR (400 MHz, DMSO-d$_6$); δ 8.82 (s, 1H), 7.89-7.87 (m, 3H), 7.58-7.54 (m, 3H), 7.24 (t, J=8.0 Hz, 1H), 7.16-7.11 (m, 2H), 6.71-6.69 (m, 1H); LC-MS 320 (MH+)

Example 15

4-(4-(3-hydroxyphenylamino)thieno[3,2-d]pyrimidine-6-yl)benzonitrile

The synthesis of (4-(4-(3-hydroxyphenylamino)thieno[3,2-d]pyrimidin-6-yl)benzonitrile) (LCB03-0013)

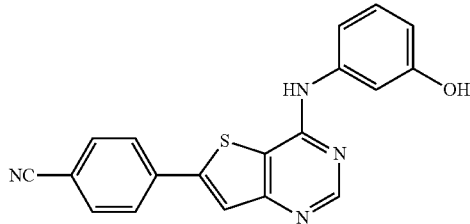 [SMILES: N#Cc1ccc(-c2cc3ncnc(Nc4cccc(O)c4)c3s2)cc1]

$^1$H-NMR (400 MHz, MeOH-d$_4$); δ 8.43 (s, 1H), 7.90 (d, J=8.4 Hz, 2H), 7.76 (d, J=8.4 Hz, 2H), 7.71 (s, 1H), 7.16 (t, J=2.0 Hz, 1H), 7.11 (t, J=8.0 Hz, 1H), 7.01-6.99 (m, 1H), 6.57-6.55 (m, 1H); LC-MS 345 (MH+)

Example 16

3-(6-(4-chlorophenyl)thieno[3,2-d]pyrimidine-4-ylamino)phenol

The synthesis of (3-(6-(4-chlorophenyl)thieno[3,2-d]pyrimidin-4-ylamino)phenol) (LCB03-0019)

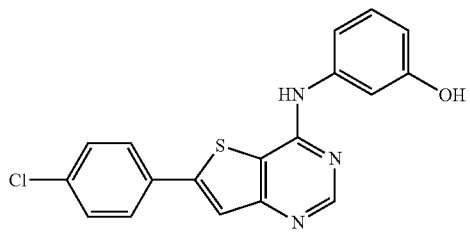 [SMILES: Oc1cccc(Nc2ncnc3cc(-c4ccc(Cl)cc4)sc23)c1]

¹H-NMR (400 MHz, DMSO-d₆); δ 9.59 (s, 1H), 9.40 (s, 1H), 8.53 (s, 1H), 7.93 (s. 1H), 7.84 (d, J=6.8 Hz, 2H), 7.52-7.49 (m, 1H), 7.26 (t, J=2.0 Hz, 1H), 7.14-7.07 (m, 2H), 6.50-6.47 (m, 1H); LC-MS 354 (MH+)

Example 17

N-(3-methoxyphenyl)-6-(4-(2-morpholinoethoxy)phenyl)thieno[3,2-d]pyrimidine-4-amine The synthesis of (N-(3-methoxyphenyl)-6-(4-(2-morpholinoethoxy)phenyl)thieno[3,2-d]pyrimidin-4-amine) (LCB03-0018)

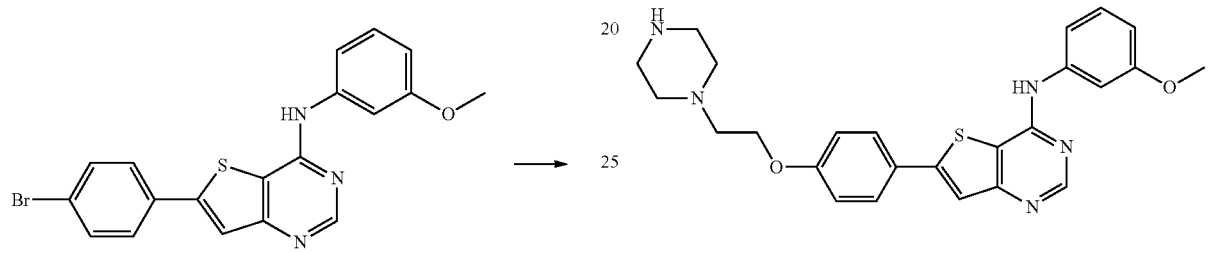

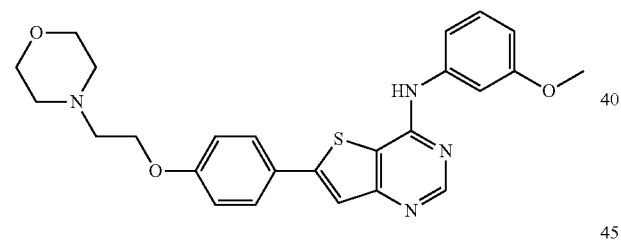

N-(3-methoxyphenyl)-6-(4-bromophenyl)thieno[3,2-d]pyrimidine-4-amine (0.26 g, 0.76 mmol) was dissolved in 5 ml of degassed dimethylformamide and added with 4-(2-hydroxyethyl)morpholine (0.12 ml, 0.92 mmol) and triphenylphosphine (241 mg, 0.92 mmol). The mixture was further added with DIAD (0.18 ml, 0.92 mmol) at 0° C. and stirred at room temperature for 15 hours. It was extracted with 50 ml saturated sodium bicarbonate and 50 ml of ethylacetate and the organic layer was washed with 50 ml of water twice, dried with magnesium sulfate and filtered. After concentration under vacuum, column chromatography (dichloromethane/methanol, 15/1) was done. The title compound (100 mg, 29%) was obtained as ivory colored solid.

¹H-NMR (400 MHz, CDCl₃); δ 8.69 (s, 1H), 7.61 (d, J=8.8 Hz, 2H), 7.49 (s, 1H), 7.32 (t, J=7.6 Hz, 1H), 7.26 (t, J=2.0 Hz, 1H), 7.12-7.10 (m, 1H), 6.97 (d, J=8.8 Hz, 2H), 6.86 (brs, 1H), 6.81-6.78 (m, 1H), 4.16 (t, J=6.0 Hz, 2H), 3.76-3.73 (m, 4H), 2.83 (t, J=5.6 Hz, 2H), 2.60-2.58 (m, 4H); LC-MS 463 (MH+)

The following compounds were synthesized by the methods similar to the one described in the preferred embodiment 17 described above.

Example 18

N-(3-methoxyphenyl)-6-(4-(2-(piperazine-1-yl)ethoxy)phenyl)thieno[3,2-d]pyrimidine-4-amine The synthesis of (N-(3-methoxyphenyl)-6-(4-(2-(piperazin-1-yl)ethoxy)phenyl)thieno[3,2-d]pyrimidin-4-amine) (LCB03-0029)

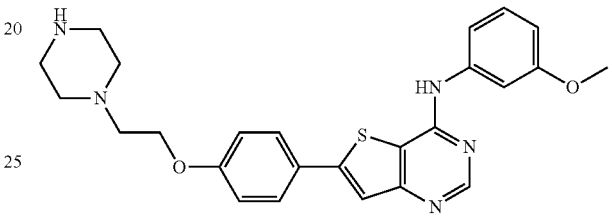

¹H-NMR (400 MHz, DMSO-d₆); δ 9.64 (s, 1H), 8.58 (s, 1H), 7.82-7.79 (m, 3H), 7.48-7.42 (m, 2H), 7.27 (t, J=8.4 Hz, 1H), 7.10 (d, J=8.8 Hz, 2H), 6.70-6.82 (m, 1H), 4.16 (t, J=5.6 Hz, 2H), 2.95-2.92 (m, 4H), 2.76 (t, J=5.6 Hz, 2H), 2.59-2.51 (m, 4H); LC-MS 463 (MH+)

Example 19 t-butyl 4-(2-(4-(3-methoxyphenylamino)thieno[3,2-d]pyrimidine-6-yl)phenoxy)ethyl)piperazine-1-carboxylate The synthesis of (tert-butyl 4-(2-(4-(4-(3-methoxyphenylamino)thieno[3,2-d]pyrimidin-6-yl)phenoxy)ethyl)piperazine-1-carboxylate) (LCB03-0025)

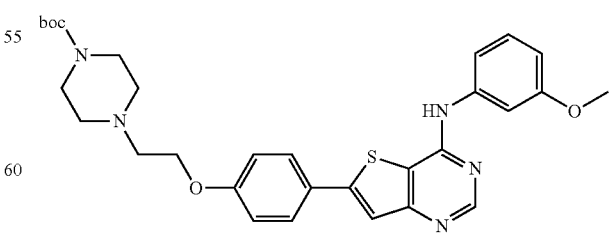

¹H-NMR (400 MHz, CDCl₃); δ 8.70 (s, 1H), 7.62 (d, J=8.8 Hz, 2H), 7.51 (s, 1H), 7.34-7.30 (m, 2H), 7.12-7.0 (m, 1H), 6.97 (d, J=8.8 Hz, 2H), 6.81-6.78 (m, 1H), 6.70 (s, 1H), 4.16

(t, J=5.6 Hz, 2H), 3.47-3.45 (m, 4H), 2.84 (t, J=5.6 Hz, 2H), 2.55-2.50 (m, 4H), 1.55 (s, 9H); LC-MS 562 (MH+)

Example 20

N-(3-methoxyphenyl)-6-(4-(2-(pyrrolidine-1-yl)ethoxy)phenyl)thieno[3,2-d]pyrimidine-4-amine The synthesis of (N-(3-methoxyphenyl)-6-(4-(2-(pyrrolidin-1-yl)ethoxy)phenyl)thieno[3,2-d]pyrimidin-4-amine) (LCB03-0026)

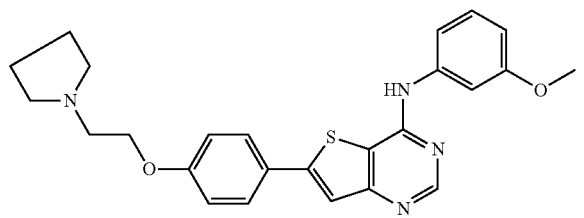 [SMILES: COc1cccc(Nc2ncnc3cc(-c4ccc(OCCN5CCCC5)cc4)sc23)c1]

$^1$H-NMR (400 MHz, CDCl$_3$); δ 8.69 (s, 1H), 7.62 (d, J=8.8 Hz, 2H), 7.49 (s, 1H), 7.34-7.28 (m, 2H), 7.12-7.10 (m, 1H), 6.98 (d, J=8.8 Hz, 2H), 6.81-6.78 (m, 1H), 6.71 (brs 1H), 4.17 (t, J=6.4 Hz, 2H), 2.96-2.95 (m, 3H), 2.67-2.66 (m, 2H), 2.07-2.02 (m, 1H), 1.83-1.80 (m, 2H), 1.65-1.63 (m, 2H); LC-MS 447 (MH+)

Example 21

N-(3-methoxyphenyl)-6-(4-phenethoxyphenyl)thieno[3,2-d]pyrimidine-4-amine

The synthesis of (N-(3-methoxyphenyl)-6-(4-phenethoxyphenyl)thieno[3,2-d]pyrimidin-4-amine) (LCB03-0021)

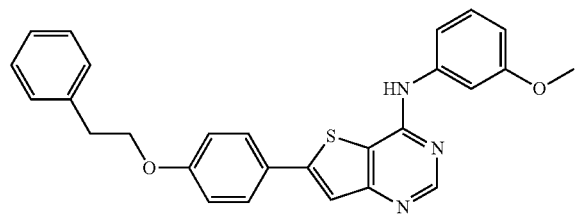 [SMILES: COc1cccc(Nc2ncnc3cc(-c4ccc(OCCc5ccccc5)cc4)sc23)c1]

$^1$H-NMR (400 MHz, CDCl$_3$); δ 8.69 (s, 1H), 7.61 (d, J=8.8 Hz, 2H), 7.49 (s, 1H), 7.35-7.30 (m, 8H), 7.12 7.10 (m, 1H), 6.96 (d, J=8.8 Hz, 1H), 6.81-6.95 (m, 1H), 6.71 (brs, 1H), 4.23 (t, J=7.2 Hz, 2H), 3.84 (s, 3H), 3.13 (t, J=6.8 Hz, 2H); LC-MS 454 (MH+)

Example 22

N-(3-methoxyphenyl)-6-(4-(2-(pyridine-2-yl)ethoxy)phenyl)thieno[3,2-d]pyrimidine-4-amine The synthesis of (N-(3-methoxyphenyl)-6-(4-(2-(pyridin-2-yl)ethoxy)phenyl)thieno[3,2-d]pyrimidin-4-amine) (LCB03-0022)

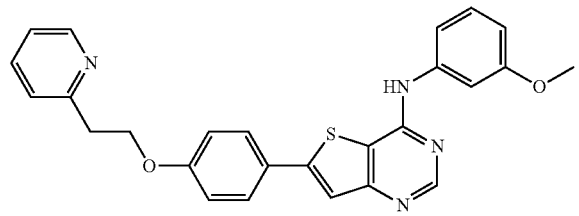 [SMILES: COc1cccc(Nc2ncnc3cc(-c4ccc(OCCc5ccccn5)cc4)sc23)c1]

$^1$H-NMR (400 MHz, CDCl$_3$); δ 10.07 (s, 1H), 9.65 (s, 1H), 8.58 (s, 1H), 7.72-7.70 (m, 4H), 7.48 (t, J=2.0 Hz, 1H), 7.45-7.44 (m, 1H), 7.30-7.29 (m, 1H), 6.92 (d, J=8.8 Hz, 2H), 6.81 (d, J=7.6 Hz, 1H), 6.69 (dd, J=2.0, 8.4 Hz, 1H), 3.76 (s, 3H), 3.72-3.71 (m, 2H), 3.20-3.17 (m, 2H); LC-MS 454 (MH+)

Example 23

3-(6-(4-(2-morpholinoethoxy)phenyl)thieno[3,2-d]pyrimidine-4-ylamino)phenol

The synthesis of (3-(6-(4-(2-morpholinoethoxy)phenyl)thieno[3,2-d]pyrimidin-4-ylamino)phenol) (LCB03-0020)

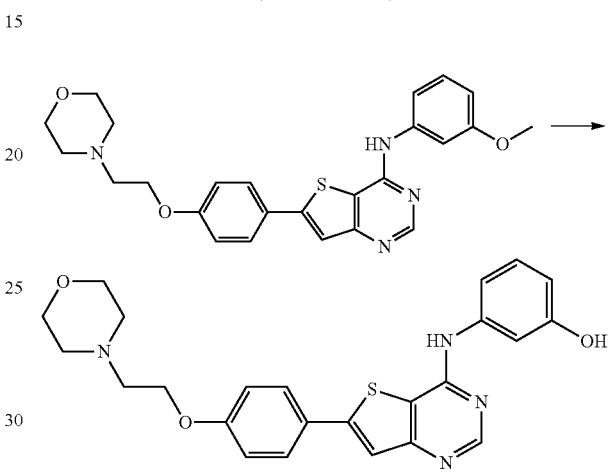

The compound (75 mg, 0.16 mmol) synthesized in the preferred embodiment 17 was dissolved in 1 ml of dichloromethane and added slowly with 1M borontribromide (0.73 ml, 0.64 mmol) at 0° C., followed by stirring for 12 hours at room temperature. The mixture was extracted with 30 ml of dichloromethane and 20 ml of sodium bicarbonate solution and concentrated under vacuum followed by column chromatography (dichloromethane/methanol, 15/1). The title compound (22 mg, 30%) was obtained as yellowish solid.

$^1$H-NMR (400 MHz, DMSO-d$_6$); δ 9.49 (brs, 1H), 9.38 (s, 1H), 8.50 (s, 1H), 7.73 (t, J=8.0 Hz, 2H), 7.26 (s, 1H), 7.12-7.03 (m, 4H), 6.46 (d, J=6.8 Hz, 1H), 4.13-4.11 (m, 2H), 3.53 (m, 4H), 3.12-3.10 (m, 4H), 2.67-2.66 (m, 2H); LC-MS 449 (MH+)

Example 24

3-(6-(4-(morpholinomethyl)phenyl)thieno[3,2-d]pyrimidine-4-ylamino)phenol

The synthesis of (3-(6-(4-(morpholinomethyl)phenyl)thieno[3,2-d]pyrimidin-4-ylamino)phenol) (LCB03-0032)

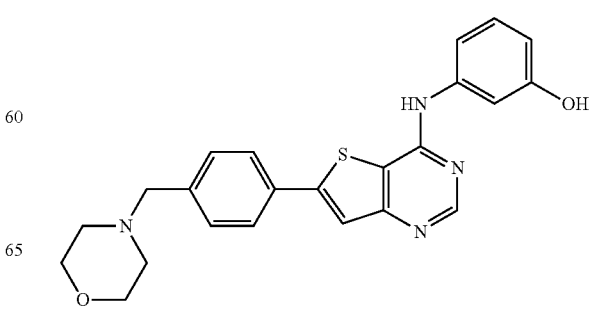

¹H-NMR (400 MHz, DMSO-d₆); δ 11.67 (br, 1H), 10.99 (br, 1H), 8.84 (s, 1H), 7.97-7.94 (m, 3H), 7.83 (d, J=8.4 Hz, 2H), 7.24 (t, J=8.0 Hz, 1H), 7.17 (brs, 1H), 7.12 (d, J=8.0 Hz, 1H), 6.72 (d, J=7.6 Hz, 1H), 4.40 (s, 2H), 3.95-3.92 (m, 2H), 3.87-3.81 (m, 2H), 3.25-3.23 (m, 2H), 3.14-3.12 (m, 2H); LC-MS 419 (MH+)

Example 25

3-(6-(4-(piperazine-1-ylmethyl)phenyl)thieno[3,2-d]pyrimidine-4-ylamino)phenol

The synthesis of (3-(6-(4-(piperazine-1-ylmethyl)phenyl)thieno[3,2-d]pyrimidin-4-ylamino)phenol) (LCB03-0033)

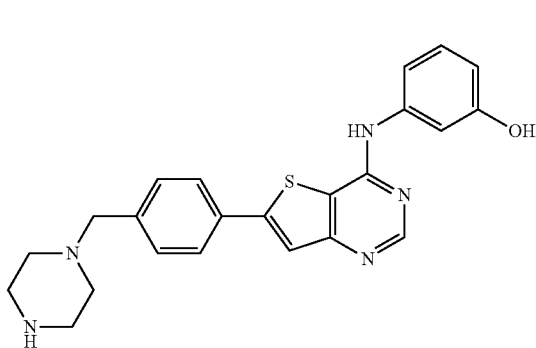 [SMILES: Oc1cccc(Nc2ncnc3cc(-c4ccc(CN5CCNCC5)cc4)sc23)c1]

¹H-NMR (400 MHz, DMSO-d₆); δ 9.59 (br, 2H), 8.80 (s, 1H), 7.97-7.95 (m, 3H), 7.83-7.81 (m, 2H), 7.23 (t, J=7.6 Hz, 1H), 7.21 (s, 1H), 7.14-7.12 (m, 1H), 6.70 (d, J=7.6 Hz, 1H), 4.43 (s, 2H), 3.57-3.37 (m, 4H), 3.36-3.30 (M, 2H), 2.53-2.50 (m, 2H); LC-MS 418 (MH+)

Example 26

3-(6-(4-(piperidine-ylmethyl)phenyl)thieno[3,2-d]pyrimidine-4-ylamino)phenol

The synthesis of (3-(6-(4-(piperidin-1-ylmethyl)phenyl)thieno[3,2-d]pyrimidin-4-ylamino)phenol) (LCB03-0035)

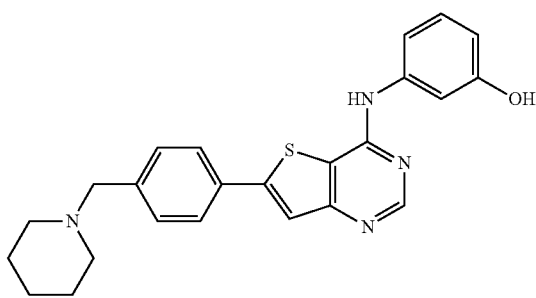 [SMILES: Oc1cccc(Nc2ncnc3cc(-c4ccc(CN5CCCCC5)cc4)sc23)c1]

¹H-NMR (400 MHz, DMSO-d₆); δ 10.99 (brs, 1H), 10.82 (brs, 1H), 8.82 (s, 1H), 7.97 (s, 1H), 7.95 (d, J=8.0 Hz, 2H), 7.81 (d, J=8.0 Hz, 2H), 7.24 (t, J=8.0 Hz, 1H), 7.22 (brs, 1H), 7.13 (d, J=7.6 Hz, 1H), 6.71 (d, J=8.0 Hz, 1H), 4.33 (s, 2H), 3.71-3.67 (m, 1H), 3.50-3.28 (m, 5H), 2.87-2.85 (m, 1H), 1.79-1.68 (m, 3H); LC-MS 417 (MH+)

Example 27

3-(6-(4-((4-methylpiperazine-1-yl-methyl)phenyl)thieno[3,2-d]pyrimidine-4-ylamino)phenol The synthesis of (3-(6-(4-((4-methylpiperazin-1-yl)methyl)phenyl)thieno[3,2-d]pyrimidin-4-ylamino)phenol) (LCB03-0036)

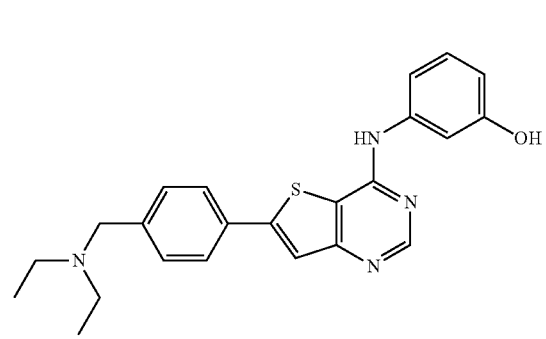 [SMILES: CCN(CC)Cc1ccc(-c2cc3ncnc(Nc4cccc(O)c4)c3s2)cc1]

¹H-NMR (400 MHz, DMSO-d₆); δ 11.03 (brs, 1H), 8.84 (s, 1H), 7.96 (s, 1H), 7.95 (d, J=8.4 Hz, 2H), 7.83-7.81 (m, 2H), 7.25 (t, J=8.4 Hz, 1H), 7.17 (s, 1H), 7.12 (d, J=7.6 Hz, 1H), 6.73 (d, J=7.6 Hz, 1H), 4.39 (s, 2H), 3.73-3.34 (m, 6H), 3.26-3.24 (m, 2H), 2.89 (s, 3H); LC-MS 432 (MH+)

Example 28

3-((6-(4-((diethylamino)methyl)phenyl)thieno[3,2-d]pyrimidine-4-ylamino)phenol

The synthesis of (3-((6-(4-((diethylamino)methyl)phenyl)thieno[3,2-d]pyrimidin-4-ylamino)phenol) (LCB03-0037)

¹H-NMR (400 MHz, DMSO-d₆); δ 10.86 (brs, 1H), 8.83 (s, 1H), 7.97 (s, 1H), 7.95 (d, J=8. Hz, 2H), 7.85 (d, J=8.4 Hz, 2H), 7.24 (t, J=8.4 Hz, 1H), 7.18 (s, 1H), 7.12 (d, J=8.0 Hz, 1H), 6.73 (d, J=8.4 Hz, 1H), 4.36 (d, J=5.2 Hz, 2H), 3.07-3.04 (m, 4H), 1.27 (t, J=7.2 Hz, 6H); LC-MS 405 (MH+)

Example 29

3-((6-(4-((cyclopropylmethylamino)methyl)phenyl)thieno[3,2-d]pyrimidine-4-ylamino)phenol The synthesis of (3-((6-(4-((cyclopropylmethylamino)methyl)phenyl)thieno[3,2-d]pyrimidin-4-ylamino)phenol) (LCB03-0040)

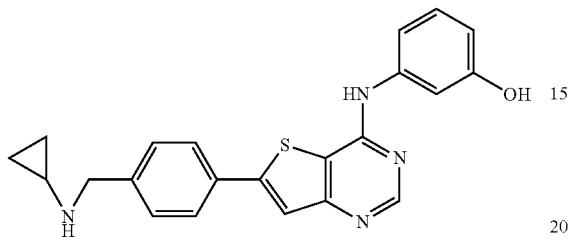

¹H-NMR (400 MHz, DMSO-d₆); δ 9.50-9.48 (m, 2H), 8.77 (s, 1H), 7.95-7.93 (m, 3H), 7.73 (d, J=8.0 Hz, 2H), 7.24-7.13 (m, 3H), 6.67 (d, J=7.6 Hz, 1H), 4.30 (s, 2H), 3.70-3.67 (m, 1H), 0.91-0.75 (m, 2H), 0.59-0.54 (m, 2H); LC-MS 389 (MH+)

Example 30

3-((6-(4-((isobutylamino)methyl)phenyl)thieno[3,2-d]pyrimidine-4-ylamino)phenol

The synthesis of (3-((6-(4-((isobutylamino)methyl)phenyl)thieno[3,2-d]pyrimidin-4-ylamino)phenol) (LCB03-0041)

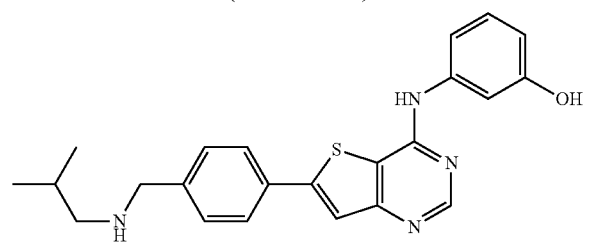

¹H-NMR (400 MHz, DMSO-d₆); δ 9.20 (brs, 2H), 8.78 (s, 1H), 7.95-7.93 (m, 3H), 7.75 (d, J=8.0 Hz, 2H), 7.24-7.12 (m, 3H), 6.68 (d, J=7.2 Hz, 1H), 4.21 (s, 2H), 2.75-2.74 (m, 2H), 2.08-2.02 (m, 1H), 0.95 (d, J=6.8 Hz, 6H); LC-MS 405 (MH+)

Example 31

3-((6-(4-((ethylamino)methyl)phenyl)thieno[3,2-d]pyrimidine-4-ylamino)phenol

The synthesis of (3-((6-(4-((ethylamino)methyl)phenyl)thieno[3,2-d]pyrimidin-4-ylamino)methyl)phenol) (LCB03-0042)

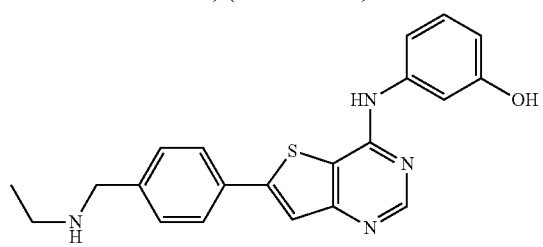

¹H-NMR (400 MHz, DMSO-d₆); δ 9.11 (brs, 2H), 8.73 (s, 1H), 7.95-7.94 (m, 3H), 7.70 (d, J=8.4 Hz, 2H), 7.22-7.13 (m, 3H), 6.64 (d, J=7.2 Hz, 1H), 4.20 (s, 2H), 3.01-3.98 (m, 2H), 1.24 (t, J=7.2 Hz, 3H); LC-MS 377 (MH+)

Example 32

(3-(4-(3-hydroxyphenylamino)thieno[3,2-d]pyrimidine-6-yl)phenyl(pyrrolidine-1-yl)methanone The synthesis of ((3-(4-(3-hydroxyphenylamino)thieno[3,2-d]pyrimidin-6-yl)phenyl)(pyrrolidin-1-yl)methanone)) (LCB03-0053)

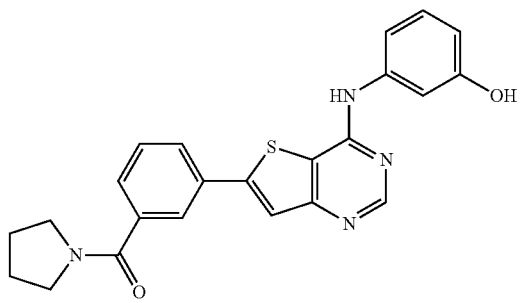 [SMILES: O=C(c1cccc(-c2cc3ncnc(Nc4cccc(O)c4)c3s2)c1)N1CCCC1]

¹H-NMR (600 MHz, DMSO-d₆); δ 11.09 (brs, 1H), 8.85 (s, 1H), 7.99-7.97 (m, 2H), 7.93 (d, J=7.2 Hz, 1H), 7.67 (d, J=7.2 Hz, 1H), 7.63 (t, J=7.8 Hz, 1H), 7.25 (t, J=8.4 Hz, 1), 7.17 (s, 1H), 7.12 (d, J=7.8 Hz, 1H), 6.73 (d, J=7.2 Hz, 1H), 3.52-3.49 (m, 2H), 3.44-3.42 (m, 2H), 1.91-1.82 (m, 4H); LC-MS 417 (MH+)

Example 33

N,N-diethyl-3-(4-(3-hydroxyphenylamino)thieno[3,2-d]pyrimidine-6-yl)benzamide

The synthesis of (N,N-diethyl-3-(4-(3-hydroxyphenylamino)thieno[3,2-d]pyrimidin-6-yl)benzamide)) (LCB03-0054)

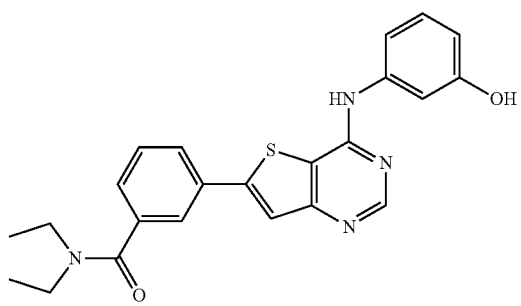 [SMILES: CCN(CC)C(=O)c1cccc(-c2cc3ncnc(Nc4cccc(O)c4)c3s2)c1]

¹H-NMR (600 MHz, DMSO-d₆); δ 8.82 (s, 1H), 7.99 (s, 1H), 7.91 (d, J=7.8 Hz, 1H), 7.82 (s, 1H), 7.63 (t, J=7.8 Hz, 1H), 7.50 (d, J=7.2 Hz, 1H), 7.24 (t, J=7.8 Hz, 1H), 7.17 (s, 1H), 7.12 (d, J=7.2 Hz, 1H), 6.70 (d, J=7.2 Hz, 1H), 3.47-3.45 (m, 2H), 3.22-3.21 (m, 2H), 1.19-1.18 (m, 3H), 1.10-1.07 (m, 3H); LC-MS 419 (MH+)

Example 34

(3-(4-(3-hydroxyphenylamino)thieno[3,2-d]pyrimidine-6-yl)phenyl(4-methylpiperazine-1-yl)methanone The synthesis of ((3-(4-(3-hydroxyphenylamino)thieno[3,2-d]pyrimidin-6-yl)phenyl)(4-methylpiperazin-1-yl)methanone)) (LCB03-0055)

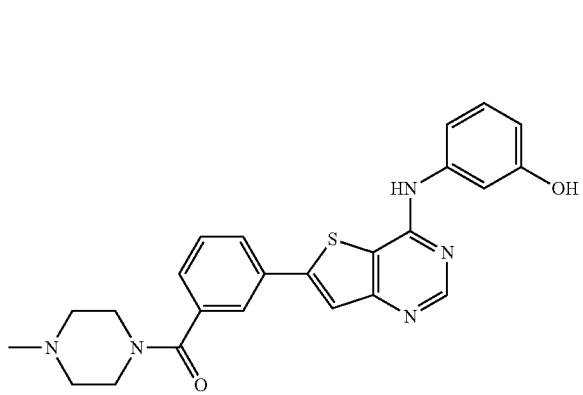 [SMILES: CN1CCN(C(=O)c2cccc(-c3cc4ncnc(Nc5cccc(O)c5)c4s3)c2)CC1]

$^1$H-NMR (600 MHz, DMSO-d$_6$); δ 9.70 (brs, 1H), 8.78 (s, 1H), 8.03-7.95 (m, 3H), 7.66-7.59 (m, 2H), 7.23-7.15 (m, 4H), 6.68 (s, 1H), 3.71-3.66 (m, 2H), 3.46-3.39 (m, 2H), 3.16-3.12 (m, 4H), 2.81 (s, 3H); LC-MS 482 (MH+)

Example 35

3-(6-(4-morpholinophenyl)thieno[3,2-d]pyrimidine-4-ylamino)phenol

The synthesis of (3-(6-(4-morpholinophenyl)thieno[3,2-d]pyrimidin-4-ylamino)phenol) (LCB03-0082)

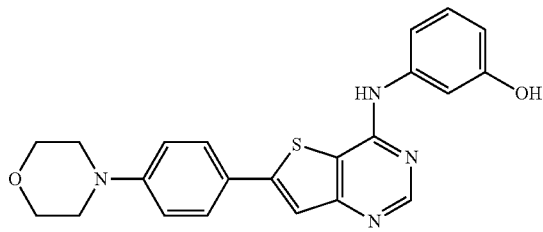 [SMILES: Oc1cccc(Nc2ncnc3cc(-c4ccc(N5CCOCC5)cc4)sc23)c1]

$^1$H-NMR (600 MHz, DMSO-d$_6$); δ 9.50 (s, 1H), 8.53 (s, 1H), 7.71 (m, 3H), 7.32 (s, 1H), 7.15 (m, 2H), 7.06 (d, J=8.82 Hz, 1H), 6.52 (d, J=8.0 Hz, 1H), 3.76 (t, J=4.8 Hz, 4H), 3.23 (t, J=4.8 Hz, 4H); LC-MS 405 (MH+)

Example 36

Step 1

N-(3-(tert-butyldimethylsiloxy)phenyl)-6-(4-(pyrrolidine-1-ylmethyl)phenyl)thieno[3,2-d]pyrimidine-4-amine The synthesis of (N-(3-(tert-butyldimethylsilyloxy)phenyl)-6-(4-(pyrrolidin-1-ylmethyl)phenyl)thieno[3,2-d]pyrimidin-4-amine)

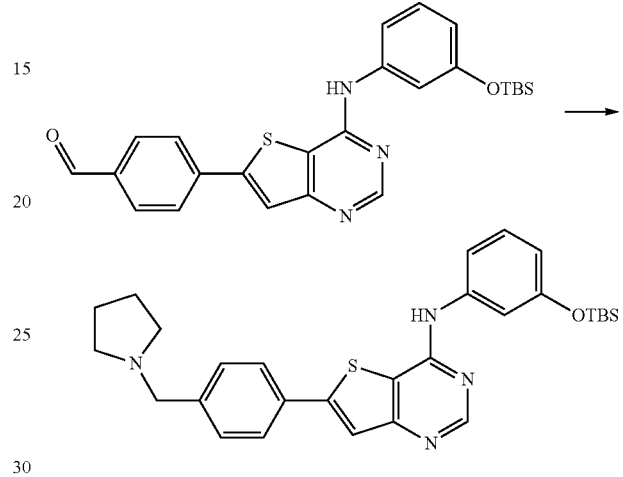

The compound (1.7 g, 3.68 mmol) synthesized in the example of synthesis 6 and pyrrolidine (0.46 ml, 5.52 mmol) were dissolved sequentially into 1 ml of dichloroethane and stirred for 20 minutes and further stirred for 7 hours at room temperature after adding sodium acetate (0.44 g, 5.52 mmol) and sodium triacethoxyborohydride (1.56 g, 7.36 mmol). The reaction mixture was extracted with 130 ml of dichloromethane and 130 ml of saturated ammonium chloride solution. The organic layer was dried with sodium sulfate and concentrated under vacuum followed by column chromatography (dichloromethane/methanol, 1/15) to obtain the title compound (1.4 g, 73.7%).

$^1$H-NMR (400 MHz, CDCl$_3$); δ 8.68 (s, 1H), 7.62 (d, J=8.0 Hz, 2H), 7.58 (s, 1H), 7.41 (d, J=8.0 Hz, 2H), 7.28-7.24 (m, 1H), 7.17-7.14 (m, 1H), 7.20-7.19 (m, 1H), 6.99 (brs, 1H), 6.76-6.74 (m, 1H), 3.68 (s, 2H), 2.56 (m, 4H), 1.85-1.78 (m, 4H), 1.00 (s, 9H), 0.23 (s, 6H); LC-MS 517 (MH+)

Step 2

3-(6-(4-(pyrrolidine-1-ylmethyl)phenyl)thieno[3,2-d]pyrimidine-4-ylamino)phenol HCl salt The synthesis of (3-(6-(4-(pyrrolidin-1-ylmethyl)phenyl)thieno[3,2-d]pyrimidin-4-ylamino)phenol. HCl) (LCB03-0034)

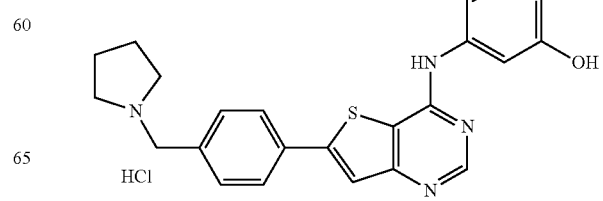

67

The compound (15 mg, 0.03 mmol) synthesized in the step 1 described above was dissolved in 1 ml of dichloromethane 1 ml and added with 1 ml of 4 M c HCl/1,4-dioxane and stirred at room temperature for 15 hours and concentrated under vacuum. The reaction mixture was further azotrope-concentration using dichloromethane, methanol, diethylether and vacuum-dried to obtain the title compound (12 mg, 94%) as a yellowish solid.

¹H-NMR (400 MHz, DMSO-d₆); δ 11.29 (brs, 1H), 11.03 (brs, 1H), 8.84 (s, 1H), 7.96 (s, 1H), 7.94 (d, J=8.0 Hz, 2H), 7.82 (d, J=8.0 Hz, 2H), 7.25 (t, J=8.0 Hz, 2H), 7.17 (s, 1H), 7.12 (d, J=7.6 Hz, 1H), 6.73 (d, J=7.2 Hz, 1H), 4.42 (d, J=6.0 Hz, 2H), 3.39-3.36 (m, 2H), 3.08-3.04 (m, 2H), 2.02-1.89 (m, 4H); LC-MS: 403 (MH+)

The following compounds were synthesized by the method similar to the one described in the preferred embodiment 36 described above.

Example 37

Step 1 methyl 1-(4-(4-(3-(tert-butyldimethylsiloxy)phenylamino)thieno[3,2-d]pyrimidine-6-yl)benzyl)pyrrolidine-2-carboxylate The synthesis of (methyl 1-(4-(4-(3-(tert-butyldimethylsilyloxy)phenylamino)thieno[3,2-d]pyrimidin-6-yl)benzyl)pyrrolidine-2-carboxylate)

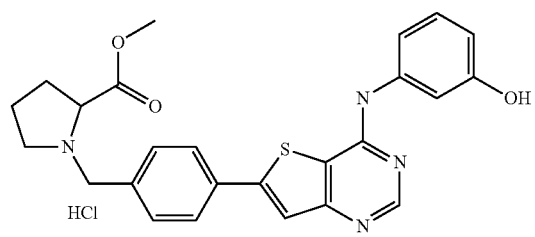 [SMILES: COC(=O)C1CCCN1Cc1ccc(-c2cc3ncnc(Nc4cccc(O)c4)c3s2)cc1 ; Cl]

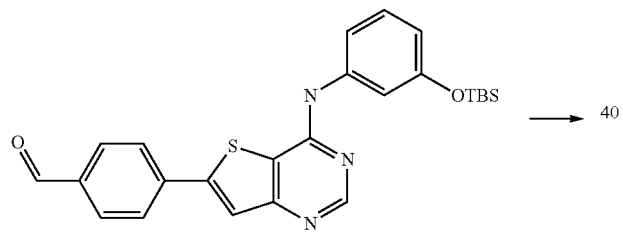

¹H-NMR (600 MHz, CDCl₃); δ 8.67 (s, 1H), 7.60 (d, J=7.8 Hz, 2H), 7.57 (s, 1H), 7.39 (d, J=7.8 Hz, 2H), 7.24-7.23 (m, 2H), 7.17 (t, J=2.4 Hz, 1H), 7.13-7.12 (m, 1H), 6.74-6.72 (m, 1H), 3.94 (d, J=7.2 Hz, 1H), 3.64 (s, 3H), 3.57 (d, J=7.2 Hz, 1H), 3.28-3.25 (m, 1H), 3.05-3.02 (m, 1H), 2.37 (q, J=8.4 Hz, 1H), 2.15-2.12 (m, 1H), 1.98-1.76 (m, 3H), 1.04 (s, 9H), 0.23 (s, 6H); LC-MS 575 (MH+)

68

Step 2 methyl 1-(4-(4-(3-hydroxyphenylamino)thieno[3,2-d]pyrimidine-6-yl)benzyl)pyrrolidine-2-carboxylate HCl salt The synthesis of (methyl 1-(4-(4-(3-hydroxyphenylamino)thieno[3,2-d]pyrimidin-6-yl)benzyl)pyrrolidine-2-carboxylate, HCl) (LCB03-0056)

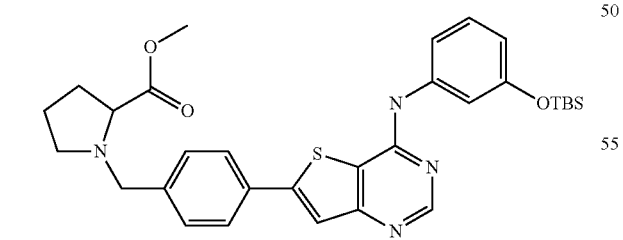

¹H-NMR (600 MHz, DMSO-d₆); δ 10.75 (brs, 1H), 9.72 (brs, 1H), 8.79 (s, 1H), 7.94 (s, 1H), 7.92 (d, J=7.8 Hz, 2H), 7.69 (d, J=6.6 Hz, 2H), 7.20 (t, J=7.8 Hz, 1H), 7.16 (s, 1H), 7.10 (d, J=7.2 Hz, 1H), 6.78 (d, J=7.2 Hz, 1H), 4.57-4.40 (m, 3H), 3.46-3.44 (m, 2H), 3.28-3.27 (m, 1H), 2.03-2.02 (m, 2H), 1.89-1.88 (m, 1H); LC-MS: 461 (MH+)

Example 38

Step 1

N-(3-(t-butyldimethylsiloxy)phenyl)-6-(4-((4-methylpiperidin-1-yl)methyl)phenylthieno[3,2-d]pyrimidine-4-amine The synthesis of (N-(3-(tert-butyldimethylsilyloxy)phenyl)-6-(4-(4-(4-methylpiperidin-1-yl)methyl)phenyl)thieno[3,2-d]pyrimidin-4-amine)

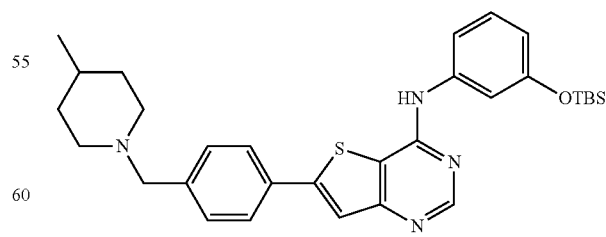

¹H-NMR (600 MHz, CDCl₃); δ 7.63 (d, J=7.8 Hz, 2H), 7.59 (s, 1H), 7.40 (d, J=8.4 Hz, 2H), 7.28 (t, J=8.4 Hz, 1H), 7.20-7.19 (m, 2H), 7.16-7.15 (m, 1H), 6.75 (dd, J=2.4, 8.4 Hz, 1H), 6.73 (brs, 1H), 3.52 (s, 2H), 2.86-2.84 (m, 2H), 2.10-

1.94 (m, 3H), 1.62-1.60 (m, 4H), 1.00 (s, 9H), 0.93 (d, J=7.2 Hz, 3H), 0.09 (s, 6H); LC-MS 545 (MH+)

Step 2

3-(6-(4-((4-methylpiperidine-1-yl)methyl)phenyl) thieno[3,2-d]pyrimidine-4-ylamino)phenol HCl salt The synthesis of (3-(6-(4-((4-methylpiperidin-1-yl) methyl)phenyl)thieno[3,2-d]pyrimidin-4-ylamino) phenol. HCl) (LCB03-0058)

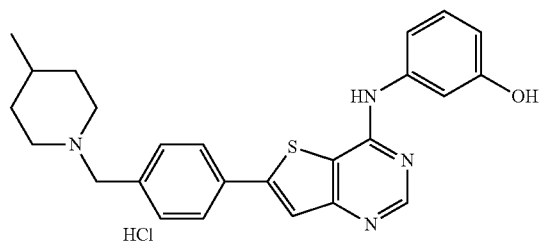 [SMILES: CC1CCN(Cc2ccc(-c3cc4ncnc(Nc5cccc(O)c5)c4s3)cc2)CC1 ; Cl]

¹H-NMR (600 MHz, DMSO-d₆); δ 8.79 (s, 1H), 8.00-7.95 (m, 3H), 7.78 (d, J=7.8 Hz, 1H), 7.14 (d, J=7.8 Hz, 1H), 6.70-6.69 (m, 1H), 4.32 (d, J=4.8 Hz, 2H), 3.32-3.31 (m, 1H), 2.93-2.88 (m, 1H), 1.80-1.76 (m, 2H), 1.49-1.43 (m, 2H), 1.10-1.09 (m, 1H), 0.91 (d, J=6.0 Hz, 3H); LC-MS: 431 (MH+)

Example 39

Step 1

N-(3-(tert-butyldimethylsiloxy)phenyl)-6-(4-(pyrrolidine-1-ylmethyl)phenyl)thieno[3,2-d]pyrimidine-4-amine The synthesis of (N-(3-(tert-butyldimethylsilyloxy) phenyl)-6-(4-(pyrrolidin-1-ylmethyl)phenyl)thieno [3,2-d]pyrimidin-4-amine)

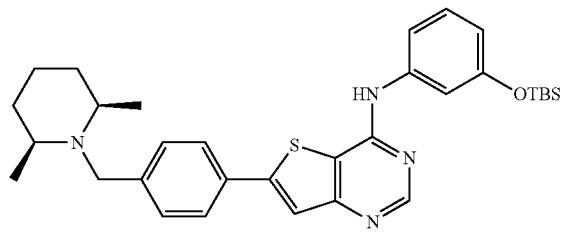 [SMILES: C[C@@H]1CCC[C@H](C)N1Cc1ccc(-c2cc3ncnc(Nc4cccc(O[Si](C)(C)C(C)(C)C)c4)c3s2)cc1]

¹H-NMR (600 MHz, CDCl₃); δ 8.67 (s, 1H), 7.60 (d, J=7.8 Hz, 2H), 7.59 (s, 1H), 7.48 (d, J=8.4 Hz, 2H), 7.28-7.23 (m, 1H), 7.20-7.19 (m, 1H), 7.18-7.17 (m, 1H), 7.15-7.13 (m, 1H), 6.76-6.75 (m, 1H), 3.83 (s, 2H), 2.51-2.50 (m, 2H), 2.04-2.02 (m, 1H), 1.67-1.65 (m, 1H), 1.60-1.58 (m, 2H), 1.35-1.32 (m, 2H), 1.07 (d. J=6.6 Hz, 6H), 1.00 (s, 9H), 0.23 (s, 6H); LC-MS 559 (MH+)

Step 2

3-(6-(4-(((2R,6S)-2,6-dimethylpiperidine-1-yl)methyl)phenyl)thieno[3,2-d]pyrimidine-4-ylamino)phenol HCl salt The synthesis of (3-(6-(4-(((2R,6S)-2,6-dimethylpiperidin-1-yl)methyl)phenyl)thieno[3,2-d]pyrimidin-4-ylamino)phenol. HCl) (LCB03-0059)

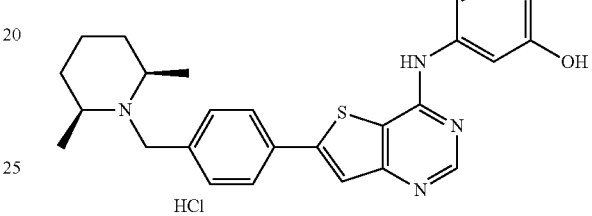

¹H-NMR (600 MHz, DMSO-d₆); δ 8.78 (s, 1H), 7.99-7.93 (m, 3H), 7.78 (d, J=8.4 Hz, 1H), 7.74 (d, J=8.4 Hz, 1H), 7.24-7.21 (m, 2H), 7.14-7.13 (m, 1H), 6.89-6.88 (m, 1H), 4.56 (s, 1H), 4.39 (s, 1H), 3.38-3.36 (m, 2H), 3.09-3.08 (m, 1H), 1.85-1.82 (m, 1H), 1.76-1.70 (m, 3H), 1.68-1.60 (m, 1H), 1.56 (d, J=6.0 Hz, 3H), 1.30 (d, J=6.6 Hz, 3H); LC-MS: 445 (MH+)

Example 40

Step 1

1-(4-(4-(3-(tert-butyldimethylsiloxy)phenylamino) thieno[3,2-d]pyrimidine-6-yl)benzyl)pyrrolidine-2-carboxamide The synthesis of (1-(4-(4-(3-(tert-butyldimethylsilyloxy)phenylamino)thieno[3,2-d]pyrimidin-6-yl)benzyl)pyrrolidine-2-carboxamide)

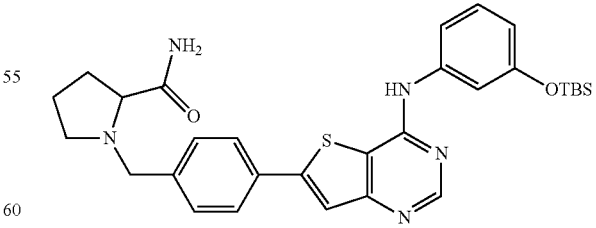

¹H-NMR (600 MHz, CDCl₃); δ 8.72 (s, 1H), 7.66 (d, J=7.8 Hz, 2H), 7.60 (s, 1H), 7.38 (d, J=7.8 Hz, 2H), 7.29 (t, J=7.2 Hz, 1H), 7.20-7.15 (m, 2H), 6.87 (brs, 1H), 6.76 (dd, J=2.4, 8.4 Hz, 1H), 5.40 (s, 1H), 3.98 (d, J=13.8 Hz, 1H), 3.55 (d, J=13.8 Hz, 1H), 3.22 (dd, J=5.4, 10.2 Hz, 1H), 3.08-3.00 (m, 1H), 2.40-2.35 (m, 1H), 2.29-2.24 (m, 1H), 2.08-1.94 (m, 2H), 1.84-1.76 (m, 2H), 1.00 (s, 9H), 0.25 (s, 6H); LC-MS 560 (MH+)

Step 2

1-(4-(4-(3-hydroxyphenylamino)thieno[3,2-d]pyrimidine-6-yl)benzyl)pyrrolidine-2-carboxamide HCl salt The synthesis of (1-(4-(4-(3-hydroxyphenylamino)thieno[3,2-d]pyrimidin-6-yl)benzyl)pyrrolidine-2-carboxamide. HCl) (LCB03-0068)

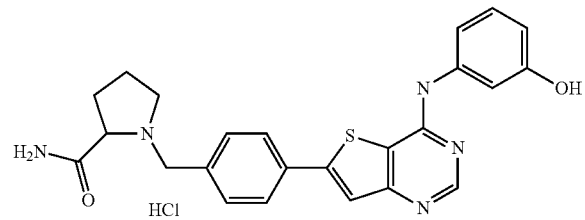 [SMILES: NC(=O)C1CCCN1Cc1ccc(-c2cc3ncnc(Nc4cccc(O)c4)c3s2)cc1 ; Cl]

$^1$H-NMR (400 MHz, DMSO-d$_6$); δ 9.78 (brs, 1H), 8.81 (s, 1H), 8.06 (s, 1H), 7.97 (s, 1H), 7.93 (d, J=8.0 Hz, 2H), 7.70-7.68 (m, 1H), 7.46 (brs, 1H), 7.25-7.10 (m, 3H), 6.70 (d, J=8.0 Hz, 1H), 4.49-4.40 (m, 3H), 4.17 (br, 2H), 3.35-3.32 (m, 2H), 2.08-2.07 (m, 2H), 1.91-1.84 (m, 2H); LC-MS: 446 (MH+)

Example 41

Step 1

2-(4-(4-(3-(tert-butyldimethylsiloxy)phenylamino)thieno[3,2-d]pyrimidine-6-yl)benzylamino)ethanol The synthesis of (2-(4-(4-(3-(tert-butyldimethylsilyloxy)phenylamino)thieno[3,2-d]pyrimidin-6-yl)benzylamino)ethanol)

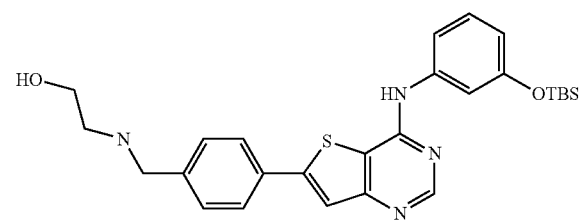 [SMILES: CC(C)(C)[Si](C)(C)Oc1cccc(Nc2ncnc3cc(-c4ccc(CNCCO)cc4)sc23)c1]

$^1$H-NMR (400 MHz, CDCl$_3$); δ 8.67 (s, 1H), 7.61 (d, J=8.0 Hz, 2H), 7.57 (s, 1H), 7.39 (d, J=8.0 Hz, 2H), 7.26 (t, J=8.0 Hz, 1H), 7.19-7.14 (m, 2H), 6.77-6.74 (m, 1H), 3.88 (s, 2H), 3.66-3.64 (m, 2H), 2.04-2.01 (m, 2H), 1.00 (s, 9H), 0.23 (s, 6H); LC-MS 507 (MH+)

Step 2

3-(6-(4-((2-hydroxyethylamino)methyl)phenyl)thieno[3,2-d]pyrimidine-4-ylamino)phenol HCl salt The synthesis of (3-(6-(4-((2-hydroxyethylamino)methyl)phenyl)thieno[3,2-d]pyrimidin-4-ylamino)phenol. HCl) (LCB03-0070)

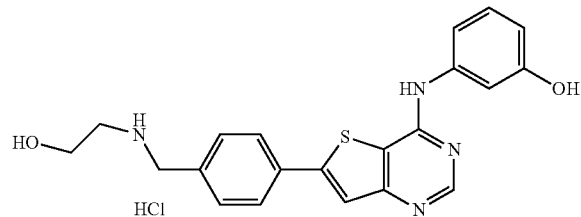 [SMILES: OCCNCc1ccc(-c2cc3ncnc(Nc4cccc(O)c4)c3s2)cc1 ; Cl]

$^1$H-NMR (600 MHz, DMSO-d$_6$); δ 9.23 (brs, 2H), 8.77 (s, 1H), 7.95 (s, 1H), 7.94 (d, J=7.2 Hz, 2H), 7.72 (d, J=7.2 Hz, 2H), 7.23-7.20 (m, 2H), 7.14-7.13 (m, 1H), 6.67-6.66 (m, 1H), 4.23 (t, J=5.4 Hz, 2H), 3.72-3.67 (m, 2H), 2.99-2.98 (m, 2H); LC-MS 393 (MH+)

Example 42

6-(4-(pyrrolidine-1-ylmethyl)phenyl)-N-(3-(trifluoromethyl)phenyl)thieno[3,2-d]pyrimidine-4-amine The synthesis of (6-(4-(pyrrolidin-1-ylmethyl)phenyl)-N-(3-(trifluoromethyl)phenyl)thieno[3,2-d]pyrimidin-4-amine) (LCB03-0077)

$^1$H-NMR (400 MHz, CDCl$_3$); δ 8.76 (s, 1H), 7.99 (s, 1H), 7.89 (d, J=8 Hz, 1H), 7.66-7.63 (m, 3H), 7.53 (t, J=8 Hz, 1H), 7.44 (m, 3H), 7.05 (br, 1H), 3.68 (s, 2H), 2.55 (s, 4H), 1.81 (s, 4H); LC-MS 454 (MH+)

Example 43

N-(3-(difluoromethyl)phenyl)-6-(4-(pyrrolidine-1-ylmethyl)phenyl)thieno[3,2-d]pyrimidine-4-amine The synthesis of (N-(3-(difluoromethyl)phenyl)-6-(4-(pyrrolidin-1-ylmethyl)phenyl)thieno[3,2-d]pyrimidin-4-amine) (LCB03-0078)

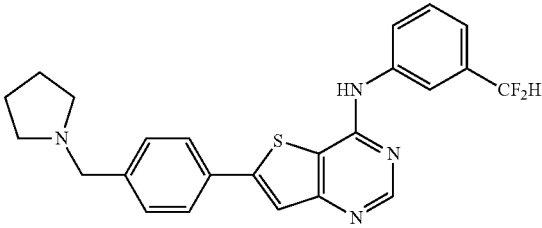 [SMILES: FC(F)c1cccc(Nc2ncnc3cc(-c4ccc(CN5CCCC5)cc4)sc23)c1]

¹H-NMR (400 MHz, CDCl₃); δ 8.75 (s, 1H), 7.87 (s, 1H), 7.79 (d, J=8.0 Hz, 1H), 7.69-7.63 (m, 3H), 7.51 (m, 2H), 7.36 (d, J=8.0 Hz, 1H), 6.90 (brs, 1H), 6.70 (t, J=56.4 Hz, 1H), 3.79 (s, 2H), 2.69 (s, 4H), 1.88 (s, 4H); LC-MS 436 (MH+)

Example 44

Step 1

1-(4-(4-(3-(t-butyldimethylsiloxy)phenylamino)thieno[3,2-d]pyrimidine-6-yl)benzyl)pyrrolidine-3-ol The synthesis of (1-(4-(4-(3-(tert-butyldimethylsilyloxy)phenylamino)thieno[3,2-d]pyrimidin-6-yl)benzyl)pyrrolidin-3-ol)

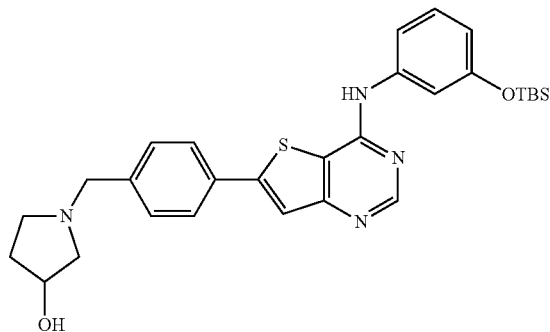 [SMILES: CC(C)(C)[Si](C)(C)Oc1cccc(Nc2ncnc3cc(-c4ccc(CN5CCC(O)C5)cc4)sc23)c1]

¹H-NMR (400 MHz, CDCl₃); δ 8.69 (s, 1H), 7.63 (d, J=5.2 Hz, 2H), 7.59 (s, 1H), 7.41 (d, J=5.6 Hz, 2H), 7.28-7.25 (m, 1H), 7.19 (t, J=1.6 Hz, 1H), 7.15 (d, J=5.2 Hz, 1H), 6.18 (br, 1H), 6.75 (d, J=5.2 Hz, 1H), 4.36-4.35 (m, 1H), 3.69 (s, 2H), 2.93-2.89 (m, 1H), 2.72 (d, J=6.4 Hz, 1H), 2.59-2.56 (m, 1H), 2.36-2.33 (m, 1H), 2.25-2.19 (m, 1H), 2.04-2.02 (m, 1H), 1.80-1.76 (m, 1H), 1.00 (s, 9H), 0.24 (s, 6H); LC-MS 533.2 (MH+)

Step 2

1-(4-(4-(3-hydroxyphenylamino)thieno[3,2-d]pyrimidine-6-yl)benzyl)pyrrolidine-3-ol HCl salt The synthesis of (1-(4-(4-(3-hydroxyphenylamino)thieno[3,2-d]pyrimidin-6-yl)benzyl)pyrrolidin-3-ol.HCl) (LCB03-0072)

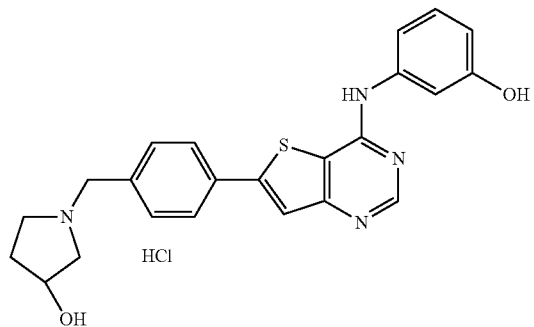 [SMILES: Oc1cccc(Nc2ncnc3cc(-c4ccc(CN5CCC(O)C5)cc4)sc23)c1 ; Cl]

¹H-NMR (400 MHz, DMSO-d₆); δ 10.82 (br, 1H), 9.71 (br, 1H), 8.74 (s, 1H), 7.96 (m, 3H), 7.76 (m, 2H), 7.20 (m, 3H), 6.65 (d, J=8.4 Hz, 1H), 4.45 (m, 4H), 3.71-3.43 (m, 3H), 2.40 (m, 1H), 2.13 (m, 1H), 2.02 (m, 1H)); LC-MS 419.2 (MH+)

Example 45

3-(6-(4-((2-(hydroxymethyl)pyrrolidine-1-yl)methyl)phenyl)thieno[3,2-d]pyrimidine-4-ylamino)phenol HCl salt The synthesis of (3-(6-(4-((2-(hydroxymethyl)pyrrolidin-1-yl)methyl)phenyl)thieno[3,2-d]pyrimidin-4-ylamino)phenol, HCl) (LCB03-0057)

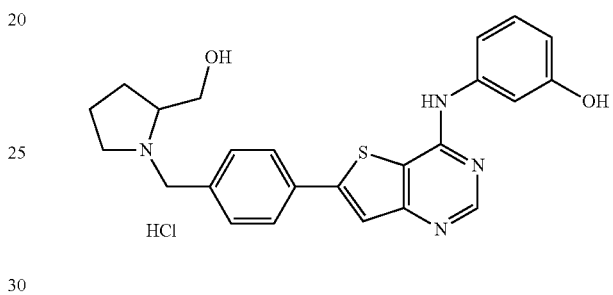

¹H-NMR (400 MHz, DMSO-d₆); δ 8.89 (s, 1H), 8.02 (s, 1H), 8.17-7.98 (m, 2H), 7.77-7.76 (m, 2H), 7.30-7.27 (m, 1H), 7.26 (s, 1H), 7.17 (d, J=7.2 Hz, 1H), 6.75 (d, J=7.2 Hz, 1H), 4.69 (dd, J=2.8, 8.8 Hz, 1H), 4.38 (dd, J=4.4, 8.8 Hz, 1H), 3.75-3.64 (m, 3H), 3.32-3.31 (m, 1H), 3.21-3.17 (m, 1H), 2.18-2.13 (m, 1H), 2.02-2.00 (m, 1H), 1.91-1.80 (m, 2H); LC-MS: 433 (MH+)

Example 46

1-(4-(4-(3-hydroxyphenylamino)thieno[3,2-d]pyrimidine-6-yl)benzyl)pyrrolidine-2-carboxylic acid HCl salt The synthesis of (1-(4-(4-(3-hydroxyphenylamino)thieno[3,2-d]pyrimidin-6-yl)benzyl)pyrrolidine-2-carboxylic acid. HCl) (LCB03-0069)

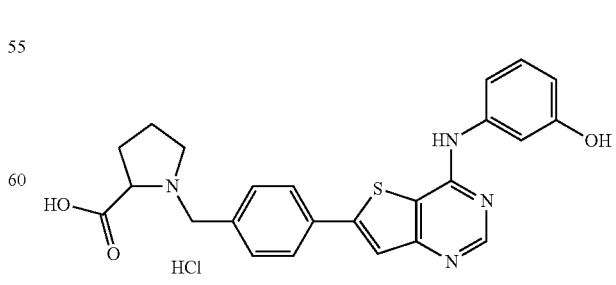

¹H-NMR (400 MHz, DMSO-d₆); δ 8.65 (s, 1H), 7.98 (s, 1H), 7.96 (d, J=8.4 Hz, 2H), 7.68 (d, J=8.4 Hz, 2H), 7.27 (s,

1H), 7.18-7.17 (m, 2H), 6.59-6.58 (m, 1H), 4.55-4.39 (m, 2H), 3.45-3.40 (m, 3H), 2.51-2.49 (m, 2H); LC-MS: 447 (MH+)

Example 47

4-(4-(3-hydroxyphenylamino)thieno[3,2-d]pyrimidine-6-yl)-N-(1-hydroxyprophane-2-yl)benzamide HCl salt The synthesis of (4-(4-(3-hydroxyphenylamino) thieno[3,2-d]pyrimidin-6-yl)-N-(1-hydroxypropan-2-yl)benzamide. HCl)) (LCB03-0074)

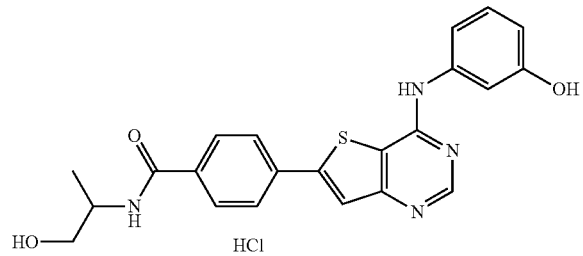 [SMILES: CC(CO)NC(=O)c1ccc(-c2cc3ncnc(Nc4cccc(O)c4)c3s2)cc1 ; Cl]

$^1$H-NMR (400 MHz, DMSO-d$_6$); δ 10.65 (brs, 1H), 8.80 (s, 1H), 8.29 (d, J=8.0 Hz, 1H), 8.04-7.95 (m, 4H), 7.24 (d, J=8.0 Hz, 1H), 7.21 (s, 1H), 7.14 (d, J=7.6 Hz, 1H), 6.68 (d, J=8.4 Hz, 1H), 4.07-4.02 (m, 1H), 3.52-3.49 (m, 2H), 1.10 (d, J=8.0 Hz, 3H); LC-MS 421 (MH+)

Example 48

Step 1

N-(3-(t-butyldimethylsiloxy)phenyl)-6-(3-(piperidine-1-ylmethyl)phenyl)thieno[3,2-d]pyrimidine-4-amine The synthesis of (N-(3-(tert-butyldimethylsilyloxy) phenyl)-6-(3-(piperidin-1-ylmethyl)phenyl)thieno[3,2-d]pyrimidin-4-amine)

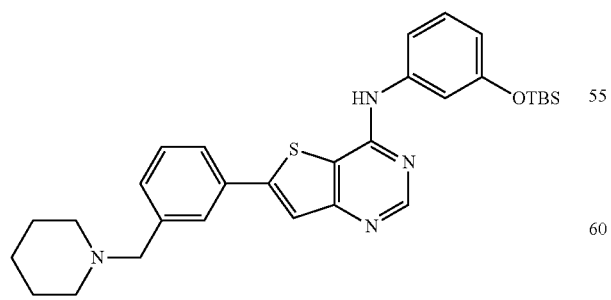

$^1$H-NMR (400 MHz, CDCl$_3$); δ 8.70 (s, 1H), 7.66 (s, 1H), 7.62 (s, 1H), 7.57-7.56 (m, 1H), 7.39-7.38 (m, 2H), 7.27-7.25 (m, 1H), 7.21 (m, 1H), 7.17-7.16 (m, 1H), 6.76-6.73 (m, 2H), 3.52 (s, 2H), 2.41-2.39 (m, 4H), 1.62-1.58 (m, 4H), 1.45-1.44 (m, 2H), 1.00 (s, 9H), 0.24 (s, 6H); LC-MS 531 (MH+)

Step 2

3-(6-(3-(piperidine-1-ylmethyl)phenyl)thieno[3,2-d] pyrimidine-4-ylamino)phenol HCl salt The synthesis of (3-(6-(3-(piperidin-1-ylmethyl)phenyl)thieno[3,2-d]pyrimidin-4-ylamino)phenol. HCl) (LCB03-0060)

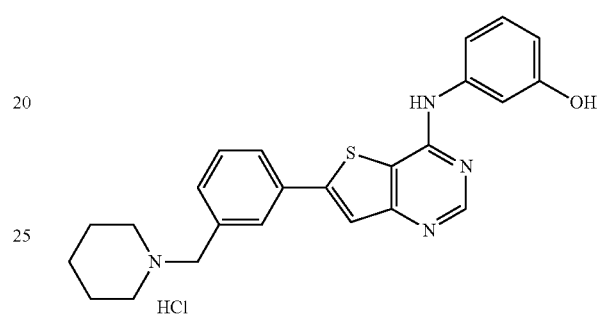

$^1$H-NMR (400 MHz, DMSO-d$_6$); δ 10.54 (br, 1H), 9.65 (br, 1H), 8.76 (s, 1H), 8.23 (s, 1H), 7.95 (s, 1H), 7.89 (m, 1H), 7.70-7.69 (m, 1H), 7.66-7.63 (t, J=5.2 Hz, 1H), 7.21 (m, 2H), 7.14 (d, J=4.8 Hz, 1H), 6.65 (m, 1H), 4.36 (s, 2H), 3.40-3.32 (m, 4H), 1.79 (m, 4H), 1.37 (m, 2H); LC-MS 417 (MH+)

Example 49

Step 1

N-(3-(t-butyldimethylsiloxy)phenyl)-6-(3-((4-methylpiperazine-1-yl)methyl)phenyl)thieno[3,2-d]pyrimidine-4-amine The synthesis of (N-(3-(tert-butyldimethylsilyloxy) phenyl)-6-(3-((4-methylpiperazin-1-yl)methyl)phenyl)thieno[3,2-d]pyrimidin-4-amine)

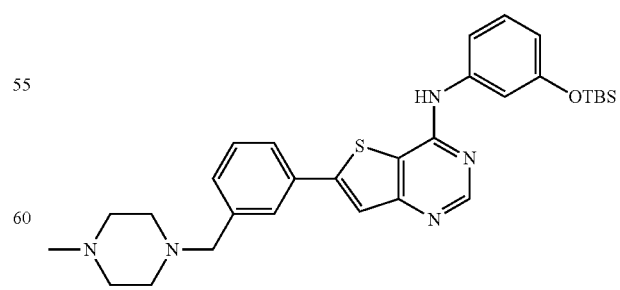

$^1$H-NMR (400 MHz, CDCl$_3$); δ 8.70 (s, 1H), 7.66 (s, 1H), 7.62 (s, 1H), 7.59-7.57 (m, 1H), 7.40-7.37 (m, 2H), 7.27-7.25 (m, 1H), 7.22-7.21 (m, 1H), 7.18-7.16 (m, 1H), 6.78 (br, 1H), 6.76-6.73 (m, 1H), 3.64 (s, 2H), 2.65-2.64 (m, 4H), 2.44 (s, 3H), 1.47-1.45 (m, 4H), 1.00 (s, 9H), 0.24 (s, 6H); LC-MS 546.2 (MH+)

Step 2

3-(6-(3-((4-methylpiperazine-1-yl)methyl)phenyl)thieno[3,2-d]pyrimidine-4-ylamino)phenol HCl salt The synthesis of (3-(6-(3-((4-methylpiperazin-1-yl)methyl)phenyl)thieno[3,2-d]pyrimidin-4-ylamino)phenol. HCl) (LCB03-0061)

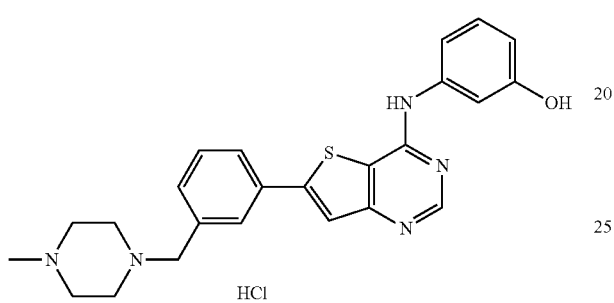

¹H-NMR (400 MHz, DMSO-d₆); δ 10.54 (br, 1H), 9.65 (brs, 1H), 8.84 (s, 1H), 7.94 (s, 1H), 7.87 (m, 1H), 7.76 (m, 1H), 7.64 (t, J=4.8 Hz, 1H), 7.26-7.23 (m, 2H), 7.18 (m, 1H), 7.14-7.12 (m, 1H), 6.72 (m, 1H), 3.76 (s, 2H), 2.81-2.80 (m, 4H), 2.47 (s, 3H), 1.41 (m, 4H); LC-MS 432 (MH+)

Example 50

Step 1

(N-(3-(tert-butyldimethylsilyloxy)phenyl)-6-(3-(pyrrolidin-1-ylmethyl)phenyl)thieno[3,2-d]pyrimidin-4-amine)

The synthesis of (N-(3-(tert-butyldimethylsilyloxy)phenyl)-6-(3-(pyrrolidin-1-ylmethyl)phenyl)thieno[3,2-d]pyrimidin-4-amine)

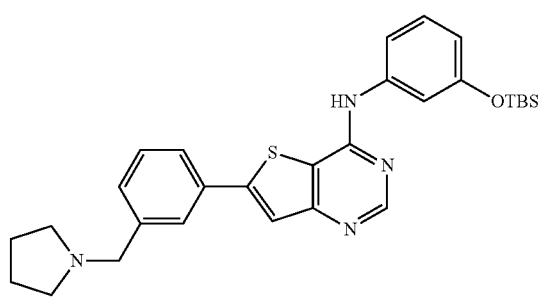 [SMILES: CC(C)(C)[Si](C)(C)Oc1cccc(Nc2ncnc3cc(-c4cccc(CN5CCCC5)c4)sc23)c1]

¹H-NMR (400 MHz, CDCl₃); δ 8.70 (s, 1H), 7.73 (s, 1H), 7.62-7.60 (m, 2H), 7.46-7.40 (m, 2H), 7.29-7.25 (m, 1H), 7.22 (m, 1H), 7.18-7.17 (m, 1H), 6.88 (br, 1H), 6.75-6.73 (m, 1H), 3.79 (s, 2H), 2.68-2.65 (m, 4H), 1.87-1.85 (m, 4H), 1.00 (s, 9H), 0.24 (s, 6H); LC-MS 518 (MH+)

Step 2

3-(6-(3-(pyrrolidine-1-ylmethyl)phenyl)thieno[3,2-d]pyrimidine-4-ylamino)phenol salt The synthesis of (3-(6-(3-(pyrrolidin-1-ylmethyl)phenyl)thieno[3,2-d]pyrimidin-4-ylamino)phenol. HCl) (LCB03-0062)

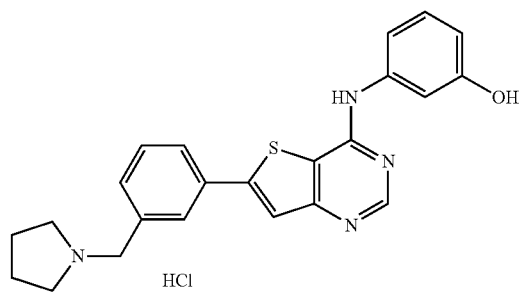 [SMILES: Oc1cccc(Nc2ncnc3cc(-c4cccc(CN5CCCC5)c4)sc23)c1 ; Cl]

¹H-NMR (400 MHz, DMSO-d₆); δ 11.22 (br, 1H), 9.65 (br, 1H), 8.81 (s, 1H), 8.27 (s, 1H), 7.96 (s, 1H), 7.86 (m, 1H), 7.75-7.73 (m, 1H), 7.64 (t, J=4.8 Hz, 1H), 7.25-7.22 (m, 2H), 7.14-7.12 (m, 1H), 6.69 (m, 1H), 4.45 (d J=4.0 Hz, 2H), 3.51-3.46 (m, 2H), 3.38-3.37 (m, 2H), 2.04 (m, 2H), 1.91 (m, 2H); LC-MS 403 (MH+)

Example 51

Step 1

N-(3-(t-butyldimethylsiloxy)phenyl)-6-(3-((diethylamino)methyl)phenylthieno[3,2-d]pyrimidine-4-amine The synthesis of (N-(3-(tert-butyldimethylsilyloxy)phenyl)-6-(3-((diethylamino)methyl)phenyl)thieno[3,2-d]pyrimidin-4-amine)

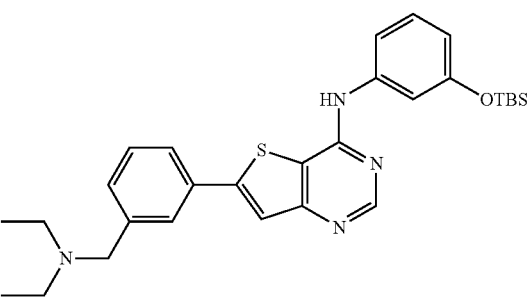 [SMILES: CCN(CC)Cc1cccc(-c2cc3ncnc(Nc4cccc(O[Si](C)(C)C(C)(C)C)c4)c3s2)c1]

¹H-NMR (400 MHz, CDCl₃); δ 8.68 (s, 1H), 7.67 (s, 1H), 7.62-7.58 (m, 2H), 7.47-7.39 (m, 2H), 7.28-7.24 (m, 1H), 7.20-7.16 (m, 2H), 6.76-6.73 (m, 1H), 3.76 (s, 2H), 2.70-2.68 (m, 4H), 1.15 (t, J=7.2 Hz, 6H), 0.99 (s, 9H), 0.24 (s, 6H); LC-MS 519.2 (MH+)

Step 2

3-(6-(3-((diethylamino)methyl)phenyl)thieno[3,2-d]pyrimidine-4-ylamino)phenol HCl salt The synthesis of (3-(6-(3-((diethylamino)methyl)phenyl)thieno[3,2-d]pyrimidin-4-ylamino)phenol. HCl) (LCB03-0063)

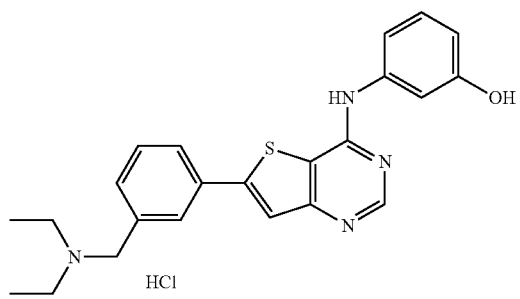 [SMILES: CCN(CC)Cc1cccc(-c2cc3ncnc(Nc4cccc(O)c4)c3s2)c1 ; Cl]

$^1$H-NMR (400 MHz, DMSO-d$_6$); δ 10.86 (brs 1H), 9.79 (m, 1H), 8.81 (s, 1H), 8.32 (s, 1H), 7.97 (s, 1H), 7.87 (s, 1H), 7.75 (s, 1H), 7.64 (s, 1H), 7.21 (m, 2H), 7.14 (s, 1H), 6.68 (s, 1H), 4.39 (s, 2H), 3.08 (m, 4H), 1.28 (s, 6H); LC-MS 405 (MH+)

Example 52

Step 1 t-butyl 4-(3-(4-(3-(t-butyldimethylsiloxy)phenylamino) 사이에토 [3,2-d]piperazine-1-carboxylate The synthesis of (tert-butyl 4-(3-(4-(3-(tert-butyldimethylsilyloxy)phenylamino)thieno[3,2-d]pyrimidin-6-yl)benzyl)piperazine-1-carboxylate)

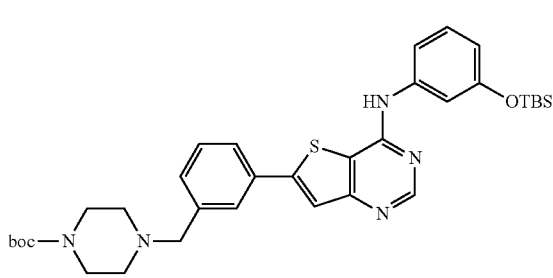

$^1$H-NMR (400 MHz, CDCl$_3$); δ 8.70 (s, 1H), 7.73 (s, 1H), 7.62-7.60 (m, 2H), 7.46-7.40 (m, 2H), 7.29-7.25 (m, 1H), 7.21 (m, 1H), 7.18-7.16 (m, 1H), 6.84 (br, 1H), 6.76-6.73 (m, 1H), 3.56 (d, J=3.6 Hz, 2H), 3.45 (m, 4H), 2.42 (m, 4H), 1.46 (s, 9H), 1.00 (s, 9H), 0.24 (s, 6H); LC-MS 632.5 (MH+)

Step 2

3-(6-(3-(piperazine-1-ylmethyl)phenyl)thieno[3,2-d]pyrimidine-4-ylamino)phenol HCl salt The synthesis of (3-(6-(3-(piperazin-1-ylmethyl)phenyl)thieno[3,2-d]pyrimidin-4-ylamino)phenol. HCl) (LCB03-0064)

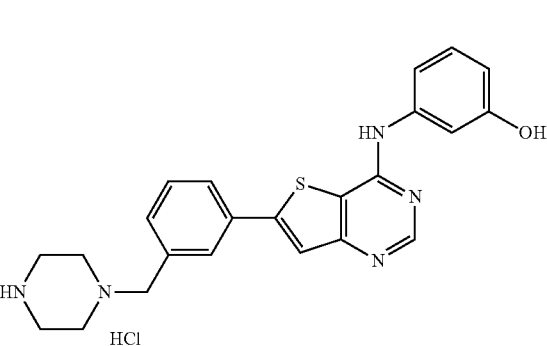 [SMILES: Oc1cccc(Nc2ncnc3cc(-c4cccc(CN5CCNCC5)c4)sc23)c1 ; Cl]

$^1$H-NMR (400 MHz, DMSO-d$_6$); δ 10.75 (br, 1H), 9.44 (br, 1H), 8.80 (s, 1H), 8.24 (s, 1H), 7.95 (s, 1H), 7.89 (d, J=5.2 Hz, 1H), 7.74 (d, J=4.4 Hz, 1H), 7.65 (t, J=5.2 Hz, 1H), 7.23 (t, J=5.6 Hz, 1H), 7.19 (s, 1H), 7.13 (d, J=5.2 Hz, 1H), 6.69 (d, J=5.2 Hz, 1H), 3.76 (s, 2H), 2.81-2.80 (m, 4H), 2.47 (m, 4H); LC-MS 418 (MH+)

Example 53

Step 1

N-(3-(t-butyldimethylsiloxy)phenyl)-6-(3-((ethylamino)methyl)phenyl)thieno[3,2-d]pyrimidine-4-amine The synthesis of (N-(3-(tert-butyldimethylsilyloxy)phenyl)-6-(3-((ethylamino)methyl)phenyl)thieno[3,2-d]pyrimidin-4-amine)

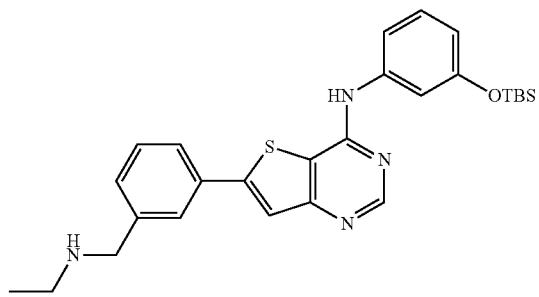 [SMILES: CCNCc1cccc(-c2cc3ncnc(Nc4cccc(O[Si](C)(C)C(C)(C)C)c4)c3s2)c1]

$^1$H-NMR (400 MHz, CDCl$_3$); δ 8.70 (s, 1H), 7.67 (s, 1H), 7.62 (s, 1H), 7.57-7.55 (m, 1H), 7.42-7.38 (m, 1H), 7.29-7.25 (m, 1H), 7.21 (t, J=1.2 Hz, 1H), 7.17 (m, 1H), 6.75-6.73 (m,

2H), 3.87 (s, 2H), 2.74 (q, J=4.8 Hz, 2H), 1.18 (t, J=4.8 Hz, 3H), 1.00 (s, 9H), 0.24 (s, 6H); LC-MS 491.2 (MH+)

Step 2

3-(6-(3-((ethylamino)methyl)phenyl)thieno[3,2-d]pyrimidine-4-ylamino)phenol HCl salt The synthesis of (3-(6-(3-((ethylamino)methyl)phenyl)thieno[3,2-d]pyrimidin-4-ylamino)phenol. HCl) (LCB03-0065)

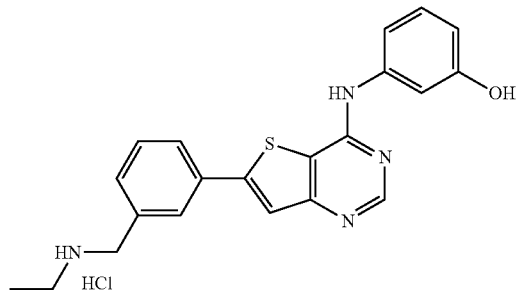 [SMILES: CCNCc1cccc(-c2cc3ncnc(Nc4cccc(O)c4)c3s2)c1 ; Cl]

¹H-NMR (400 MHz, DMSO-d₆); δ 9.68 (br, 1H), 9.24 (br, 1H), 8.78 (s, 1H), 8.14 (s, 1H), 7.93 (s, 1H), 7.88 (m, 1H), 7.67 (m, 1H), 7.63 (m, 1H), 7.22 (m, 2H), 7.14 (m, 1H), 6.68 (m, 1H), 4.23 (m, 2H), 3.01 (m, 2H), 1.25 (t, J=4.8 Hz, 3H); LC-MS 377 (MH+)

Example 54

Step 1

N-(3-(t-butyldimethylsiloxy)phenyl)-6-(3-(morpholinomethyl)phenyl)thieno[3,2-d]pyrimidine-4-amine The synthesis of (N-(3-(tert-butyldimethylsilyloxy)phenyl)-6-(3-(morpholinomethyl)phenyl)thieno[3,2-d]pyrimidin-4-amine)

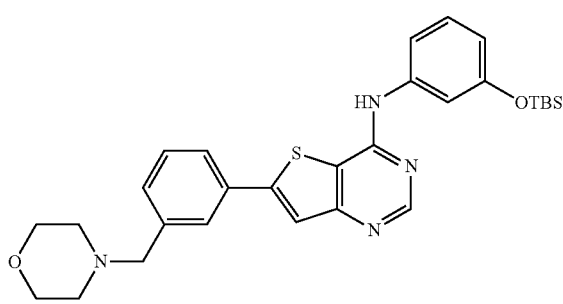 [SMILES: CC(C)(C)[Si](C)(C)Oc1cccc(Nc2ncnc3cc(-c4cccc(CN5CCOCC5)c4)sc23)c1]

¹H-NMR (400 MHz, CDCl₃); δ 8.69 (s, 1H), 7.73 (s, 1H), 7.62-7.60 (m, 2H), 7.46-7.40 (m, 2H), 7.29 (m, 1H), 7.25-7.24 (m, 2H), 7.21-7.19 (m, 1H), 6.73-6.71 (m, 1H), 3.73 (t, J=2.8 Hz, 4H), 3.55 (s, 2H), 2.48 (br, 4H), 0.99 (s, 9H), 0.24 (s, 6H); LC-MS 533.5 (MH+)

Step 2

3-(6-(3-(morpholinomethyl)phenyl)thieno[3,2-d]pyrimidine-4-ylamino)phenol HCl salt The synthesis of (3-(6-(3-(morpholinomethyl)phenyl)thieno[3,2-d]pyrimidin-4-ylamino)phenol. HCl) (LCB03-0066)

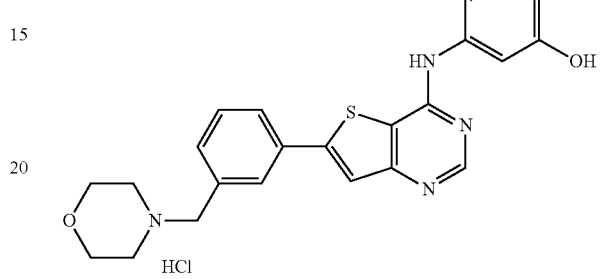

¹H-NMR (400 MHz, DMSO-d₆); δ 10.86 (br, 1H), 9.80 (br, 1H), 8.81 (s, 1H), 8.28 (s, 1H), 7.95 (s, 1H), 7.90 (d, J=7.6 Hz, 1H), 7.73 (d, J=7.6 Hz, 1H), 7.65 (t, J=8.0 Hz, 1H), 7.25-7.19 (m, 2H), 7.13 (d, J=8.0 Hz, 1H), 6.69 (d, J=7.6 Hz, 1H), 4.44 (s, 2H), 3.93-3.85 (m, 3H), 3.82 (t, J=12 Hz, 1H), 2.48 (br, 4H); LC-MS 419 (MH+)

Example 55

Step 1

N-(3-(t-butyldimethylsiloxy)phenyl)-6-(3-((isobutylamino)methyl)phenyl)thieno[3,2-d]pyrimidine-4-amine The synthesis of (N-(3-(tert-butyldimethylsilyloxy)phenyl)-6-(3-((isobutylamino)methyl)phenyl)thieno[3,2-d]pyrimidin-4-amine)

¹H-NMR (400 MHz, CDCl₃); δ 8.69 (s, 1H), 7.66 (s, 1H), 7.61 (s, 1H), 7.55 (d, J=4.4 Hz, 1H), 7.40-7.38 (m, 2H), 7.26 (t, J=5.2 Hz, 1H), 7.20 (t, J=1.2 Hz, 1H), 7.16 (d, J=5.2 Hz, 1H), 7.08 (br, 1H), 6.75 (d, J=4.4 Hz, 1H), 3.85 (s, 2H), 2.47 (d, J=4.8 Hz, 2H), 1.79 (m, 1H), 0.99 (s, 9H), 0.94 (d, J=4.4 Hz, 6H), 0.24 (s, 6H); LC-MS 519 (MH+)

Step 2

3-(6-(3-((isobutylamino)methyl)phenyl)thieno[3,2-d]pyrimidine-4-ylamino)phenol HCl salt The synthesis of (3-(6-(3-((isobutylamino)methyl)phenyl)thieno[3,2-d]pyrimidin-4-ylamino)phenol. HCl) (LCB03-0067)

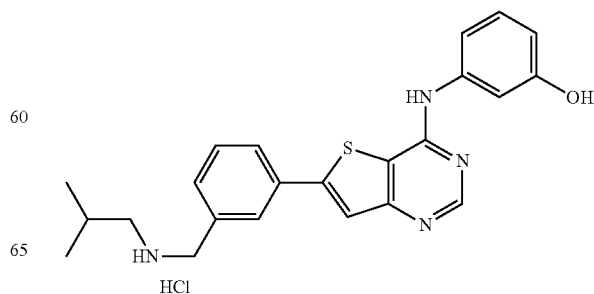

¹H-NMR (400 MHz, DMSO-d₆); δ 10.82 (br, 1H), 9.71 (br, 1H), 9.27 (br, 1H), 8.81 (s, 1H), 8.21 (s, 1H), 7.94 (s, 1H), 7.87 (d, J=7.6 Hz, 1H), 7.71 (d, J=7.2 Hz, 1H), 7.62 (t, J=7.2 Hz, 1H), 7.25-7.19 (m, 2H), 7.13 (d, J=7.6 Hz, 1H), 6.70 (d, J=8.8 Hz, 1H), 4.25 (s, 2H), 2.77-2.75 (m, 2H), 2.06-2.05 (m, 1H), 0.96 (d, J=6.4 Hz, 6H); LC-MS 405 (MH+)

Example 56

Step 1

N-(3-(t-butyldimethylsiloxy)phenyl)-6-(furan-2-yl)thieno[3,2-d]pyrimidine-4-amine The synthesis of (N-(3-(tert-butyldimethylsilyloxy)phenyl)-6-(furan-2-yl)thieno[3,2-d]pyrimidin-4-amine)

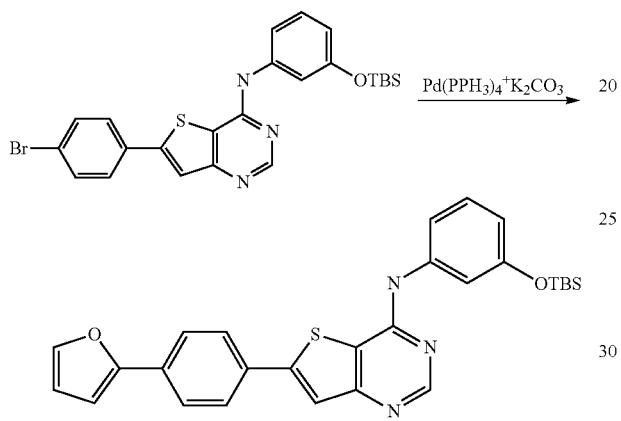

The compound (0.1 mg, 0.23 mmol) synthesized in the example of synthesis 5, 2-furanboric acid (2-furanboronic acid) (33 mg, 0.27 mmol), palladium tetrakistriphenylphosphine (53 mg, 0.04 mmol), and 2N sodium carbonate (0.23 ml, 0.46 mmol) were added into 2 ml of 1,4-dioxane 2 ml and the mixture was refluxed for 2 hours. The reaction mixture was extracted with 50 ml of saturated sodium bicarbonate and 50 ml of dichloromethane and the organic layer was further extracted with 50 ml of saturated sodium bicarbonate twice and dried using anhydrous sodium sulfate and concentrated under vacuum. The column chromatography (ethylacetate/n-hexane, 1/3) was done to obtain the title compound (76.3 mg, 78.9%) as yellowish solid.

¹H-NMR (400 MHz, CDCl₃); δ 8.68 (s, 1H), 7.51-7.50 (m, 2H), 7.29-7.25 (m, 1H), 7.61-7.12 (m, 2H), 6.81 (brs, 1H), 6.78-6.75 (m, 2H), 6.52-6.51 (m, 1H), 1.00 (s, 9H), 0.23 (s, 6H); LC-MS 422 (MH+)

Step 2

3-(6-(furan-2-yl)thieno[3,2-d]pyrimidine-4-ylamino)phenol HCl salt

The synthesis of (3-(6-(furan-2-yl)thieno[3,2-d]pyrimidin-4-ylamino)phenol. HCl) (LCB03-0038)

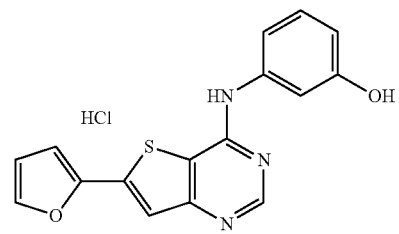 [SMILES: Oc1cccc(Nc2ncnc3cc(-c4ccco4)sc23)c1 ; Cl]

¹H-NMR (400 MHz, DMSO-d₆); δ 11.10 (brs, 1H), 8.86 (s, 1H), 8.53 (s, 1H), 7.92 (t, J=1.8 Hz, 1H), 7.71 (s, 1H), 7.24 (t, J=8.0 Hz, 1H), 7.13 (s, 1H), 7.10-7.08 (m, 2H), 6.73 (dd, J=1.6, 8.0 Hz, 1H); LC-MS 310 (MH+)

The following compounds were synthesized by the methods similar to the one described in the preferred embodiment 56 described above.

Example 57

Step 1

N-(3-(t-butyldimethylsiloxy)phenyl)-6-(furan-3-yl)thieno[3,2-d]pyrimidine-4-amine The synthesis of (N-(3-(tert-butyldimethylsilyloxy)phenyl)-6-(furan-3-yl)thieno[3,2-d]pyrimidin-4-amine)

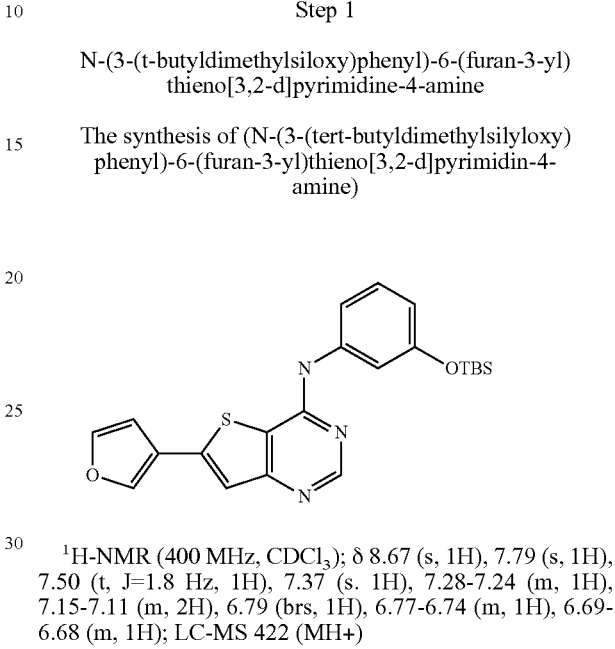

¹H-NMR (400 MHz, CDCl₃); δ 8.67 (s, 1H), 7.79 (s, 1H), 7.50 (t, J=1.8 Hz, 1H), 7.37 (s. 1H), 7.28-7.24 (m, 1H), 7.15-7.11 (m, 2H), 6.79 (brs, 1H), 6.77-6.74 (m, 1H), 6.69-6.68 (m, 1H); LC-MS 422 (MH+)

Step 2

3-(6-(furan-3-yl)thieno[3,2-d]pyrimidine-4-ylamino)phenol HCl salt

The synthesis of (3-(6-(furan-3-yl)thieno[3,2-d]pyrimidin-4-ylamino)phenol. HCl) (LCB03-0039)

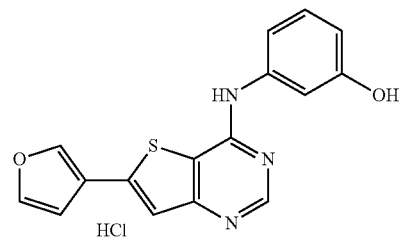 [SMILES: Oc1cccc(Nc2ncnc3cc(-c4ccoc4)sc23)c1 ; Cl]

The compound (63 mg, 0.15 mmol) synthesized in the step 1 described above was dissolved into 1 ml of dichloromethane 1 ml and added with 1 ml of 4 M c HCl/1,4-dioxane and 0.2 ml of methanol 0.2 ml, then stirred at room temperature for 15 hours. The reaction mixture was concentrated under vacuum and then subject to azotrope-concentration with 2 ml of dichloromethane, 2 ml of methanol 2 ml, 2 ml of dichloromethane and 2 ml of diethylether followed by vacuum-dry. The title compound (42 mg, 90%) was obtained as yellowish solid.

¹H-NMR (400 MHz, DMSO-d₆); δ 11.03 (brs, 1H), 8.84 (s, 1H), 7.94 (s, 1H), 7.72 (s, 1H), 7.39 (d, J=3.6 Hz, 1H), 7.26 (t, J=8.0 Hz, 1H), 7.12 (s, 1H), 7.09 (d, J=8.4 Hz, 1H), 6.78-6.74 (m, 2H); LC-MS 310 (MH+)

Example 581

Step 1

N-(3-(4-methoxybenzyloxy)phenyl)-6-(5-(pyrrolidine-1-ylmethyl)thiophene-2-yl)thieno[3,2-d]pyrimidine-4-amine The synthesis of (N-(3-(4-methoxybenzyloxy)phenyl)-6-(5-pyrrolidin-1-ylmethyl)thiophene-2-yl)thieno[3,2-d]pyrimidin-4-amine)

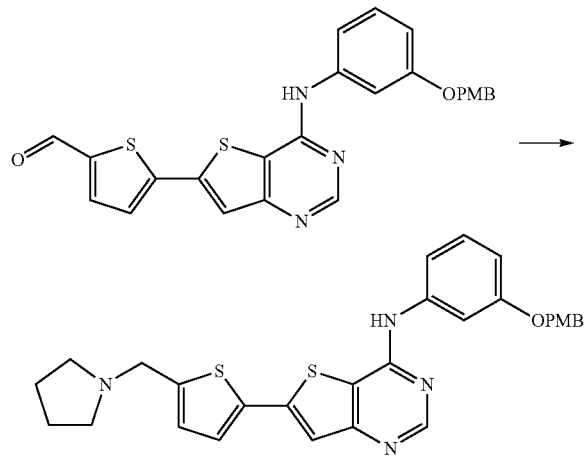

The compound (24 mg, 0.05 mmol) synthesized in the example of synthesis 18 and pyrrolidine (6.3 μl, 0.07 mmol) were added sequentially into 1 ml of dichloroethane 1 ml and stirred for 20 minutes and then further stirred for 7 hours at room temperature after adding sodium acetate (13 mg, 0.15 mmol) and sodium triacethoxyborohydride (64 mg, 0.30 mmol). The reaction mixture was extracted with 10 ml of dichloromethane and 10 ml of saturated ammonium chloride solution. The organic layer was dried with sodium sulfate and concentrated under vacuum followed by column chromatography (dichloromethane/methanol, 40/1). The title compound (21 mg, 78.6%) was obtained as a yellowish solid.

$^1$H-NMR (400 MHz, CDCl$_3$); δ 8.64 (s, 1H), 7.41 (d, J=8.8 Hz, 2H), 7.43 (s, 1H), 7.38-7.35 (m, 3H), 7.17 (d, J=3.6 Hz, 1H), 6.89 (d, J=8.8 HZ, 2H), 6.84-6.83 (m, 3H), 5.02 (s, 2H), 3.92 (s, 2H), 3.79 (s, 3H), 2.78-2.70 (m, 4H), 1.87-1.85 (m, 4H); LC-MS 529 (MH+)

Step 2

3-(6-(5-(pyrrolidine-1-ylmethyl)thiophene-2-yl)thieno[3,2-d]pyrimidine-4-ylamino)phenol trifluoroacetic acid The synthesis of (3-(6-(5-(pyrrolidin-1-ylmethyl)thiophene-2-yl)thieno[3,2-d]pyrimidin-4-ylamino)phenol. TFA) (LCB03-0085)

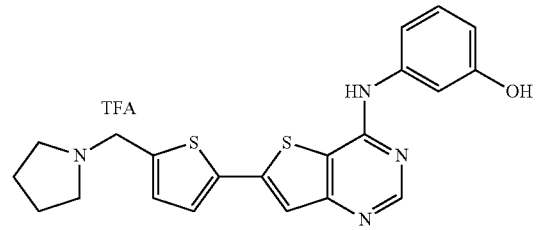 [SMILES: Oc1cccc(Nc2ncnc3cc(-c4ccc(CN5CCCC5)s4)sc23)c1]

$^1$H-NMR (400 MHz, Acetone-d$_6$); δ 8.59 (s, 1H), 7.26-7.21 (m, 5H), 7.01 (d, J=3.6 Hz, 1H), 6.84 (d, J=8.0 Hz, 1H), 6.81 (d, J=3.6 Hz, 1H), 6.75 (dd, J=1.6, 8.4 Hz, 1H), 3.81 (s, 2H), 2.69-2.65 (m, 4H), 2.04-2.02 (m, 4H); LC-MS 409 (MH+)

The following compounds were synthesized by the methods similar to the one described in the preferred embodiment 58 described above.

Example 59

Step 1

N-(3-(4-methoxybenzyloxy)phenyl)-6-(5-((4-methylpiperazine-1-yl)methyl)thiophene-2-yl)thieno[3,2-d]pyrimidine-4-amine The synthesis of (N-(3-(4-methoxybenzyloxy)phenyl)-6-(5-((4-methylpiperazin-1-yl)methyl)thiophene-2-yl)thieno[3,2-d]pyrimidin-4-amine)

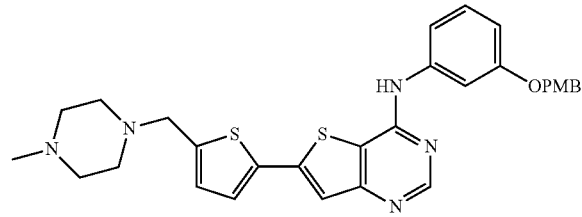

$^1$H-NMR (400 MHz, CDCl$_3$); δ 8.67 (s, 1H), 7.39 (s, 1H), 7.37 (d, J=8.8 Hz, 2H), 7.34-7.29 (m, 2H), 7.18 (d, J=3.6 Hz, 1H), 7.09-7.07 (m, 1H), 6.91 (d, J=8.4 Hz, 2H), 6.88 (d, J=2.8 Hz, 1H), 6.86 (d, J=2.4 Hz, 1H), 6.73 (brs, 1H), 5.03 (s, 2H), 3.81 (s, 3H), 3.71 (s, 2H), 2.50 (m, 4H), 2.20 (s, 3H), 1.62 (m, 4H); LC-MS 558 (MH+)

Step 2

3-(6-(5-((4-methylpiperazine-1-yl)methyl)thiophene-2-yl)thieno[3,2-d]pyrimidine-4-ylamino)phenol trifluoroacetic acid The synthesis of (3-(6-(5-((4-methylpiperazin-1-yl)methyl)thiophene-2-yl)thieno[3,2-d]pyrimidin-4-ylamino)phenol. TFA) (LCB03-0092)

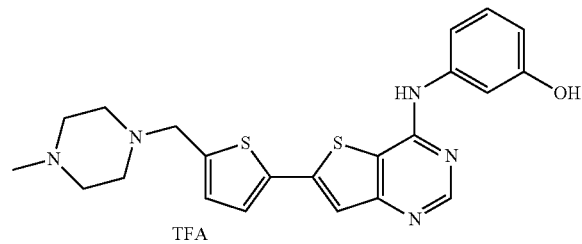 [SMILES: CN1CCN(Cc2ccc(-c3cc4ncnc(Nc5cccc(O)c5)c4s3)s2)CC1]

$^1$H-NMR (600 MHz, DMSO-d$_6$); δ 9.90 (brs, 1H), 8.62 (s, 1H), 7.61 (s, 1H), 7.53 (d, J=3.6 Hz, 1H), 7.24 (s, 1H), 7.18-7.09 (m, 3H), 6.58 (d, J=7.2 Hz, 1H), 3.86 (s, 2H), 3.47-3.46 (m, 4H), 3.05-3.03 (m, 4H), 2.80 (s, 3H); LC-MS 438 (MH+)

Example 60

Step 1

N-(3-(4-methoxybenzyloxy)phenyl)-6-(5-(piperidine-1-ylmethyl)thiophene-2-yl)thieno[3,2-d]pyrimidine-4-amine The synthesis of (N-(3-(4-methoxybenzyloxy)phenyl)-6-(5-(piperidin-1-ylmethyl)thiophene-2-yl)thieno[3,2-d]pyrimidin-4-amine)

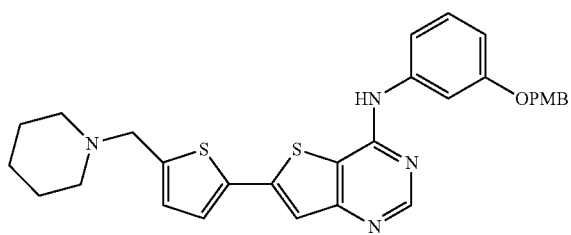

$^1$H-NMR (400 MHz, CDCl$_3$); δ 8.67 (s, 1H), 7.39 (s, 1H), 7.37 (d, J=8.4 Hz, 2H), 7.34-7.29 (m, 2H), 7.19 (d, J=3.6 Hz, 1H), 7.09-7.07 (m, 1H), 6.91 (d, J=8.4 Hz, 2H), 6.88-6.86 (m, 2H), 6.77 (brs, 1H), 5.03 (s, 2H), 3.81 (s, 3H), 3.68 (s, 2H), 2.46 (m, 4H), 1.62-1.60 (m, 4H), 1.47-1.45 (m, 2H); LC-MS 543 (MH+)

Step 2

3-(6-(5-(piperidine-1-ylmethyl)thiophene-2-yl)thieno[3,2-d]pyrimidine-4-ylamino)phenol trifluoroacetic acid The synthesis of (3-(6-(5-(piperidin-1-ylmethyl)thiophene-2-yl)thieno[3,2-d]pyrimidin-4-ylamino)phenol. TFA) (LCB03-0093)

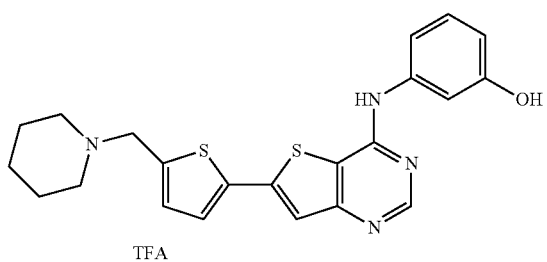 [SMILES: Oc1cccc(Nc2ncnc3cc(-c4ccc(CN5CCCCC5)s4)sc23)c1]

$^1$H-NMR (600 MHz, DMSO-d$_6$); δ 9.97 (brs, 1H), 9.98 (brs, 1H), 8.61 (s, 1H), 7.75 (s, 1H), 7.66 (d, J=3.6 Hz, 1H), 7.38 (d, J=30 Hz, 1H), 7.25 (s, 1H), 7.18-7.14 (m, 2H), 6.38 (d, J=8.4 Hz, 1H), 6.57 (d, J=7.2 Hz, 1H), 4.59 (s, 2H), 3.73-3.70 (m, 2H), 2.93-2.91 (m, 2H), 1.86-1.84 (m, 2H), 1.70-1.62 (m, 3H), 1.38-1.36 (m, 1H); LC-MS 438 (MH+)

Example 61

Step 1

N-(3-(4-methoxybenzyloxy)phenyl)-6-(5-(morpholinomethyl)thiophene-2-yl)thieno[3,2-d]pyrimidine-4-amine The synthesis of (N-(3-(4-methoxybenzyloxy)phenyl)-6-(5-(morpholinomethyl)thiophene-2-yl)thieno[3,2-d]pyrimidin-4-amine)

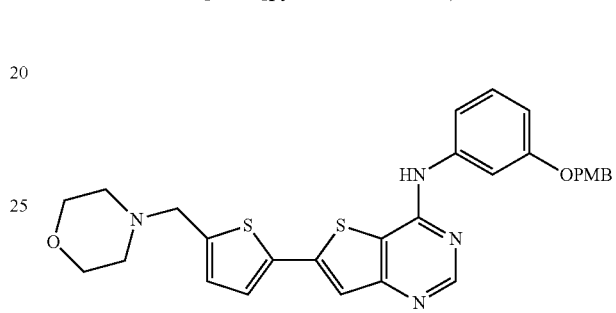

$^1$H-NMR (400 MHz, CDCl$_3$); δ 8.68 (s, 1H), 7.49 (s, 1H), 7.38-7.31 (m, 4H), 7.08 (dd, J=1.6, 7.6 Hz, 1H), 6.92 (brs, 1H), 6.90-6.85 (m, 3H), 6.70 (d, J=3.2 Hz, 1H), 6.35 (d, J=3.2 Hz, 1H), 5.03 (s, 2H), 3.80 (s, 3H), 3.74-3.72 (m, 4H), 3.62 (s, 2H), 2.56-2.53 (m, 4H); LC-MS 545 (MH+)

Step 2

3-(6-(5-(morpholinomethyl)thiophene-2-yl)thieno[3,2-d]pyrimidine-4-ylamino)phenol trifluoroacetic acid The synthesis of (3-(6-(5-(morpholinomethyl)thiophene-2-yl)thieno[3,2-d]pyrimidin-4-ylamino)phenol. TFA) (LCB03-0096)

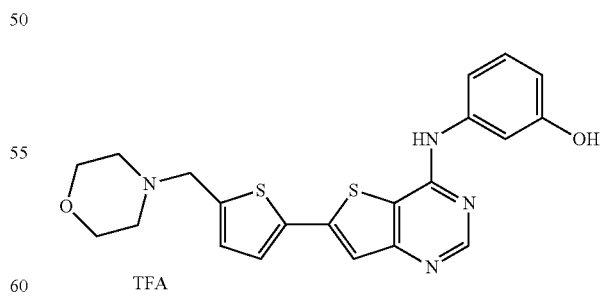

$^1$H-NMR (400 MHz, Acetone-d$_6$); δ 8.74 (s, 1H), 7.74 (s, 1H), 7.55-7.53 (m, 1H), 7.42-7.41 (m, 1H), 7.35-7.32 (m, 1H), 7.27 (t, J=8.0 Hz, 1H), 7.20-7.18 (m, 1H), 6.83-6.82 (m, 1H), 4.67 (s, 2H), 3.96-3.94 (m, 4H), 3.35-3.33 (m, 4H); LC-MS 425 (MH+)

Example 62

Step 1 t-butyl 4-((5-(4-(3-(4-methoxybenzyloxy)phenylamino)thieno[3,2-d]pyrimidine-6-yl)thiophene-2-yl)methyl)piperazine-1-carboxylate The synthesis of (tert-butyl 4-((5-(4-(3-(4-methoxybenzyloxy)phenylamino)thieno[3,2-d]pyrimidin-6-yl)thiophene-2-yl)methyl)piperazine-1-carboxylate)

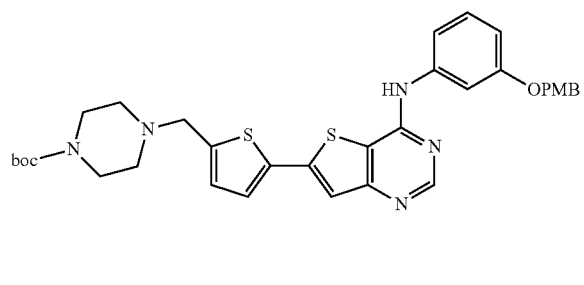

$^1$H-NMR (400 MHz, CDCl$_3$); δ 8.68 (s, 1H), 7.40 (s, 1H), 7.38 (d, J=8.4 Hz, 2H), 7.34-7.33 (m, 1H), 7.31 (t, J=7.8 Hz, 1H), 7.19 (d, J=3.6 Hz, 1H), 6.91 (d, J=8.4 Hz, 2H), 6.88-6.86 (m, 3H), 6.77 (brs, 1H), 5.04 (s, 2H), 3.81 (s, 3H), 3.72 (s, 2H), 3.44-3.42 (m, 4H), 2.47-2.46 (m, 4H), 1.48 (s, 9H); LC-MS 644 (MH+)

Step 2

3-(6-(5-(piperazine-1-ylmethyl)thiophene-2-yl)thieno[3,2-d]pyrimidine-4-ylamino)phenol trifluoroacetic acid The synthesis of (3-(6-(5-(piperazin-1-ylmethyl)thiophene-2-yl)thieno[3,2-d]pyrimidin-4-ylamino)phenol. TFA) (LCB03-0094)

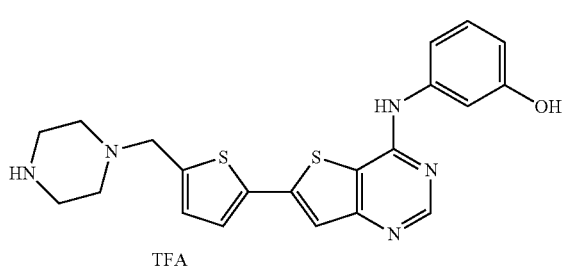 [SMILES: Oc1cccc(Nc2ncnc3cc(-c4ccc(CN5CCNCC5)s4)sc23)c1]

$^1$H-NMR (400 MHz, Acetone-d$_6$); δ 8.71 (s, 1H), 7.67 (s, 1H), 7.46 (d, J=3.6 Hz, 1H), 7.38 (s, 1H), 7.29-7.20 (m, 2H), 7.16-7.10 (m, 1H), 6.84-6.78 (m, 1H), 4.04 (s, 2H), 3.51-3.43 (m, 4H), 3.05-3.04 (m, 4H); LC-MS 538 (MH+)

Example 63

Step 1

6-(5-((ethylamino)methyl)thiophene-2-yl)-N-(3-(4-methoxybenzyloxy)phenyl)thieno[3,2-d]pyrimidine-4-amine The synthesis of (6-(5-((ethylamino)methyl)thiophene-2-yl)-N-(3-(4-methoxybenzyloxy)phenyl)thieno[3,2-d]pyrimidin-4-amine)

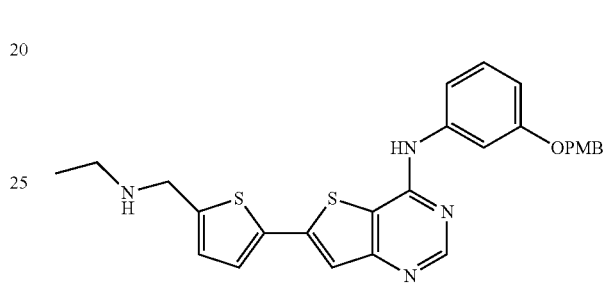

$^1$H-NMR (400 MHz, CDCl$_3$); δ 8.67 (s, 1H), 7.39 (s, 1H), 7.37 (d, J=7.8 Hz, 2H), 7.34-7.29 (m, 2H), 7.20 (d, J=3.6 Hz, 1H), 7.07 (d, J=7.8 Hz, 1H), 6.91 (d, J=7.2 Hz, 2H), 6.90 (d, J=3.6 Hz, 1H), 6.87 (d, J=7.8 Hz, 1H), 6.75 (brs, 1H), 5.03 (s, 1H), 4.00 (s, 2H), 3.81 (s, 3H), 2.74 (q, J=7.2 Hz, 2H), 1.17 (t, J=7.2 Hz, 3H; LC-MS 503 (MH+)

Step 2

3-(6-(5-((ethylamino)methyl)thiophene-2-yl)thieno[3,2-d]pyrimidine-4-ylamino)phenol trifluoroacetic acid The synthesis of (3-(6-(5-((ethylamino)methyl)thiophene-2-yl)thieno[3,2-d]pyrimidin-4-ylamino)phenol. TFA) (LCB03-0095)

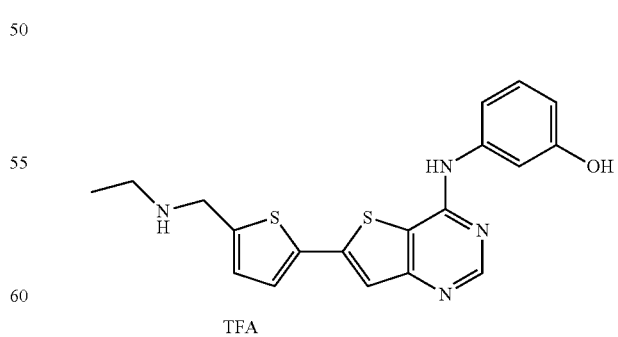

$^1$H-NMR (600 MHz, Acetone-d$_6$); δ 8.65 (s, 1H), 7.60 (s, 1H), 7.47-7.42 (m, 3H), 7.23-7.21 (m, 3H), 6.74-6.73 (m, 1H), 4.64 (s, 2H), 3.32-3.30 (m, 2H), 1.39 (t, J=6.4 Hz, 3H); LC-MS 383 (MH+)

Example 64

Step 1

N-(3-(4-methoxybenzyloxy)phenyl)-6-(5-(pyrrolidine-1-ylmethyl)furan-2-yl)thieno[3,2-d]pyrimidine-4-amine The synthesis of (N-(3-(4-methoxybenzyloxy)phenyl)-6-(5-(pyrrolidin-1-ylmethyl)furan-2-yl)thieno[3,2-d]pyrimidin-4-amine)

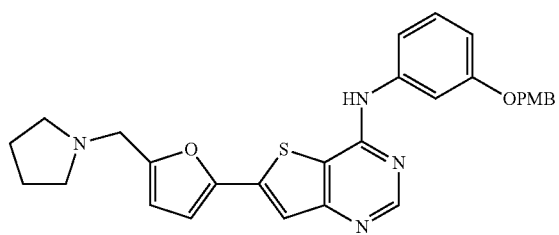

$^{1}$H-NMR (600 MHz, Acetone-d$_6$); δ 8.74 (brs, 1H), 8.62 (s, 1H), 7.73 (s, 1H), 7.57 (s, 1H), 7.43 (d, J=8.4 Hz, 2H), 7.40 (d, J=7.8 Hz, 1H), 7.27 (t, J=8.4 Hz, 1H), 7.00 (d, J=3.0 Hz, 1H), 6.95 (d, J=8.4 Hz, 2H), 6.80-6.78 (m, 1H), 6.55 (s, 1H), 5.07 (s, 2H), 3.84 (s, 2H), 3.80 (s, 3H), 3.59-3.57 (m, 3H), 2.65 (brm 5H); LC-MS 513 (MH+)

Step 2

3-(6-(5-(pyrrolidine-1-ylmethyl)furan-2-yl)thieno[3,2-d]pyrimidine-4-ylamino)phenol trifluoroacetic acid The synthesis of (3-(6-(5-(pyrrolidin-1-ylmethyl)furan-2-yl)thieno[3,2-d]pyrimidin-4-ylamino)phenol. TFA) (LCB03-0086)

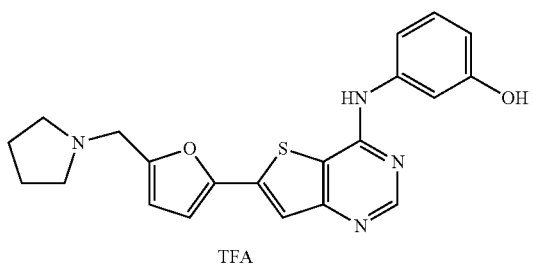 [SMILES: Oc1cccc(Nc2ncnc3cc(-c4ccc(CN5CCCC5)o4)sc23)c1]

$^{1}$H-NMR (600 MHz, CDCl$_3$); δ 8.60 (s, 1H), 7.31 (s, 1H), 7.27-7.26 (m, 1H), 7.22 (t, J=7.8 Hz, 1H), 6.81 (d, J=7.8 Hz, 1H), 6.82 (brs, 1H), 6.69 (dd, J=2.4, 8.4 Hz), 6.60 (d, J=3.0 Hz, 1H), 6.31 (d, J=3.0 Hz, 1H), 3.76 (s, 2H), 2.78-2.77 (m, 4H), 1.88-1.86 (m, 4H); LC-MS 330 (MH+)

Example 65

Step 1

N-(3-(4-methoxybenzyloxy)phenyl)-6-(5-((4-methylpiperazine-1-yl)methyl)furan-2-yl)thieno[3,2-d]pyrimidine-4-amine The synthesis of (N-(3-(4-methoxybenzyloxy)phenyl)-6-(5-((4-methylpiperazin-1-yl)methyl)furan-2-yl)thieno[3,2-d]pyrimidin-4-amine)

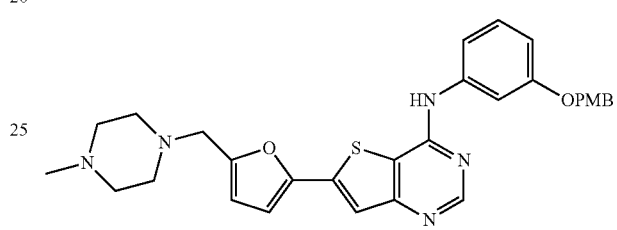

$^{1}$H-NMR (400 MHz, Acetone-d$_6$); δ 8.72 (brs, 1H), 8.62 (s, 1H), 7.74 (t, J=2.0 Hz, 1H), 7.55 (s, 1H), 7.44-7.40 (m, 3H), 7.27 (t, J=8.0 Hz, 1H), 6.99 d, J=3.2 Hz, 1H), 6.95 (d, J=8.8 Hz, 2H), 6.79 (dd, J=2.4, 8.4 Hz, 1H), 6.48 (d, J=3.6 Hz, 1H), 5.07 (s, 2H), 3.80 (s, 3H), 3.61 (s, 2H), 2.51-2.21 (m, 8H), 2.20 (s, 3H); LC-MS 542 (MH+)

Step 2

3-(6-(5-((4-methylpiperazine-1-yl)methyl)furan-2-yl)thieno[3,2-d]pyrimidine-4-ylamino)phenol trifluoroacetic acid The synthesis of (3-(6-(5-((4-methylpiperazin-1-yl)methyl)furan-2-yl)thieno[3,2-d]pyrimidin-4-ylamino)phenol. TFA) (LCB03-0087)

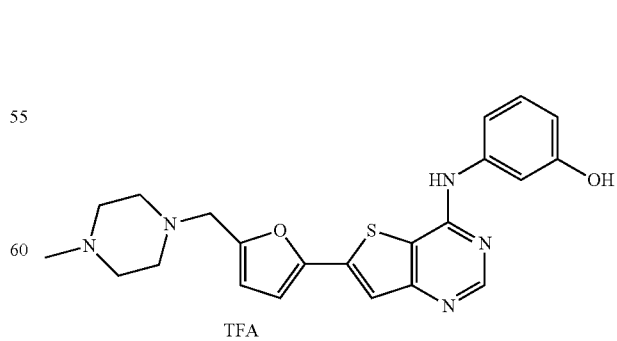

$^{1}$H-NMR (600 MHz, Acetone-d$_6$); δ 8.70 (brs, 1H), 8.61 (s, 1H), 7.58-7.53 (m, 2H), 7.28 (s, 1H), 7.21 (t, J=8.4H, 1H), 7.02 (s, 1H), 6.66 (d, J=7.8 Hz, 1H), 6.55 (s, 1H), 3.72 (s, 2H), 2.88-2.86 (m, 4H), 2.60-2.58 (m, 4H), 2.27 (s, 3H); LC-MS 422 (MH+)

Example 66

Step 1

N-(3-(4-methoxybenzyloxy)phenyl)-6-(5-(piperidine-1-ylmethyl)furan-2-yl)thieno[3,2-d]pyrimidine-4-amine The synthesis of (N-(3-(4-methoxybenzyloxy)phenyl)-6-(5-(piperidin-1-ylmethyl)furan-2-yl)thieno[3,2-d]pyrimidin-4-amine)

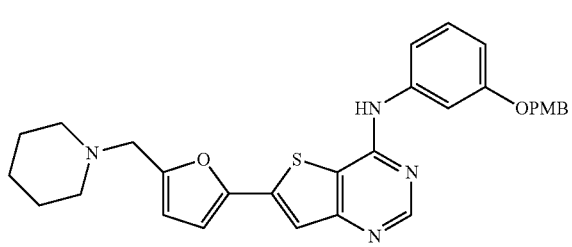

$^1$H-NMR (400 MHz, Acetone-d$_6$); δ 8.71 (brs, 1H), 8.62 (s, 1H), 7.74 (t, J=2.0 Hz, 1H), 7.54 (s, 1H), 7.44-7.39 (m, 4H), 7.28 (t, J=8.0 Hz, 1H), 6.98 (d, J=2.4 Hz, 1H), 6.95 (d, J=8.8 Hz, 2H), 6.80-6.77 (m, 1H), 6.45 (d, J=3.2 Hz, 1H), 5.07 (s, 2H), 3.80 (s, 3H), 3.57 (s, 2H), 2.46-2.45 (m, 4H), 1.59-1.53 (m, 4H), 1.42-1.41 (m, 2H); LC-MS 527 (MH+)

Step 2

3-(6-(5-(piperidine-1-ylmethyl)furan-2-yl)thieno[3,2-d]pyrimidine-4-ylamino)phenol trifluoroacetic acid The synthesis of (3-(6-(5-(piperidin-1-ylmethyl)furan-2-yl)thieno[3,2-d]pyrimidin-4-ylamino)phenol. TFA) (LCB03-0088)

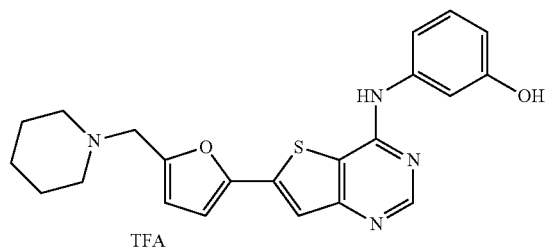 [SMILES: Oc1cccc(Nc2ncnc3cc(-c4ccc(CN5CCCCC5)o4)sc23)c1]

$^1$H-NMR (400 MHz, Acetone-d$_6$); δ 8.66 (s, 1H), 7.71 (s, 1H), 7.58 (s, 1H), 7.23-7.22 (m, 2H), 7.11 (d, J=4.8 Hz, 1H), 6.93 (d, J=4.8 Hz, 1H), 6.72-6.70 (m, 1H), 4.51 (s, 2H), 3.61 (brm, 6H), 1.93-1.91 (m, 4H); LC-MS 407 (MH+)

Example 67

Step 1

N-(3-(4-methoxybenzyloxy)phenyl)-6-(5-(morpholinomethyl)furan-2-yl)thieno[3,2-d]pyrimidine-4-amine The synthesis of (N-(3-(4-methoxybenzyloxy)phenyl)-6-(5-(morpholinomethyl)furan-2-yl)thieno[3,2-d]pyrimidin-4-amine)

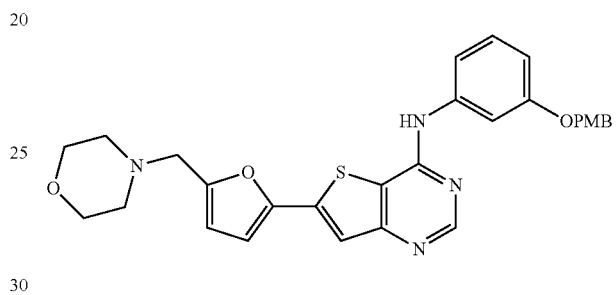

$^1$H-NMR (400 MHz, CDCl$_3$); δ 8.68 (s, 1H), 7.49 (s, 1H), 7.38-7.31 (m, 4H), 7.08 (dd, J=1.6, 7.6 Hz, 1H), 6.92 (brs, 1H), 6.90-6.85 (m, 3H), 6.70 (d, J=3.2 Hz, 1H), 6.35 (d, J=3.2 Hz, 1H), 5.03 (s, 2H), 3.80 (s, 3H), 3.74-3.72 (m, 4H), 3.62 (s, 2H), 2.56-2.53 (m, 4H); LC-MS 529 (MH+)

Step 2

3-(6-(5-(morpholinomethyl)furan-2-yl)thieno[3,2-d]pyrimidine-4-ylamino)phenol trifluoroacetic acid The synthesis of (3-(6-(5-(morpholinomethyl)furan-2-yl)thieno[3,2-d]pyrimidin-4-ylamino)phenol. TFA) (LCB03-0089)

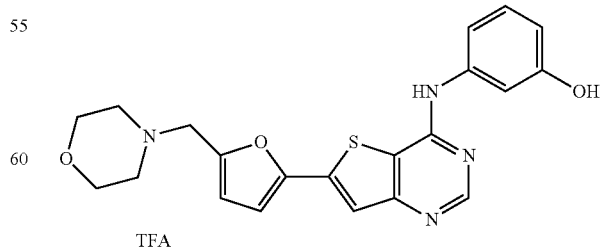

$^1$H-NMR (400 MHz, CDCl$_3$); δ 8.69 (s, 1H), 7.75 (s, 1H), 7.45 (s, 1H), 7.23 (d, J=5.2 Hz, 2H), 7.09 (d, J=3.2H, 1H), 6.90 (d, J=3.6 Hz, 1H), 6.76-6.71 (m, 1H), 4.48 (s, 2H), 3.94-3.93 (m, 4H), 3.34-3.31 (m, 4H); LC-MS 409 (MH+)

Example 68

Step 1 t-butyl 4-((5-(4-(3-(4-methoxybenzyloxy)phenylamino)thieno[3,2-d]pyrimidine-6-yl)furan-2-yl)methyl)piperazine-1-carboxylate The synthesis of (tert-butyl 4-((5-(4-(3-(4-methoxybenzyloxy)phenylamino)thieno[3,2-d]pyrimidin-6-yl)furan-2-yl)methyl)piperazine-1-carboxylate)

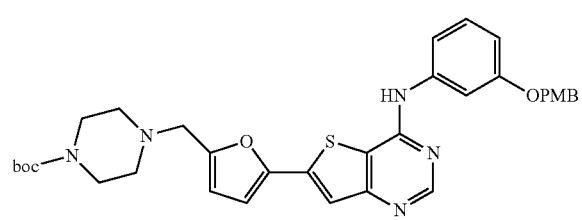

¹H-NMR (400 MHz, CDCl₃); δ 8.67 (s, 1H), 7.47 (s, 1H), 7.37-7.34 (m, 4H), 7.28 (t, J=8.0 Hz, 1H), 7.10-7.08 (m, 1H), 6.91-6.85 (m, 3H), 6.90 (d, J=3.2 Hz, 1H), 6.33 (d, J=3.6 Hz, 1H), 5.02 (s, 2H), 3.80 (s, 3H), 3.63 (s, 2H), 3.48-3.44 (m, 4H), 2.49-2.47 (m, 4H), 1.45 (s, 9H); LC-MS 628 (MH+)

Step 2

3-(6-(5-(piperazine-1-ylmethyl)furan-2-yl)thieno[3,2-d]pyrimidine-4-ylamino)phenol trifluoroacetic acid The synthesis of (3-(6-(5-(piperazin-1-ylmethyl)furan-2-yl)thieno[3,2-d]pyrimidin-4-ylamino)phenol. TFA) (LCB03-0090)

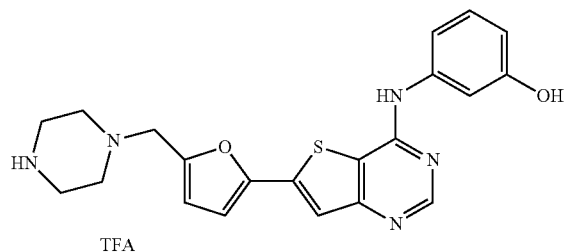 [SMILES: Oc1cccc(Nc2ncnc3cc(-c4ccc(CN5CCNCC5)o4)sc23)c1]

¹H-NMR (400 MHz, Acetone-d₆); δ 8.76 (brs, 1H), 7.74 (s, 1H), 7.37-7.36 (m, 1H), 7.28 (t, J=7.6 Hz, 1H), 7.20-7.28 (m, 1H), 7.12-7.10 (m, 2H), 6.84-6.82 (m, 2H), 6.67 (d, J=3.2 Hz, 1H), 3.95 (s, 2H), 3.53 (m, 4H), 3.14 (m, 4H); LC-MS 408 (MH+)

Example 69

Step 1

6-(5-((ethylamino)methyl)furan-2-yl)-N-(3-(4-methoxybenzyloxy)phenyl)thieno[3,2-d]pyrimidine-4-amine The synthesis of (6-(5-((ethylamino)methyl)furan-2-yl)-N-(3-(4-methoxybenzyloxy)phenyl)thieno[3,2-d]pyrimidin-4-amine)

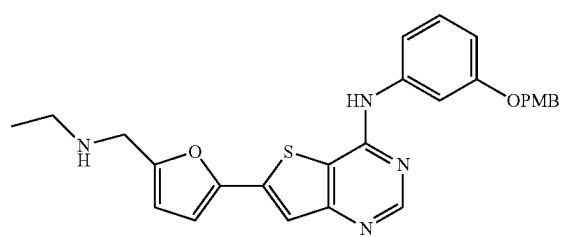

¹H-NMR (400 MHz, CDCl₃); δ 8.67 (s, 1H), 7.46 (s, 1H), 7.38-7.28 (m, 4H), 7.08 (dd, J=1.2, 8.0 Hz, 1H), 6.90 (d, J=8.8 Hz, 2H), 6.86 (dd, J=1.6, 7.6 Hz, 1H), 6.68 (d, J=3.0 Hz, 1H), 6.32 (d, J=3.2 Hz, 1H), 5.02 (s, 2H), 3.87 (s, 2H), 3.80 (s, 3H), 3.48 (q, J=7.2 Hz, 2H), 2.74 (q, J=7.2 Hz, 2H), 1.17 (t, J=7.2 Hz, 3H); LC-MS 487 (MH+)

Step 2

3-(6-(5-((ethylamino)methyl)furan-2-yl)thieno[3,2-d]pyrimidine-4-ylamino)phenol trifluoroacetic acid The synthesis of (3-(6-(5-((ethylamino)methyl)furan-2-yl)thieno[3,2-d]pyrimidin-4-ylamino)phenol. TFA) (LCB03-0091)

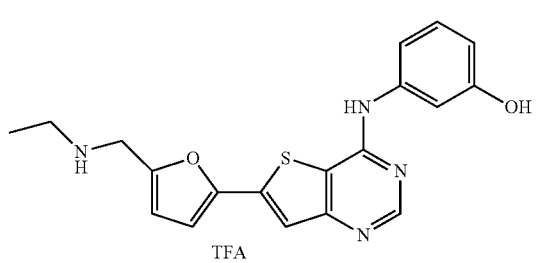 [SMILES: CCNCc1ccc(-c2cc3ncnc(Nc4cccc(O)c4)c3s2)o1]

¹H-NMR (400 MHz, CDCl₃); δ 8.67 (brs, 1H), 7.68 (s, 1H), 7.41 (s, 1H), 7.26-7.19 (m, 3H), 7.01 (d, J=3.2 Hz, 1H), 6.86 (d, J=3.2 Hz, 1H), 6.75-6.73 (m, 1H), 4.55 (s, 2H), 3.34 (q, J=6.8 Hz, 2H), 1.41 (t, J=7.2 Hz, 3H); LC-MS 367 (MH+)

Example 70

Step 1

N-(3-(4-methoxybenzyloxy)phenyl)-6-(4-(morpholinomethyl)thiophene-2-yl)thieno[3,2-d]pyrimidine-4-amine The synthesis of (N-(3-(4-methoxybenzyloxy)phenyl)-6-(4-(morpholinomethyl)thiophene-2-yl)thieno[3,2-d]pyrimidin-4-amine)

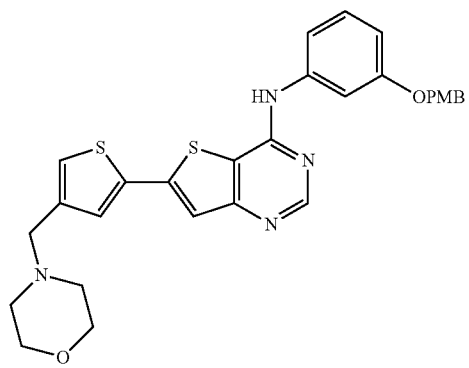

$^1$H-NMR (400 MHz, CDCl$_3$); δ 8.68 (s, 1H), 7.44 (s, 1H), 7.38 (d, J=8.8 Hz, 2H), 7.32 (m, 3H), 7.19 (s, 1H), 7.09 (d, J=8.0 Hz, 1H), 6.92 (d, J=8.8 Hz, 2H), 6.89 (m, 1H), 6.83 (br, 1H), 5.03 (s, 2H), 3.80 (s, 3H), 3.68 (m, 2H), 3.47-3.44 (m, 4H), 2.48 (m, 4H); LC-MS 423 (MH+)

Step 2

3-(6-(4-(morpholinomethyl)thiophene-2-yl)thieno[3,2-d]pyrimidine-4-ylamino)phenol trifluoroacetic acid The synthesis of (3-(6-(4-(morpholinomethyl)thiophene-2-yl)thieno[3,2-d]pyrimidin-4-ylamino)phenol. TFA) (LCB03-0104)

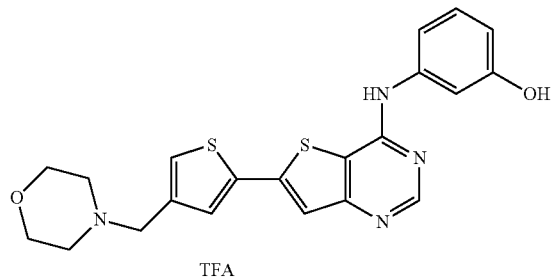 [SMILES: Oc1cccc(Nc2ncnc3cc(-c4cc(CN5CCOCC5)cs4)sc23)c1]

$^1$H-NMR (400 MHz, Acetone-d$_6$); δ 8.89 (s, 1H), 7.98 (s, 1H), 7.82 (s, 1H), 7.72 (s, 1H), 7.42 (s, 1H), 7.28 (m, 2H), 7.15 (m, 1H), 6.87 (m, 1H), 6.79 (s, 1H), 4.51 (m, 2H), 3.77 (m, 2H), 3.45 (m, 2H), 1.15 (m, 4H); LC-MS 425 (MH+)

Example 71

Step 1 t-butyl 4-((5-(4-(3-(4-methoxybenzyloxy)phenylamino)thieno[3,2-d]pyrimidin-6-yl)thiophene-3-yl)methyl)piperazine-1-carboxylate The synthesis of (tert-butyl 4-((5-(4-(3-(4-methoxybenzyloxy)phenylamino)thieno[3,2-d]pyrimidin-6-yl)thiophene-3-yl)methyl)piperazine-1-carboxylate)

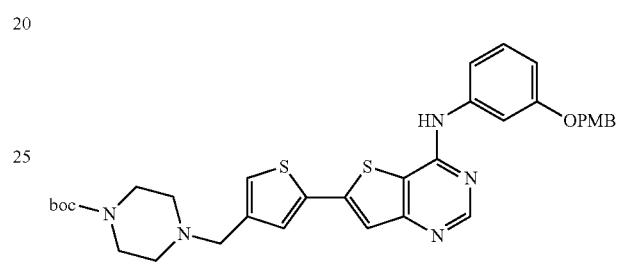

$^1$H-NMR (400 MHz, CDCl$_3$); δ 8.68 (s, 1H), 7.42 (s, 1H), 7.36 (d, J=6.0 Hz, 2H), 7.33-7.31 (m, 3H), 7.19 (s, 1H), 7.11 (d, J=5.6 Hz, 1H), 6.68-6.66 (m, 3H), 5.02 (s, s 2H), 3.70 (s, 3H), 3.47-3.44 (m, 4H), 3.43 (s, 2H), 2.44-2.42 (m, 4H), 1.46 (s, 9H); LC-MS 524 (MH+)

Step 2

3-(6-(4-(piperazine-1-ylmethyl)thiophene-2-yl)thieno[3,2-d]pyrimidine-4-ylamino)phenol trifluoroacetic acid The synthesis of (3-(6-(4-(piperazin-1-ylmethyl)thiophene-2-yl)thieno[3,2-d]pyrimidin-4-ylamino)phenol. TFA) (LCB03-0105)

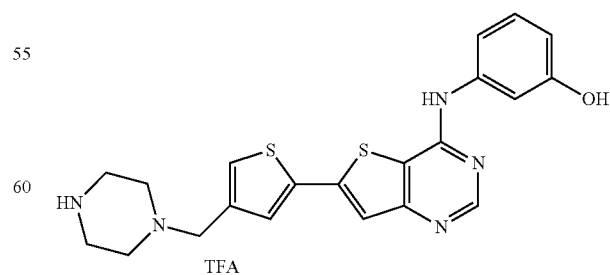

$^1$H-NMR (400 MHz, DMSO-d$_6$); δ 8.95 (s, 1H), 8.15 (s, 1H), 7.40-7.37 (m, 2H), 7.32-7.27 (m, 1H), 7.13-7.11 (m,

2H), 6.93 (m, 1H), 6.86 (m, 1H), 4.29 (s, 2H), 3.75 (brm, 4H), 1.98-1.97 (m, 4H); LC-MS 422 (MH+)

Example 72

Step 1

N-(3-(4-methoxybenzyloxy)phenyl)-6-(4-(pyrrolidine-1-ylmethyl)thiophene-2-yl)thieno[3,2-d]pyrimidine-4-amine The synthesis of (N-(3-(4-methoxybenzyloxy)phenyl)-6-(4-(pyrrolidin-1-ylmethyl)thiophene-2-yl)thieno[3,2-d]pyrimidin-4-amine)

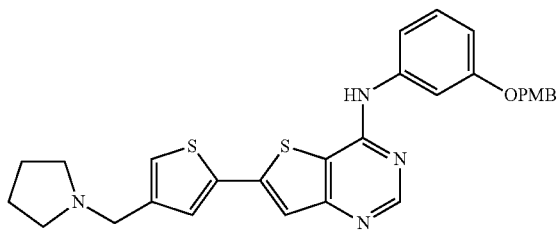

$^1$H-NMR (400 MHz, CDCl$_3$); δ 8.66 (s, 1H), 7.42 (s, 1H), 7.-7.36 (m, 3H), 7.66 (t, J=1.6 Hz, 1H), 7.31 (d, J=5.6 Hz, 1H), 7.25 (s, 1H), 7.10 (d, J=3.6 Hz, 1H), 6.91 (d, J=6.0 Hz, 2H), 6.87 (d, J=5.6 Hz, 1H), 3.68 (s, 2H), 2.64 (m, 4H), 1.85 (m, 4H); LC-MS 409 (M+H+)

Step 2

3-(6-(4-(pyrrolidine-1-ylmethyl)thiophene-2-yl)thieno[3,2-d]pyrimidine-4-ylamino)phenoltrifluoroacetic acid The synthesis of (3-(6-(4-(pyrrolidin-1-ylmethyl)thiophene-2-yl)thieno[3,2-d]pyrimidin-4-ylamino)phenol. TFA) (LCB03-0101)

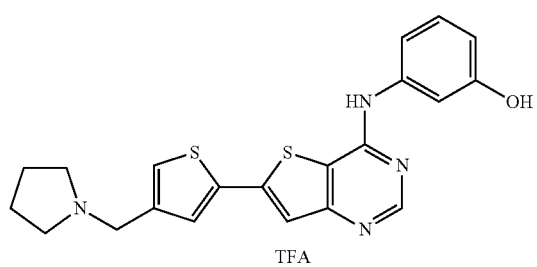 [SMILES: Oc1cccc(Nc2ncnc3cc(-c4cc(CN5CCCC5)cs4)sc23)c1]

$^1$H-NMR (400 MHz, CDCl$_3$); δ 8.59 (s, 1H), 7.26-7.21 (m, 1H), 7.14-7.11 (m, 2H), 7.01 (d, J=3.6 Hz, 1H), 6.84 (d, J=8.0 Hz, 1H), 6.81 (d, J=3.6 Hz, 1H), 6.75 (dd, J=1.6, 8.4 Hz, 1H), 3.81 (s, 2H), 2.69 (brm, 4H), 2.04-2.02 (m, 4H); LC-MS 409 (MH+)

Example 73

Step 1

6-(4-((ethylamino)methyl)thiophene-2-yl)-N-(3-(4-methoxybenzyloxy)phenyl)thieno[3,2-d]pyrimidine-4-amine The synthesis of (6-(4-((ethylamino)methyl)thiophene-2-yl)-N-(3-(4-methoxybenzyloxy)phenyl)thieno[3,2-d]pyrimidin-4-amine)

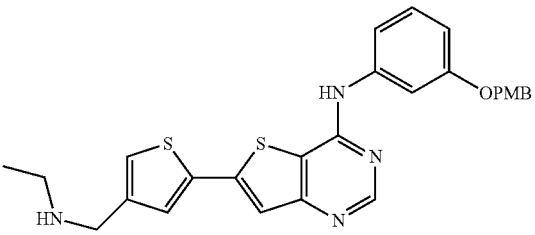

$^1$H-NMR (600 MHz, CDCl$_3$); δ 8.68 (s, 1H), 7.42 (s, 1H), 7.38 (d, J=6.0 Hz, 2H), 7.33 (m, 3H), 7.19 (s, 1H), 7.09 (d, J=5.6 Hz, 1H), 6.68 (m, 3H), 3.80 (s, 2H), 2.71 (m, 2H), 1.06 (m, 3H); LC-MS 383 (MH+)

Step 2

3-(6-(4-((ethylaminomethyl)thiophene-2-yl)thieno[3,2-d]pyrimidine-4-ylamino)phenol trifluoroacetic acid The synthesis of (3-(6-(4-((ethylamino)methyl)thiophene-2-yl)thieno[3,2-d]pyrimidin-4-ylamino)phenol. TFA) (LCB03-0106)

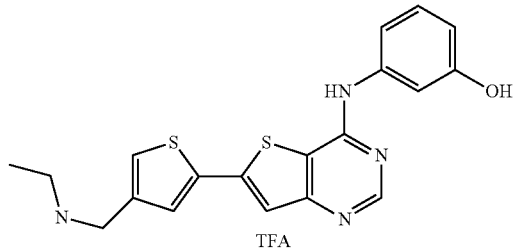 [SMILES: CCNCc1csc(-c2cc3ncnc(Nc4cccc(O)c4)c3s2)c1]

$^1$H-NMR (600 MHz, Acetone-d$_6$); δ 8.65 (s, 1H), 7.60 (s, 1H), 7.47-7.42 (m, 3H), 7.23-7.21 (m, 3H), 6.74-6.73 (m, 1H), 4.64 (s, 2H), 3.32-3.30 (m, 2H), 1.39 (t, J=6.4 Hz, 3H); LC-MS 383 (MH+)

Example 74

Step 1

N-(3-(4-methoxybenzyloxy)phenyl)-6-(4-(pyrrolidine-1-ylmethyl)furan-2-yl)thieno[3,2-d]pyrimidine-4-amine The synthesis of (N-(3-(4-methoxybenzyloxy)phenyl)-6-(4-(pyrrolidin-1-ylmethyl)furan-2-yl)thieno[3,2-d]pyrimidin-4-amine)

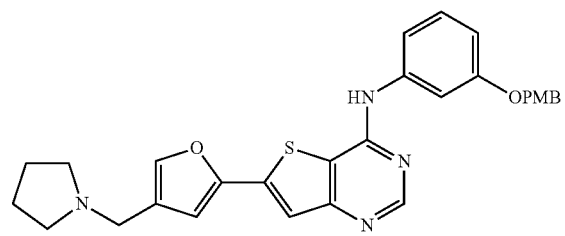

¹H-NMR (400 MHz, CDCl₃); δ 8.96 (s, 1H), 8.73 (s, 1H), 8.17 (s, 1H), 7.41-7.36 (m, 2H), 7.32-7.26 (m, 2H), 7.14-7.10 (m, 2H), 6.92 (d, J=8.4 Hz, 2H), 6.85 (m, 1H), 5.07 (s, 2H), 4.16 (s, 2H), 3.76 (s, 3H), 3.57 (m, 4H), 1.95 (m, 4H); LC-MS 393 (MH+)

Step 2

3-(6-(4-(pyrrolidine-1-ylmethyl)furan-2-yl)thieno[3,2-d]pyrimidine-4-ylamino)phenol trifluoroacetic acid The synthesis of (3-(6-(4-(pyrrolidin-1-ylmethyl)furan-2-yl)thieno[3,2-d]pyrimidin-4-ylamino)phenol. TFA) (LCB03-0113)

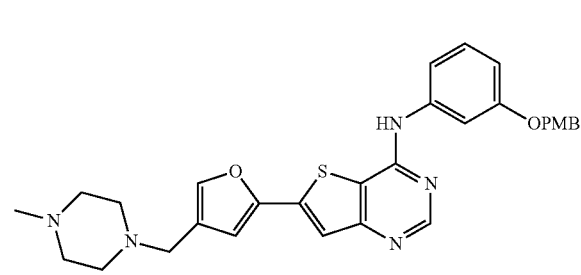

¹H-NMR (400 MHz, DMSO-d₆); δ 8.76 (s, 1H), 8.16 (s, 1H), 7.41-7.37 (m, 2H), 7.32-7.26 (m, 1H), 7.14-7.11 (m, 2H), 6.93 (m, 1H), 6.86 (m, 1H), 4.50 (s, 2H), 2.48 (m, 4H), 1.72 (m, 4H); LC-MS 393 (MH+)

Example 75

Step 1

N-(3-(4-methoxybenzyloxy)phenyl)-6-(4-((4-methylpiperazine-1-yl)methyl)furan-2-yl)thieno[3,2-d]pyrimidine-4-amine The synthesis of (N-(3-(4-methoxybenzyloxy)phenyl)-6-(4-((4-methylpiperazin-1-yl)methyl)furan-2-yl)thieno[3,2-d]pyrimidin-4-amine)

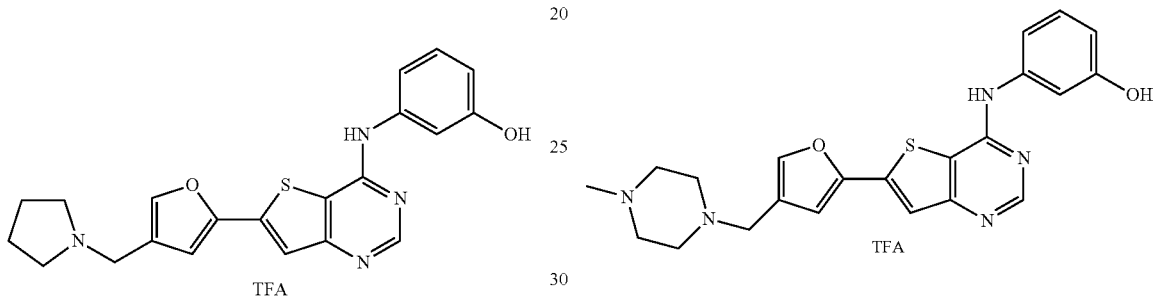

¹H-NMR (600 MHz, CDCl₃); δ 8.95 (s, 1H), 8.73 (s, 1H), 8.19 (s, 1H), 7.37-7.29 (m, 3H), 7.11 (d, J=8.4 Hz, 2H), 6.92-6.86 (m, 3H), 6.79 (s, 1H), 5.02 (s, 2H), 3.74 (s, 3H), 3.45 (s, 2H), 3.57 (m, 4H), 1.95 (m, 4H), 2.27 (s, 3H); LC-MS 542 (MH+)

Step 2

3-(6-(4-((4-methylpiperazine-1-yl)furan-2-yl)thieno[3,2-d]pyrimidine-4-ylamino)phenol trifluoroacetic acid The synthesis of (3-(6-(4-((4-methylpiperazin-1-yl)methyl)furan-2-yl)thieno[3,2-d]pyrimidin-4-ylamino)phenol. TFA) (LCB03-0114)

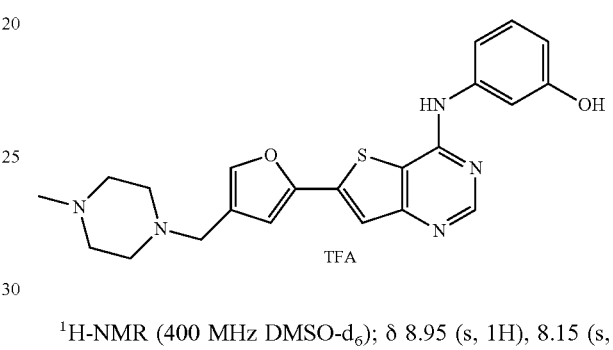

¹H-NMR (400 MHz DMSO-d₆); δ 8.95 (s, 1H), 8.15 (s, 1H), 7.40-7.37 (m, 2H), 7.32-7.27 (m, 1H), 7.13-7.11 (m, 2H), 6.93 (m, 1H), 6.86 (m, 1H), 4.29 (s, 2H), 2.65-2.63 (m, 4H), 2.44 (s, 3H), 1.47-1.45 (m, 4H); LC-MS 422 (MH+)

Example 76

Step 1

N-(3-(4-methoxybenzyloxy)phenyl)-6-(4-(piperidine-1-ylmethyl)furan-2-yl)thieno[3,2-d]pyrimidine-4-amine The synthesis of (N-(3-(4-methoxybenzyloxy)phenyl)-6-(4-(piperidin-1-ylmethyl)furan-2-yl)thieno[3,2-d]pyrimidin-4-amine)

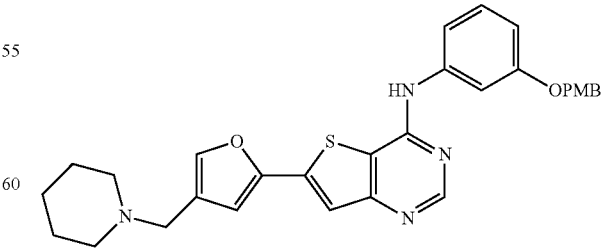

¹H-NMR (600 MHz, CDCl₃); δ 8.92 (s, 1H), 8.75 (s, 1H), 8.19 (s, 1H), 7.39-7.36 (m, 3H), 7.30 (t, J=7.8 Hz, 1H), 7.12 (d, J=8.4 Hz, 1H), 6.92 (d, J=8.4 Hz, 2H), 6.86 (d, J=8.4 Hz,

1H), 6.80 (s, 1H), 5.02 (s, 2H), 4.19 (s, 2H), 3.81 (s, 3H), 3.43 (m, 4H) 1.64 (m, 6H); LC-MS 527 (MH+)

Step 2

3-(6-(4-(piperidine-1-ylmethyl)furan-2-yl)thieno[3,2-d]pyrimidine-4-ylamino)phenol The synthesis of (3-(6-(4-(piperidin-1-ylmethyl)furan-2-yl)thieno[3,2-d]pyrimidin-4-ylamino)phenol) (LCB03-0115)

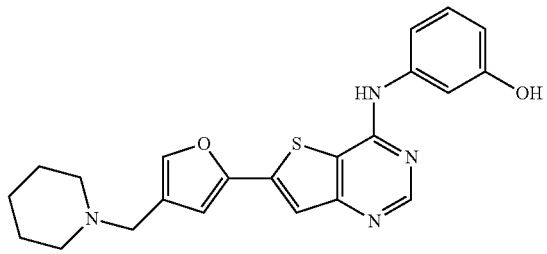 [SMILES: Oc1cccc(Nc2ncnc3cc(-c4cc(CN5CCCCC5)co4)sc23)c1]

$^1$H-NMR (400 MHz, Acetone-d$_6$); δ 8.79 (brs, 1H), 7.74 (s, 1H), 7.37-7.36 (m, 1H), 7.28 (t, J=7.6 Hz, 1H), 7.20-7.18 (m, 1H), 7.12-7.10 (m, 2H), 6.84-6.82 (m, 2H), 6.67 (d, J=3.2 Hz, 1H), 4.50 (s, 2H), 2.48 (m, 4H), 1.72 (m, 4H), 1.37 (m, 2H); LC-MS 407.0 (MH+)

Example 77

3-(6-(4-(piperidine-1-ylmethyl)thiophene-2-yl)thieno[3,2-d]pyrimidine-4-ylamino)phenol trifluoroacetic acid The synthesis of (3-(6-(4-(piperidin-1-ylmethyl)thiophene-2-yl)thieno[3,2-d]pyrimidin-4-ylamino)phenol. TFA) (LCB03-0103)

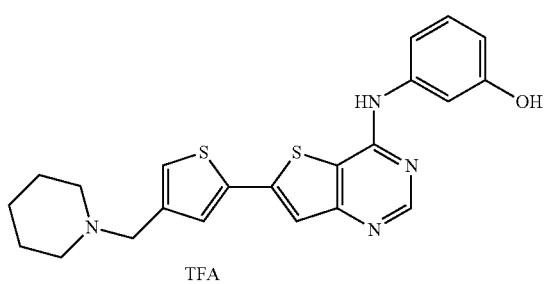 [SMILES: Oc1cccc(Nc2ncnc3cc(-c4cc(CN5CCCCC5)cs4)sc23)c1]

$^1$H-NMR (400 MHz, DMSO-d$_6$); δ 8.76 (s, 1H), 8.16 (s, 1H), 7.41-7.37 (m, 2H), 7.32-7.26 (m, 1H), 7.14-7.11 (m, 2H), 6.93 (m, 1H), 6.86 (m, 1H), 4.50 (s, 2H), 2.48 (m, 4H), 1.72 (m, 4H) 1.56-1.54 (m, 2H); LC-MS 393 (MH+)

Example 78

3-(6-(4-((4-methylpiperazine-1-yl)methyl)thiophene-2-yl)thieno[3,2-d]pyrimidine-4-ylamino)phenol The synthesis of (3-(6-(4-((4-methylpiperazin-1-yl)methyl)thiophene-2-yl)thieno[3,2-d]pyrimidin-4-ylamino)phenol) (LCB03-0102)

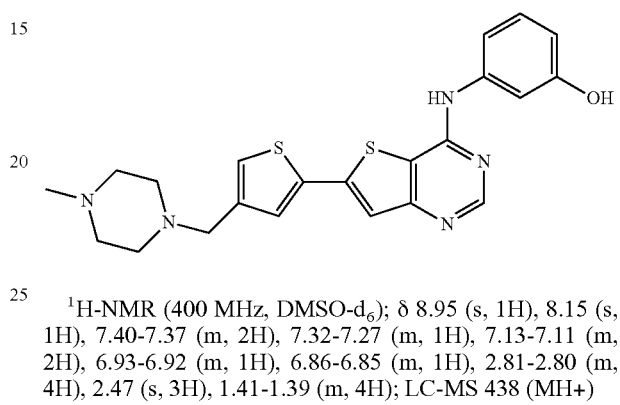

$^1$H-NMR (400 MHz, DMSO-d$_6$); δ 8.95 (s, 1H), 8.15 (s, 1H), 7.40-7.37 (m, 2H), 7.32-7.27 (m, 1H), 7.13-7.11 (m, 2H), 6.93-6.92 (m, 1H), 6.86-6.85 (m, 1H), 2.81-2.80 (m, 4H), 2.47 (s, 3H), 1.41-1.39 (m, 4H); LC-MS 438 (MH+)

Example 79

Step 1

N-(3-(4-methoxybenzyloxy)phenyl)-2-(4-(piperidine-1-ylmethyl)phenyl)thieno[3,2-b]pyridine-7-amine The synthesis of (N-(3-(4-methoxybenzyloxy)phenyl)-2-(4-(piperidin-1-ylmethyl)phenyl)thieno[3,2-b]pyridin-7-amine)

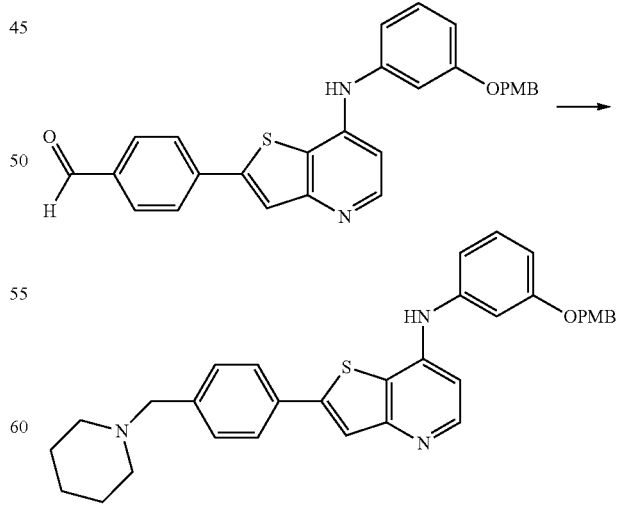

The compound (50 mg, 0.10 mmol) synthesized in the example of synthesis 24 and piperidine (92 mg, 1.07 mmol) were added sequentially into 1 ml of dichloroethane and stirred for 20 minutes, and then further stirred for 5 hours at room temperature after adding sodium acetate (26 mg, 0.32 mmol) and sodium triacethoxyborohydride (136 mg, 0.64 mmol). The resultant reaction mixture was extracted with 30 ml of dichloromethane and 30 ml of saturated ammonium chloride solution. The organic layer was dried with sodium sulfate and concentrated under vacuum. After column chromatography (dichloromethane/methanol, 1/25), the title compound (42 mg, 73%) was obtained.

$^1$H-NMR (400 MHz, CDCl$_3$); δ 8.35 (d, J=5.6 Hz, 1H), 7.74-7.72 (m, 1H), 7.62 (d, J=5.6 Hz, 1H), 7.39-7.29 (m, 4H), 6.91-6.78 (m, 6H), 6.16 (s, 1H), 5.01 (s, 2H), 3.81 (s, 3H), 3.55 (s, 2H), 2.44 (m, 4H), 2.12 (m, 2H), 1.61 (m, 4H); LC-MS: 536 (MH+)

Step 2

3-(2-(4-(piperidine-1-ylmethyl)phenyl)thieno[3,2-b]pyridine-7-ylamino)phenol trifluoroacetic acid The synthesis of (3-(2-(4-(piperidin-1-ylmethyl)phenyl)thieno[3,2-b]pyridin-7-ylamino)phenol. TFA) (LCB03-0097)

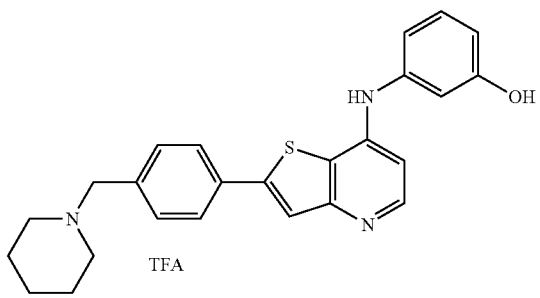 [SMILES: Oc1cccc(Nc2ccnc3cc(-c4ccc(CN5CCCCC5)cc4)sc23)c1]

The compound (15 mg, 0.03 mmol) synthesized in the step 1 described above was dissolved in 1 ml of dichloromethane. It was further stirred at room temperature for 15 hours after adding 1 ml of trifluoroacetic acid and anisole (40 mg, 0.38 mmol) and concentrated under vacuum. The resultant reaction mixture was subject to azotrope-concentration using dichloromethane, methanol, and diethylether and vacuum-dried to obtain the title compound (14 mg, 99%) as yellowish solid.

$^1$H-NMR (400 MHz, CDCl$_3$); δ 8.41-8.40 (m, 1H), 8.17 (s, 1H), 7.83 (d, J=8.4 Hz, 2H), 7.74 (d, J=8.4 Hz, 2H), 7.34 (t, J=8.4 Hzm 1H), 7.08-7.06 (m, 1H), 7.01-6.99 (m, 2H), 6.96-6.90 (m, 2H), 4.41 (s, 2H), 3.83-3.80 (m, 4H), 2.95-2.93 (m, 2H), 1.90-1.88 (m, 4H); LC-MS 416 (MH+)

The following compounds were synthesized by the method similar to the one described in the preferred embodiment 79 described above.

Example 80

Step 1

N-(3-(4-methoxybenzyloxy)phenyl)-2-(4-((4-methylpiperazine-1-ylmethyl)phenyl)thieno[3,2-b]pyridine-7-amine (N-(3-(4-methoxybenzyloxy)phenyl)

The synthesis of 2-(4-((4-methylpiperazin-1-yl)methyl)phenyl)thieno[3,2-b]pyridin-7-amine)

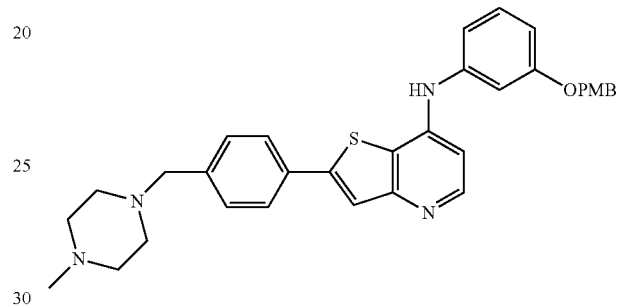

$^1$H-NMR (400 MHz, CDCl$_3$); δ 8.36 (d, J=5.2 Hz, 1H), 7.70-7.68 (m, 3H), 7.41 (d, J=7.2 Hz, 2H), 7.36 (d, J=6.8 Hz, 2H), 7.31 (t, J=8.4 Hz, 1H), 6.93 (d, J=6.8 Hz, 2H), 6.89-6.84 (m, 3H), 6.80 (d, J=7.6 Hz, 1H), 6.01 (s, 1H), 5.02 (s, 2H), 3.82 (s, 3H), 3.56 (s, 2H), 2.52 (m, 4H), 2.32 (s, 3H), 1.76 (m, 4H); LC-MS: 538 (MH+)

Step 2

3-(2-(4-((4-methylpiperazine-1-ylmethyl)phenyl)thieno[3,2-b]pyridine-7-ylamino)phenol trifluoroacetic acid The synthesis of (3-(2-(4-((4-methylpiperazin-1-yl)methyl)phenyl)thieno[3,2-b]pyridin-7-ylamino)phenol. TFA) (LCB03-0084)

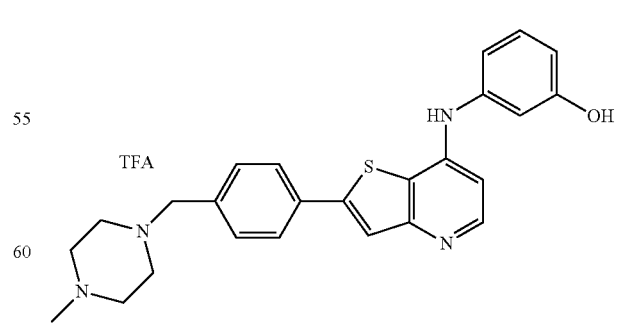

$^1$H-NMR (600 MHz, Acetone-d$_6$); δ 9.98 (brs, 1H), 8.41 (brs, 1H), 8.04 (s, 1H), 7.81 (d, J=7.2 Hz, 2H), 7.69 (d, J=7.2 Hz, 2H), 7.36 (t, J=8.4 Hz, 1H), 7.11 (d, J=8.4 Hz, 2H), 6.99

(s, 1H), 6.92-6.91 (m, 1H), 6.82 (d, J=8.4 Hz, 2H), 4.40 (s, 2H), 3.75-3.74 (m, 4H), 3.66-3.65 (m, 4H), 3.00 (s, 3H); LC-MS: 431 (MH+)

Example 81

Step 1

N-(3-(4-methoxybenzyloxy)phenyl)-2-(4-(pyrrolidine-1-ylmethyl)phenyl)thieno[3,2-b]pyridine-7-amine The synthesis of (N-(3-(4-methoxybenzyloxy)phenyl)-2-(4-(pyrrolidin-1-ylmethyl)phenyl)thieno[3,2-b]pyridin-7-amine)

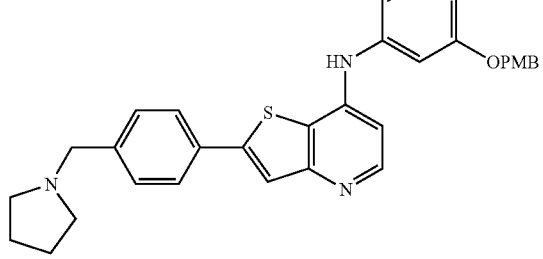

$^1$H-NMR (400 MHz, CDCl$_3$); δ 8.36 (s, 1H), 7.75-7.73 (m, 1H), 7.66-7.65 (m, 1H), 7.41-7.29 (m, 5H), 6.93-6.79 (m, 6H), 6.14 (s, 1H), 5.05 (s, 2H), 3.82 (s, 3H), 3.76 (s, 2H), 2.62 (m, 4H), 1.83 (m, 4H); LC-MS: 523 (MH+)

Step 2

3-(2-(4-(pyrrolidine-1-ylmethyl)phenyl)thieno[3,2-b]pyridine-7-ylamino)phenol trifluoroacetic acid The synthesis of (3-(2-(4-(pyrrolidin-1-ylmethyl)phenyl)thieno[3,2-b]pyridin-7-ylamino)phenol. TFA) (LCB03-0080)

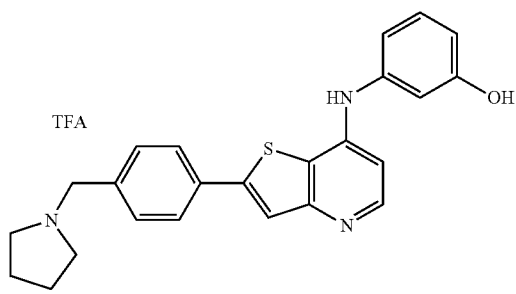 [SMILES: Oc1cccc(Nc2ccnc3cc(-c4ccc(CN5CCCC5)cc4)sc23)c1]

$^1$H-NMR (400 MHz, Acetone-d$_6$); δ 8.41-8.40 (m, 1H), 8.17 (s, 1H), 7.83 (d, J=8.4 Hz, 2H), 7.74 (d, J=8.4 Hz, 2H), 7.34 (t, J=8.4 Hz, 1H), 7.08-7.06 (m, 1H), 7.01-6.99 (m, 2H), 6.96-6.90 (m, 2H), 4.41 (s, 2H), 3.83-3.80 (m, 4H), 1.90-1.88 (m, 4H); LC-MS 402 (MH+)

Example 82

Step 1

N-(3-(4-methoxybenzyloxy)phenyl)-2-(4-(morpholinomethyl)phenyl)thieno[3,2-b]pyridine-7-amine The synthesis of (N-(3-(4-methoxybenzyloxy)phenyl)-2-(4-(morpholinomethyl)phenyl)thieno[3,2-b]pyridin-7-amine)

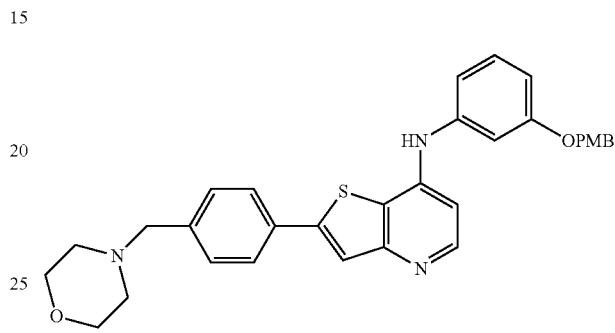

$^1$H-NMR (400 MHz, CDCl$_3$); δ 8.38 (d, J=5.2 Hz, 1H), 7.72-7.70 (m, 3H), 7.44 (d, J=7.2 Hz, 2H), 7.35 (d, J=7.2 Hz, 2H), 7.32-7.29 (m, 1H), 6.94 (d, J=6.8 Hz, 2H), 6.90-6.81 (m, 4H), 6.02 (s, 1H), 5.03 (s, 2H), 3.84 (s, 3H), 3.74-3.73 (m, 4H), 2.50-2.49 (m, 4H); LC-MS: 551 (MH+)

Step 2

3-(2-(4-(morpholinomethyl)phenyl)thieno[3,2-b]pyridine-7-ylamino)phenol trifluoroacetic acid The synthesis of (3-(2-(4-(morpholinomethyl)phenyl)thieno[3,2-b]pyridin-7-ylamino)phenol. TFA) (LCB03-0083)

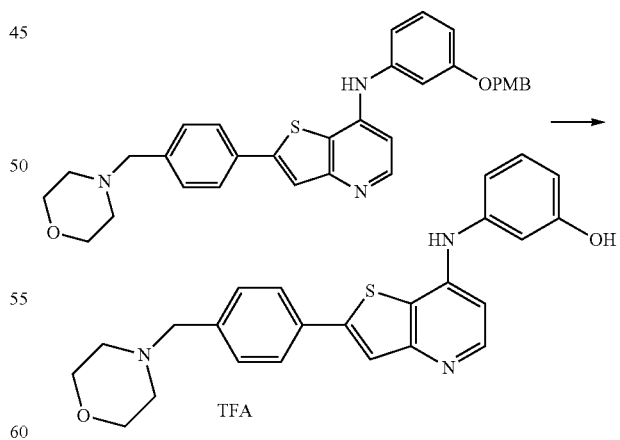

The compound (15 mg, 0.03 mmol) synthesized in the step 1 described above was dissolved into 1 ml of dichloromethane and stirred at room temperature for 15 hours after adding 1 ml of trifluoroacetic acid and anisole (40 mg, 0.38 mmol), followed by concentration under vacuum. This reaction mixture was subject to azotrope-concentration using dichloromethane, methanol, and diethylether and vacuum-dried. The title compound (14 mg, 99%) was obtained as pale yellowish solid.

¹H-NMR (600 MHz, Acetone-d₆); δ 10.61 (brs, 1H), 8.34 (brs, 1H), 8.00 (s, 1H), 7.77-7.70 (m, 3H), 7.33 (t, J=8.4 Hz, 1H), 7.11 (d, J=7.8 Hz, 2H), 6.99 (s, 1H), 6.90 (d, J=7.8 Hz, 1H), 6.83 (d, J=8.4 Hz, 2H), 4.49 (s, 2H), 3.96-3.93 (m, 4H), 3.28-3.26 (m, 4H); LC-MS: 418 (MH+)

Example 83

Step 1

N-(3-(4-methoxybenzyloxy)phenyl)-2-(4-(pipera-zine-1-ylmethyl)phenyl)thieno[3,2-b]pyridine-7-amine The synthesis of (N-(3-(4-methoxybenzyloxy)phe-nyl)-2-(4-(piperazin-1-ylmethyl)phenyl)thieno[3,2-b]pyridin-7-amine)

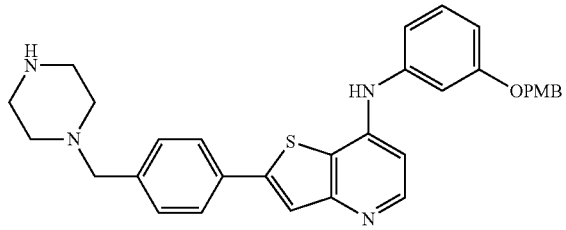

¹H-NMR (400 MHz, Acetone-d₆); δ 8.44 (d, J=6.8 Hz, 1H), 8.15 (s, 1H), 8.01 (s, 1H), 7.81 (d, J=8.4 Hz, 2H), 7.62 (d, J=8.0 Hz, 2H), 7.37 (t, J=8.0 Hz, 1H), 7.30 (t, J=8.4 Hz, 1H), 7.10 (m, 2H), 7.01 (m, 2H), 6.94 (m, 1H), 5.00 (s, 2H), 3.97 (s, 2H), 3.84 (s, 2H), 3.54-3.52 (m, 4H), 3.12-3.10 (m, 4H); LC-MS 537 (MH+)

Step 2

3-(2-(4-(piperazine-1-ylmethyl)phenyl)thieno[3,2-b]pyridine-7-ylamino)phenol trifluoroacetic acid The synthesis of (3-(2-(4-(piperazin-1-ylmethyl)phenyl)thieno[3,2-b]pyridin-7-ylamino)phenol. TFA) (LCB03-0098)

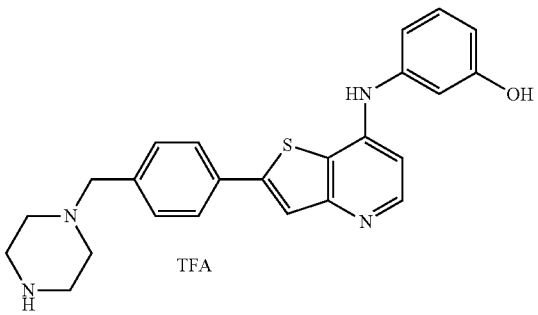 [SMILES: Oc1cccc(Nc2ccnc3cc(-c4ccc(CN5CCNCC5)cc4)sc23)c1]

¹H-NMR (400 MHz, Acetone-d₆); δ 8.44 (d, J=6.8 Hz, 1H), 8.15 (s, 1H), 7.81 (d, J=8.4 Hz, 2H), 7.62 (d, J=8.0 Hz, 2H), 7.37 (t, J=8.0 Hz, 1H), 7.10 (m, 2H), 7.01 (m, 2H), 6.94 (m, 1H), 3.97 (s, 2H), 3.54-3.52 (m, 4H), 3.12-3.10 (m, 4H); LC-MS 418 (MH+)

Example 84

Step 1

2-(4-((ethylamino)methyl)phenyl)-N-(3-(4-methoxy-benzyloxy)phenyl)thieno[3,2-b]pyridine-7-amine The synthesis of (2-(4-((ethylamino)methyl)phenyl)-N-(3-(4-methoxybenzyloxy)phenyl)thieno[3,2-b]pyridin-7-amine)

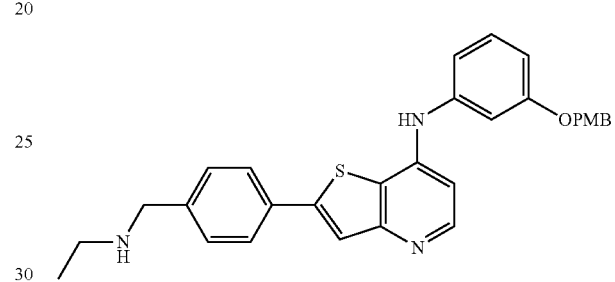

¹H-NMR (400 MHz, Acetone-d₆); δ 9.99 (brs, 1H), 8.36 (d, J=6.8 Hz, 1H), 7.97 (s, 1H), 7.98 (s, 1H), 7.72 (d, J=8.4 Hz, 2H), 7.68 (d, J=8.0 Hz, 2H), 7.64 (t, J=7.8 Hz, 1H), 7.33 (t, J=8.0 Hz, 1H), 7.03 (m, 2H), 6.91 (m, 2H), 6.86-6.83 (m, 2H), 4.99 (s, 2H), 3.80 (s, 3H), 3.78 (s, 2H), 3.28 (q, J=6.8 Hz, 2H), 1.38 (t, J=6.8 Hz, 3H); LC-MS 496 (MH+)

Step 2

3-(2-(4-((ethylamino)methyl)phenyl)thieno[3,2-b]pyridine-7-ylamino)phenol trifluoroacetic acid The synthesis of (3-(2-(4-((ethylamino)methyl)phe-nyl)thieno[3,2-b]pyridin-7-ylamino)phenol. TFA) (LCB03-0099)

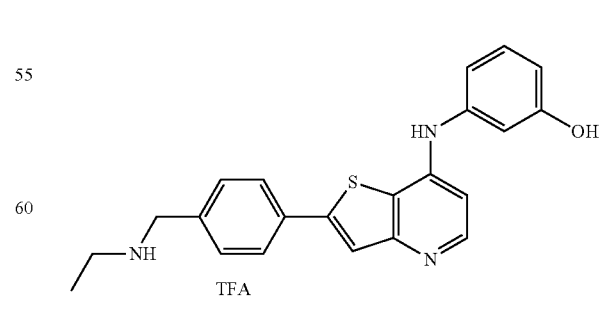

¹H-NMR (400 MHz, Acetone-d₆); δ 8.36 (d, J=6.8 Hz, 1H), 7.97 (s, 1H), 7.72 (d, J=8.4 Hz, 2H), 7.68 (d, J=8.0 Hz, 2H), 7.33 (t, J=8.0 Hz, 1H), 7.03 (m, 2H), 6.91 (m, 2H), 4.37 (s, 2H), 3.28 (q, J=6.8 Hz, 2H), 1.38 (t, J=6.8 Hz, 3H); LC-MS 376 (MH+)

Example 85

Step 1

N-(4-chloro-3-(4-methoxybenzyloxy)phenyl)-6-(4-pyrrolidine-1-ylmethyl)phenyl)thieno[3,2-d]pyrimidine-4-amine The synthesis of (N-(4-chloro-3-(4-methoxybenzyloxy)phenyl)-6-(4-(pyrrolidin-1-ylmethyl)phenyl)thieno[3,2-d]pyrimidin-4-amine)

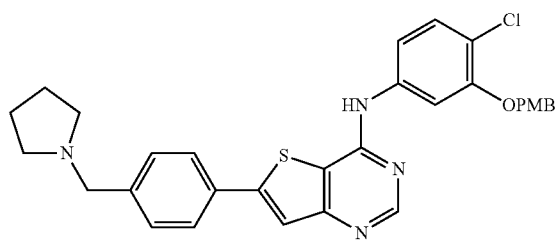

$^1$H-NMR (400 MHz, CDCl$_3$); δ 8.69 (s, 1H), 7.63-7.59 (m, 3H), 7.53 (d, J=2.0 Hz, 1H), 7.43-7.36 (m, 6H), 7.03 (dd, J=2.0, 8.4 Hz 1H), 6.89 (d, J=8.8 Hz, 2H), 5.12 (s, 2H), 3.78 (s, 3H), 3.67 (s, 2H), 2.55 (m, 4H), 1.80 (m, 4H); LC-MS 558 (MH+)

Step 2

4-chloro-5-(6-(4-(pyrrolidine-1-ylmethyl)phenyl)thieno[3,2-d]pyrimidine-4-ylamino)phenol trifluoroacetic acid The synthesis of (4-chloro-5-(6-(4-(pyrrolidin-1-ylmethyl)phenyl)thieno[3,2-d]pyrimidin-4-ylamino)phenol. TFA) (LCB03-0081)

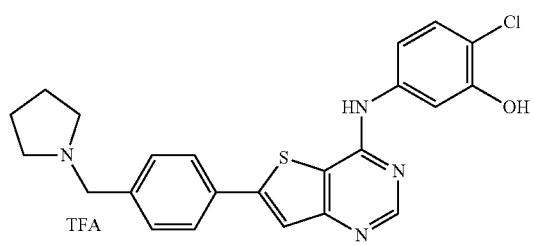 [SMILES: Oc1cc(Nc2ncnc3cc(-c4ccc(CN5CCCC5)cc4)sc23)ccc1Cl]

$^1$H-NMR (400 MHz, CDCl$_3$); δ 8.51 (s, 1H), 7.86 (d, J=8.4 Hz, 2H), 7.67 (s, 1H), 7.55 (d, J=8.0 Hz, 2H), 7.50 (d, J=2.4 Hz, 1H), 7.25 (d, J=8.8 Hz, 1H), 7.09 (d, J=8.6 Hz, 1H), 4.80 (s, 1H), 4.09 (s, 2H), 3.01 (s, 4H), 1.97 (s, 4H); LC-MS 437 (MH+)

Example 86

Step 1

N-(3-(4-methoxybenzyloxy)phenyl)-2-(3-(piperidine-1-ylmethyl)phenyl)thieno[3,2-b]pyridine-7-amine The synthesis of (N-(3-(4-methoxybenzyloxy)phenyl)-2-(3-(piperidin-1-ylmethyl)phenyl)thieno[3,2-b]pyridin-7-amine)

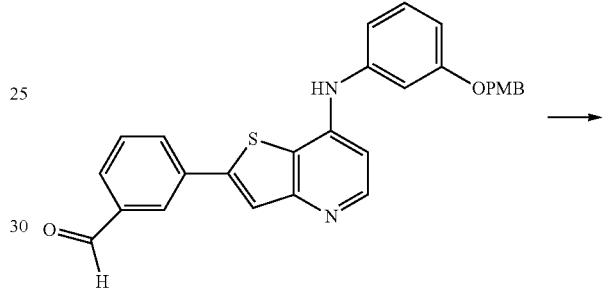

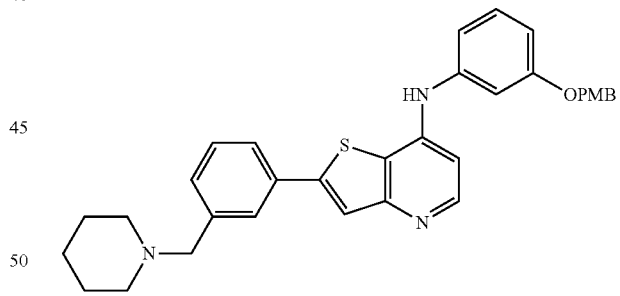

The compound (30 mg, 0.06 mmol) synthesized in the example of synthesis 25 and piperidine (64 μl, 0.61 mmol) were added sequentially into 1 ml of DCE and stirred for 20 minutes. It was further stirred for 5 hours at room temperature after adding sodium acetate (16 mg, 0.19 mmol) and sodium triacethoxyborohydride (82 mg, 0.38 mmol). The resultant reaction mixture was extracted with 30 ml of dichloromethane and 30 ml of saturated ammonium chloride solution. The organic layer was dried using sodium sulfate and concentrated under vacuum. The column chromatography (dichloromethane/methanol, 1/25) was done to obtain the title compound (17 mg, 48%).

$^1$H-NMR (400 MHz, CDCl$_3$); δ 8.35 (d, J=5.6 Hz, 1H), 7.72-7.70 (m, 1H), 7.62 (d, J=5.6 Hz, 1H), 7.40-7.29 (m, 5H), 6.93-6.78 (m, 6H), 6.16 (s, 1H), 5.01 (s, 2H), 3.81 (s, 3H), 3.55 (s, 2H), 2.44 (m, 4H), 2.12 (m, 2H), 1.61 (m, 4H); LC-MS: 536 (MH+)

Step 2

3-(2-(3-(piperidine-1-ylmethyl)phenyl)thieno[3,2-b]pyridine-7-ylamino)phenol trifluoroacetic acid The synthesis of (3-(2-(3-(piperidin-1-ylmethyl)phenyl)thieno[3,2-b]pyridin-7-ylamino)phenol. TFA) (LCB03-0109)

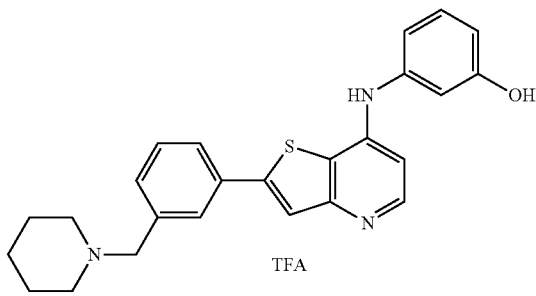 [SMILES: Oc1cccc(Nc2ccnc3cc(-c4cccc(CN5CCCCC5)c4)sc23)c1]

¹H-NMR (600 MHz, Acetone-d₆); δ 8.32 (brs, 1H), 8.02 (brs, 1H), 7.99 (s, 1H), 7.71 (t, J=7.2 Hz, 2H), 7.53 (t, J=7.2 Hz, 1H), 7.31-7.26 (m, 2H), 7.03 (s, 1H), 6.98 (t, J=6.6 Hz, 1H), 6.92-6.88 (m, 3H), 4.43 (s, 2H), 3.59-3.56 (m, 2H), 3.56-3.54 (m, 2H), 2.06-2.04 (m, 2H), 1.90-1.89 (m, 4H); LC-MS 416 (MH+)

The following compounds were synthesized by the methods similar to the one described in the preferred embodiment 86 described above.

Example 87

Step 1

N-(3-(4-methoxybenzyloxy)phenyl)-2-(3-(pyrrolidine-1-ylmethyl)phenyl)thieno[3,2-b]pyridine-7-amine The synthesis of (N-(3-(4-methoxybenzyloxy)phenyl)-2-(3-(pyrrolidin-1-ylmethyl)phenyl)thieno[3,2-b]pyridin-7-amine)

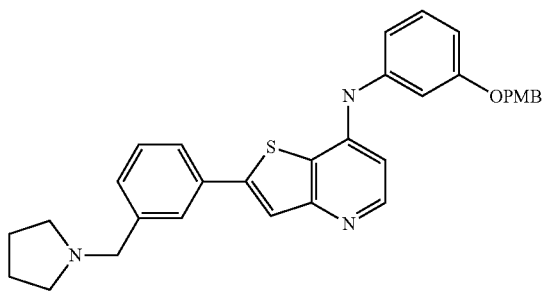

¹H-NMR (400 MHz, CDCl₃); δ 8.36 (s, 1H), 7.73-7.72 (m, 1H), 7.64-7.63 (m, 1H), 7.41-7.29 (m, 5H), 6.93-6.79 (m, 6H), 6.14 (s, 1H), 5.01 (s, 2H), 3.82 (s, 3H), 3.74 (s, 2H), 2.62 (m, 4H), 1.83 (m, 4H); LC-MS: 523 (MH+)

Step 2

3-(2-(3-(pyrrolidine-1-ylmethyl)phenyl)thieno[3,2-b]pyridine-7-ylamino)phenol trifluoroacetic acid The synthesis of (3-(2-(3-(pyrrolidin-1-ylmethyl)phenyl)thieno[3,2-b]pyridin-7-ylamino)phenol. TFA) (LCB03-0107)

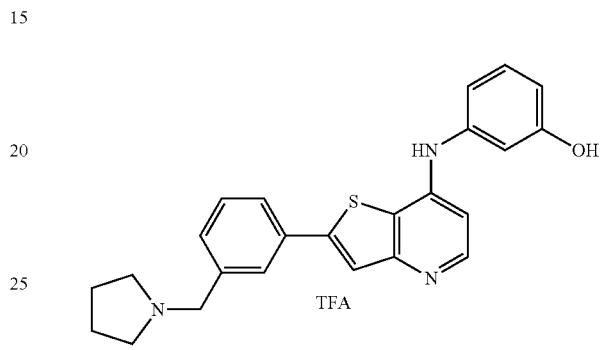

¹H-NMR (600 MHz, Acetone-d₆); δ 10.07 (brs, 1H), 8.35-8.33 (m, 1H), 8.06 (s, 1H), 7.99 (s, 1H), 7.73 (t, J=8.4 Hz, 2H), 7.54 (t, J=7.8 Hz, 1H), 7.33 (t, J=7.8 Hz, 1H), 7.04 (s, 1H), 7.01 (t, J=6.6 Hz, 1H), 6.93 (s, 1H), 6.92-6.89 (m, 2H), 4.55 (s, 2H), 3.66-3.64 (m, 2H), 3.29-3.28 (m, 2H), 2.16-2.14 (m, 4H); LC-MS: 402 (MH+)

Example 88

Step 1

N-(3-(4-methoxybenzyloxy)phenyl)-6-(3-((4-methylpiperazine-1-yl)methyl)phenyl)thieno[3,2-b]pyridine-7-amine The synthesis of (N-(3-(4-methoxybenzyloxy)phenyl)-6-(3-((4-methylpiperazin-1-yl)methyl)phenyl)thieno[3,2-d]pyrimidin-4-amine)

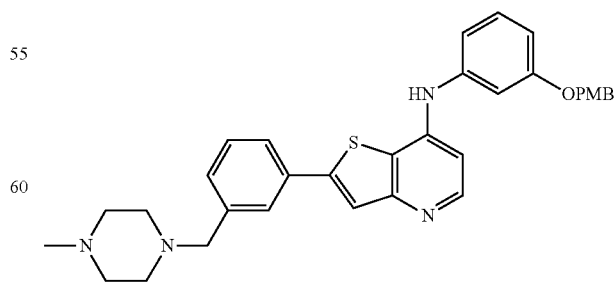

¹H-NMR (400 MHz, CDCl₃); δ 8.35 (d, J=5.6 Hz, 1H), 7.72-7.71 (m, 2H), 7.62 (d, J=7.2 Hz, 1H), 7.41-7.30 (m, 5H), 6.93-6.79 (m, 6H), 6.19 (s, 1H), 5.01 (s, 2H), 3.82 (s, 3H), 3.57 (s, 3H), 3.47-3.46 (m, 2H), 2.63 (m, 4H), 2.09 (m, 4H); LC-MS: 523 (MH+)

Step 2

3-(2-(3-((4-methylpiperazine-1-yl)methyl)phenyl)thieno[3,2-b]pyridine-7-ylamino)phenol trifluoroacetic acid The synthesis of (3-(2-(3-((4-methylpiperazin-1-yl)methyl)phenyl)thieno[3,2-b]pyridin-7-ylamino)phenol. TFA) (LCB03-0108)

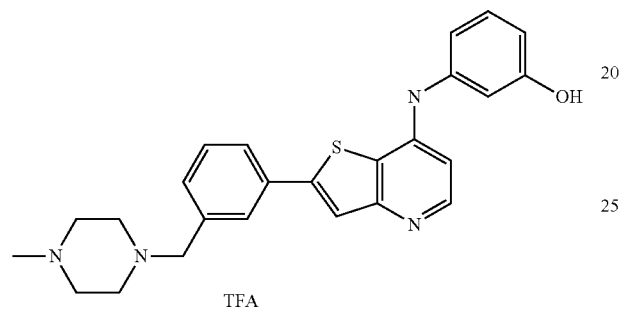

$^1$H-NMR (600 MHz, Acetone-$d_6$); δ 9.99 (brs, 1H), 8.39 (brs, 1H), 8.08 (s, 1H), 7.29 (s, 1H), 7.71 (d, J=7.8 Hz, 2H), 7.59 (d, J=7.8 Hz, 1H), 7.53 (t, J=7.8 Hz, 1H), 7.35 (t, J=7.8 Hz, 1H), 7.13-7.12 (m, 1H), 7.12-7.10 (m, 2H), 6.96-6.92 (m, 2H), 6.83-6.82 (m, 1H), 4.03 (s, 2H), 3.86-3.85 (m, 2H), 3.74 (s, 3H), 3.62-3.61 (m, 3H), 3.19-3.18 (m, 3H), 2.09 (s, 3H); LC-MS: 431 (MH+)

Example 89

Step 1

N-(3-(4-methoxybenzyloxy)phenyl)-6-(3-(morpholinomethyl)phenyl)thieno[3,2-b]pyridine-7-amine The synthesis of (N-(3-(4-methoxybenzyloxy)phenyl)-6-(3-(morpholinomethyl)phenyl)thieno[3,2-d]pyrimidin-4-amine)

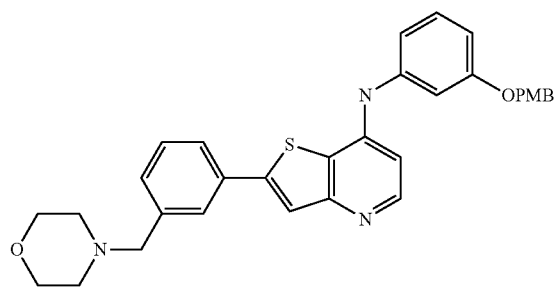

$^1$H-NMR (400 MHz, CDCl$_3$); δ 8.20 (d, J=5.6 Hz, 1H), 7.79 (s, 1H), 7.69 (s, 1H), 7.57 (s, 1H), 7.37-7.28 (m, 4H), 6.94-6.83 (m, 6H), 6.19 (s, 1H), 5.01 (s, 2H), 3.80 (s, 3H), 3.74-3.73 (m, 3H), 3.52-3.50 (m, 4H), 2.49-2.48 (m, 3H); LC-MS: 538 (MH+)

Step 2

3-(2-(3-(morpholinomethyl)phenyl)thieno[3,2-b]pyridine-7-ylamino)phenol trifluoroacetic acid The synthesis of (3-(2-(3-(morpholinomethyl)phenyl)thieno[3,2-b]pyridin-7-ylamino)phenol. TFA) (LCB03-0110)

$^1$H-NMR (600 MHz, Acetone-$d_6$); δ 8.37 (d, J=6.0 Hz, 1H), 8.08 (brs, 1H), 8.02 (s, 1H), 7.77-7.73 (m, 2H), 7.57 t, J=7.8 Hz, 1H), 7.33 (t, J=8.4 Hz, 1H), 7.29-7.26 (m, 1H), 7.02-7.01 (m, 1H), 6.93-6.91 (m, 3H), 4.52 (s, 2H), 4.07-4.03 (m, 4H), 3.59-3.55 (m, 4H); LC-MS: 418 (MH+)

Example 90

Step 1 t-butyl 4-(3-(7-(3-(4-methoxybenzyloxy)phenylamino)thieno[3,2-b]pyridine-2-yl)benzyl)piperazine-1-carboxylate The synthesis of (tert-butyl 4-(3-(7-(3-(4-methoxybenzyloxy)phenylamino)thieno[3,2-b]pyridin-2-yl)benzyl)piperazine-1-carboxylate)

$^1$H-NMR (400 MHz, CDCl$_3$); δ 8.34 (d, J=5.6 Hz, 1H), 7.72-7.63 (m, 3H), 7.56-7.53 (m, 1H), 7.48-7.46 (m, 1H), 7.41-7.27 (m, 4H), 6.93-6.85 (m, 4H), 6.80-6.78 (m, 1H), 6.48 (s, 1H), 5.00 (s, 2H), 3.81 (s, 3H), 3.40-3.38 (m, 2H), 2.47 (m, 4H), 2.20 (m, 4H), 1.49 (s, 9H); LC-MS 637 (MH+)

Step 2

3-(2-(3-(piperazine-1-ylmethyl)phenyl)thieno[3,2-b]pyridine-7-ylamino)phenol trifluoroacetic acid The synthesis of (3-(2-(3-(piperazin-1-ylmethyl)phenyl)thieno[3,2-b]pyridin-7-ylamino)phenol. TFA) (LCB03-0111)

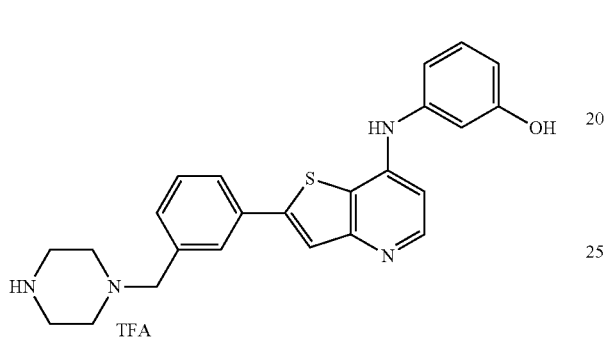

$^1$H-NMR (600 MHz, Acetone-d$_6$); δ 8.45 (d, J=7.2 Hz, 1H), 8.12 (brs, 1H), 8.02 (s, 1H), 7.86 (d, J=7.8 Hz, 1H), 7.78 (d, J=7.8 Hz, 1H), 7.63 (t, J=7.8 Hz, 1H), 7.28-7.24 (m, 1H), 7.12 (d, J=6.6 Hz, 1H), 6.98-6.95 (m, 1H), 6.92-6.60 (m, 3H), 4.61 (s, 2H), 3.94-3.87 (m, 4H), 3.72-3.52 (m, 4H); LC-MS: 417 (MH+)

Example 91

Step 1

2-(3-((ethylamino)methyl)phenyl)-N-(3-(4-methoxybenzyloxyphenyl)thieno[3,2-b]pyridine-7-amine The synthesis of (2-(3-((ethylamino)methyl)phenyl)-N-(3-(4-methoxybenzyloxy)phenyl)thieno[3,2-b]pyridin-7-amine)

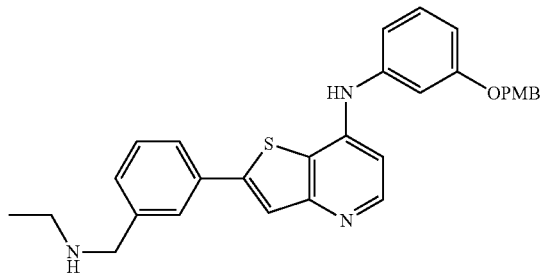

$^1$H-NMR (400 MHz, CDCl$_3$); δ 8.31 (d, J=5.6 Hz, 1H), 7.75-7.74 (m, 1H), 7.71 (s, 1H), 7.62-7.61 (m, 1H), 7.46-7.29 (m, 5H), 6.93-6.87 (m, 5H), 6.81-6.79 (m, 1H), 5.01 (s, 2H), 3.90 (s, 2H), 3.82 (s, 3H), 2.80 (q, J=6.8 Hz, 2H), 1.24-1.22 (m, 3H); LC-MS 496 (MH+)

Step 2

3-(2-(3-((ethylamino)methyl)phenyl)thieno[3,2-b]pyridine-7-ylamino)phenol trifluoroacetic acid The synthesis of (3-(2-(3-((ethylamino)methyl)phenyl)thieno[3,2-b]pyridin-7-ylamino)phenol. TFA) (LCB03-0112)

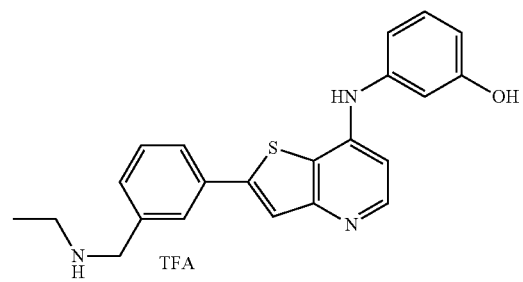 [SMILES: CCNCc1cccc(-c2cc3nccc(Nc4cccc(O)c4)c3s2)c1]

$^1$H-NMR (600 MHz, Acetone-d$_6$); δ 8.35 (d, J=6.0 Hz, 1H), 8.09 (brs, 1H), 7.96 (s, 1H), 7.70 (t, J=7.8 Hz, 2H), 7.51 (t, J=7.8 Hz, 1H), 7.34 (t, J=7.8 Hz, 1H), 7.29-7.26 (m, 1H), 7.05-6.94 (m, 2H), 6.92-6.89 (m, 3H), 4.43 (s, 2H), 3.41-3.40 (m, 2H), 1.40 (t, J=7.2 Hz, 3H); LC-MS 376 (MH+)

Example 92

Step 1

2-(4-(4-(3-(t-butyldimethylsiloxy)phenylamino)thieno[3,2-d]pyrimidine-6-yl)phenyl)ethanol The synthesis of (2-(4-(4-(3-(tert-butyldimethylsilyloxy)phenylamino)thieno[3,2-d]pyrimidin-6-yl)phenyl)ethanol)

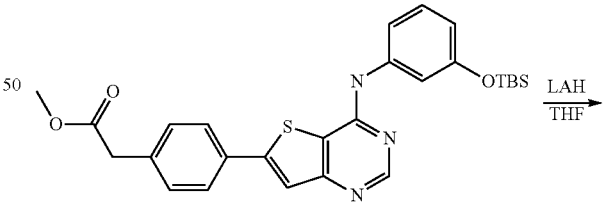

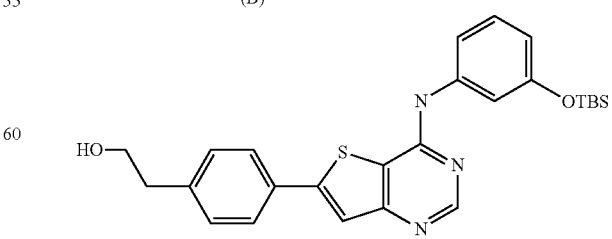

Lithumaluminumhydride (44 mg, 1.16 mmol) was added into 3 ml of dried dimethylformamide. The mixture was further added slowly at 0° C. with the compound (0.49 mg, 0.96 mmol) synthesized in the example of synthesis 28 dissolved in 7 ml of dried tetrahydrofuran under nitrogen and stirred for 2 hours. 44 μl of water, 44 μl of 15% NaOH, and 132 μl of water were added sequentially to the reaction mixture at 0° C. slowly. Then the mixture was dried by adding a small amount of anhydrous sodium sulfate and filtered. The solid was washed with dichloromethane and concentrated under vacuum. After trituration using n-hexane, the title compound (0.34 g, 76%) was obtained as a yellowish solid.

$^1$H-NMR (400 MHz, DMSO-d$_6$); δ 9.64 (s, 1H), 8.58 (s, 1H), 7.86 (s, 1H), 7.79 (d, J=8.4 Hz, 2H), 7.50-7.48 (m, 1H), 7.44 (t, J=2.0 Hz, 1H), 7.38 (d, J=8.4 Hz, 2H), 6.60-6.58 (m, 1H), 4.70 (t, J=5.2 Hz, 1H), 3.65 (q, J=6.8 HZ, 2H), 2.79 (t, J=7.2 HZ, 2H), 0.98 (s, 9H), 0.22 (s, 6H); LC-MS: 478 (MH+)

Step 2

4-(4-(3-(t-butyldimethylsiloxy)phenylamino)thieno[3,2-d]pyrimidine-6-yl)phenethyl methanesulfonate The synthesis of (4-(4-(3-(tert-butyldimethylsilyloxy)phenylamino)thieno[3,2-d]pyrimidin-6-yl) phenethyl methanesulfonate)

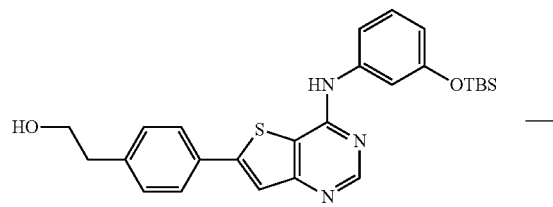

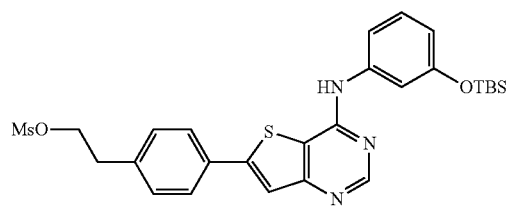

The compound (0.33 g, 0.69 mmol) synthesized in the step 1 described above was dissolved into 5 ml of dichloromethane and the mixture was added slowly with triethylamine (116 μl, 0.83 mmol), and chloromethanesulfonic acid (56 μl, 0.72 mmol) at 0° C. The mixture was stirred for 30 minutes at 0° C. and then further stirred at room temperature for 2 hours. After the reaction mixture was poured into 2 N c HCl (50 mL) solution, it was extracted with ethyl acetate (50 mL×2) and the organic layer was washed with water (100 mL×2) and dried with anhydrous sodium sulfate. After concentration under vacuum and column chromatography (ethylacetate/n-hexane, 1:2), the title compound (0.22 g, 57%) was obtained as yellowish solid.

$^1$H-NMR (400 MHz, CDCl$_3$); δ 8.53 (s, 1H), 7.73 (s, 1H), 7.58-7.52 (m, 2H), 7.32-7.14 (m, 5H), 6.89 (d, J=6.0 Hz, 1H), 4.43 (brm, 2H), 3.08 (brm, 2H), 2.91 (s, 3H), 0.88 (s, 9H), 0.02 (s, 6H); LC-MS 556 (MH+)

Step 3

N-(3-(t-butyldimethylsiloxy)phenyl)-6-(4-(2-morpholinoethyl)phenyl)thieno[3,2-d]pyrimidine-4-amine The synthesis of (N-(3-(tert-butyldimethylsilyloxy)phenyl)-6-(4-(2-morpholinoethyl)phenyl)thieno[3,2-d]pyrimidin-4-amine)

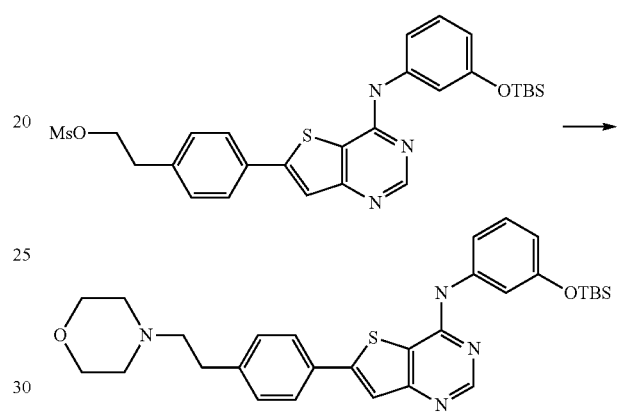

The compound (50 mg, 0.089 mmol) synthesized in the step 2 described above was dissolved into 1 ml toluene and mixed with diisopropylamine (24 μl, 0.13 mmol), and morpholine (12 μl, 0.13 mmol) followed by reflux. After concentration under vacuum and separation with column chromatography (ethylacetate/n-hexane, 1:1), the title compound (15 mg, 31%) was obtained as yellowish solid.

$^1$H-NMR (400 MHz, CDCl$_3$); δ 8.69 (s, 1H), 7.61-7.57 (m, 3H), 7.30-7.24 (m, 3H), 7.19 (t, J=2.0 Hz, 1H), 7.16-7.13 (m, 1H), 6.84 (br, 1H), 6.76-6.74 (m, 1H), 3.75 (t, J=4.4 Hz, 2H), 2.87-2.83 (m, 2H), 2.64-2.60 (m, 4H), 2.55-2.54 (m, 4H), 0.99 (s, 9H), 0.24 (s, 6H); LC-MS: 547 (MH+)

Step 4

3-(6-(4-(2-morpholinoethyl)phenyl)thieno[3,2-d]pyrimidine-4-ylamino)phenol HCl salt (3-(6-(4-(2-morpholinoethyl)phenyl)thieno[3,2-d]pyrimidin-4-ylamino)phenol. HCl) (LCB03-0046)
의 synthesis

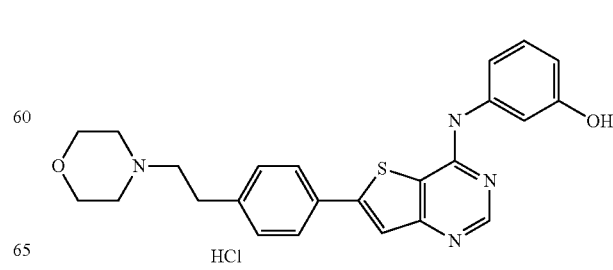

The title compound (12 mg, 93%) was obtained as yellowish solid from the compound (15 mg, 0.02 mmol) synthesized in the step 3 described above by the method similar to the preferred embodiment 9.

$^1$H-NMR (400 MHz, DMSO-d$_6$); δ 11.25 (brs, 1H), 8.80 (s, 1H), 7.89 (s, 1H), 7.86 (d, J=8.0 Hz, 2H), 7.48 (d, J=8.0 Hz, 2H), 7.25-7.11 (m, 3H), 6.69 (d, J=7.6 Hz, 1H), 4.01-3.99 (m, 2H), 3.83-3.78 (m, 2H), 3.51-3.46 (m, 2H), 3.40-3.35 (m, 2H), 3.17-3.10 (m, 4H); LC-MS 433 (MH+)

The following compounds were synthesized by the methods similar to the one described in the preferred embodiment 92 described above.

Example 93

3-((6-(4-(2-(pyrrolidine-1-yl)ethyl)phenyl)thieno[3,2-d]pyrimidine-4-ylamino)phenol (3-((6-(4-(2-(pyrrolidin-1-yl)ethyl)phenyl)thieno[3,2-d]pyrimidin-4-ylamino)phenol) (LCB03-0043) 의 synthesis

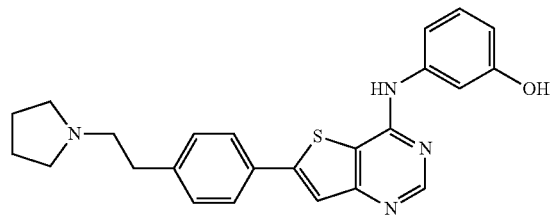 [SMILES: Oc1cccc(Nc2ncnc3cc(-c4ccc(CCN5CCCC5)cc4)sc23)c1]

$^1$H-NMR (400 MHz, DMSO-d$_6$); δ 7.87-7.85 (m, 3H), 7.49-7.47 (m, 2H), 7.22-7.15 (m, 4H), 6.66-6.65 (m, 1H), 3.55 (s, 2H), 3.17-3.11 (m, 4H), 2.34-2.32 (m, 2H), 2.01-1.89 (m, 4H); LC-MS 417 (MH+)

Example 94

3-((6-(4-(2-(piperidine-1-yl)ethyl)phenyl)thieno[3,2-d]pyrimidine-4-ylamino)phenol The synthesis of (3-((6-(4-(2-(piperidin-1-yl)ethyl)phenyl)thieno[3,2-d]pyrimidin-4-ylamino)phenol) (LCB03-0044)

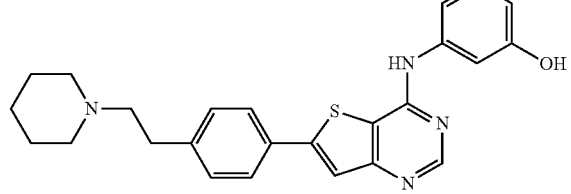

$^1$H-NMR (400 MHz, DMSO-d$_6$); δ 10.44 (brs, 1H), 8.78 (s, 1H), 7.89-7.84 (m, 3H), 7.48-7.46 (m, 2H), 7.20-7.14 (m, 3H), 6.70-6.69 (m, 1H), 3.49 (s, 2H), 3.39-3.37 (m, 2H), 3.37-3.27 (m, 2H), 3.20-3.18 (m, 2H), 2.90-2.89 (m, 2H), 1.90-1.87 (m, 3H), 1.38-1.35 (m, 3H); LC-MS 431 (MH+)

Example 95

3-((6-(4-(2-(4-methylpiperazine-1-yl)ethyl)phenyl)thieno[3,2-d]pyrimidine-4-ylamino)phenol The synthesis of (3-((6-(4-(2-(4-methylpiperazin-1-yl)ethyl)phenyl)thieno[3,2-d]pyrimidin-4-ylamino)phenol) (LCB03-0045)

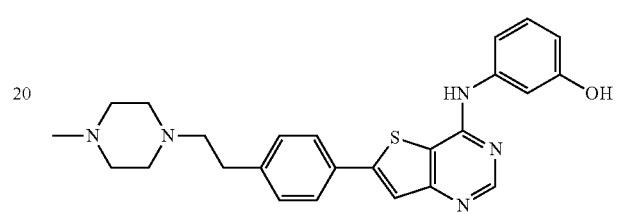

$^1$H-NMR (400 MHz, DMSO-d$_6$); δ 8.75 (s, 1H), 7.88 (S, 1H), 7.85 (d, J=7.6 Hz, 2H), 7.48 (d, J=7.6 Hz, 2H), 7.23-7.12 (m, 3H), 6.66 (d, J=7.2 Hz, 1H), 3.72-3.68 (m, 2H), 3.51-3.47 (m, 2H), 3.44-3.37 (m, 4H), 3.16-3.12 (m, 4H), 2.83 (s, 3H); LC-MS 446 (MH+)

Example 96

3-(6-(3-(2-(pyrrolidine-1-yl)ethyl)phenyl)thieno[3,2-d]pyrimidine-4-ylamino)phenol HCl salt The synthesis of (3-(6-(3-(2-(pyrrolidin-1-yl)ethyl)phenyl)thieno[3,2-d]pyrimidin-4-ylamino)phenol. HCl) (LCB03-0076)

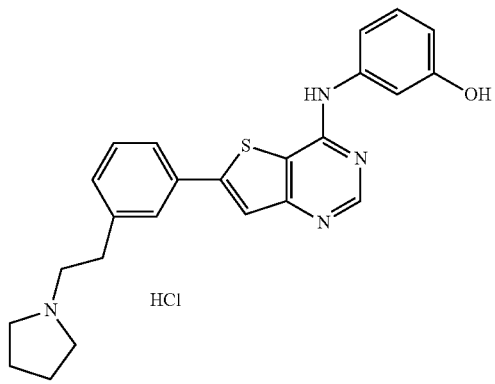 [SMILES: Oc1cccc(Nc2ncnc3cc(-c4cccc(CCN5CCCC5)c4)sc23)c1 ; Cl]

$^1$H-NMR (400 MHz, CDCl$_3$); δ 8.53 (s, 1H), 7.72 (br, 1H), 7.58 (s, 1H), 7.34-7.26 (m, 3H), 7.22-7.12 (m, 3H), 6.88 (d,

J=7.6 Hz, 1H), 6.69 (d, J=8 Hz, 1H), 2.89-2.87 (m, 4H), 2.74-2.72 (m, 4H), 1.86 (s, 4H); LC-MS 417.2 (MH+)

Example 97

3-(6-(3-(2-(piperazine-1-yl)ethyl)phenyl)thieno[3,2-d]pyrimidine-4-ylamino)phenol The synthesis of (3-(6-(3-(2-(piperazin-1-yl)ethyl)phenyl)thieno[3,2-d]pyrimidin-4-ylamino)phenol) (LCB03-0079)

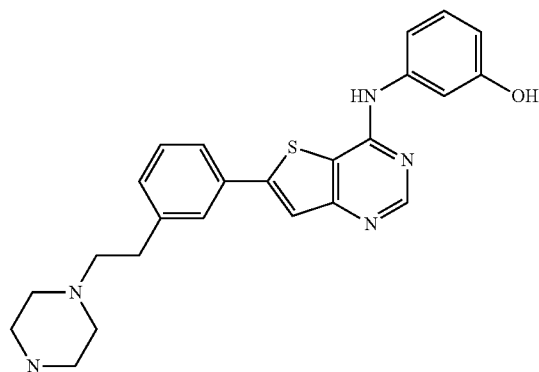 [SMILES: Oc1cccc(Nc2ncnc3cc(-c4cccc(CCN5CCNCC5)c4)sc23)c1]

¹H-NMR (400 MHz, DMSO-d₆); δ 9.83 (brs, 1H), 8.85 (s, 1H), 7.93 (s, 1H), 7.83-7.73 (m, 2H), 7.54-7.48 (m, 2H), 7.23-7.13 (m, 3H), 6.73 (s, 1H), 3.75-3.71 (m, 2H), 3.66-3.64 (m, 2H), 3.33-3.31 (m, 4H), 3.17-3.15 (m, 4H); LC-MS 432 (MH+)

Example 98

Step 1

2-(4-(4-(3-hydroxyphenylamino)thieno[3,2-d]pyrimidine-6-yl)phenylacetic acid

The synthesis of (2-(4-(4-(3-hydroxyphenylamino)thieno[3,2-d]pyrimidin-6-yl)phenyl)acetic acid)

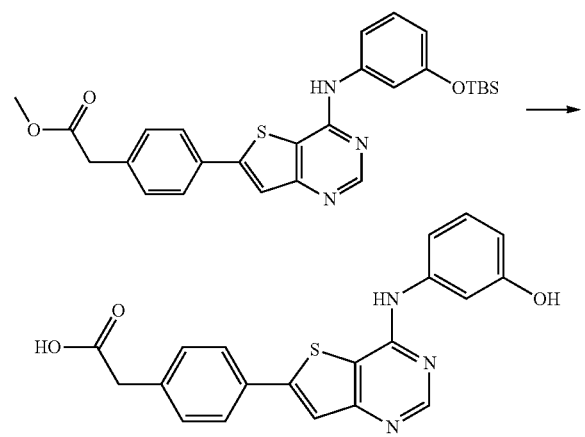

The compound (0.2 g, 0.39 mmol) synthesized in the example of synthesis 27 was dissolved into 1 ml of tetrahydrofuran and 1 ml of methanol 1 ml and the mixture was added slowly with lithumhydroxide (166 mg, 3.95 mmol) dissolved in 1 ml of water at 0° C. The resultant mixture was stirred at room temperature for 15 hours and its pH was adjusted to pH 4 using 2N c HCl before concentration under vacuum to remove reaction solvent. After extraction with ethylacetate (50 ml) and water (50 ml), and removing the organic solvents by vacuum-evaporation, the title compound (0.13 mg, 87.2%) was obtained.

¹H-NMR (400 MHz, CDCl₃); δ 10.78 (brs, 1H), 9.69 (brs, 1H), 8.80 (s, 1H), 7.87 (s, 1H), 7.82 (d, J=8.0 Hz, 2H), 7.45 (d, J=8.0 Hz, 2H), 7.25 (t, J=8.0 Hz, 1H), 7.19 (s, 1H), 7.14-7.12 (m, 1H), 6.71-6.68 (m, 1H), 3.68 (s, 2H; LC-MS 378 (MH+)

Step 2

2-(4-(4-(3-hydroxyphenylamino)thieno[3,2-d]pyrimidine-6-yl)phenyl)-1-(4-methylpiperazine-1-yl)ethanone The synthesis of (2-(4-(4-(3-hydroxyphenylamino)thieno[3,2-d]pyrimidin-6-yl)phenyl)-1-(4-methylpiperazin-1-yl)ethanone)) (LCB03-0047)

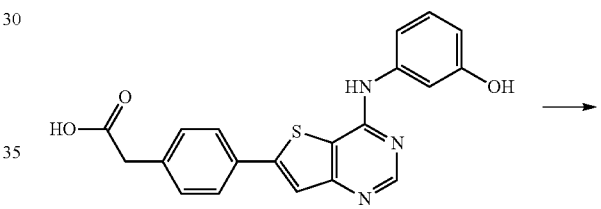

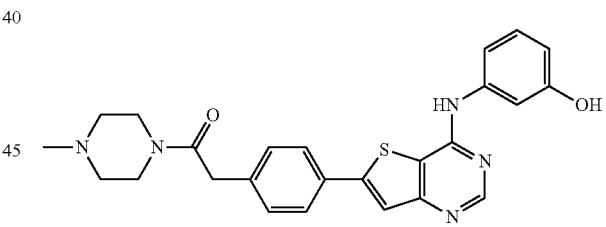

The compound (30 mg, 0.08 mmol) synthesized in the step 1 described above was dissolved in 2 ml of degassed dimethylformamide and added with (benzotriazol-1-yloxy)tripyrrolidinophosphonium hexafluorophosphate (62 mg, 0.12 mmol) and N-methylpiperazine (44 μl, 0.40 mmol), then the mixture was stirred for 15 hours at room temperature. The reaction mixture was extracted using 50 ml of saturated ammonium chloride and 50 ml of ethyl acetate and the organic layer was washed with 50 ml of water twice before vacuum-distillation. The synthesized solid was solidified using n-hexane and the title compound (20 mg, 54.8%) was obtained as beige colored solid.

¹H-NMR (400 MHz, DMSO-d₆); δ 8.87 (s, 1H), 7.88 (s, 1H), 7.82 (d, J=8.0 Hz, 2H), 7.41 (d, J=8.0 Hz, 2H), 7.26 (t, J=8.0 Hz, 1H), 7.14 (s, 1H), 7.10 (d, J=8.0 Hz, 1H), 6.76-6.74 (m, 1H), 3.60 (s, 2H), 3.54 (s, 3H), 3.49-3.39 (m, 6H), 2.77-2.76 (m, 2H); LC-MS: 460 (MH+)

The following compounds were synthesized by the method similar to the one described in the preferred embodiment 98 described above.

Example 99

2-(4-(4-(3-hydroxyphenylamino)thieno[3,2-d]pyrimidine-6-yl)phenyl)-1-(pyrrolidine-1-yl)ethanone The synthesis of (2-(4-(4-(3-hydroxyphenylamino)thieno[3,2-d]pyrimidin-6-yl)phenyl)-1-(pyrrolidin-1-yl)ethanone)) (LCB03-0049)

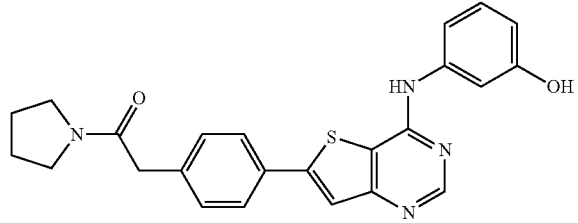

¹H-NMR (400 MHz, DMSO-d₆); δ 9.61 (brs, 1H), 9.43 (s, 1H), 8.57 (s, 1H), 7.86 (s, 1H), 7.80 (d, J=8.0 Hz, 2H), 7.39 (d, J=8.0 Hz, 2H), 7.33 (s, 1H), 7.20-7.12 (m, 2H), 6.53-6.51 (m, 1H), 3.70 (s, 2H), 3.50 (t, J=6.4 Hz, 2H), 3.40-3.29 (m, 2H), 1.89 (p, J=7.0 Hz, 2H), 1.78 (p, J=7.0 Hz, 2H); LC-MS: 431 (MH+)

Example 100

N,N-diethyl-2-(4-(4-(3-hydroxyphenylamino)thieno[3,2-d]pyrimidine-6-yl)phenyl)acetamide The synthesis of (N,N-diethyl-2-(4-(4-(3-hydroxyphenylamino)thieno[3,2-d]pyrimidin-6-yl)phenyl)acetamide)) (LCB03-0050)

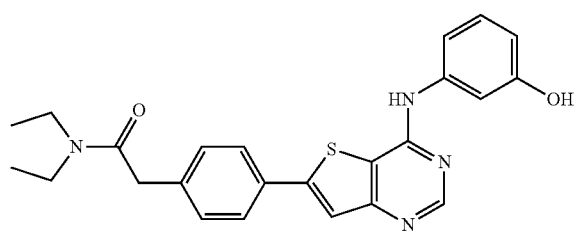 [SMILES: CCN(CC)C(=O)Cc1ccc(-c2cc3ncnc(Nc4cccc(O)c4)c3s2)cc1]

¹H-NMR (400 MHz, DMSO-d₆): δ 8.72 (s, 1H), 7.57 (d, J=8.4 Hz, 2H), 7.54 (s, 1H), 7.31-7.28 (m, 3H), 6.93 (d, J=8.4 Hz, 2H), 6.76 (dd, J=2.0, 8.0 Hz, 1H), 3.91 (s, 2H), 3.42 (q, J=7.2 HZ, 2H), 3.34 (q, J=7.2 Hz, 2H), 1.13-1.10 (m, 6H); LC-MS 433 (MH+)

Example 101

Step 1

(4-(4-(3-(t-butyldimethylsiloxy)phenylamino)thieno[3,2-d]pyrimidine-6-yl)phenyl)(4-methylpiperazine-1-yl)methanone The synthesis of ((4-(4-(3-(tert-butyldimethylsilyloxy)phenylamino)thieno[3,2-d]pyrimidin-6-yl)phenyl)(4-methylpiperazin-1-yl)methanone)

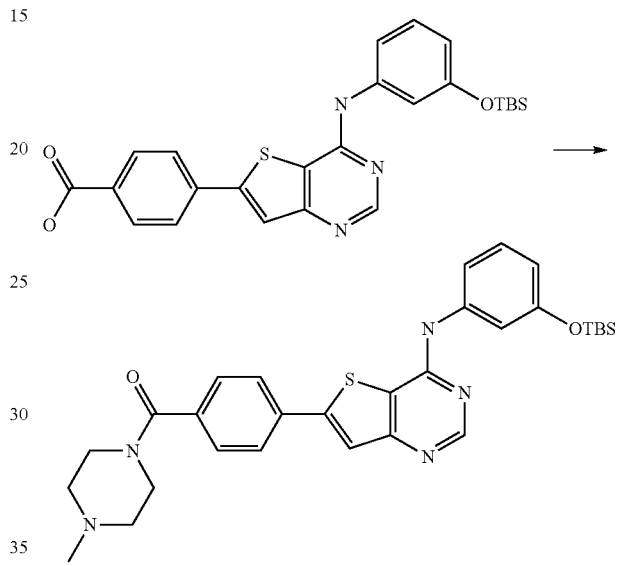

¹H-NMR (400 MHz, CDCl₃); δ 7.71 (s, 1H), 7.70 (d, J=8.4 Hz, 2H), 7.64 (s, 1H), 7.49 (d, J=8.0 Hz, 2H), 7.27 (t, J=8.0 Hz, 2H), 7.19-7.15 (m, 2H), 6.85 (brs, 1H), 6.77 (dd, J=2.4, 8.0 Hz, 1H), 3.82 (brm, 2H), 3.48 (brm, 2H), 3.44-3.33 (m, 1H), 2.50 (brm, 2H), 2.38-2.37 (m, 1H), 2.33 (s, 3H), 1.00 (s, 9H), 0.24 (s, 6H); LC-MS 560 (MH+)

Step 2

(4-(4-(3-hydroxyphenylamino)thieno[3,2-d]pyrimidine-6-yl)phenyl)(4-methylpiperazine-1-yl)methanone HCl salt The synthesis of ((4-(4-(3-hydroxyphenylamino)thieno[3,2-d]pyrimidin-6-yl)phenyl)(4-methylpiperazin-1-yl)methanone. HCl)) (LCB03-0052)

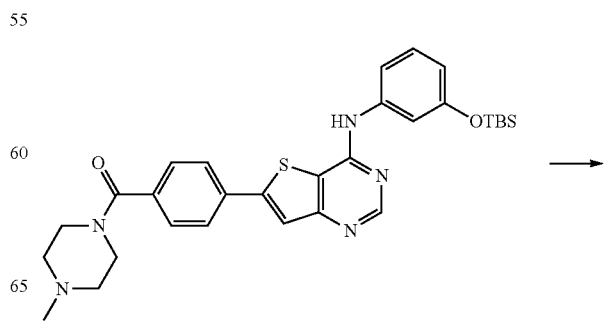

-continued

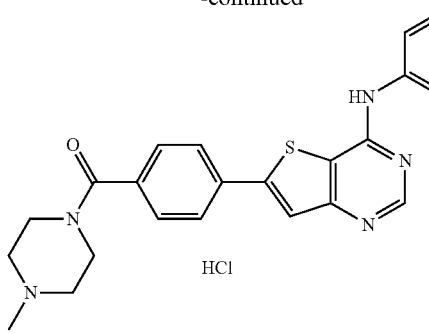

¹H-NMR (400 MHz, DMSO-d₆); δ 10.65 (brs, 1H), 9.68 (brs, 1H), 7.99 (s, 1H), 7.97 (d, J=8.0 Hz, 2H), 7.64 (d, J=8.0 Hz, 2H), 7.24-7.13 (m, 4H), 6.68 (d, J=8.0 Hz, 1H), 3.50-3.39 (m, 4H), 3.33-3.32 (m, 2H), 3.11-3.08 (m, 2H), 2.78 (s, 3H); LC-MS 446 (MH+)

Example 102

Step 1 methyl 2-(4-(4-(3-(t-butyldimethylsiloxy) phenylamino)thieno[3,2-d]pyrimidine-6-yl)benzamido)propanoate The synthesis of (methyl 2-(4-(4-(3-(tert-butyldimethylsilyloxy)phenylamino)thieno[3,2-d]pyrimidin-6-yl)benzamido)propanoate)

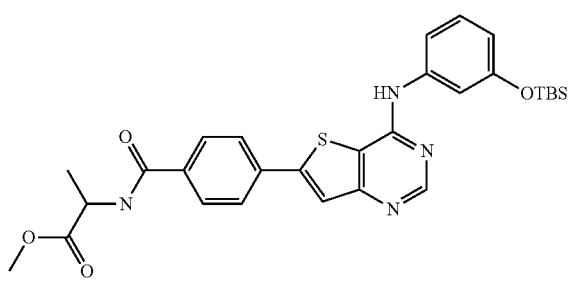 [SMILES: COC(=O)C(C)NC(=O)c1ccc(-c2cc3ncnc(Nc4cccc(O[Si](C)(C)C(C)(C)C)c4)c3s2)cc1]

¹H-NMR (400 MHz, CDCl₃); δ 8.69 (s, 1H), 7.68-7.63 (m, 3H), 7.47-7.44 (m, 2H), 7.29-7.26 (m, 1H), 7.17-7.14 (m, 2H), 6.92 (d, J=5.2 Hz, 1H), 6.77 (d, J=3.6 Hz, 1H), 4.81 (m, 1H), 3.80 (s, 3H), 1.55 (d, J=5.2 Hz, 3H), 0.99 (s, 9H), 0.23 (s, 6H); LC-MS 563 (MH+)

Step 2 methyl 2-(3-(4-(3-hydroxyphenylamino)thieno[3,2-d]pyrimidine-6-yl)benzamido)propanoate The synthesis of (methyl 2-(3-(4-(3-hydroxyphenylamino)thieno[3,2-d]pyrimidin-6-yl)benzamido)propanoate)) (LCB03-0071)

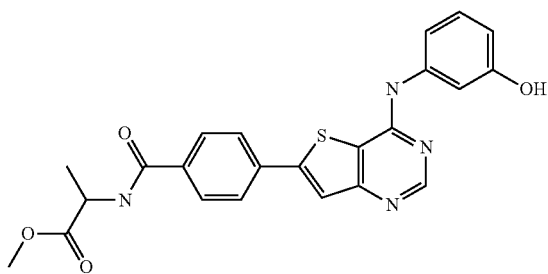 [SMILES: COC(=O)C(C)NC(=O)c1ccc(-c2cc3ncnc(Nc4cccc(O)c4)c3s2)cc1]

¹H-NMR (600 MHz, DMSO-d₆); δ 9.64 (brs, 1H), 8.91 (d, J=6.6 Hz, 1H), 8.56 (s, 1H), 8.00-7.99 (m, 3H), 7.95 (d, J=8.4 Hz, 2H), 7.29 (brs, 1H), 7.15 (d, J=7.2 Hz, 1H), 7.11 (t, J=7.8 Hz, 1H), 6.49 (d, J=7.8 Hz, 1H), 4.48-4.46 (1H), 3.61 (s, 3H), 1.38 (d, J=7.2 Ha, 3H); LC-MS 449 (MH+)

Example 103

3-(4-(3-hydroxyphenylamino)thieno[3,2-d]pyrimidine-6-yl)benzo 산

The synthesis of (3-(4-(3-hydroxyphenylamino) thieno[3,2-d]pyrimidin-6-yl)benzoic acid)) (LCB03-0051)

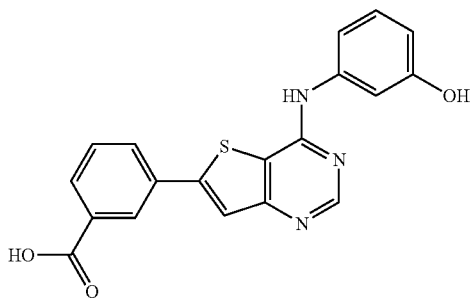 [SMILES: O=C(O)c1cccc(-c2cc3ncnc(Nc4cccc(O)c4)c3s2)c1]

¹H-NMR (400 MHz, DMSO-d₆); δ 9.70 (brs, 1H), 8.61 (s, 1H), 8.35 (s, 1H), 8.19 (d, J=7.6 Hz, 1H), 8.04-8.01 (m, 2H), 7.68 (t, J=7.6 Hz, 1H), 7.50 (d, J=8.4 Hz, 1H), 7.45 (s, 1H), 7.24 (t, J=8.0 Hz, 1H), 6.61 (d, J=8.0 Hz, 1H); LC-MS 364 (MH+)

Example 104

3-(6-(4-(ethoxymethyl)phenyl)thieno[3,2-d]pyrimidine-4-ylamino)phenol

The synthesis of (3-(6-(4-(ethoxymethyl)phenyl) thieno[3,2-d]pyrimidin-4-ylamino)phenol)) (LCB03-0073)

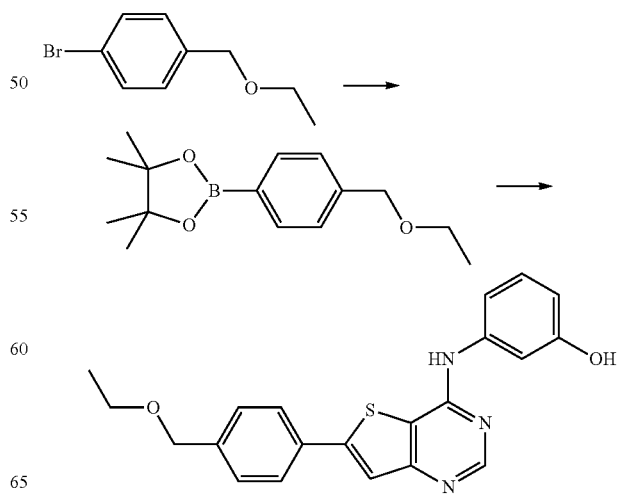

Bis(pinacolate)diborane (0.16 g, 0.63 mmol), PdCl₂ dppf (13 mg, 0.015 mmol), and potassium acetate (0.15 g, 1.57 mmol) were mixed in a reaction vessel and vacuum-dried. The compound (0.11 g, 0.52 mmol) synthesized in the example of synthesis 30 was dissolved in 3 ml of dimethylformamide degassed with N₂ and added into the reaction mixture in the reaction vessel followed by stirring for 15 hours at 85° C. The reaction mixture was cooled to room temperature and extracted with 50 ml of ethyl acetate and 50 ml of saturated ammonium chloride 50 ml. The organic layer was washed with 50 ml of ammonium chloride twice, and then dried with anhydrous sodium sulfate and concentrated under vacuum to obtain 2-(4-(ethoxymethyl)phenyl)-4,4,5,5-tetramethyl-1,3,2-dioxaborane as brown oil type. This compound, the compound synthesized in the example of synthesis 6 (50 mg, 0.11 mmol), and PdCl2 dppf (3 mg, 0.003 mmol) were sequentially added into 20 ml of degassed dimethylformamide, then 2N sodium carbonate solution (0.12 ml, 0.23 mmol) was further added. After stirring at 80° C. for 5 hours, the reaction mixture was cooled to room temperature and extracted with 100 ml of ethylacetate and 100 ml of saturated ammonium chloride. The organic layer was washed twice using 100 ml of saturated ammonium chloride and dried using sodium sulfate and concentrated under vacuum. After column chromatography (dichloromethane/methanol, 20/1) was done, the title compound (20 mg, 64%) was obtained.

¹H-NMR (400 MHz, DMSO-d₆); δ 9.60 (brs, 1H), 9.44 (brs, 1H), 8.58 (s, 1H), 7.88 (s, 1H), 7.85 (d, J=8.0 Hz, 1H), 7.47 (d, J=8.0 Hz, 2H), 7.33 (s, 1H), 7.19 (d, J=8.0 Hz, 1H), 7.14 (t, J=8.0 Hz, 2H), 6.52 (d, J=7.6 Hz, 1H), 4.52 (s, 2H), 3.52 (q, J=7.0 Hz, 2H), 1.18 (t, J=6.8 Hz, 3H); LC-MS 378 (MH+)

Example 105

2-(4-(4-(3-hydroxyphenylamino)thieno[3,2-d]pyrimidine-6-yl)benzamido)prophane acid The synthesis of (2-(4-(4-(3-hydroxyphenylamino)thieno[3,2-d]pyrimidin-6-yl)benzamido)propanoic acid)) (LCB03-0075)

¹H-NMR (400 MHz, CDCl₃); δ 10.07 (brs, 1H), 9.53 (brs, 1H), 8.82 (d, J=10.8 Hz, 1H), 8.67 (s, 1H), 8.05-7.97 (m, 4H), 7.28 (s, 1H), 7.18 (d, J=7.2 Hz, 2H), 6.59-6.58 (m, 1H), 4.44 (p, J=10.8 Hz, 1H), 1.49 (d, J=10.8 Hz, 3H); LC-MS 435 (MH+)

Example 106

Step 1

N-(3-(4-methoxybenzyloxy)phenyl)-2-(4-methylpiperazine-1-yl)thiazolo[4,5-d]pyrimidine-7-amine The synthesis of (N-(3-(4-methoxybenzyloxy)phenyl)-2-(4-methylpiperazin-1-yl)thiazolo[4,5-d]pyrimidin-7-amine)

The compound (100 mg, 0.24 mmol) synthesized in the example of synthesis 33 was dissolved in 2 ml of N-methylpyrrolidine and added with N-methylpiperazine (0.57 ml, 4.87 mmol) before reflux for 18 hours. The mixture was extracted with 40 ml of water and 40 ml of ethylacetate, dried using sodium sulfate, filtered, and then concentrated under vacuum. After column chromatography (dichloromethane/methanol, 20/1→15/1), the title compound (111 mg, 99%) was obtained.

¹H-NMR (400 MHz, CDCl₃); δ 8.52 (s, 1H), 7.35 (d, J=8.4 Hz, 2H), 7.29 (t, J=8.0 Hz, 1H), 7.00-6.99 (m, 1H), 6.91-6.86 (m, 4H), 5.01 (s, 2H), 3.81 (s, 3H), 3.66 (m, 4H), 2.50-2.47 (m, 4H), 2.33 (s, 3H); LC-MS 463 (MH+)

Step 2

3-(2-(4-methylpiperazine-1-yl)thiazolo[4,5-d]pyrimidine-7-ylamino)phenol trifluoroacetic acid The synthesis of (3-(2-(4-methylpiperazin-1-yl)thiazolo[4,5-d]pyrimidin-7-ylamino)phenol. TFA)) (LCB03-0100)

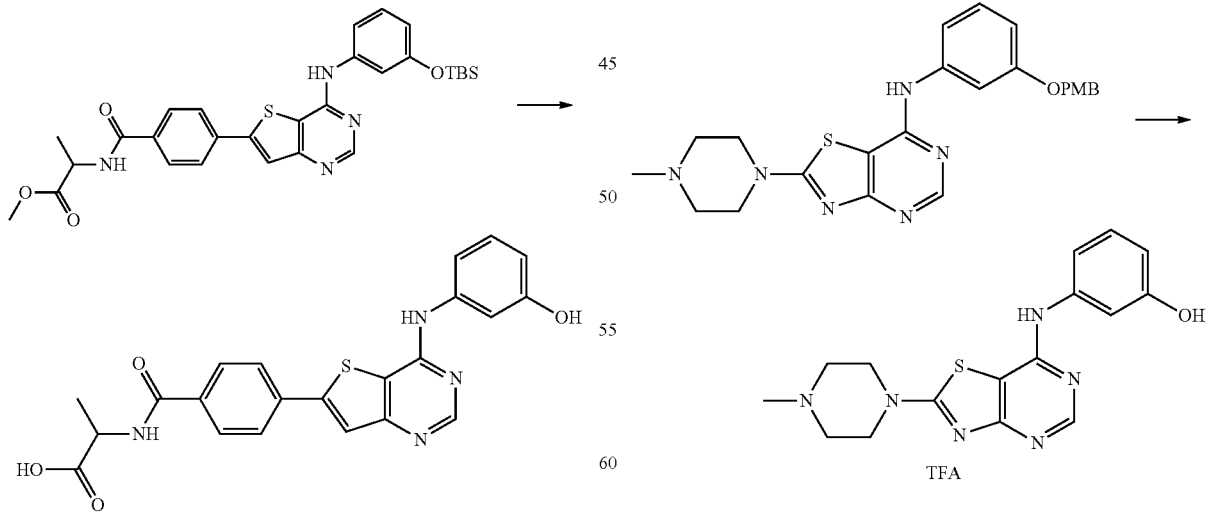

The title compound (18 mg, 60%) was obtained from the compound (40 mg, 0.07 mmol) synthesized in the step 1 of the preferred embodiment 102 by the method similar to the preferred embodiment 31.

The compound (50 mg, 0.108 mmol) synthesized in the step 1 described above was dissolved in 2 ml of dichloromethane and added 2 ml of trifluoroacetic acid and anisole (59 μl, 0.54 mmol) before stirring at room temperature for 10 hours. After the reaction mixture was concentrated under vacuum, it was subject to azotrope-concentration using dichloromethane and methanol, diethylether to obtain the title compound (48 mg, 99%).

$^1$H-NMR (600 MHz, Acetone-$d_6$); δ 8.69 (s, 1H), 7.31-7.28 (m, 1H), 7.15-7.13 (m, 1H), 7.02-6.98 (m, 1H), 6.87-6.84 (m, 1H), 4.13-4.10 (m, 4H), 3.59-3.58 (m, 4H), 3.02 (s, 3H); LC-MS 343 (MH+)

Comparative Example

The Synthesis of Control Compound 1~3

In order to confirm the excellent efficacy of the compounds of the present invention, Inventors synthesized the following three control compounds. These compounds have the pharmacophore of thieno pyridine as similarly to the compounds of the present invention, however they were not included in the chemical formula 1 defined in the present invention. The preferred embodiments for the synthesis of the control compounds were described in the following examples of synthesis.

Control compound 1

Control compound 2

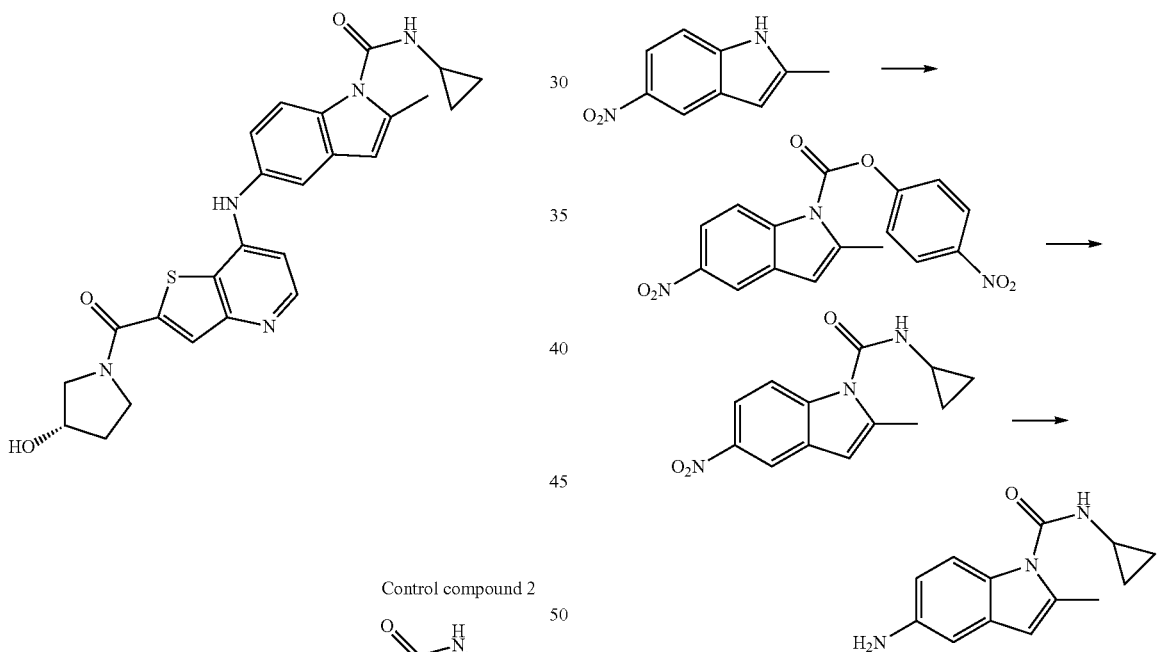

Control compound 3

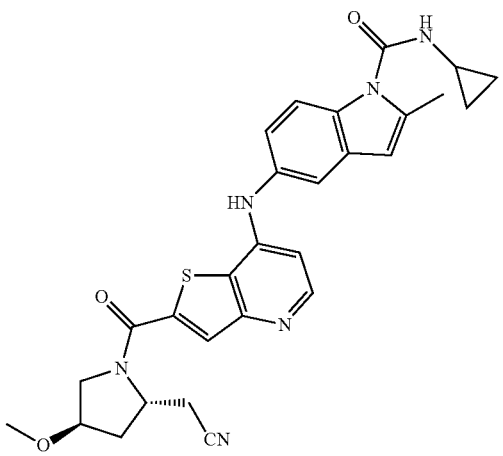

Comparative Preparation Example 1

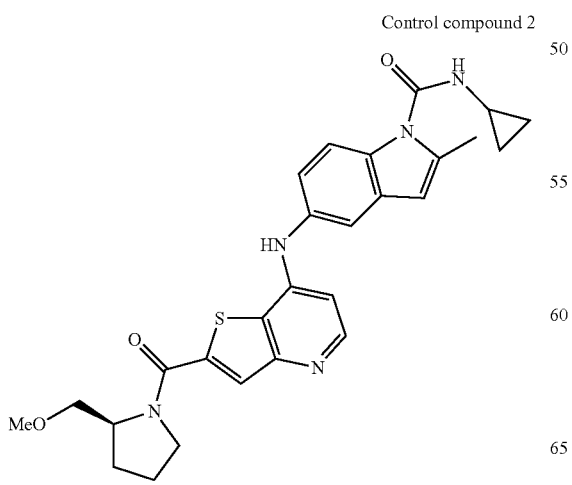

Comparative Preparation Example 1-1

2-methyl-5-nitroindole (2 g, 8.78 mmol) was dissolved into 80 ml of dichloromethane, and then sodium hydroxide (1.1 g, 26.36 mmol), tetrabutylammonium bromide (32 mg, 0.87 mmol), and 4-nitrophenyl chloroformate (1.86 g, 9.22 mmol) were sequentially added followed by stirring at room temperature for 1 hour. After filtering out the solid made in the reaction, the reaction mixture was washed with dichloromethane. The resultant liquid layer was concentrated and 2-methyl-5-nitro-1-(4-nitrophenoxycarbonyl)indole (2.9 g, 96%) was obtained as yellow solid.

$^1$H-NMR (600 MHz, DMSO-d$_6$); δ 8.73 (d, J=4.8 Hz, 1H), 8.13 (s, 1H), 7.69 (d, J=4.8 Hz, 1H), 5.08 (brs, 1H), 4.40~4.34 (m, 1H), 4.02~3.95 (m, 2H), 3.69~3.59 (m, 2H), 2.05~1.94 (m, 2H) LC-MS 342 (MH+)

Comparative Preparation Example 1-2

After 2-methyl-5-nitro-1-(4-nitrophenoxycarbonyl)indole (1.9 g, 5.56 mmol) was dissolved into 25 ml of tetrahydrofuran, cycloprophyl amine (3.1 ml, 44.53 mmol) was added and the mixture was stirred at room temperature for 3 hours. After extraction with water and ethylacetate, the solid made in the reaction was removed by filtering. Then, column chromatography (ethylacetate/n-hexane, 1/4) was performed to obtain 2-methyl-5-nitro indole-1-carboxyacid cycloprophylamide (660 mg, 46%) as yellow solid.

$^1$H-NMR (600 MHz, CDCl$_3$); δ 8.40 (d, J=2.4 Hz, 1H), 8.09 (dd, J=9.6, 2.4 Hz, 1 Hz), 7.65 (d, J=9.6 Hz, 1H), 6.47 (s, 1H), 5.79 (brs, 1H), 2.98~2.82 (m, 1H), 2.59 (s, 3H), 0.99~0.97 (m, 2H), 0.79~0.74 (m, 2H) LC-MS 476 (MH+)

Comparative Preparation Example 1-3

After 2-methyl-5-nitro indole-1-carboxyacid methylamide (860 mg, 3.32 mmol) was dissolved into ethylacetate/tetrahydrofuran (30 ml/24 ml), 10% Pd/C (354 mg, 0.33 mmol) was added, followed by stirring at room temperature for 2 hours. After removing Pd with cellite, vacuum-concentration was carried out. Then, column chromatography (dichloromethane/methanol, 98/2) was performed to obtain 5-amino-2-methyl-indole-1-carboxyacid cyclorophylamide (490 mg, 64%) as orange-colored solid.

$^1$H-NMR (600 MHz, CDCl$_3$); δ 7.32 (d, J=8.4 Hz, 1H), 6.76 (d, J=2.4 Hz, 1H), 6.56 (dd, J=8.4, 2.4 Hz, 1H), 6.136 (s, 1H), 5.84 (brs, 1H), 3.55 (brs, 1H), 2.89~2.86 (m, 1H), 2.53 (s, 3H), 0.92~0.88 (m, 2H), 0.71~0.69 (m, 2H) LC-MS 230 (MH+)

Comparative Preparation Example 2

The synthesis of 5-[2-(3R-hydroxy-pyrrolidine-1-carbonyl)-thieno[3,2-b]pyridine-7-ylamino]-2-methyl-indole-1-carboxyacid cycloprophylamide

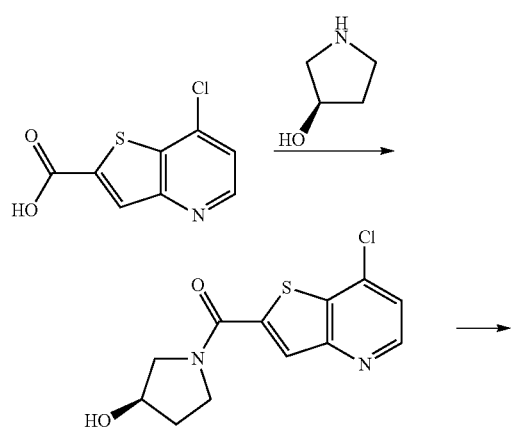

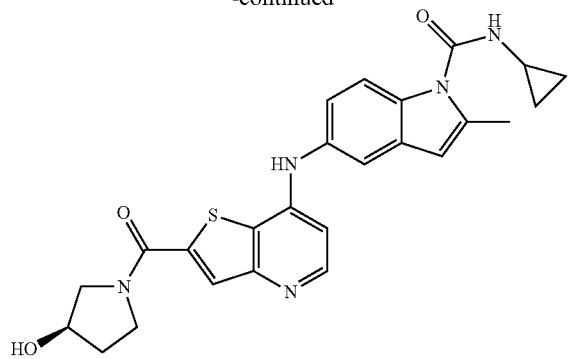

Comparative Preparation Example 2-1

The starting material (0.1 g, 0.46 mmol) synthesized by the method similar to the example of synthesis 6 was dissolved into 5 ml of dichloromethane and thionylchloride (0.05 ml, 0.70 mol) and 1 drop of dimethylformamide were added, followed by reflux for 2 hours. After removing the solvent in the reactant by vacuum-distillation, R-3-pyrrolidinol (45 mg, 0.51 mmol) dissolved in 1 ml of dichloromethane was added slowly at room temperature and stirred for 2 hours. After removing the solvent in the reactant by vacuum-distillation, column chromatography (dichloromethane/methanol, 98/2) was performed to obtain the intermediate (98 mg, 74%) as white solid.

$^1$H-NMR (600 MHz, DMSO-d$_6$); δ 8.73 (d, J=4.8 Hz, 1H), 8.13 (s, 1H), 7.69 (d, J=4.8 Hz, 1H), 5.08 (brs, 1H), 4.40~4.34 (m, 1H), 4.02~3.95 (m, 2H), 3.69~3.59 (m, 2H), 2.05~1.94 (m, 2H)

LCMS 283 (MH+)

Comparative Preparation Example 2-2

The obtained intermediate (97 mg, 0.34 mmol) and the compound obtained in the example of synthesis 1 for the control compound (87 mg, 0.38 mmol) were dissolved in 0.6 ml of dichloromethane and 6 ml of ethanol and added with 0.08 ml of 4M HCl/dioxane, followed by reflux for 20 hours. After removing the solvent in the reactant by vacuum-distillation, column chromatography (dichloromethane/methanol, 97/3) was performed to obtain the title compound (100 mg, 60%) as yellow solid.

$^1$H-NMR (600 MHz, DMSO-d$_6$); δ 9.11 (brs, 1H), 8.52 (s, 1H), 8.29 (d, J=5.4 Hz, 1H), 7.83 (d, J=39.6 Hz, 1H), 7.55 (d, J=8.4 Hz, 1H), 7.37 (s, 1H), 7.10, (8.4 Hz, 1H), 6.73 (d, 4.8 Hz, 1H), 6.36 (s, 1H), 5.07 (d, J=8.4 Hz, 1H), 4.35 (d, J=33 Hz, 1H), 3.95~3.90 (m, 2H), 3.64~3.55 (m, 2H), 3.46~3.44 (m, 1H), 2.88~2.82 (m, 1H), 2.47 (s, 3H), 2.03~1.85 (m, 2H), 0.77~0.76 (m, 2H), 0.69~0.64 (m, 2H)

LCMS 476 (MH+)

Comparative Preparation Example 3

The synthesis of 5-(2-[(S)-2-(methoxymethyl)pyrrolidine-1-carbonyl]thieno[3,2-b]pyridine-7-ylamino)-2-methylindole-1-carboxyacid cycloprophylamide

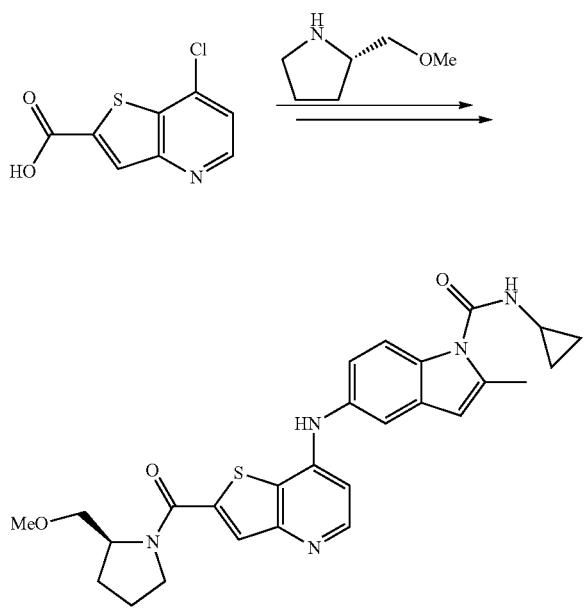

The title compound was obtained by the similar method of the example of synthesis 2 for the control compound.

$^1$H-NMR (600 MHz, CDCl$_3$); δ 8.32 (d, J=6.0 Hz, 1H), 7.77 (brs, 1H), 7.61 (d, J=8.4 Hz, 1H), 7.37 (d, 1.8 Hz, 1H), 7.08 (dd, J=8.4, 2.4 Hz, 1H), 6.68 (d, J=6.0 Hz, 1H), 6.29 (s, 1H), 6.19 (s, 1H), 6.12 (brs, 1H), 4.49 (brs, 1H), 3.87~3.83 (m, 2H), 3.65~3.61 (m, 2H), 3.38 (s, 3H), 2.96~2.92 (m, 1H), 2.59 (s, 3H), 2.08~1.79 (m, 5H), 0.98~0.92 (m, 2H), 0.88~0.86 (m, 2H)

LCMS 504 (MH+)

Comparative Preparation Example 4

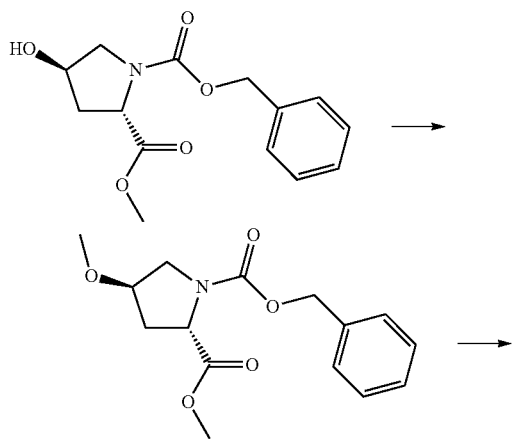

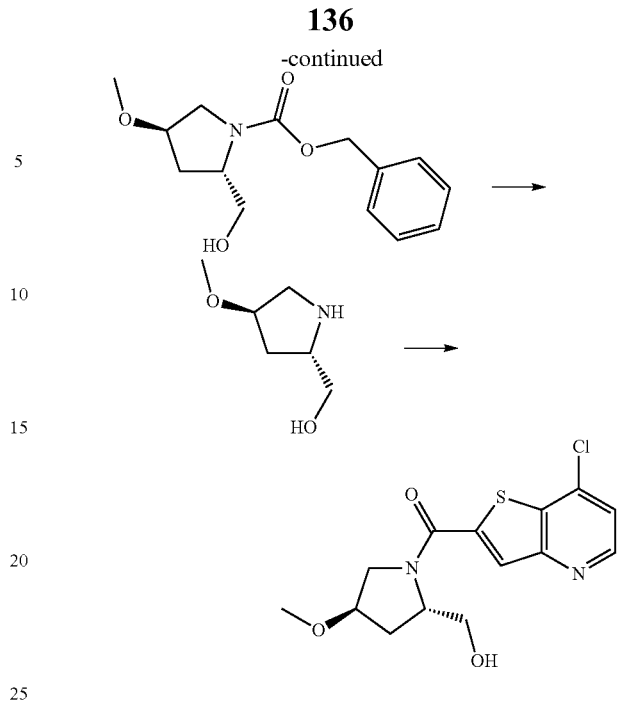

(2S,4R)-4-hydroxypyrrolidine-1,2-dicarboxyacid 1-benzylester 2-methylester (1.6 g, 6.03 mmol) was dissolved in 16 ml of acetone and then silver oxide (4.7 g, 20.50 mol) and iodomethane (1.3 ml, 21.10 mmol) were added, followed by stirring at 57° C. for 8 hours. After removing silver oxide using cellite, the reaction mixture was washed with methanol and vacuum concentrated. Column chromatography (ethylacetate/n-hexane, 1/9) was performed to obtain (2S,4R)-4-methoxypyrrolidine-1,2-dicarboxyacid 1-benzylester 2-methylester (1.53 g, 87%) as oil.

$^1$H-NMR (600 MHz, CDCl$_3$); δ 7.31~7.23 (m, 5H), 5.22~5.00 (m, 2H), 4.44~4.40 (m, 1H), 4.10~4.02 (m, 1H), 3.76 (s, 3H), 3.69 (m, 1H), 3.54 (s, 2H), 3.29 (brs, 3H), 2.42~2.30 (m, 1H)

(2S,4R)-4-methoxypyrrolidine-1,2-dicarboxyacid 1-benzylester 2-methylester (1.53 g, 5.25 mmol) was dissolved in 7 ml of tetrahydrofuran and added slowly with 3.15 ml of lithiumborohydride (2.0M/THF) at 0° C., followed by stirring for 4 hours. After terminating the reaction by adding 1 ml of saturated sodiumbicarbonate, the reaction mixture was extracted using ethylacetate and sodiumbicarbonate and then vacuum-concentrated. Column chromatography (ethylacetate/n-hexane, 1/9) was performed to obtain (2S,4R)-2-hydroxymethyl-4-methoxypyrrolidine-1-carboxyacid benzylester (1.3 g, 93%) as transparent oil.

$^1$H-NMR (600 MHz, CDCl$_3$); δ 7.51~7.38 (m, 5H), 5.24~5.00 (m, 2H), 4.45~4.40 (m, 1H), 4.23~4.18 (m, 2H), 3.95~3.73 (m, 3H), 3.51~3.42 (m, 1H), 3.31 (s, 3H), 2.22~2.14 (m, 1H)

(2S,4R)-2-hydroxymethyl-4-methoxypyrrolidine-1-carboxyacid benzylester (1.25 g, 4.71 mmol) was dissolved in methanol and added with 10% Pd/C, followed by stirring for 15 hours. After removing Pd using cellite and vacuum-concentration, ((2S,4R)-4-methoxypyrrolidine-2-yl)methanol (606 mg, 98%) was obtained.

$^1$H-NMR (600 MHz, CDCl$_3$); δ 4.11~4.08 (m, 2H), 4.00~3.98 (m, 1H), 3.82~3.79 (m, 1H), 3.51~3.49 (m, 1H), 3.41~3.88 (m 1H), 3.32 (s, 3H), 2.17~2.14 (m, 1H), 2.03~1.99 (m, 1H)

The title compound was obtained from ((2S,4R)-4-methoxypyrrolidine-2-yl)methanol using the method similar to the example of synthesis 2 for the control compound.

$^1$H-NMR (600 MHz, CDCl$_3$); δ 8.65 (d, J=4.8 Hz, 1H), 7.58 (s, 1H), 7.37 (d, J=4.8 Hz, 1H), 4.61~4.57 (m, 1H), 4.12~4.05 (m, 2H), 4.01 (brs, 1H), 3.94~3.87 (m, 2H), 3.77~3.74 (brs, 1H) 3.28 (s, 3H), 2.34~2.30 (m, 1H), 1.87~1.82 (m, 1H) LC-MS 327 (MH+)

Comparative Preparation Example 5

The synthesis of 5-[2-((2S,4R)-2-hydroxymethyl-4-methoxy-pyrrolidine-1-carbonyl)-benzo[b]thiophene-7-ylamino]-2-methyl-indole-1-carboxy-acid cycloprophylamide

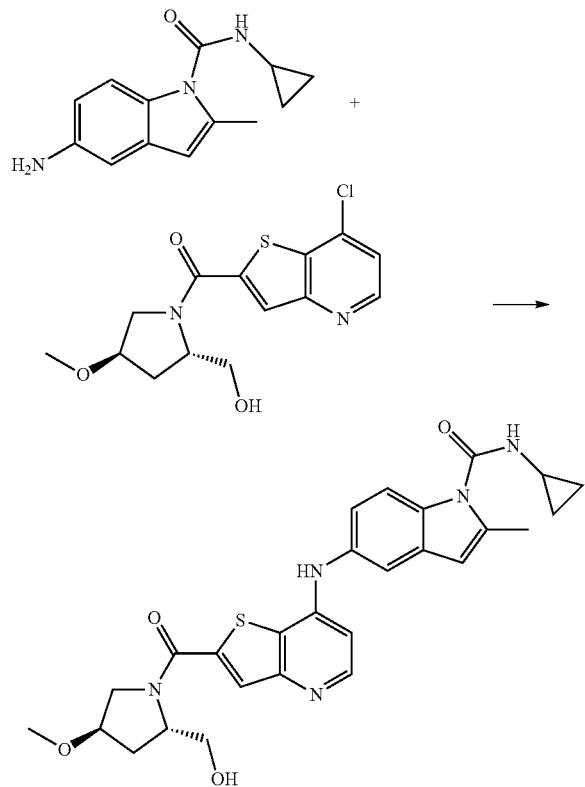

The title compound shown above was obtained by the methods similar to the example of synthesis 2-2 for the control compound from the compound (22 mg, 0.09 mmol) synthesized in the example of synthesis 1 for the control compound and the compound (28 mg, 0.08 mmol) synthesized in the example of synthesis 4 for the control compound.

$^1$H-NMR (600 MHz, CDCl$_3$); δ 8.94 (s, 1H), 8.58 (d, J=3.0 Hz, 1H), 8.34 (d, J=5.3 Hz, 1H), 7.84 (s, 1H), 7.61 (d, J=8.6 Hz, 1H), 7.43 (d, J=1.8 Hz, 1H), 7.16 (dd, J=8.8, 2.0 Hz, 1H), 6.78 (d, J=5.6 Hz, 1H), 6.54 (s, 1H), 6.43 (s, 1H), 4.86 (t, J=5.5 Hz, 1H), 4.28 (brs, 1H), 4.09 (brs, 1H), 3.95~3.89 (m, 2H), 3.78-3.75 (m, 1H), 3.60~3.58 (m, 1H), 3.23 (s, 3H), 2.94~2.89 (m, 1H), 2.56 (m, 3H), 2.15 (t, J=7.3 Hz, 2H), 0.84~0.82 (m, 2H), 0.74~0.71 (m, 2H) LC-MS 520 (MH+)

Experimental Example 1

In Vitro Measurement of the Inhibitory Activity Against c-Src Family and Discoidin Domain Receptor Family Tyrosine Kinases The compounds denoted as chemical formula 1 and the three control compounds for comparison were assayed for their in vitro inhibitory activity against c-Src, Hck, Fgr, Lyn tyrosine kinase of Src family tyrosine kinase that plays a central role in the activation of various inflammatory cells. In addition, the compounds denoted as chemical formula 1 and the three control compounds for comparison were assayed for their in vitro inhibitory activity against the tyrosine kinase activity of discoidin domain receptor family, DDR1 and DDR2 that also are known to play an important role in the activation of some immune cells and alpha smooth muscle cells, and fibroblast. Human recombinant tyrosine kinase proteins of c-Src, Hck, Fgr Lyn used in the experiments were purified in insect cells by a conventional method after their expression using the baculovirus expression system. DDR1 and DDR2 kinase domain proteins fused with Glutathione-S-transferase (GST) were used after their activation and purification according to the method as described in the previous paper (Yang K. et al, J Biol. Chem.; 280(47):39058-66, 2005). More specifically, the kinase domain fragment of the site exposed into the cytoplasm in the entire human DDR1 and DDR2 protein were fused to GST protein and c-Src protein were co-expressed in insect cells using conventional baculovirus expression system to activate the DDR1 and DDR2 tyrosine kinase domain fused to GST and the activated kinase proteins were purified by column chromatography method using glutathione-agarose beads. The inhibitory activity measurement against the kinases mentioned above was measured in the kinase inhibition reaction mixture containing 2 ul purified kinase protein (10-50 ng), 20 mM Tris-HCl, pH 8.0, 5 mM MgCl$_2$, 0.5 mM dithiothreitol, 0.01 mM ATP, 4 ug of poly(D$_4$Y)$_n$ peptide substrate (Promega), 0.2 uCi of $^{32}$P-ATP and the each compound shown in table 1. The mixture was incubated for 15 min at 30° C. and the reaction was then ended by adding a half volume of 30% phosphoric acid solution. Subsequently, the reaction mixture solution was spotted in avidin coated membrane (Promega). This membrane was washed using 50 mM phosphate, 0.1N NaCl buffer (pH 6.0) solution for 10 min 5 times and then the radioactivity of each spot was quantified by using a BAS image analyzer (Fuji).

Table 1 shows % inhibition of compounds described in the preferred embodiment and the three control compounds used for comparison at the concentration of 1 uM against c-Src, Hck, Fgr, Lyn, DDR1 and DDR2 tyrosine kinase.

TABLE 1

| compound | c-Src | Hck | Fgr | Lyn | DDR1 | DDR2 |
|---|---|---|---|---|---|---|
| LCB 03-0008 | >70% | >70% | >70% | >70% | >70% | >70% |
| LCB 03-0013 | >70% | >70% | >60% | >70% | >60% | >60% |
| LCB 03-0015 | >60% | >60% | >60% | >60% | >20% | >20% |
| LCB 03-0016 | >70% | >70% | >70% | >70% | >20% | >20% |
| LCB 03-0017 | >60% | >60% | >60% | >60% | >70% | >70% |
| LCB 03-0018 | >70% | >70% | >70% | >70% | >70% | >70% |
| LCB 03-0019 | >60% | >60% | >60% | >60% | >70% | >70% |
| LCB 03-0020 | >70% | >70% | >70% | >70% | >60% | >60% |
| LCB 03-0021 | >50% | >60% | >60% | >60% | >30% | >30% |
| LCB 03-0022 | >60% | >60% | >60% | >60% | >10% | >10% |
| LCB 03-0023 | >40% | >40% | >40% | >40% | >60% | >60% |
| LCB 03-0024 | >30% | >30% | >30% | >30% | >70% | >70% |
| LCB 03-0026 | >60% | >60% | >60% | >40% | >20% | >20% |
| LCB 03-0027 | >40% | >40% | >40% | >40% | >70% | >70% |
| LCB 03-0028 | >30% | >30% | >30% | >30% | >50% | >50% |
| LCB 03-0029 | >60% | >60% | >60% | >60% | >20% | >20% |
| LCB 03-0030 | >40% | >30% | >30% | >40% | >70% | >70% |
| LCB 03-0031 | >40% | >40% | >40% | >30% | >70% | >70% |
| LCB 03-0032 | >80% | >80% | >80% | >80% | >80% | >80% |
| LCB 03-0033 | >60% | >60% | >60% | >60% | >80% | >80% |
| LCB 03-0034 | >80% | >70% | >80% | >80% | >80% | >80% |
| LCB 03-0035 | >80% | >80% | >80% | >80% | >80% | >80% |
| LCB 03-0036 | >80% | >80% | >80% | >80% | >80% | >80% |

TABLE 1-continued

| compound | c-Src | Hck | Fgr | Lyn | DDR1 | DDR2 |
|---|---|---|---|---|---|---|
| LCB 03-0037 | >80% | >80% | >70% | >80% | >80% | >80% |
| LCB 03-0038 | >60% | >50% | >50% | >60% | >70% | >70% |
| LCB 03-0039 | >50% | >50% | >50% | >50% | >70% | >70% |
| LCB 03-0040 | >80% | >80% | >80% | >80% | >80% | >80% |
| LCB 03-0041 | >80% | >80% | >80% | >80% | >80% | >80% |
| LCB 03-0042 | >80% | >80% | >80% | >80% | >80% | >80% |
| LCB 03-0043 | >30% | >30% | >30% | >30% | >80% | >80% |
| LCB 03-0044 | >30% | >30% | >30% | >30% | >80% | >80% |
| LCB 03-0045 | >30% | >20% | >20% | >30% | >80% | >80% |
| LCB 03-0046 | >30% | >30% | >30% | >30% | >80% | >80% |
| LCB 03-0047 | >30% | >30% | >30% | >20% | >70% | >70% |
| LCB 03-0049 | >40% | >40% | >40% | >40% | >80% | >80% |
| LCB 03-0050 | >40% | >40% | >40% | >40% | >80% | >80% |
| LCB 03-0051 | N/D | N/D | N/D | N/D | >80% | >80% |
| LCB 03-0052 | >60% | >60% | >50% | >60% | >80% | >80% |
| LCB 03-0053 | >70% | >70% | >70% | >70% | >80% | >80% |
| LCB 03-0054 | >60% | >60% | >60% | >50% | >80% | >80% |
| LCB 03-0055 | >50% | >50% | >50% | >50% | >80% | >80% |
| LCB 03-0056 | >50% | >50% | >50% | >50% | >80% | >80% |
| LCB 03-0057 | >50% | >50% | >50% | >50% | >80% | >80% |
| LCB 03-0058 | >40% | >40% | >40% | >40% | >80% | >80% |
| LCB 03-0059 | >50% | >50% | >50% | >50% | >80% | >80% |
| LCB 03-0060 | >80% | >80% | >80% | >80% | >80% | >80% |
| LCB 03-0061 | >80% | >80% | >80% | >80% | >80% | >80% |
| LCB 03-0062 | >80% | >80% | >80% | >80% | >80% | >80% |
| LCB 03-0063 | >80% | >80% | >80% | >80% | >80% | >80% |
| LCB 03-0064 | >80% | >80% | >80% | >80% | >80% | >80% |
| LCB 03-0065 | >80% | >80% | >80% | >80% | >70% | >70% |
| LCB 03-0066 | >80% | >80% | >80% | >80% | >80% | >80% |
| LCB 03-0067 | >80% | >80% | >80% | >80% | >80% | >80% |
| LCB 03-0068 | N/D | N/D | N/D | N/D | >80% | >80% |
| LCB 03-0069 | N/D | N/D | N/D | N/D | >50% | >50% |
| LCB 03-0070 | >80% | >80% | >80% | >80% | >80% | >80% |
| LCB 03-0071 | N/D | N/D | N/D | N/D | >70% | >70% |
| LCB 03-0072 | N/D | N/D | N/D | N/D | >80% | >80% |
| LCB 03-0073 | >30% | >30% | >30% | >30% | >80% | >80% |
| LCB 03-0074 | >30% | >30% | >30% | >30% | >80% | >80% |
| LCB 03-0075 | >30% | >30% | >30% | >30% | >80% | >80% |
| LCB 03-0076 | >80% | >80% | >80% | >80% | >80% | >80% |
| LCB 03-0079 | >80% | >80% | >80% | >80% | >80% | >80% |
| LCB 03-0080 | >60% | >60% | >60% | >60% | >80% | >80% |
| LCB 03-0082 | >70% | >70% | >70% | >70% | N/D | N/D |
| LCB 03-0083 | >60% | >60% | >60% | >60% | >80% | >80% |
| LCB 03-0084 | >60% | >60% | >60% | >60% | >80% | >80% |
| LCB 03-0085 | >70% | >70% | >70% | >70% | >80% | >80% |
| LCB 03-0086 | >70% | >70% | >70% | >70% | >80% | >80% |
| LCB 03-0087 | >70% | >70% | >70% | >70% | >70% | >70% |
| LCB 03-0088 | >70% | >70% | >70% | >70% | >90% | >90% |
| LCB 03-0089 | >70% | >70% | >70% | >70% | >70% | >70% |
| LCB 03-0090 | >70% | >70% | >70% | >70% | >70% | >70% |
| LCB 03-0091 | >70% | >70% | >70% | >70% | >70% | >70% |
| LCB 03-0092 | >60% | >60% | >50% | >60% | >80% | >80% |
| LCB 03-0093 | >60% | >60% | >60% | >60% | >80% | >80% |
| LCB 03-0094 | >60% | >60% | >60% | >60% | >80% | >80% |
| LCB 03-0095 | >60% | >50% | >60% | >60% | >80% | >80% |
| LCB 03-0097 | >30% | >30% | >30% | >30% | >80% | >80% |
| LCB 03-0098 | >30% | >30% | >30% | >30% | >80% | >80% |
| LCB 03-0099 | >30% | >30% | >30% | >30% | >80% | >80% |
| LCB 03-0100 | >30% | >30% | >30% | >30% | >70% | >70% |
| LCB 03-0101 | >70% | >70% | >70% | >70% | >70% | >70% |
| LCB 03-0102 | >60% | >60% | >60% | >60% | >70% | >70% |
| LCB 03-0103 | >50% | >50% | >50% | >50% | >70% | >70% |
| LCB 03-0104 | >50% | >50% | >50% | >50% | >80% | >80% |
| LCB 03-0105 | >50% | >50% | >50% | >50% | >70% | >70% |
| LCB 03-0106 | >70% | >70% | >70% | >70% | >70% | >70% |
| LCB 03-0107 | >70% | >70% | >70% | >70% | >80% | >80% |
| LCB 03-0108 | >80% | >80% | >80% | >80% | >80% | >80% |
| LCB 03-0109 | >70% | >70% | >70% | >70% | >80% | >80% |
| LCB 03-0110 | >90% | >80% | >80% | >90% | >90% | >90% |
| LCB 03-0111 | >80% | >80% | >80% | >80% | >90% | >90% |
| LCB 03-0112 | >80% | >80% | >80% | >80% | >80% | >80% |
| LCB 03-0113 | >50% | >50% | >50% | >50% | >70% | >70% |
| LCB 03-0114 | >50% | >50% | >50% | >50% | >70% | >70% |
| LCB 03-0115 | >50% | >50% | >50% | >50% | >70% | >70% |
| Control compound 1 | <20% | <20% | <20% | <20% | <20% | <20% |
| Control compound 2 | <20% | <20% | <20% | <20% | <20% | <20% |
| Control compound 3 | <20% | <20% | <20% | <20% | <20% | <20% |

(>; more than <; less than, ND; not determined)

The compounds of the present invention shown in table 1 were found to inhibit Src family tyrosine kinase activity by average more than 65% at the concentration of 1 uM. Especially, the compounds of LCB 03-0032~37, LCB 03-0040~42, LCB 03-0060~67, LCB 03-0070, LCB 03-0076, LCB 03-0079~95, LCB 03-0107~112 that have common structural characters generally showed a high inhibition effect by more than 70-80% inhibition. On the other hand, all the three control compounds used for comparison showed an inhibition ability by less than 20% against Src family tyrosine kinases as compared with the compounds of the preferred embodiment in the present invention shown in table 1. Also the compounds shown in table 1 in the present invention inhibited the activity of discoidin domain receptor family tyrosine kinases by an average of more than 70% at the concentration of 1 uM. Especially, the compounds of LCB 03-0032~37, LCB 03-0040~68, LCB 03-0070, LCB 03-0072~80, LCB 03-0083~99, LCB 03-0107~112 that have common structural characters generally showed a high inhibition effect by more than 70-80% inhibition. On the other hand, all the three control compounds used for comparison showed low inhibition ability by less than 20% against discoidin domain receptor family tyrosine kinases as compared with the compounds of the preferred embodiment in the present invention shown in table 1. These facts showed that the compounds of the present invention that are derivatives having a common pharmacophore such as hydroxy anilino pyrimidine or hydroxy anilino pyridine generally have a strong inhibitory activity against discoidin domain receptor family tyrosine kinases and Src family tyrosine kinases. In contrast, the control compounds used for comparison have a significantly different pharmaceutical action mechanism from the compounds of the present invention since these control compounds have a weak inhibition activity against Src or discoidin family tyrosine kinases. From these facts, it can be concluded that the compounds of present invention are useful for the prevention or treatment of inflammatory diseases due to their effective suppression of the Src tyrosine kinase activity associated with inflammatory diseases, and particularly these compounds can be used effectively for the suppression of the inflammatory diseases that accompany tissue fibrosis and hypertrophy by activated fibroblast, epitherial cells and/or alpha smooth muscle cells since they inhibit together the discoidin domain receptor family tyrosine kinase activity which is important for the activations of fibroblast, epitherial cell or alpha smooth muscle cells.

Experimental Example 2

The Measurement of the Inhibition Activity Against Nitric Oxide (NO) and TNF-α Synthesis in Macrophages Activated by Treatment with LPS (Lipo-Poly-Saccharide)

When LPS is treated at in vivo and in vitro experiment, the increase of immune cytokines such as TNF-α, IL-6, IL-12 and iNOS (inducible nitric oxide synthase) that produce NO are induced mainly in macrophage cells. Currently the compounds to suppress the synthesis of such inflammatory immune modulators are considered to have an anti-inflammatory activity. The compounds of the present invention were treated into activated macrophages for measuring the inhibitory activity against the synthesis of TNF-α and NO at in vitro experiment. Specifically, J744A.1 macrophages were cultured in 24 well dish using DMEM medium containing 10% FBS. After the culture medium was replaced with DMEM supplemented with 1% FBS, the compounds of the preferred embodiment were treated at the concentration of 10 μM, then 100 ng/ml of LPS was treated after 30 minutes. Taken with culture medium after 6 hours, the amount of synthesized TNF-α was quantified using enzyme-linked immunosorbent assay kit (R & D Systems). As compared to the amount of TNF-α synthesized without the compound treatment, the reduced amount by the treatment of each compound was described as % inhibition in table 2.

TABLE 2

| compound | Inhibition (%) |
|---|---|
| LCB03-0008 | 67 |
| LCB03-0015 | 71 |
| LCB03-0018 | 68 |
| LCB03-0030 | 80 |
| LCB03-0032 | 77 |
| LCB03-0033 | 59 |
| LCB03-0034 | 75 |
| LCB03-0035 | 65 |
| LCB03-0036 | 61 |
| LCB03-0037 | 73 |
| LCB03-0038 | 85 |
| LCB03-0039 | 80 |
| LCB03-0040 | 84 |
| LCB03-0041 | 87 |
| LCB03-0042 | 98 |
| LCB03-0048 | 42 |
| LCB03-0049 | 57 |
| LCB03-0053 | 83 |
| LCB03-0054 | 77 |
| LCB03-0057 | 64 |
| LCB03-0058 | 58 |
| LCB03-0059 | 74 |
| LCB03-0060 | 78 |
| LCB03-0061 | 91 |
| LCB03-0062 | 82 |
| LCB03-0063 | 85 |
| LCB03-0064 | 73 |
| LCB03-0065 | 79 |
| LCB03-0066 | 93 |
| LCB03-0067 | 83 |
| LCB03-0070 | 77 |
| LCB03-0072 | 59 |
| LCB03-0076 | 90 |
| LCB03-0079 | 67 |
| LCB03-0080 | 59 |
| LCB03-0082 | 77 |
| LCB03-0083 | 62 |
| LCB03-0084 | 64 |
| LCB03-0085 | 74 |
| LCB03-0086 | 68 |
| LCB03-0087 | 68 |
| LCB03-0088 | 73 |
| LCB03-0089 | 71 |
| LCB03-0090 | 63 |
| LCB03-0091 | 68 |
| LCB03-0092 | 64 |
| LCB03-0093 | 53 |
| LCB03-0094 | 56 |
| LCB03-0101 | 71 |
| LCB03-0106 | 63 |
| LCB03-0107 | 45 |
| LCB03-0108 | 53 |
| LCB03-0109 | 56 |
| LCB03-0110 | 64 |
| LCB03-0111 | 57 |
| LCB03-0112 | 46 |
| Control compound1 | 16 |
| Control compound2 | 39 |
| Control compound3 | 19 |

The compounds of the present invention inhibited TNF-alpha synthesis at the concentration of 10 μM as shown in Table 2. Especially, the compounds of LCB 03-0032~37, LCB 03-0040~68, LCB 03-0070, LCB 03-0072~80, LCB 03-0083~99, LCB 03-0107~112 that have common structural characters showed around 70% or higher inhibitory effect and the compound of LCB 03-0108~0111 that have a common structural characteristic also showed the inhibitory activity by more than 50%. However, the three control compounds used for comparison showed significantly less inhibitory activities against TNF-alpha synthesis when compared with the compounds of the present invention as shown in Table 2. Form these facts, it can be concluded that the compounds of the present invention can be useful for prevention and/or treatment of inflammatory diseases due to their effective suppression of TNF-alpha production which is directly associated with the inflammatory diseases. Also, J744A.1 macrophage activated by the same method as mentioned above was cultured for 24 hours and 100 ul of the culture medium was mixed with the same volume of Griess reagent. The absorbance at 540 nm wavelength was estimated after 15 minutes to measure the relative amount of synthesized nitric oxide (NO) in the macrophage. Compared to the amount of NO without treatment of the compound, the reduced amount of NO by each compound treatment was described as % inhibition in table 3.

TABLE 3

| Compound | Inhibition (%) |
|---|---|
| LCB03-0008 | 87 |
| LCB03-0017 | 82 |
| LCB03-0018 | 89 |
| LCB03-0030 | 96 |
| LCB03-0032 | 92 |
| LCB03-0033 | 77 |
| LCB03-0034 | 90 |
| LCB03-0035 | 91 |
| LCB03-0036 | 81 |
| LCB03-0037 | 93 |
| LCB03-0038 | 88 |
| LCB03-0039 | 80 |
| LCB03-0040 | 93 |
| LCB03-0041 | 91 |
| LCB03-0042 | 91 |
| LCB03-0043 | 66 |
| LCB03-0047 | 56 |
| LCB03-0049 | 88 |
| LCB03-0053 | 94 |
| LCB03-0054 | 92 |
| LCB03-0057 | 87 |
| LCB03-0058 | 80 |
| LCB03-0059 | 88 |
| LCB03-0060 | 93 |
| LCB03-0061 | 92 |
| LCB03-0062 | 93 |
| LCB03-0063 | 89 |
| LCB03-0064 | 79 |

TABLE 3-continued

| Compound | Inhibition (%) |
|---|---|
| LCB03-0065 | 84 |
| LCB03-0066 | 87 |
| LCB03-0067 | 85 |
| LCB03-0070 | 90 |
| LCB03-0072 | 76 |
| LCB03-0073 | 85 |
| LCB03-0076 | 91 |
| LCB03-0079 | 74 |
| LCB03-0080 | 78 |
| LCB03-0082 | 90 |
| LCB03-0083 | 71 |
| LCB03-0084 | 85 |
| LCB03-0085 | 93 |
| LCB03-0086 | 72 |
| LCB03-0087 | 83 |
| LCB03-0088 | 97 |
| LCB03-0089 | 86 |
| LCB03-0090 | 90 |
| LCB03-0091 | 92 |
| LCB03-0092 | 90 |
| LCB03-0093 | 79 |
| LCB03-0094 | 77 |
| LCB03-0095 | 59 |
| LCB03-0101 | 76 |
| LCB03-0102 | 97 |
| LCB03-0107 | 81 |
| LCB03-0108 | 92 |
| LCB03-0109 | 90 |
| LCB03-0110 | 97 |
| LCB03-0111 | 92 |
| LCB03-0112 | 81 |
| Control compound1 | 32 |
| Control compound2 | 45 |
| Control compound3 | 21 |

The compounds of the present invention inhibited NO synthesis at the concentration of 10 μM as shown in Table 3. Especially, the compounds of LCB 03-0030, LCB 03-0031~38, LCB 03-0040~42, LCB 03-0053~54, LCB 03-0060~67, LCB 03~0070, LCB 03~0076, LCB 03~0082, LCB 03-0084~94, and LCB 03-0107~112 that have common structural characters showed generally around 80% or higher inhibitory effects. However, the three control compounds used for comparison showed significantly less inhibitory activities against NO synthesis when compared with the compounds of the present invention as shown in Table 3. These facts demonstrate that the compounds of the present invention can be useful for prevention and/or treatment of inflammatory diseases due to their effective suppression of TNF-alpha and/or NO which are important inflammatory modulators associated with the inflammatory diseases. In addition such activity of the compounds in the present invention is superior to ones of the three control compounds used for comparison.

Experimental Example 3

The Measurement of the Inhibition Activity Against Increased Alpha-Smooth Muscle Actin Protein Expression or Cell Migration in Activated Fibroblast Stimulated by Type 1 Collagen and TGF-β1

When fibroblast, epitherial cells and alpha smooth muscle cells are converted to myofibroblast by activation, one of characteristic features is that α-smooth muscle actin protein expression is increased. Also myoblast cells with the increased α-smooth muscle actin expression have a character of an increased migration. These phenomena appear together with the activation of inflammatory cells and the activated myoblast-type cells are known to contribute directly to the pathology of inflammatory diseases. We inventors confirm that the expression of alpha smooth muscle actin is highly increased by western blotting on the cell lysate using its specific antibosy when skin fibroblast cells isolated from Balb/C mouse were treated with 10 ng/ml of TGF-β1 for 48 hours after they were plated on 24 well culture dish coated with 200 ul of 100 ug/ml type I collagen. In this experiment, the expression level of alpha smooth muscle actin can be quantificated by measuring the density of α-smooth muscle actin protein band with densitometer after developing the X-ray film of chemiluminescence signal in western blotting experiment. In this experiment, the degree of inhibition against the increase of the α-smooth muscle actin at treatment of 0.5 uM of each compound was shown as % inhibition by comparison with the degree of inhibition without treatment of the compounds.

TABLE 4

| compound | Inhibition (%) |
|---|---|
| LCB03-0032 | 56 |
| LCB03-0033 | 60 |
| LCB03-0034 | 67 |
| LCB03-0035 | 55 |
| LCB03-0036 | 63 |
| LCB03-0037 | 55 |
| LCB03-0040 | 55 |
| LCB03-0041 | 66 |
| LCB03-0042 | 69 |
| LCB03-0059 | 56 |
| LCB03-0060 | 65 |
| LCB03-0061 | 68 |
| LCB03-0062 | 64 |
| LCB03-0063 | 61 |
| LCB03-0064 | 66 |
| LCB03-0065 | 58 |
| LCB03-0066 | 75 |
| LCB03-0067 | 49 |
| LCB03-0070 | 42 |
| LCB03-0072 | 39 |
| LCB03-0076 | 57 |
| LCB03-0079 | 61 |
| LCB03-0080 | 62 |
| LCB03-0083 | 55 |
| LCB03-0084 | 57 |
| LCB03-0085 | 51 |
| LCB03-0086 | 33 |
| LCB03-0087 | 29 |
| LCB03-0088 | 52 |
| LCB03-0089 | 25 |
| LCB03-0090 | 44 |
| LCB03-0091 | 39 |
| LCB03-0092 | 37 |
| LCB03-0093 | 43 |
| LCB03-0094 | 41 |
| LCB03-0095 | 37 |
| LCB03-0097 | 45 |
| LCB03-0098 | 51 |
| LCB03-0099 | 39 |
| LCB03-0107 | 71 |
| LCB03-0108 | 75 |
| LCB03-0109 | 67 |
| LCB03-0110 | 82 |
| LCB03-0111 | 79 |
| LCB03-0112 | 71 |
| Control compound1 | 16 |
| Control compound2 | 22 |
| Control compound3 | 8 |

As shown in table 4, the compounds of the present invention inhibit the α-smooth muscle actin protein expression at the concentration of 0.5 uM and the average of inhibition was by 55.3%. Especially, the compounds of LCB 03-0032~37, LCB 03-0040~42, LCB 03-0059~67, LCB 03-0070, 03-0076 LCB, LCB 03-0079~80, LCB 03-0083~85, LCB 03-0088, LCB 03-0107~112 that have common structural characters showed generally around 60% or higher inhibitory effects. However, the three control compounds used for comparison showed significantly less inhibitory activities as shown in table 4 when compared with the compounds of the present invention in the same experimental condition.

As fibroblast activated by collagen and TGF-β1 showed an increased migration, the inhibitory activity against the migration by the compounds of the present invention was measured. The high-density culture of mouse skin fibroblast in collagen-coated 6 well culture plate using DMEM medium containing 10% FBS were allowed to grow overnight to a mono layer culture of nearly 100% confluency next day. The straight line of regular width was made using a micro pipette tip for a scratch wound on the mono-layer culture, and then the culture was exchanged to DMEM medium and incubated with 10 ng/ml of TGF-β1 in cell culture incubator of 37° C. for 24 hours. The cultured cells were fixed using formalin and stained with crystal violet. Photo-pictures were taken at 100× magnification in five location selected randomly in the scratched wound site of each stained culture dish and then the number of the cells moved into the scratched wound area was counted and averaged. The average reduced number of migrated cells into the wound site by treating the compound of the present invention shown in table 5 was depicted as inhibition % of each compound in table 5 when the average number of the migrated cells without treatment of the compound was assigned by 100%.

TABLE 5

| compound | Inhibition (%) |
| --- | --- |
| LCB03-0032 | 35 |
| LCB03-0033 | 30 |
| LCB03-0034 | 32 |
| LCB03-0035 | 31 |
| LCB03-0036 | 39 |
| LCB03-0037 | 37 |
| LCB03-0040 | 43 |
| LCB03-0041 | 39 |
| LCB03-0042 | 46 |
| LCB03-0059 | 29 |
| LCB03-0060 | 42 |
| LCB03-0061 | 44 |
| LCB03-0062 | 41 |
| LCB03-0063 | 36 |
| LCB03-0064 | 41 |
| LCB03-0065 | 35 |
| LCB03-0066 | 54 |
| LCB03-0067 | 33 |
| LCB03-0070 | 30 |
| LCB03-0072 | 27 |
| LCB03-0076 | 45 |
| LCB03-0079 | 41 |
| LCB03-0080 | 41 |
| LCB03-0083 | 33 |
| LCB03-0084 | 36 |
| LCB03-0085 | 35 |
| LCB03-0086 | 21 |
| LCB03-0087 | 24 |
| LCB03-0088 | 27 |
| LCB03-0089 | 19 |
| LCB03-0090 | 26 |
| LCB03-0091 | 39 |
| LCB03-0092 | 28 |

TABLE 5-continued

| compound | Inhibition (%) |
| --- | --- |
| LCB03-0093 | 31 |
| LCB03-0094 | 29 |
| LCB03-0095 | 23 |
| LCB03-0097 | 34 |
| LCB03-0098 | 34 |
| LCB03-0099 | 29 |
| LCB03-0107 | 58 |
| LCB03-0108 | 56 |
| LCB03-0109 | 48 |
| LCB03-0110 | 65 |
| LCB03-0111 | 58 |
| LCB03-0112 | 38 |
| Control compound1 | 17 |
| Control compound2 | 14 |
| Control compound3 | 11 |

As shown in table 5, the compounds of the present invention inhibit the migration of the activated fibroblast at the concentration of 0.5 uM and the average of the inhibition was by 36.9%. Especially, the compounds of LCB 03-0032, LCB 03-0036~37, LCB 03-0040~42, LCB 03-0060~67, LCB 03-0076, LCB 03-0079~80, LCB 03-0084~85, LCB 03-0091, and LCB 03-0107~112 that have common structural characters generally showed around the average inhibition value or higher. However, the three control compounds used for comparison showed significantly decreased inhibitory activities when compared with the compounds of the present invention as shown in table 5 in the same experimental condition. These results indicate that the compounds of present invention show an excellent efficacy for suppression against the activation of fibroblast into myoblast cell type. However the three control compounds for comparison have a significantly less inhibition activity. Therefore, the compounds of the present invention can be considered to show preventive and/or therapeutic efficacy for inflammatory diseases, wound treatment or scar formation that are associated with activated myoblast cells.

Experimental Example 4

Measurement of Anti-Inflammatory Efficacy in Mouse Skin Inflammatory Model Induced by Oxazolone The compounds of the present invention were evaluated for their effective anti-inflammatory activity using a skin inflammatory animal model of 8 weeks old Balb/C mouse ears induced by oxazolone. First, 8 weeks Balb/C mice were sensitized by applying 50 ul of 3% oxazolone dissolved in acetone:olive oil (4:1) on a shaved dorsal area for two consecutive days. After 4 days, the thickness of ear was measured using a caliper for the thickness value of ear before the induction of inflammation. Subsequently 20 ul of 0.1% each compound dissolved in ethanol were applied to inner and outer side of the ear. After 30 minutes the 20 ul of 0.5% oxazolone dissolved in acetone:olive oil (4:1) were applied to inner and outer side of the mouse ear. After 36 hours, the thickness of ear was measured for the increased thickness induced by inflammation. As the increased amount of ear thickness in the group treated with 20 ul of the carrier solution only was assigned as 100%, the increased amount of ear thickness in the group treated with each compound was represented as % value as well. The average value was obtained in each group (n=4). From this experiment, the % amount of suppression against the increase of ear thickness that is proportional with the degree of inflammation was obtained and shown in table 6 when 0.1% of the compounds of the present invention and the three control compounds were treated respectively.

TABLE 6

| compound | Inhibition (%) |
| --- | --- |
| LCB03-0032 | 27 |
| LCB03-0033 | 22 |
| LCB03-0034 | 29 |
| LCB03-0035 | 31 |
| LCB03-0036 | 28 |
| LCB03-0037 | 33 |
| LCB03-0040 | 31 |
| LCB03-0041 | 29 |
| LCB03-0042 | 33 |
| LCB03-0059 | 59 |
| LCB03-0060 | 66 |
| LCB03-0061 | 55 |
| LCB03-0062 | 57 |
| LCB03-0063 | 51 |
| LCB03-0064 | 63 |
| LCB03-0065 | 52 |
| LCB03-0066 | 67 |
| LCB03-0067 | 54 |
| LCB03-0070 | 55 |
| LCB03-0072 | 48 |
| LCB03-0076 | 54 |
| LCB03-0079 | 51 |
| LCB03-0080 | 53 |
| LCB03-0083 | 47 |
| LCB03-0084 | 49 |
| LCB03-0085 | 53 |
| LCB03-0086 | 48 |
| LCB03-0087 | 43 |
| LCB03-0088 | 51 |
| LCB03-0089 | 59 |
| LCB03-0090 | 56 |
| LCB03-0091 | 49 |
| LCB03-0092 | 47 |
| LCB03-0093 | 51 |
| LCB03-0094 | 49 |
| LCB03-0095 | 43 |
| LCB03-0107 | 59 |
| LCB03-0108 | 63 |
| LCB03-0109 | 52 |
| LCB03-0110 | 72 |
| LCB03-0111 | 71 |
| LCB03-0112 | 68 |
| Control compound1 | 3 |
| Control compound3 | 22 |

As shown in table 6, the compounds of the present invention inhibit the inflammation on the mouse ear at the concentration of 0.1% and the average of the inhibition was by 49.4%. Especially, the compounds of LCB 03-0059~67, LCB 03-0070, LCB 03-0072, LCB 03-0076, LCB 03-0079~80, LCB 03-0093~94, LCB 03-0107~112 that have common structural characters generally showed a high inhibitory activity by around 50% or higher. The compounds of the present invention showed generally a significantly higher anti-inflammatory activity than the two control compounds used for comparison in the same experimental condition. Therefore the compounds of the present invention have an excellent anti-inflammatory activity which is superior to the two control compounds used for comparison.

Experimental Example 5

The Estimation of Inhibitory Activities of LCB 03-0110 Against Various Tyrosine Kinases In order to determine inhibitory activity of LCB 03-0110, the representative one of the compounds provided by this invention, against various kinases, we performed in vitro experiments. Measurement of $IC_{50}$ value of compounds against various kinases can be carried out using the method to measure in vitro kinase activity as described in the preferred embodiment 1 of above or by a CRO company, for example, Reaction Biology Corp. (Palo Alto, USA). Following table 7 shows $IC_{50}$ value of LCB 03-0110 against various tyrosine kinases involved in various immune cell activation.

TABLE 7

| Kinase | IC50 (nM) | Kinase | IC50 (nM) |
| --- | --- | --- | --- |
| c-Src | 1.3 | Blk | 50.7 |
| Lck | 21.6 | Btk1 | 17.7 |
| Lyn | 4.3 | Syk1 | 25.2 |
| Fyn | 2.3 | VEGFR2 | 4.6 |
| Yes | 2.1 | EPHA3 | 5.1 |
| Fgr | 3.7 | FLT3 | 26.1 |
| Hck | 4.4 | | |

As shown in table 7, $IC_{50}$ value of LCB 03-0110 compound against Src family tyrosine kinase which plays an important role in immune cell activation is 1.3-50.7 nM. This compound also inhibits strongly against Syk1, Btk1, EphA3, and FLT3 tyrosine kinase which plays a key role in immune cell signaling by giving $IC_{50}$ values from 4.6 nM to 26.1 nM. Therefore these results suggest this compound can inhibit effectively the activity of kinases involved in immune cell activation. Therefore, since LCB 03-0110 and the compounds similar in structure and activity thereto, provided by the present invention, can inhibit effectively the activity of Syk1, Btk1, EphA3, and FLT3 tyrosine kinase as well as Src family which plays an important role in inflammatory and immune reactions, they can be useful in the prevention and/or treatment of inflammatory diseases or autoimmune disorder. In addition, since LCB 03-0110 and the compounds similar in structure and activity thereto, provided by the present invention, can inhibit effectively the activity of VEGFR2 tyrosine kinase which plays an important role in neovascularization, they can be useful in the prevention or treatment of diabetic retinopathy.

Experimental Example 6

The Estimation of Inhibitory Activities of LCB 03-0110 Against the Synthesis of Cytokines and NO in Activated Macrophage As described in the preferred embodiment 2, J774A.1 macrophage was stimulated with LPS after being treated with various concentrations of the compound LCB 03-0110. After 6 hours, the culture medium was collected to quantify TNF-alpha, IL-6, and IL-12 by enzyme-linked immunosorbent assay and after 24 hours, the culture medium was collected to quantify the amount of NO synthesis. These results were shown in FIG. 1. As shown in FIG. 1, the concentration of the compound LCB 03-0110 required to inhibit the synthesis of TNF-alpha and NO by 50% was approximately 2 μM and its concentration to inhibit the synthesis of IL-6 by 50% was about 7 μM. In particular, in case of IL-12 synthesis, the treatment of compound LCB 03-0110 at the concentration of 1 μM inhibited its induction of synthesis by LPS by nearly 100%.

From the data, LCB 03-0110 and the compounds similar in structure and activity thereto, provided by the present invention, can effectively suppress the expression of the immune cytokines such as TNF-alpha, IL-6 and IL-12 and inflammatory immune mediators such as NO. Therefore they can be useful for the prevention or treatment of inflammatory diseases.

Experimental Example 7

Figure 2:
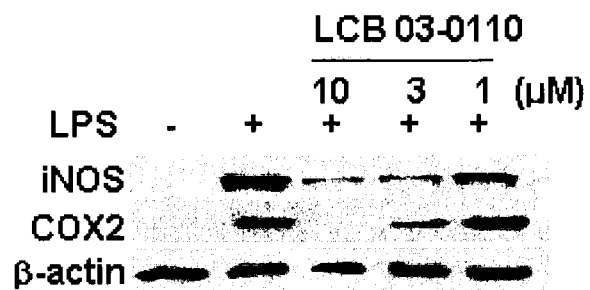
FIG. 2 shows western blotting data to depict the inhibition effect of a compound mentioned in the preferred embodiment described in the present invention against the synthesis of iNOS and COX-2 in activated macrophage

The Estimation of Inhibitory Activities of LCB 03-0110 Against COX-2, and iNOS Protein Synthesis in Activated Macrophages by LPS in vitro experiments were performed to estimate the inhibition against the induced expression of COX-2 and iNOS in macrophage when various concentrations of LCB 03-0110 of the present invention were treated. As the preferred embodiment, J744A.1 macrophage was treated with various concentrations of LCB 03-0110. After 30 minutes, 100 ng/ml of LPS was added and the cells were further incubated for 24 hours. Cell lysate was prepared from the cultured cells and mixed with the equal volume of 2× Laemmli buffer, followed by boiling for two minutes. An equal amount of the total cell lysates was subjected to 10% SDS-polyacrylamide gel electrophoresis and blotted to polyvinylidene difluoride (PVDF) membranes. Using antibodies, western blotting was performed to estimate the amount of expression of COX-2 and iNOS. As shown in FIG. 2, LPS treatment increased expression of iNOS and COX-2, but LCB 03-0110 inhibited iNOS synthesis by 50% at 1 μM and inhibited COX-2 synthesis by 50% at 2 μM. From the data, LCB 03-0110 and the compounds similar in structure and activity thereto, provided by the present invention, can effectively suppress the expression of iNOS and COX-2. Therefore they can be useful for the prevention or treatment of inflammatory diseases.

Experimental Example 8

Figure 3:
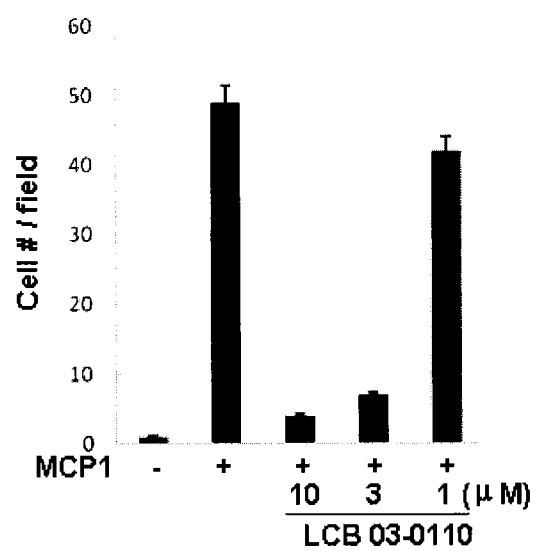
FIG. 3 shows a graph to describe the inhibition effect of a compound mentioned in the preferred embodiment described in the present invention against migration in activated macrophage.

The Estimation of Inhibitory Activity of LCB 03-0110 Against Macrophage Migration In inflammatory reactions, activated macrophages respond to the chemokines to migrate into inflammatory site and then they can recruit more macrophages at the inflammatory site to make the inflammatory reaction to continue and become stronger. The experiment was performed to determine whether LCB 03-0110 of the present invention can suppress the increased migration of activated Raw264.7 macrophage by MCP-1. As a preferred embodiment, $10^5$ of Raw264.7 macrophage cells in DMEM medium containing 1% FBS were plated into the upper chamber of 24-well transwell cell migration assay system (Corning, Co.) and treated with 100 ng/ml of LPS only or together with various concentrations of LCB 03-0110. In the lower chamber, 20 ng/ml MCP-1 was added to DMEM medium containing 1% FBS. After 8 hours of incubation, the cells on the upper side of the membrane were removed with a cotton swab and then the migrated macrophage cells on the bottom side of the membrane were stained with crystal violet. Quantification of the numbers of the migrated macrophages was shown in FIG. 3. As shown in FIG. 3, although MCP-1 increased the cell migration of LPS-activated macrophages, the treatment with 2 μM of LCB 03-0110 inhibited the migration of the cells by more than 50%. Therefore, since LCB 03-0110 and the compounds similar in structure and activity thereto, provided by the present invention effectively inhibit the migration of activated macrophages into inflammatory site, they can be useful for the prevention or treatment of inflammatory diseases.

Experimental Example 9

Figure 4:
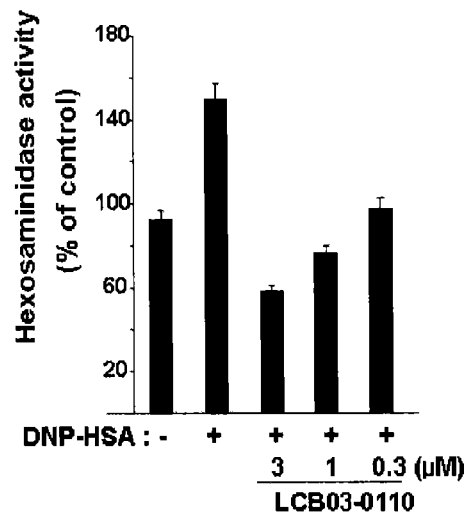
FIG. 4 shows a graph to depict the inhibition effect of a compound mentioned in the preferred embodiment described in the present invention against degranulation in activated mast cells using IgE.

The Estimation of Inhibitory Activity of LCB 03-0110 Against Degranulation in Mast Cell Mast cells are considered as one of the important immune cells that are involved in allergic immune diseases such as asthma or atopic dermatitis. In allergic immune reactions, increased IgE molecules make a complex with FcεRI receptor in the surface of mast cells. When the IgE molecules bind to an antigen, crosslinking of the FcεRI receptor via IgE-antigen complexes induces activations of Src family tyrosine kinase, Syk tyrosine kinase, and Btk1 tyrosine kinase within the cells, leading to the secretion of cytokines such as TNF-alpha, IL-4, and IL-13, etc., as well as the degranulation of mast cells. Extracellular release of various immune modulators upon degranulation of mast cells is the main cause to induce symptoms of serious allergic inflammatory diseases. The experiment was conducted to examine whether the compounds of the present invention can suppress the synthesis of inflammatory cytokines and the degranulation in mast cells activated by cell signalings from the IgE-mediated receptor activation. As a preferred embodiment, RBL-2H3 mast cells were plated at a density of $2×10^5$ cells/well into 24-well plates containing DMEM supplemented with 10% FBS, incubated with 500 ng/ml of anti-DNP IgE for 20 hrs and then washed twice with PIPES buffer containing 10% FBS and $CaCl_2$. Each well was added with 200 μL of PIPES buffer and LCB 03-0110, followed by incubation for 30 min. Next, each well was added with antigen DNP-HSA at a concentration of 25 ng/mL and incubated for 10 min before the plates was placed on ice. p-NAG, a substrate of hexosaminidase, was reacted with 100 μL of the cell culture medium taken from each well at 37° C. for 1 hr, after which the reaction was stopped with 250 μL of $Na_2CO_3/NaHCO_3$. Absorbance was read at 405 nm, and the results are given in the graph of FIG. 4. As can be seen in FIG. 4, the treatment with 0.3 μM of LCB 03-0110 inhibited hexosaminidase release from the mast cells through the degranulation by 80% or higher. Therefore, since LCB 03-0110 and the compounds similar in structure and activity thereto, provided by the present invention, can effectively inhibit the degranulation of mast cells, which is associated with the pathogenesis of asthma or atopic dermatitis, they can be useful for preventing or treating allergic immune diseases.

Experimental Example 10

Figure 5:
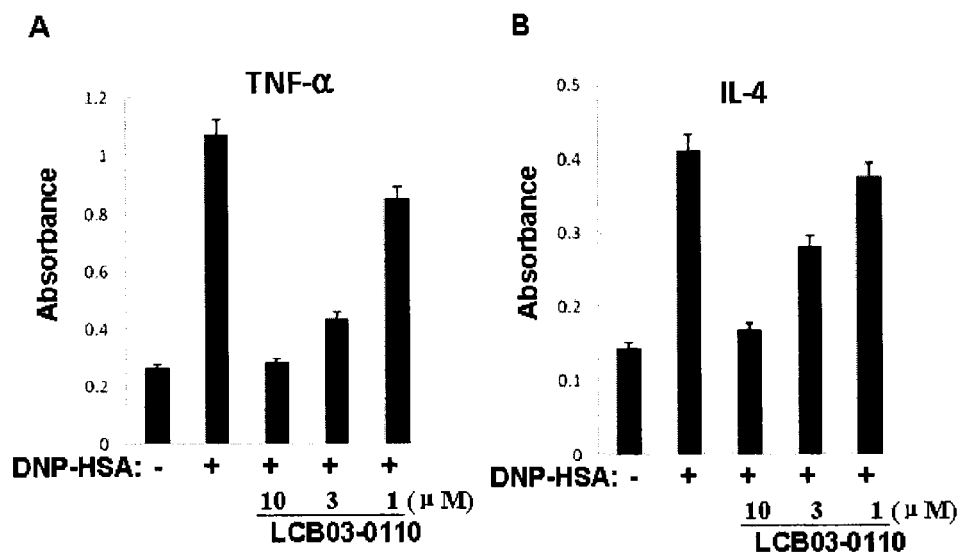
FIG. 5 shows graphs to depict the inhibition effect of a compound mentioned in the preferred embodiment described in the present invention against the synthesis TNF-alpha and IL-4 in activated mast cells using IgE.

The Estimation of Inhibitory Activities of LCB 03-0110 Against TNF-Alpha and IL-4 Synthesis in Mast Cells The experiment was conducted to examine the inhibitory activity of the compounds of the present invention against the synthesis of TNF-alpha or IL-4 in mast cells. As the preferred embodiment, RBL-2H3 mast cells were plated at a density of $2×10^5$ cells/well into 24-well plates containing DMEM supplemented with 10% FBS, added with 500 ng/ml anti-DNP IgE for 20 hrs, and then washed twice with PIPES buffer containing 10% FBS and $CaCl_2$. Each 24 well was treated with 200 μL of PIPES buffer, LCB 03-0110, and 25 ng/mL DNP-HAS sequentially with the interval of 30 min. Four hours later, TNF-alpha and IL-4 levels in the cell culture medium from each well were determined by ELISA, and the results are given in FIG. 5. As shown in FIG. 5, the synthesis of TNF-alpha and IL-4 was inhibited by 50% upon the treatment of mast cells with approximately 2 μM and 3 μM of LCB 03-0110 respectively. Therefore, since LCB 03-0110 and the compounds similar in structure and activity thereto, provided by the present invention, can effectively suppress the expression of TNF-alpha and IL-4 in activated mast cells, they can be useful for preventing or treating inflammatory diseases associated with the activity of mast cells.

Experimental Example 11

The Estimation of Anti-Atopic Dermatitis Efficacy of LCB 03-0110 in an Animal Model In order to examine the suppressive effect of the compounds of the present invention on atopic dermatitis, mice were treated with the compound, LCB 03-0110 of the present invention after the induction of atopic dermatitis, and analyzed for transepidermal water loss (TEWL), IgE level, skin thickness, and mast cell count. As a preferred embodiment, 150 μL of a 5% TNCB solution in a mixture of 3:1 acetone and olive oil was applied twice a week for two weeks to the skin of 6-week-old female Nc/Nga mice to induce atopic dermatitis. Then, four groups with five mice per each group were formed including the affected ((1) to (3)) and normal mice ((4)) as follows.
(1) transdermally administered only with 150 μL of a carrier solution of 20% ethanol: 80% PEG400 every day on the atopic mice for two weeks (TNCB group);
(2) transdermally administered with 0.1% LCB 03-0110 in the carrier solution on the atopic mice every day for two weeks (LCB 03-0110 group);
(3) Transdermally administered with 0.1% tacrolimus (FK506) in the carrier solution on the atopic mice every day for two weeks (Tacrolimus group) for comparison; and
(4) Normal mice were transdermally administered with the carrier solution alone every day for two weeks (normal group).

Figure 6:
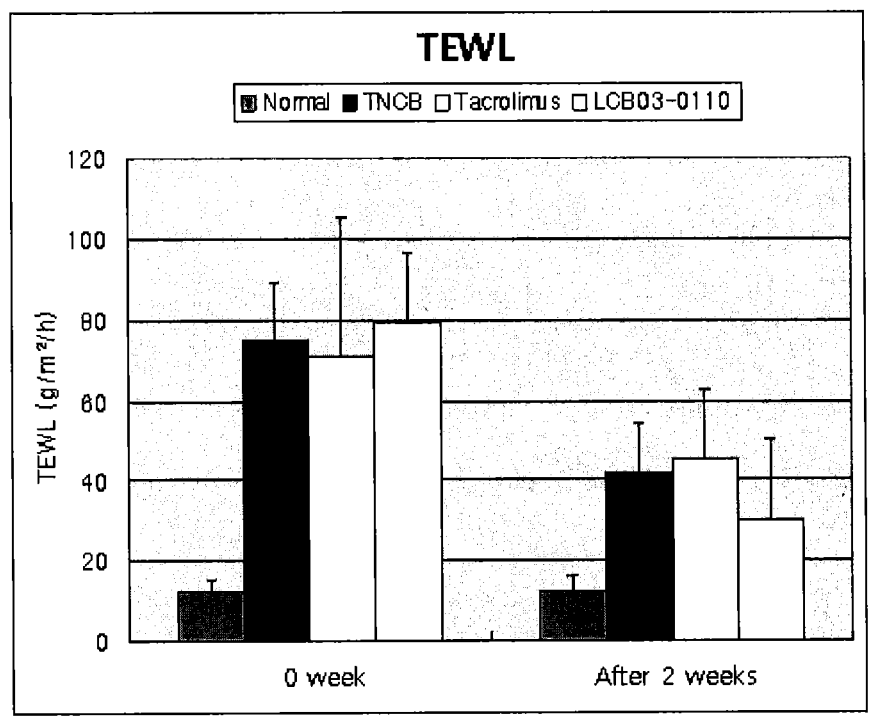
FIG. 6 shows a graph to depict the inhibition effect of a compound mentioned in the preferred embodiment described in the present invention against water loss (TEWL) in the atopic dermatitis animal model experiment.
Figure 7:
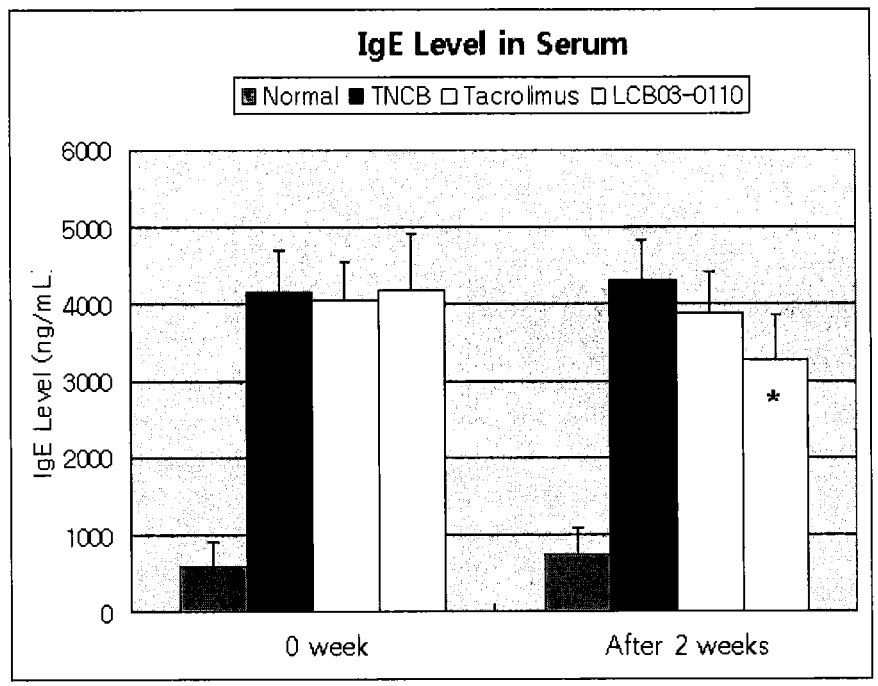
FIG. 7 shows a graph to depict the inhibition effect of a compound mentioned in the preferred embodiment described in the present invention against increase of IgE level in serum in the atopic dermatitis animal model experiment.
Figure 8:
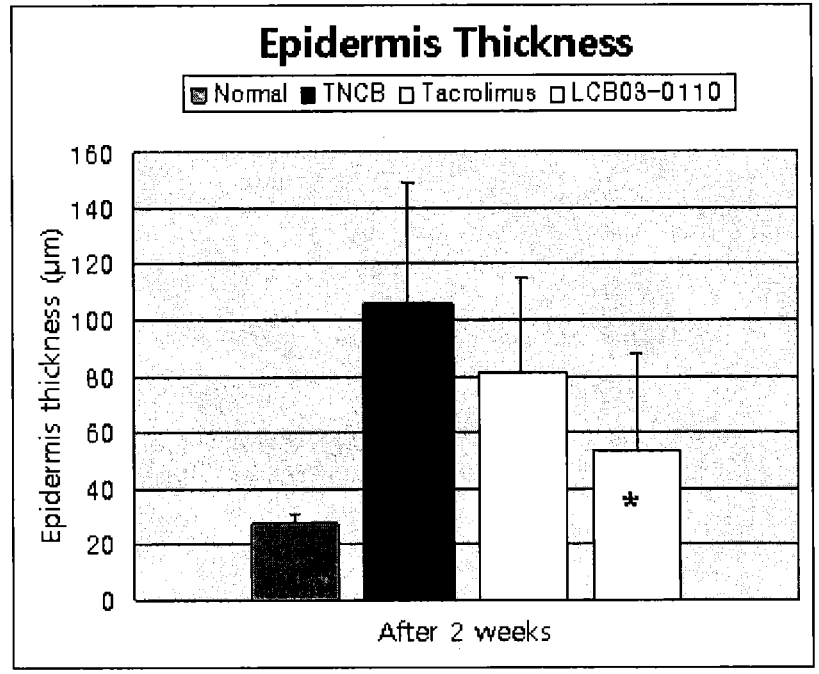
FIG. 8 shows a graph to depict the inhibition effect of a compound mentioned in the preferred embodiment described in the present invention against the increase of epidermal thickness at the dermatitis site in the atopic dermatitis animal model experiment.
Figure 9:
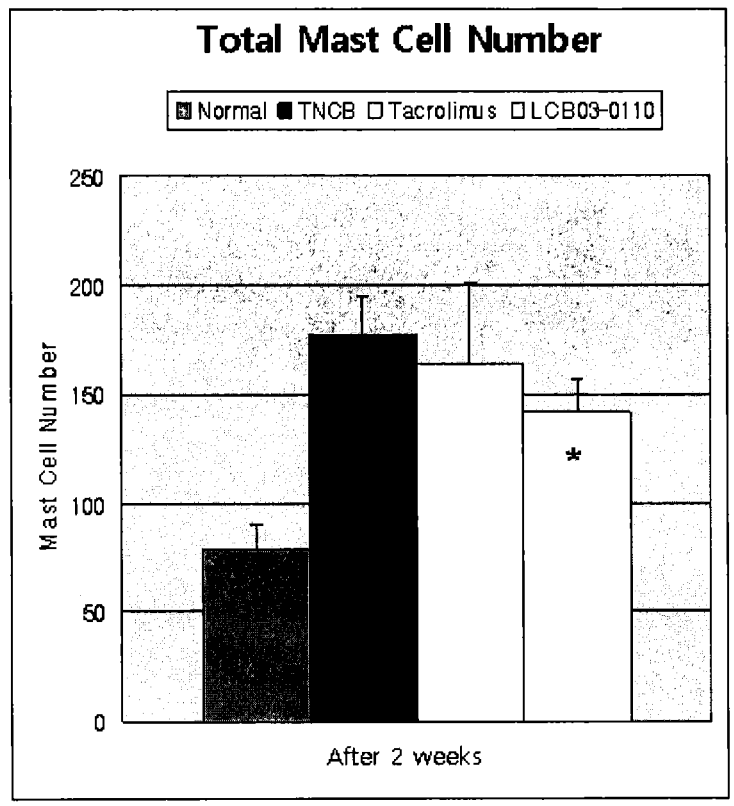
FIG. 9 shows a graph to depict the inhibition effect of a compound mentioned in the preferred embodiment described in the present invention against the increase of mast cell number at the dermatitis site in the atopic dermatitis animal model experiment.

In the four groups, TEWL of the epidermal site at which atopic dermatitis was induced was measured before and after the transdermal administration of each compound for two weeks, and the results are given in FIG. 6. In addition, approximately 100 μL of blood was taken from the each mouse before and after the administration of the each compound and quantitatively analyzed for serum IgE level using ELISA, and the result is shown in FIG. 7. Furthermore, the atopic dermatitis-induced site in each group was taken for biopsy and embedded into a paraffin block which was then sectioned into 4 μm-thick slices and stained with H&E or toluidine blue. The H&E-stained slices were used to measure the thickness of the epidermis and the result is given in FIG. 8. On the other hand, mast cells were quantitated from the toluidine blue stained slices and the result is given in FIG. 9. After two weeks, as can be seen in FIG. 6, the transepidermal water loss (TEWL) of the TNCB group was three times higher than that of the normal group. On the other hand, the LCB 03-0110 group experienced a significant reduction of TEWL by more than 30% compared to the TNCB group, and showed a lower TEWL value than even the tacrolimus group. As seen in FIG. 7, the serum IgE level was remarkably increased in the TNCB group compared to the normal group. The serum IgE level of the LCB 03-0110 group was less than that of the TNCB group by more than 20% and it was also improved over the tacrolimus group. As shown in FIG. 8, the epidermal thickness of the TNCB group was increased by four times higher than that of the normal group. However, that of the LCB 03-0110 group was less that of the TNCB group by more than 60% with significance and the LCB 03-0110 group showed a better efficacy for thinner epidermis than the tacrolimus group. As can be seen in FIG. 9, the number of mast cells was increased by about two fold compared to that of the normal group. However the LCB 03-0110 group had a reduced mast cell count by approximately 25%, compared to the TNCB group, and had a less mast cell count even than did the tacrolimus group. Therefore, since LCB 03-0110 and the compounds similar in structure and activity thereto, provided by the present invention, can effectively suppress atopic dermatitis in vivo, they can be useful for preventing or treating atopic dermatitis, with therapeutic superiority over the currently used drug, Tacrolimus.

Experimental Example 12

Figure 10:
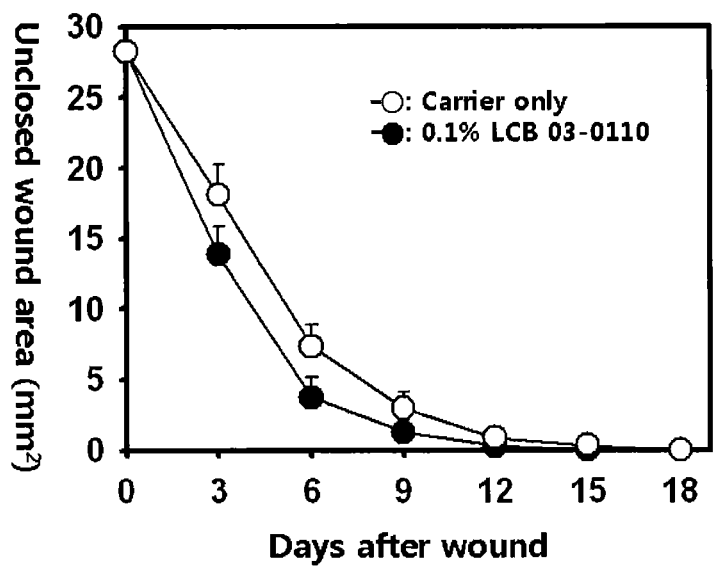
FIG. 10 shows a graph to depict the promotion of skin wound closer in the wound healing animal model experiment by a compound mentioned in the preferred embodiment described in the present invention.
Figure 11:
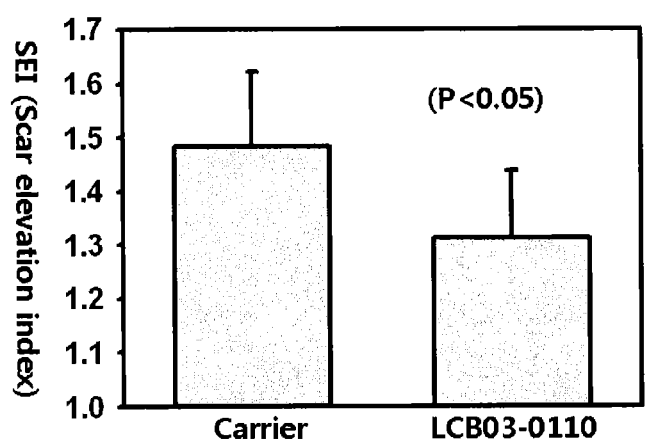
FIG. 11 shows a graph to describe the suppression of scar elevation index (SEI) after wound closing in the wound healing animal model experiment by a compound mentioned in the preferred embodiment described in the present invention.

The Estimation of the Efficacy of LCB 03-0110 for Healing Promotion or Scar Prevention in Skin Wound Healing Process After tissue injury at in vivo, the wound healing usually starts with an inflammatory response in the wound site. In this regard, inflammatory cells, such as activated macrophages, arrive at the wound site and activate surrounding fibroblast cells, epithelial cells, and alpha smooth muscle cells into proliferation, and induce the excessive synthesis of extracellular matrix proteins such as collagen. As a result, fibrotic collagen becomes accumulated to form a scar and its excess accumulation causes the disease of tissue fibrosis. In fact, the deposition of collagen takes place even in atopic dermatitis. Also, the accumulation of collagen and the excessive proliferation of activated myoblast type cells occur in asthma patients' airways to cause a serious problem of the narrowed airway. Injury to vascular tissues induces the accumulation of collagen on the blood vessel wall, resulting in arteriosclerosis. In diabetic patients, a high blood glucose level can injure vascular tissues to cause the uncontrolled formation of capillary vessels. Thus, the continuous high blood glucose level causes continuous damage on ocular tissues and renal tissues and induces inflammatory responses therein, resulting in adverse side effects such as diabetic renal failure, diabetic retinopathy, or diabetic foot ulcers. Furthermore, the accumulation of collagen during the healing process after skin tissue injury leaves an aesthetical fault, a scar. In fact, it is known that the formation of skin scars is greatly reduced in mice in which the generation of macrophage has been suppressed by a genetic manipulation. For this reason, the compounds of the present invention is expected to suppress the accumulation of fibrotic substances in tissue by preventing a scar formation in tissue fibrosis because they not only inhibit the activity of immune cells such as macrophages to suppress inflammatory responses, but simultaneously prevents the activation of fibroblast to myoblast. Moreover, the compounds of the present invention are expected to have therapeutic effects on arthritis or diabetic diseases, which are associated with both angiogenesis and inflammation, since they have an inhibitory activity against VEGFR2, which plays an important role in angiogenesis. The experiment was carried out to examine whether the compound of the present invention has the activity of suppressing scar formation and promoting wound closing by inhibiting the activity of macrophages and myoblast cells in an animal model. As a preferred embodiment, after 8-week-old New Zealand white rabbits were anesthetized by intramuscular injection of Zoletil 50® at a dose of 15 mg/kg, the hair in the inner side of ear was removed from a predetermined experimental site of each rabbit with chioglycolic acid. Using a 6 mm disposable biopsy punch (STIEFEL®), four full excisional wounds were made on the inner side of each ear. For the wound-induced rabbits, a 20% ethanol:80% PEG400 carrier solution containing 0.1% LCB 03-0110 was topically applied to the four wounds on one ear at a dose of 150 µL per wound while the four wounds on the other ear were topically treated with the 20% ethanol:80% PEG400 carrier solution alone, after which the wounds were occlusively dressed with DuoDerm (Convatec). Each group consisted of 12 wounds in rabbits (n=12). The same treatment was repeated every three days for 21 days and the longest and shortest diameter of each of the circular wounds were measured every three days for 12 days using a caliper. From the measurements, areas of the wound sites remaining unclosed were calculated, and are shown in FIG. 10. On day 21 after wounding, tissue from each wound was sampled with an 8 mm biopsy punch, fixed in 10% formalin, embedded in paraffin, and sectioned into 6 µm-thick slices before H&E staining. They were photographed at 40 magnifications. As following the Saulis' method (Saulis A S et al., Plast Reconstr Surg. 2002. 110(1): 177-83), a new epidermal and dermal area corresponding to the area before the wound (Area A in the figure below) and the area of a scar formation (Area B in the figure below) were measured using ImagePro Plus® software, and were used to calculate scar elevation index (SEI) according to Equation 1. The result is shown in FIG. 11.

[Equation 1]

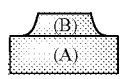

SEI=[(A new epidermal and dermal area corresponding to the area before the wound)+(Area of a scar formation)]/(A new epidermal and dermal area corresponding to the area before the wound)

Figure 12:
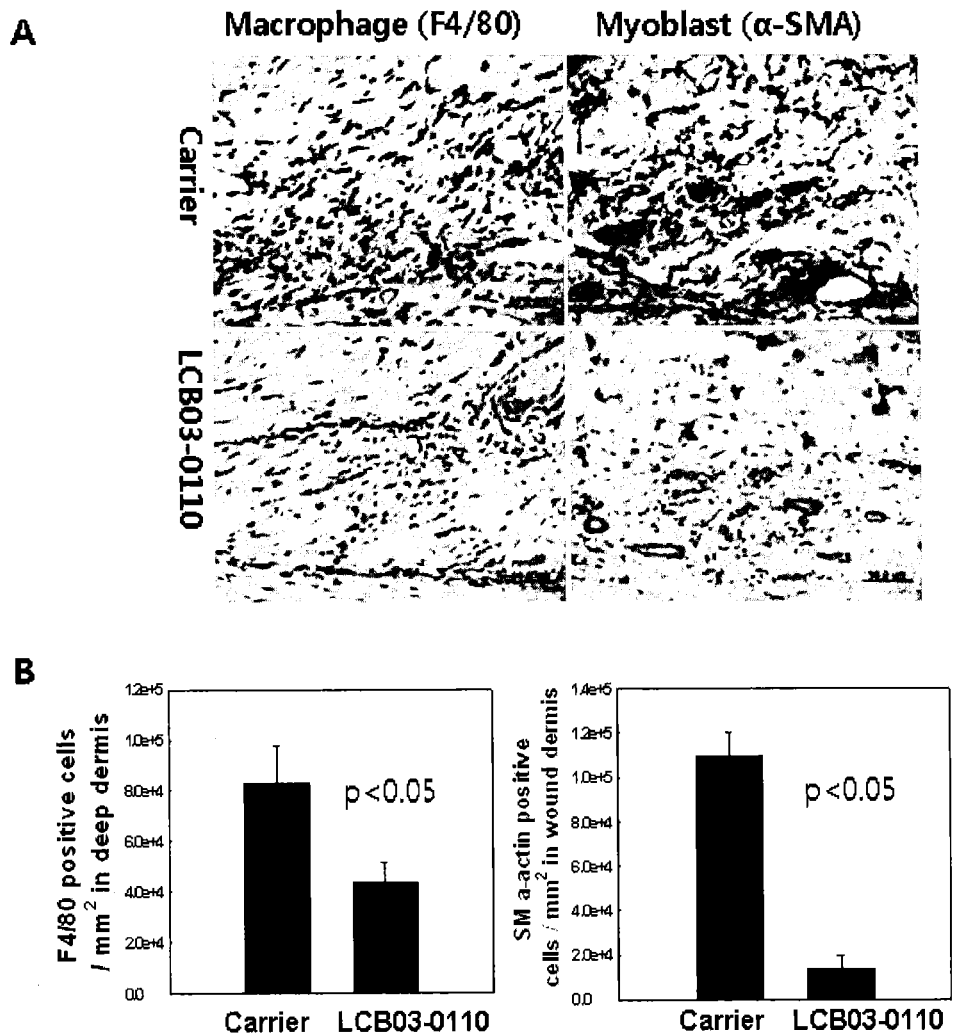
FIG. 12 shows a photo-picture (A) and a graph (B) to depict the suppression of cell populations of macrophage and myoblast cells in the wound healing animal model experiment by a compound mentioned in the preferred embodiment described in the present invention.

As can be seen in FIG. 11, the wound was closed at a higher rate by treatment with LCB 03-0110, compared to the treatment of carrier solution alone, indicating that LCB 03-0110 has the activity to promote wound healing. After the wound healing, SEI of the LCB 03-0110-treated group was reduced by approximately 30% more than that of the carrier solution-treated control with a statistical significance (p<0.05, student t-test), demonstrating the inhibitory activity of LCB 03-0110 against scar formation. The examination was performed to figure out that the inhibitory activity of LCB 03-0110 against scar formation is associated with the suppressive activity of the compound against the activation of macrophages and myoblast cells. For this, the wounds made in the same manner as described above were treated with 0.1% LCB 03-0110 or the carrier solution and covered with DuoDerm. Three days later, wound tissues were taken and embedded into paraffin blocks which were then sectioned into 6 µm-thick slices, followed by the immunostaining of macrophages and activated myoblast cells with an F4/80 antibody and an alpha smooth muscle actin-specific antibody, respectively. A new tissue site in the wound was photographed at 100 fold magnification and the pictures are shown in FIG. 12. In each photograph of the immunostained cells, the macrophages recognized by the F4/80 antibody and the activated myoblast cells expressing alpha smooth muscle actin were counted and were represented as mean±standard deviation. In this experiment, LCB 03-0110 suppressed the activation of macrophages and myoblast cells with a statistical significance (p<0.05, student t-test) during the healing of the wound tissues. Taken together, since the data obtained above demonstrate that LCB 03-0110 and the compounds similar in structure and activity thereto, provided by the present invention, are inhibitory against the activities of inflammatory cells such as macrophages and myoblast cells during wound healing, and also against a scar formation, they can be useful for preventing or treating inflammatory diseases, especially tissue fibrosis- or hypertrophy-associated inflammatory diseases, and for promoting skin wound healing, and preventing skin scar formation.

Experimental Example 13

The Estimation of Anti-Asthmatic Efficacy of LCB 03-0110

Figure 13:
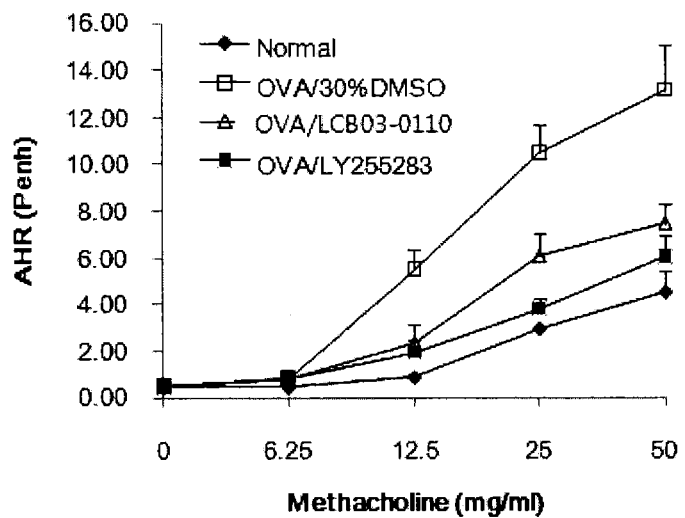
FIG. 13 shows a graph to depict the effect of improvement against AHR in the asthma animal model experiment by a compound mentioned in the preferred embodiment described in the present invention.
Figure 14:
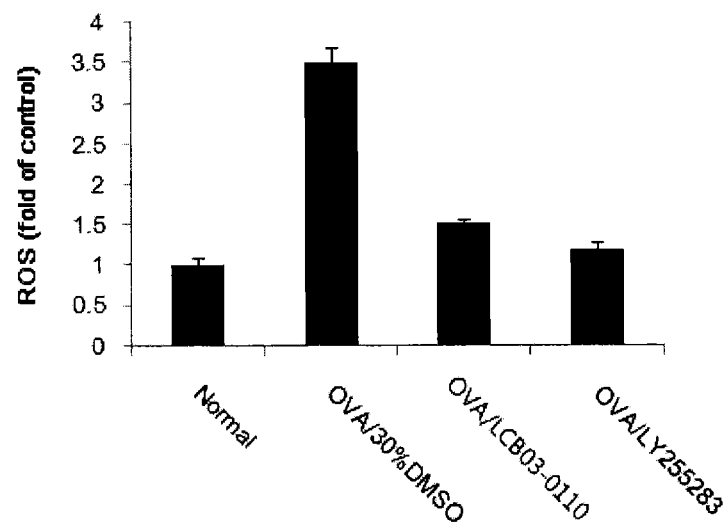
FIG. 14 shows a graph to depict the inhibitory effect of a compound mentioned in the preferred embodiment described in the present invention against ROS generation at airway in the asthma animal model experiment.
Figure 15:
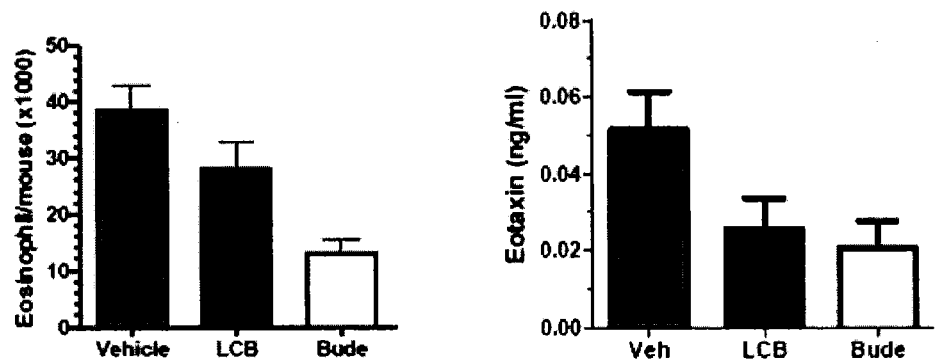
FIG. 15 shows graphs to depict the inhibitory effect of a compound mentioned in the preferred embodiment described in the present invention against number of eosinophils and immune modulator, eotaxin at lung tissue in the asthma animal model experiment.
Figure 16:
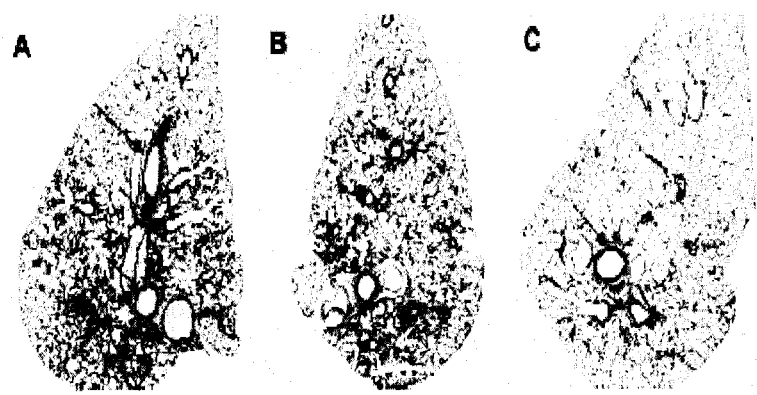
FIG. 16 shows representative photo-pictures and a graph to depict the inhibitory effect of a compound mentioned in the preferred embodiment described in the present invention against the accumulation of mucin protein at lung tissue in the asthma animal model experiment by immunohistochemical stainings of mucin in sliced lung tissue followed by histological grading.
Figure 16:

Asthma is an allergic inflammatory response in the respiratory tract tissue. To verify anti-asthma efficacy of LCB 03-0110, ovalbumin-induced asthma murine model was used. In the first experiment using asthma disease animal model, female Balb/c (8 weeks old) mouse was sensitized by ip injections of 20 mg of OVA and 2.25 mg of Al(OH)$_3$ suspended in 0.1 ml of saline on days 1 and 14. On day 21, 22 and 23 respectively, mice were challenged with 1% OVA aerosol using ultrasonic nebulizer. In this animal experiment, positive control group, was administered with BLT2 antagonist LY255283 (5 mg/kg) by i.v. injection into tails, one hour before the inhalation of ovalbumin on day 21, 22, 23 respectively (the group of OVA/LY255283). For LCB 03-0110-administered group, 0.1% LCB 03-0110 dissolved in saline containing 30% DMSO was inhaled using nebulizer one hour before inhalation of ovalbumin solution on day 21, 22, and 23 respectively. Normal group are non-treated animals (Normal). Negative control group was inhaled with only saline containing 30% DMSO using nebulizer one hour before inhalation of ovalbumin solution on day 21, 22, and 23 respectively. Respiratory tract resistance (AHR) was measured 24 hours after the last administration of ovalbumin solution by nebulizer on day 23. After 48 hours, BALF (bronchoalveolar lavage fluid) were collected from mouse using 1 ml of PBS. Each group consisted of 4~8 mice (n=4~8). As shown in FIG. 13, the group treated with 0.1% LCB03-0110 by inhalation showed a markedly improvement in AHR. When the relative amounts of reactive oxygen species (ROS) were measured in BALF collected after 48 hours, the amount of ROS decreased remarkably in the group treated with LCB 03-0110 by inhalation (FIG. 14). These results demonstrated that the inhalation of LCB 03-0110 improved markedly the ovalbumin-induced inflammatory symptoms in respiratory tract. Another animal model experiment was employed to evaluate the anti-asthma efficacy of LCB 03-0110, in which a direct intratracheal injection of 400 ng of purified house mite allergic substance was carried out on 0, 14, and 21 day respectively. LCB 03-0110 was dissolved in a concentration of 0.1% in 20% ethanol/saline solution and, 20 ul of this was injected directly intratracheal injection one hour before injection of house mite allergy substance on day 21 (LCB group). Negative control group (Vehicle group) was injected with 20 ul of 20% ethanol/saline solution only. Positive control group (Bude group) was injected with 20 ul of 0.03% of Budesonide in 20% ethanol/saline solution. Each group consisted of 4~8 mice (n=4~8). Four hours after last administration of house mite allergen, the lung tissue and BALF samples were collected to measure the amount of mucin synthesis, immune mediators and several inflammatory immune cells. As shown in FIG. 14, LCB 03-0110 administration suppressed eosinophil penetration into lung tissue (Left of FIG. 15), which was associated with the suppression of eotaxin, an inflammatory mediator, in BALF collected from LCB 03-0110 treated animals (Right of FIG. 15). In addition, periodic Schiff staining was performed to measure the amount of mucin in lung tissue, and the result was shown in FIG. 16. Administration of 20% ethanol/saline displayed a strong mucin staining (FIG. 16-A). However 0.1% LCB 03-0110 administration (FIG. 16-B) and the treatment with 0.03% Budesonide (FIG. 16-C) decreased the extent of the staining. After scoring the mucin content from the histologic staining, the value for mean and standard deviation was shown in lower of FIG. 16. The group administered with 0.1% LCB 03-0110 suppressed mucin synthesis similarly to the positive control of Budesonide-treated group with a statistical significance (p<0.05, student t-test) as compared with the group which was injected only with 20% ethanol/saline solution (Vehicle). Mucin is mainly synthesized in epithelial cells of activated respiratory tract and a major sunstance to cause a respiratory tract closure in asthmatic symptom. Since LCB 03-0110 and the compounds similar in structure and activity thereto, provided by the present invention, are inhibitory against inflammatory responses and mucin synthesis in respiratory tract, they can be useful for the prevention or treatment of asthma, COPD, or inflammatory response-related diseases.

The invention claimed is:
1. A compound of the following chemical formula 1, or pharmaceutically acceptable salts thereof:

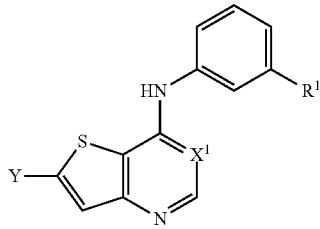

[Chemical formula 1]

wherein,
$X^1$ is N or CH;
$R^1$ is —OH or —OCH$_3$;
Y is $C_{6-10}$ aryl substituted with $R^2$, or $C_{5-10}$ heteroaryl substituted with $R^2$ or N-methylpiperazinyl;
$R^2$ is —(CH$_2$)$_n$—R$^3$, —(CH$_2$)$_n$—C(O)—R$^3$, or —O(CH$_2$)$_n$—R$^3$;
$R^3$ is —H, —CN, halogen, $C_{1-3}$ alkyl, $C_{1-3}$ alkoxy, phenyl, pyridinyl, amino, $C_{1-3}$ alkyl amino, di $C_{1-3}$ alkyl amino, hydroxyl $C_{1-3}$ alkyl amino, carboxy $C_{1-3}$ alkyl amino, $C_{3-6}$ cycloalkyl $C_{1-3}$ alkylamino, pyrolidinyl, hydroxyl pyrolidinyl, hydroxyl $C_{1-3}$ alkylpyrolidinyl, carboxypyrolidinyl, piperidinyl, $C_{1-3}$ alkylpiperidinyl, di $C_{1-3}$ alkyl piperidinyl, piperazinyl, $C_{1-3}$ alkylpiperazinyl, $C_{1-4}$ alkoxycarbonylpiperazinyl, or morpholinyl; and
n is an integer selected from 0 to 3, and
wherein the compound of the chemical formula 1 is any one selected from the group consisting of—
3(6-(phenylthieno[3,2-d]pyrimidine-4-ylamino)phenol,
4-(4-(3-methoxyphenylamino)thieno[3,2-d]pyrimidine-6-yl)benzonitrile,
4-(4-(3-hydroxyphenylamino)thieno[3,2-d]pyrimidine-6-yl)benzonitrile,
4-(4-(3-methoxyphenylamino)thieno[3,2-d]pyrimidine-6-yl)phenol,
3-[6-(4-methoxyphenyl)-thieno[3,2-d]pyrimidine-4-nylamino]-phenol,
N-(3-methoxyphenyl)-6-(4-(2-morpholinoethoxy)phenyl)thieno[3,2-d]pyrimidine-4-amine,
3-(6-(4-chlorophenyl)thieno[3,2-d]pyrimidine-4-ylamino)phenol,
3-(6-(4-(2-morpholinoethoxy)phenyl)thieno[3,2-d]pyrimidine-4-ylamino)phenol,
N-(3-methoxyphenyl)-6-(4-phenethoxyphenyl)thieno[3,2-d]pyrimidine-4-amine,
N-(3-methoxyphenyl)-6-(4-(2-(pyridine-2-yl)ethoxy)phenyl)thieno[3,2-d]pyrimidine-4-amine,
(6-furan-2-yl-thieno[3,2-d]pyrimidine-4-yl)-(3-methoxyphenol)-amine,
(6-furan-3-yl-thieno[3,2-d]pyrimidine-4-yl)-(3-methoxyphenol)-amine,
N-(3-methoxyphenyl)-6-(4-(2-(pyrolidine-1-yl)ethoxy)phenyl)thieno[3,2-d]pyrimidine-4-amine,
N-(3-methoxyphenyl)-6-(thiophene-2-yl)thieno[3,2-d]pyrimidine-4-amine,
(3-methoxyphenyl)-(6-thiophene-3-yl-thieno[3,2-d]pyrimidine-4-yl)-amine,
N-(3-methoxyphenyl)-6-(4-(2-(piperazine-1-yl)ethoxy)phenyl)thieno[3,2-d]pyrimidine-4-amine,
(3-methoxyphenyl)-(6-thiophene-2-yl-thieno[3,2-d]pyrimidine-4-yl)-amine,
3-(6-thiophene-3-yl-thieno[3,2-d]pyrimidine-4-ylamino)-phenol,
3-((6-(4-(morpholinomethyl)phenyl)thieno[3,2-d]pyrimidine-4-ylamino)phenol,
3-((6-(4-(piperazine-1-ylmethyl)phenyl)thieno[3,2-d]pyrimidine-4-ylamino)phenol,
3-(6-(4-(pyrolidine-1-ylmethyl)phenyl)thieno[3,2-d]pyrimidine-4-ylamino)phenol,
3-((6-(4-(piperidine-ylmethyl)phenyl)thieno[3,2-d]pyrimidine-4-ylamino)phenol,
3-((6-(4-((4-methylpiperazine-1-yl-methyl)phenyl)thieno[3,2-d]pyrimidine-4-ylamino)phenol,
3-((6-(4-((diethylamino)methyl)phenyl)thieno[3,2-d]pyrimidine-4-ylamino)phenol,
3-(6-(furan-2-yl)thieno[3,2-d]pyrimidine-4-ylamino)phenol,
3-(6-(furan-2-yl)thieno[3,2-d]pyrimidine-4-ylamino)phenol,
3-(6-(4-((cyclopropylmethylamino)methyl)phenyl)thieno[3,2-d]pyrimidine-4-ylamino)phenol,
3-((6-(4-((isobutylamino)methyl)phenyl)thieno[3,2-d]pyrimidine-4-ylamino)phenol,
3-((6-(4-((ethylamino)methyl)phenyl)thieno[3,2-d]pyrimidine-4-ylamino)phenol,
3-((6-(4-(2-(pyrolidine-1-yl)ethyl)phenyl)thieno[3,2-d]pyrimidine-4-ylamino)phenol,
3-((6-(4-(2-(piperidine-1-yl)ethyl)phenyl)thieno[3,2-d]pyrimidine-4-ylamino)phenol,
3-((6-(4-(2-(4-methylpiperazine-1-yl)ethyl)phenyl)thieno[3,2-d]pyrimidine-4-ylamino)phenol,
3-(6-(4-(2-morpholinoethyl)phenyl)thieno[3,2-d]pyrimidine-4-ylamino)phenol,
2-(4-(4-(3-hydroxyphenylamino)thieno[3,2-d]pyrimidine-6-yl)phenyl)-1-(4-methylpiperazine-1-yl)ethanone,
2-(4-(4-(3-hydroxyphenylamino)thieno[3,2-d]pyrimidine-6-yl)phenyl)-1-(pyrolidine-1-yl)ethanone,
N,N-diethyl-2-(4-(4-(3-hydroxyphenylamino)thieno[3,2-d]pyrimidine-6-yl)phenyl)acetamide, 3-(4-(3-hydroxyphenylamino)thieno[3,2-d]pyrimidine-6-yl)benzoic acid,
(4-(4-(3-hydroxyphenylamino)thieno[3,2-d]pyrimidine-6-yl)phenyl)(4-methylpiperazine-1-yl)methanone,
(3-(4-(3-hydroxyphenylamino)thieno[3,2-d]pyrimidine-6-yl)phenyl(pyrolidine-1-yl)methanone,
N,N-diethyl-3-(4-(3-hydroxyphenylamino)thieno[3,2-d]pyrimidine-6-yl)benzamide,
(3-(4-(3-hydroxyphenylamino)thieno[3,2-d]pyrimidine-6-yl)phenyl(4-methylpiperazine-1-yl)methanone,
methyl 1-(4-(4-(3-hydroxyphenylamino)thieno[3,2-d]pyrimidine-6-yl)benzyl)pyrolidine-2-carboxylate,
3-(6-(4-((2-(hydroxymethyl)pyrolidine-1-yl)methyl)phenyl)thieno[3,2-d]pyrimidine-4-ylamino)phenol,
3-(6-(4-((4-methylpiperidine-1-yl)methyl)phenyl)thieno[3,2-d]pyrimidine-4-ylamino)phenol,
3-(6-(4-(((2R,6S)-2,6-dimethylpiperidine-1-yl)methyl)phenyl)thieno[3,2-d]pyrimidine-4-ylamino)phenol,
3-(6-(3-(piperidine-1-ylmethyl)phenyl)thieno[3,2-d]pyrimidine-4-ylamino)phenol,
3-(6-(3-((4-methylpiperazine-1-yl)methyl)phenyl)thieno[3,2-d]pyrimidine-4-ylamino)phenol,
3-(6-(3-(pyrolidine-1-ylmethyl)phenyl)thieno[3,2-d]pyrimidine-4-ylamino)phenol,
3-(6-(3-((diethylamino)methyl)phenyl)thieno[3,2-d]pyrimidine-4-ylamino)phenol,
3-(6-(3-(piperazine-1-ylmethyl)phenyl)thieno[3,2-d]pyrimidine-4-ylamino)phenol,
3-(6-(3-((ethylamino)methyl)phenyl)thieno[3,2-d]pyrimidine-4-ylamino)phenol,
3-(6-(3-(morpholinomethyl)phenyl)thieno[3,2-d]pyrimidine-4-ylamino)phenol,
1-(4-(4-(3-hydroxyphenylamino)thieno[3,2-d]pyrimidine-6-yl)benzyl)pyrolidine-2-carboxamide HCl salt,
1-(4-(4-(3-hydroxyphenylamino)thieno[3,2-d]pyrimidine-6-yl)benzyl)pyrolidine-2-carboxylic acid HCl salt,
3-(6-(4((2-hydroxyethylamino)methyl)phenyl)thieno[3,2-d]pyrimidine-4-ylamino)phenol,
methyl 2-(3-(4-(3-hydroxyphenylamino)thieno[3,2-d]pyrimidine-6-yl)benzamido)propanoate,
1-(4-(4-(3-hydroxyphenylamino)thieno[3,2-d]pyrimidine-6-yl)benzyl)pyrolidine-3-ol HCl salt,
3-(6-(4-(ethoxymethyl)phenyl)thieno[3,2-d]pyrimidine-4-ylamino)phenol,
4-(4-(3-hydroxyphenylamino)thieno[3,2-d]pyrimidine-6-yl)-N-(1-hydroxyprophane-2-yl)benzamide,
2-(4-(4-(3-hydroxyphenylamino)thieno[3,2-d]pyrimidine-6-yl)benzamido)prophane acid,
3-(6-(3-(2-(pyrolidine-1-yl)ethyl)phenyl)thieno[3,2-d]pyrimidine-4-ylamino)phenol,
3-(6-(3-(2-(piperazine-1-yl)ethyl)phenyl)thieno[3,2-d]pyrimidine-4-ylamino)phenol,
3-(2-(4-(pyrolidine-1-ylmethyl)phenyl)thieno[3,2-b]pyridine-7-ylamino)phenol,
3-(6-(4-morpholinophenyl)thieno[3,2-d]pyrimidine-4-ylamino)phenol,
3-(2-(4-(morpholinomethyl)phenyl)thieno[3,2-b]pyridine-7-ylamino)phenol,
3-(2-(4-((4-methylpiperazine-1-ylmethyl)phenyl)thieno[3,2-b]pyridine-7-ylamino)phenol,
3-(6-(5-(pyrolidine-1-ylmethyl)thiophene-2-yl)thieno[3,2-d]pyrimidine-4-ylamino)phenol,
3-(6-(5-(pyrolidine-1-ylmethyl)furan-2-yl)thieno[3,2-d]pyrimidine-4-ylamino)phenol,
3-(6-(5((4-methylpiperazine-1-yl)methyl)furan-2-yl)thieno[3,2-d]pyrimidine-4-ylamino)phenol,
3-(6-(5-(piperidine-1-ylmethyl)furan-2-yl)thieno[3,2-d]pyrimidine-4-ylamino)phenol,
3-(6-(5-(morpholinomethyl)furan-2-yl)thieno[3,2-d]pyrimidine-4-ylamino)phenol,
3-(6-(5-(piperazine-1-ylmethyl)furan-2-yl)thieno[3,2-d]pyrimidine-4-ylamino)phenol,
3-(6-(5-((ethylamino)methyl)furan-2-yl)thieno[3,2-d]pyrimidine-4-ylamino)phenol,
3-(6-(5-((4-methylpiperazine-1-yl)methyl)thiophene-2-yl)thieno[3,2-d]pyrimidine-4-ylamino)phenol,
3-(6-(5-(piperidine-1-ylmethyl)thiophene-2-yl)thieno[3,2-d]pyrimidine-4-ylamino)phenol,
3-(6-(5-(piperazine-1-ylmethyl)thiophene-2-yl)thieno[3,2-d]pyrimidine-4-ylamino)phenol,
3-(6-(5-((ethylamino)methyl)thiophene-2-yl)thieno[3,2-d]pyrimidine-4-ylamino)phenol,
3-(2-(4-(piperidine-1-ylmethyl)phenyl)thieno[3,2-b]pyridine-7-ylamino)phenol,
3-(2-(4-(piperazine-1-ylmethyl)phenyl)thieno[3,2-b]pyridine-7-ylamino)phenol,
3-(2-(4-((ethylamino)methyl)phenyl)thieno[3,2-b]pyridine-7-ylamino)phenol,
3-(2-(4-methylpiperazine-1-yl)thiazolo[4,5-d]pyrimidine-7-ylamino)phenol,
3-(6-(4-(pyrolidine-1-ylmethyl)thiophene-2-yl)thieno[3,2-d]pyrimidine-4-ylamino)phenol,
3-(6-(4-((4-methylpiperazine-1-yl)methyl)thiophene-2-yl)thieno[3,2-d]pyrimidine-4-ylamino)phenol,
3-(6-(4-(piperidine-1-ylmethyl)thiophene-2-yl)thieno[3,2-d]pyrimidine-4-ylamino)phenol,
3-(6-(4-(morpholinomethyl)thiophene-2-yl)thieno[3,2-d]pyrimidine-4-ylamino)phenol trifluoroacetic acid)
3-(6-(4-(piperazine-1-ylmethyl)thiophene-2-yl)thieno[3,2-d]pyrimidine-4-ylamino)phenol trifluoroacetic acid
3-(6-(4-((ethylaminomethyl)thiophene-2-yl)thieno[3,2-d]pyrimidine-4-ylamino)phenol,
3-(2-(3-(pyrolidine-1-ylmethyl)phenyl)thieno[3,2-b]pyridine-7-ylamino)phenol,
3-(2-(3-((4-methylpiperazine-1-yl)methyl)phenyl)thieno[3,2-b]pyridine-7-ylamino)phenol,
3-(2-(3-(piperidine-1-ylmethyl)phenyl)thieno[3,2-b]pyridine-7-ylamino)phenol,
3-(2-(3-(morpholinomethyl)phenyl)thieno[3,2-b]pyridine-7-ylamino)phenol,
3-(2-(3-(piperazine-1-ylmethyl)phenyl)thieno[3,2-b]pyridine-7-ylamino)phenol,
3-(2-(3-((ethylamino)methyl)phenyl)thieno[3,2-b]pyridine-7-ylamino)phenol,
3-(6-(4-(pyrolidine-1-ylmethyl)furan-2-yl)thieno[3,2-d]pyrimidine-4-ylamino)phenol,
3-(6-(4-((4-methylpiperazine-1-yl)furan-2-yl)thieno[3,2-d]pyrimidine-4-ylamino)phenol trifluoroacetic acid or
3-(6-(4-(piperidine-1-ylmethyl)furan-2-yl)thieno[3,2-d]pyrimidine-4-ylamino)phenol.

2. The compound according to claim 1, wherein the compound is 3-(2-(3-(morpholinomethyl)phenyl)thieno[3,2-b]pyridine-7-ylamino)phenol.

3. The compound according to claim 1, wherein the pharmaceutically acceptable salt is inorganic salt, organic carboxylic acid salt or sulfonic acid salt.

4. The compound according to claim 3, wherein the inorganic salt is HCl salt and the organic carboxylic acid salt is trifluoroacetic acid salt.

5. A pharmaceutical composition for treating scar formation in wound healing process, asthma or atopic dermatitis, comprising the compound according to claim 1 as an active ingredient.

6. The pharmaceutical composition according to claim 5, wherein the wound is characterized by trauma, burns, pressure ulcers, or one caused by diabetic foot ulcers.

7. The pharmaceutical composition according to claim 5, wherein the pharmaceutical composition is administrated at a dose of 0.1 to 500 mg/kg body weight.

8. The pharmaceutical composition according to claim 5, wherein the pharmaceutical composition is for dermal administration.

9. The pharmaceutical composition according to claim 5, wherein the pharmaceutical composition is formulated as an ointment, cream or patch type.

10. A method for treating scar formation in wound healing process, asthma or atopic dermatitis, comprising the step of administering into a patient a therapeutically effective amount of the compound according to claim 1, or pharmaceutically acceptable salts thereof.

* * * * *